US012605444B2

(12) United States Patent
Ertl et al.

(10) Patent No.: US 12,605,444 B2
(45) Date of Patent: *Apr. 21, 2026

(54) ADENOVIRAL VECTORS ENCODING HEPATITIS B VIRAL ANTIGENS FUSED TO HERPES VIRUS GLYCOPROTEIN D AND METHODS OF USING THE SAME

(71) Applicants: VIRION THERAPEUTICS, LLC, Newark, DE (US); THE WISTAR INSTITUTE, Philadelphia, PA (US)

(72) Inventors: Hildegund CJ Ertl, Villanova, PA (US); Colin Stephen Magowan, Bishop, CA (US)

(73) Assignees: Virion Therapeutics, LLC, Newark, DE (US); The Wistar Institute, Philadelphia, PA (US)

( * ) Notice: Subject to any disclaimer, the term of this patent is extended or adjusted under 35 U.S.C. 154(b) by 824 days.

This patent is subject to a terminal disclaimer.

(21) Appl. No.: 17/790,259

(22) PCT Filed: Jan. 8, 2021

(86) PCT No.: PCT/US2021/012630
§ 371 (c)(1),
(2) Date: Jun. 30, 2022

(87) PCT Pub. No.: WO2021/142212
PCT Pub. Date: Jul. 15, 2021

(65) Prior Publication Data
US 2023/0063089 A1 Mar. 2, 2023

Related U.S. Application Data

(60) Provisional application No. 63/112,202, filed on Nov. 11, 2020, provisional application No. 63/112,219, filed on Nov. 11, 2020, provisional application No. 63/064,571, filed on Aug. 12, 2020, provisional application No. 63/064,506, filed on Aug. 12, 2020, provisional application No. 62/967,242, filed on Jan. 29, 2020, provisional application No. 62/967,104, filed on Jan. 29, 2020, provisional application No. 62/958,809, filed on Jan. 9, 2020, provisional application No. 62/958,827, filed on Jan. 9, 2020.

(51) Int. Cl.
| | |
|---|---|
| *A61P 31/12* | (2006.01) |
| *A61K 39/29* | (2006.01) |
| *C12N 7/00* | (2006.01) |
| *C12N 15/86* | (2006.01) |
| *A61K 39/00* | (2006.01) |

(52) U.S. Cl.
CPC ............ *A61K 39/292* (2013.01); *A61P 31/12* (2018.01); *C12N 7/00* (2013.01); *C12N 15/86* (2013.01); *A61K 2039/53* (2013.01); *C12N 2710/10343* (2013.01); *C12N 2730/10122* (2013.01); *C12N 2730/10134* (2013.01)

(58) Field of Classification Search
None
See application file for complete search history.

(56) References Cited

U.S. PATENT DOCUMENTS

| | | | | |
|---|---|---|---|---|
| 8,962,816 B2 * | 2/2015 | Ertl | ...................... | C07K 14/005 |
| | | | | 536/23.4 |
| 11,034,730 B2 | 6/2021 | Tangy et al. | | |
| 11,291,716 B2 * | 4/2022 | Ertl | ......................... | A61P 31/12 |
| 11,324,819 B2 | 5/2022 | Clark et al. | | |
| 11,918,645 B2 | 3/2024 | Georges et al. | | |
| 12,290,561 B2 * | 5/2025 | Ertl | ...................... | C07K 14/005 |
| 2007/0054262 A1 | 3/2007 | Baker et al. | | |
| 2021/0093712 A1 * | 4/2021 | Balsitis | .................. | A61P 37/04 |

FOREIGN PATENT DOCUMENTS

| | | | | |
|---|---|---|---|---|
| CN | 104903343 A | 9/2015 | | |
| CN | 105367662 A | 3/2016 | | |
| CN | 107074913 A | 8/2017 | | |
| CN | 109414496 A | 3/2019 | | |
| WO | 2012/109404 A1 | 8/2012 | | |
| WO | WO-2014102540 A1 * | 7/2014 | ............. | A61K 39/12 |
| WO | 2018/026547 A1 | 2/2018 | | |

OTHER PUBLICATIONS

Chen et al., Significance of quantitative determination of hepatitis B antigen and antibody in blocking mother-to-child intrauterine transmission, Chinese Journal of Neonatology, No. 5: 276-279, Sep. 2008. (English Translation Provided).
Barbara Rehermann, et al.; "The Cytotoxic T Lymphocyte Response to Multiple Hepatitis B Virus Polymerase Epitopes During and After Acute Viral Hepatitis"; The Journal of Experimental Medicine; vol. 181, Mar. 1995; pp. 1047-1059.

(Continued)

*Primary Examiner* — Stacy B Chen
(74) *Attorney, Agent, or Firm* — BakerHostetler

(57) ABSTRACT

Provided herein are non-naturally occurring variants of the hepatitis B virus (HBV) Core protein, the HBV polymerase N-terminal domain, and the HBV polymerase C-terminal domain, as well as immunogenic fragments thereof. Fusion proteins comprising the HBV variants fused to a herpes simplex virus (HSV) glycoprotein (gD) sequence, as well as methods of using the fusion proteins, are also provided.

23 Claims, 49 Drawing Sheets
Specification includes a Sequence Listing.

(56) References Cited

OTHER PUBLICATIONS

Nanna-Sophie Brinck-Jensen, et al.; "Immunogenicity of twenty peptides representing epitopes of the hepatitis B core and surface antigens by IFN-γ response in chronic and resolved HBV"; BMC Immunology; 2015; pp. 1-12.

Farina et al., "Replication-defective vector based on a chimpanzee adenovirus", J. Virol., Dec. 2001, 75(23), 11603-11613.

Hu et al., 2019 EASL, LBP-25 a phase 1 clinical trial of therapeutic vaccine t101 in chronic hepatitis b(chb) patients: a randomized, double-blind, placebo-controlled, single and multiple injections, dose escalation study, 2 pages.

Jian, et al., "The prevalence of neutralising antibodies to chimpanzee adenovirus type 6 and type 7 in healthy adult volunteers, patients with chronic hepatitis B and patients with primary hepatocel-lular carcinoma in China", Archives of Virology, vol. 159, No. 3, Sep. 22, 2013 (Sep. 22, 2013), pp. 465-470, XP055795750.

Martin et al., "TG1050, an immunotherapeutic to treat chronic hepatitis B, induces robust T cells and exerts an antiviral effect in HBV-persistent mice", Gut Microbiota, vol. 64, No. 12, Nov. 26, 2014 (Nov. 26, 2014), pp. 1961-1971, XP055565264.

Pinto et al., "Induction of CD8+ T cells to an HIV-1 antigen through a prime boost regimen with heterologous E1-deleted adenoviral vaccine carriers", J. Immunol., Dec. 15, 2003, 171(12), 6774-6779.

Reyes-Sandoval et al., "Human immunodeficiency virus type 1-spe-cific immune responses in primates upon sequential immunization with adenoviral vaccine carriers of human simian serotypes", J. Virol., Jul. 2004, 78(14), 7392-7399.

Zheng, et al., "Immunogeni city in mice of tandem repeats of an epitope from herpes simplex gD protein when expressed by recom-binant adenovirus vectors", Vaccine, Elsevier, Amsterdam, Nl, vol. 11, No. 12, Jan. 1, 1993 (Jan. 1, 1993), pp. 1191-1198, XP023710651.

* cited by examiner

FIG. 7A
FIG. 7D
Peptides within pools
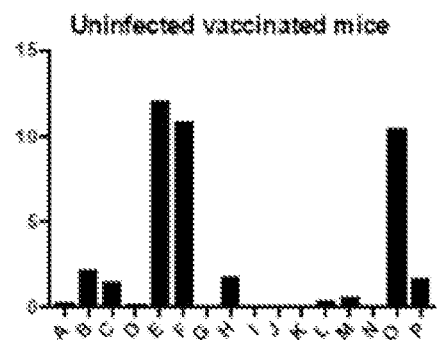
Uninfected vaccinated mice
FIG. 7B
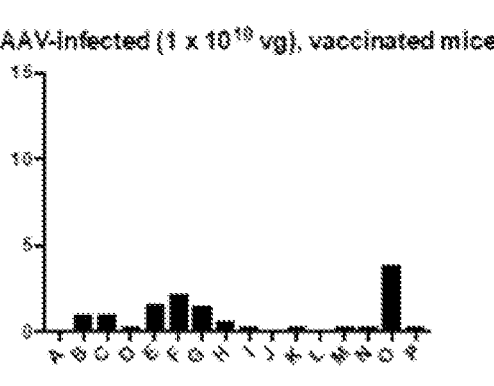
AAV-infected (1 x 10$^{10}$ vg), vaccinated mice
FIG. 7C
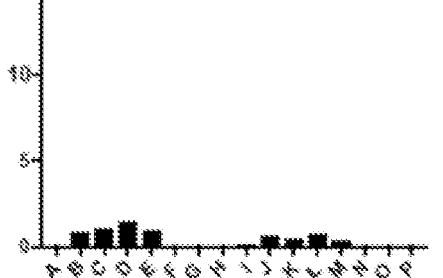
AAV-infected (1.5 x 10$^{11}$ vg), vaccinated mice
% IFN-gamma$^+$CD8$^+$/CD44$^+$CD8$^+$ cells
| | A | B | C | D | E | F | G | H |
|---|---|---|---|---|---|---|---|---|
| I | 1 | 2 | 3 | 4 | 5 | 6 | 7 | 8 |
| J | 9 | 10 | 11 | 12 | 13 | 14 | 15 | 16 |
| K | 17 | 18 | 19 | 20 | 21 | 22 | 23 | 24 |
| L | 25 | 26 | 27 | 28 | 29 | 30 | 31 | 32 |
| M | 33 | 34 | 35 | 36 | 37 | 38 | 39 | 40 |
| N | 41 | 42 | 43 | 44 | 45 | 46 | 47 | 48 |
| O | 49 | 50 | 51 | 52 | 53 | 54 | 55 | 56 |
| P | 57 | 58 | 59 | | | | | |

FIG. 7E

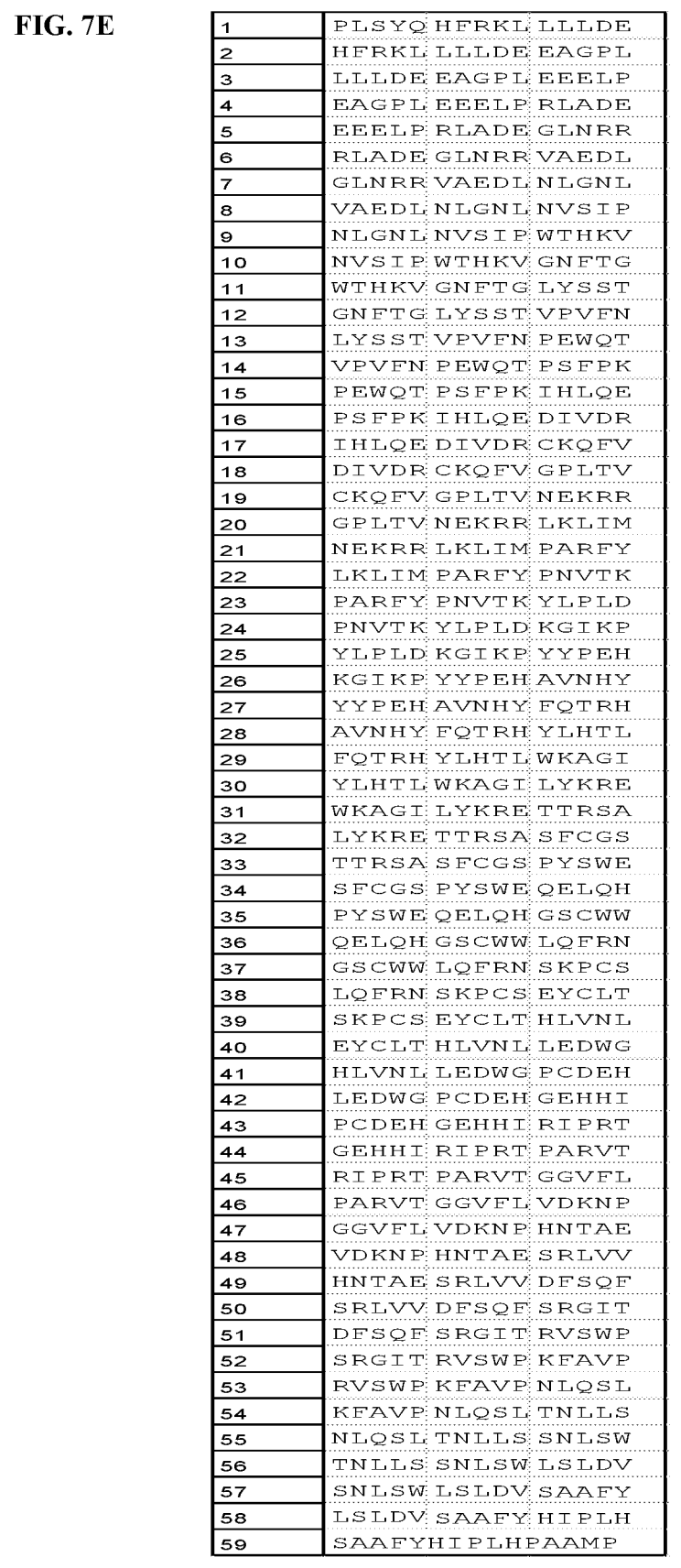

| | | | |
|---|---|---|---|
| 1 | PLSYQ | HFRKL | LLLDE |
| 2 | HFRKL | LLLDE | EAGPL |
| 3 | LLLDE | EAGPL | EEELP |
| 4 | EAGPL | EEELP | RLADE |
| 5 | EEELP | RLADE | GLNRR |
| 6 | RLADE | GLNRR | VAEDL |
| 7 | GLNRR | VAEDL | NLGNL |
| 8 | VAEDL | NLGNL | NVSIP |
| 9 | NLGNL | NVSIP | WTHKV |
| 10 | NVSIP | WTHKV | GNFTG |
| 11 | WTHKV | GNFTG | LYSST |
| 12 | GNFTG | LYSST | VPVFN |
| 13 | LYSST | VPVFN | PEWQT |
| 14 | VPVFN | PEWQT | PSFPK |
| 15 | PEWQT | PSFPK | IHLQE |
| 16 | PSFPK | IHLQE | DIVDR |
| 17 | IHLQE | DIVDR | CKQFV |
| 18 | DIVDR | CKQFV | GPLTV |
| 19 | CKQFV | GPLTV | NEKRR |
| 20 | GPLTV | NEKRR | LKLIM |
| 21 | NEKRR | LKLIM | PARFY |
| 22 | LKLIM | PARFY | PNVTK |
| 23 | PARFY | PNVTK | YLPLD |
| 24 | PNVTK | YLPLD | KGIKP |
| 25 | YLPLD | KGIKP | YYPEH |
| 26 | KGIKP | YYPEH | AVNHY |
| 27 | YYPEH | AVNHY | FQTRH |
| 28 | AVNHY | FQTRH | YLHTL |
| 29 | FQTRH | YLHTL | WKAGI |
| 30 | YLHTL | WKAGI | LYKRE |
| 31 | WKAGI | LYKRE | TTRSA |
| 32 | LYKRE | TTRSA | SFCGS |
| 33 | TTRSA | SFCGS | PYSWE |
| 34 | SFCGS | PYSWE | QELQH |
| 35 | PYSWE | QELQH | GSCWW |
| 36 | QELQH | GSCWW | LQFRN |
| 37 | GSCWW | LQFRN | SKPCS |
| 38 | LQFRN | SKPCS | EYCLT |
| 39 | SKPCS | EYCLT | HLVNL |
| 40 | EYCLT | HLVNL | LEDWG |
| 41 | HLVNL | LEDWG | PCDEH |
| 42 | LEDWG | PCDEH | GEHHI |
| 43 | PCDEH | GEHHI | RIPRT |
| 44 | GEHHI | RIPRT | PARVT |
| 45 | RIPRT | PARVT | GGVFL |
| 46 | PARVT | GGVFL | VDKNP |
| 47 | GGVFL | VDKNP | HNTAE |
| 48 | VDKNP | HNTAE | SRLVV |
| 49 | HNTAE | SRLVV | DFSQF |
| 50 | SRLVV | DFSQF | SRGIT |
| 51 | DFSQF | SRGIT | RVSWP |
| 52 | SRGIT | RVSWP | KFAVP |
| 53 | RVSWP | KFAVP | NLQSL |
| 54 | KFAVP | NLQSL | TNLLS |
| 55 | NLQSL | TNLLS | SNLSW |
| 56 | TNLLS | SNLSW | LSLDV |
| 57 | SNLSW | LSLDV | SAAFY |
| 58 | LSLDV | SAAFY | HIPLH |
| 59 | SAAFYHIPLHPAAMP | | |

Peptides

CD8+ T Cell Peptide Recognition of PolN Epitopes

-/AdC6-gDPoIN                    10$^{11}$ vg AAV8-1.3HBV

10$^{11}$ vg AAV8-1.3HBV / AdC6-gDPoIN

FIG. 13A
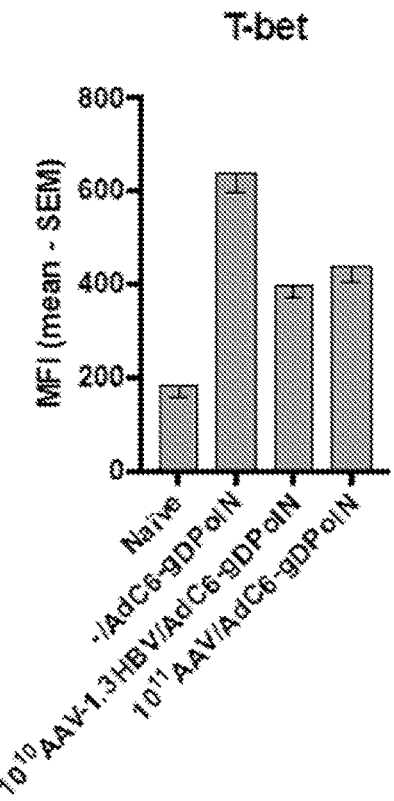
FIG. 13B
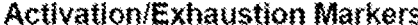
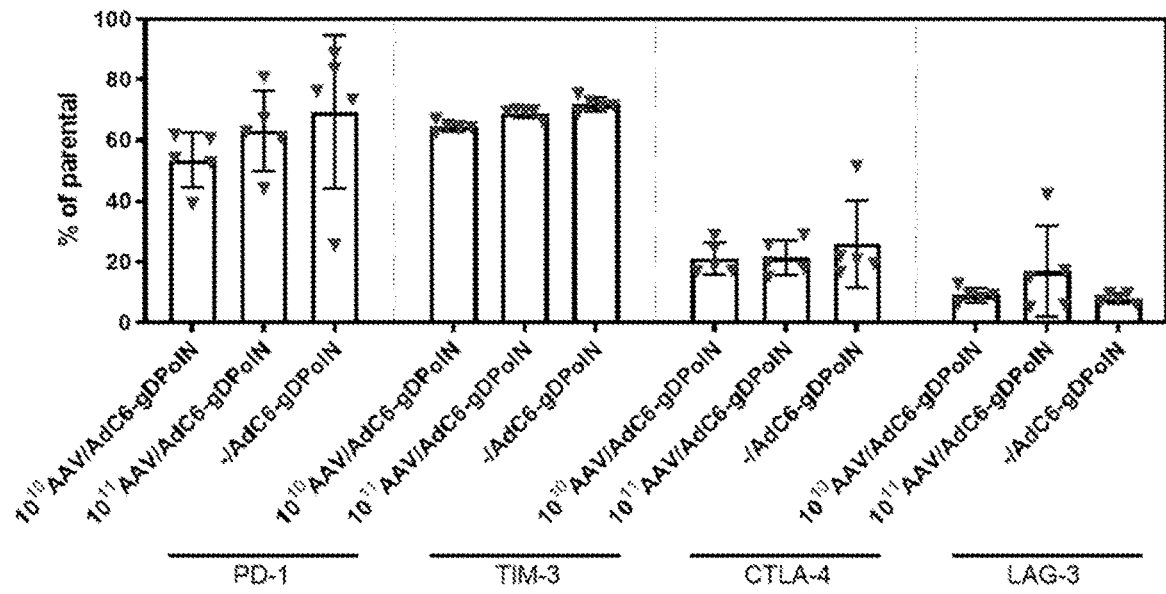

FIG. 14A                          FIG. 14B
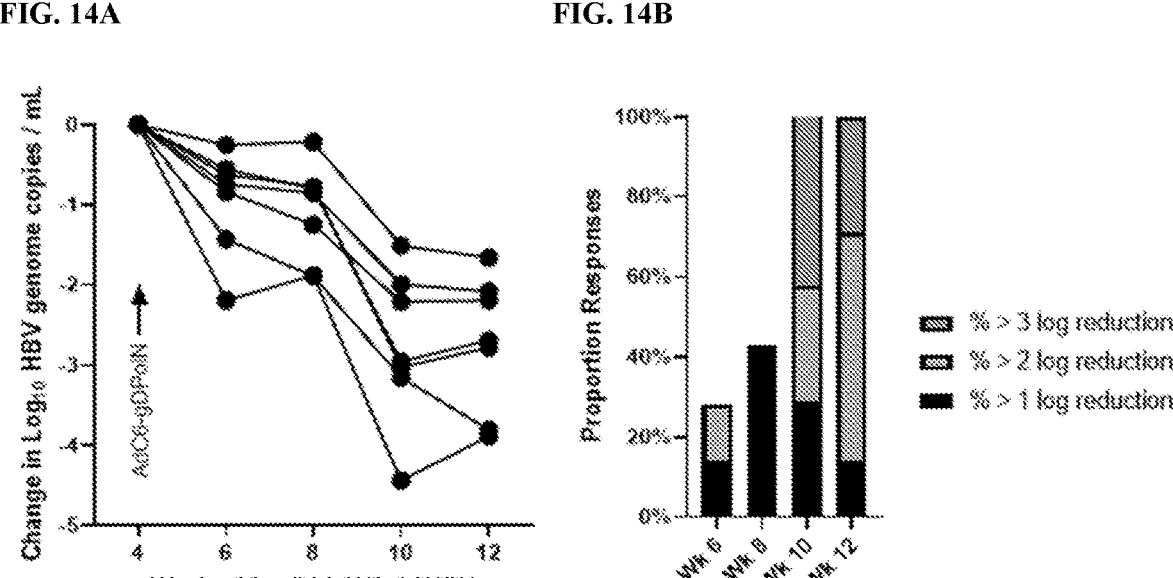

FIG. 15A
FIG. 15B
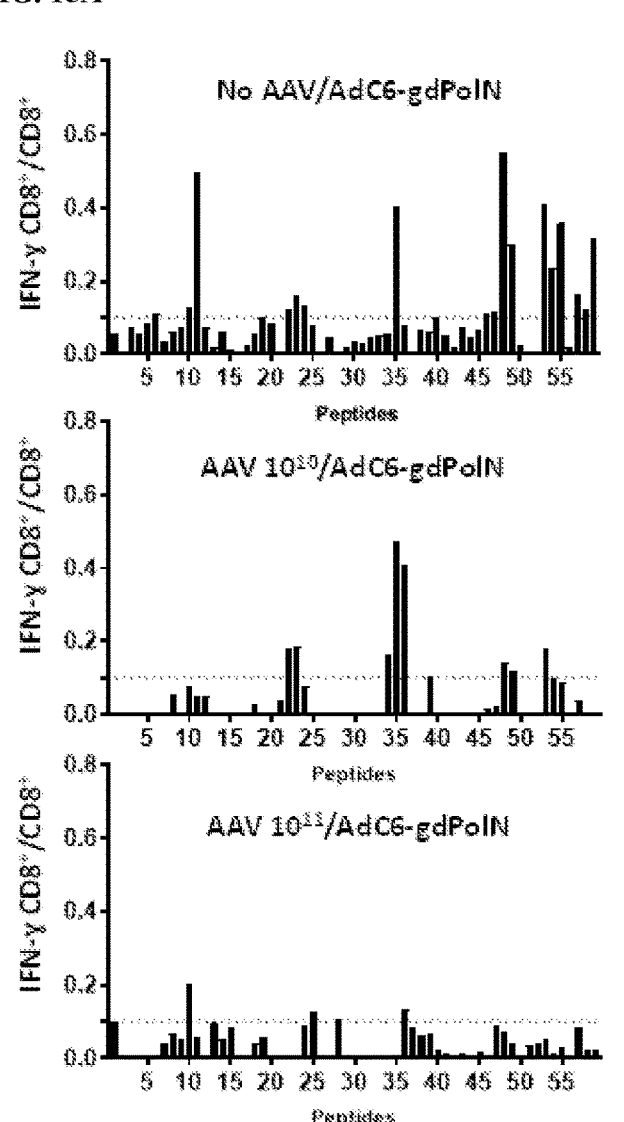
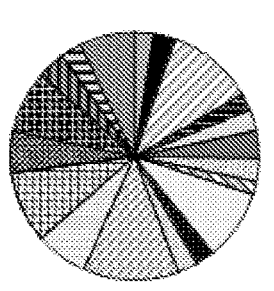
Total IFNγCD8$^+$/CD8$^+$= 4.4%
Peptides: 19
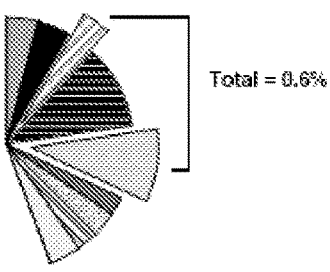
Total = 0.6%
Total IFNγCD8$^+$/CD8$^+$= 2.0%
Peptides: 9
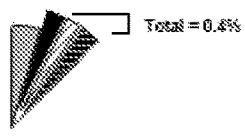
Total = 0.4%
Total IFNγCD8$^+$/CD8$^+$= 0.6%
Peptides: 4

CD8+ T cells responses in mice infected with $10^{10}$ vg of  AAV8-1.3 HBV

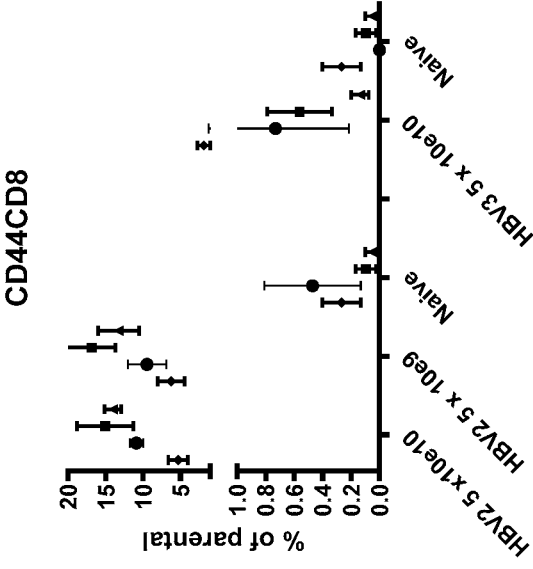
FIG. 26B
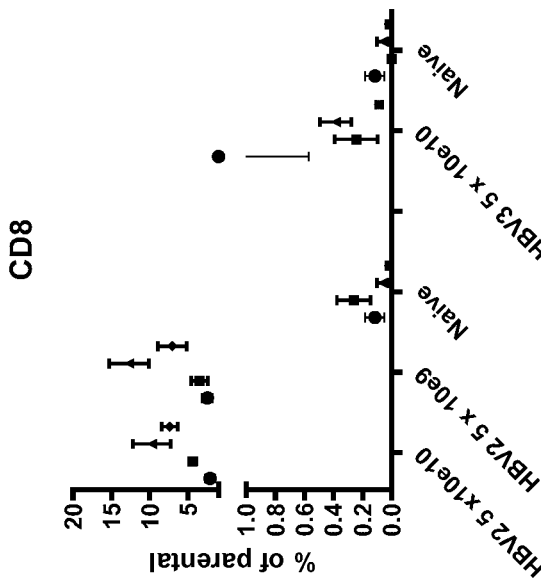
FIG. 26A
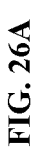

SEQUENCE LISTING

```
<160> NUMBER OF SEQ ID NOS: 233

<210> SEQ ID NO 1
<211> LENGTH: 185
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
                180                 185

<210> SEQ ID NO 2
<211> LENGTH: 183
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr

-continued

```
145              150              155              160

Pro Ser Pro Arg Arg Arg Ser Gln Ser Pro Arg Arg Arg Ser
             165              170              175

Gln Ser Arg Glu Ser Gln Cys
             180

<210> SEQ ID NO 3
<211> LENGTH: 182
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Asp Ile Asp Pro Tyr Lys Glu Phe Gly Ala Ser Val Glu Leu Leu
1               5                  10                  15

Ser Phe Leu Pro Ser Asp Phe Phe Pro Ser Ile Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
             100                 105                 110

Glu Thr Val Leu Glu Tyr Leu Val Ser Phe Gly Val Trp Ile Arg Thr
             115                 120                 125

Pro Pro Ala Tyr Arg Pro Pro Asn Ala Pro Ile Leu Ser Thr Leu Pro
     130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser Gln
             165                 170                 175

Ser Arg Glu Ser Gln Cys
             180

<210> SEQ ID NO 4
<211> LENGTH: 183
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Asp Ile Asp Pro Tyr Lys Glu Phe Gly Ala Thr Val Glu Leu Leu
1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60
```

```
Leu Met Thr Leu Ala Thr Trp Val Gly Gly Asn Leu Glu Asp Pro Ala
65                  70                  75                  80

Ser Arg Asp Leu Val Val Ser Tyr Val Asn Thr Asn Met Gly Leu Lys
                    85                  90                  95

Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
                180
```

```
<210> SEQ ID NO 5
<211> LENGTH: 184
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (12)..(12)
<223> OTHER INFORMATION: /replace="S"
<220> FEATURE:
<221> NAME/KEY: VARIANT
<222> LOCATION: (27)..(27)
<223> OTHER INFORMATION: /replace="I"
<220> FEATURE:
<221> NAME/KEY: VARIANT
<222> LOCATION: (66)..(66)
<223> OTHER INFORMATION: /replace="N"
<220> FEATURE:
<221> NAME/KEY: VARIANT
<222> LOCATION: (73)..(73)
<223> OTHER INFORMATION: /replace="S" or "G"
<220> FEATURE:
<221> NAME/KEY: VARIANT
<222> LOCATION: (82)..(82)
<223> OTHER INFORMATION: /replace="E"
<220> FEATURE:
<221> NAME/KEY: VARIANT
<222> LOCATION: (86)..(86)
<223> OTHER INFORMATION: /replace="S"
<220> FEATURE:
<221> NAME/KEY: VARIANT
<222> LOCATION: (90)..(90)
<223> OTHER INFORMATION: /replace="V"
<220> FEATURE:
<221> NAME/KEY: VARIANT
<222> LOCATION: (96)..(96)
<223> OTHER INFORMATION: /replace="F"
<220> FEATURE:
<221> NAME/KEY: VARIANT
<222> LOCATION: (115)..(115)
<223> OTHER INFORMATION: /replace="I"
<220> FEATURE:
<221> NAME/KEY: VARIANT
<222> LOCATION: (152)..(153)
<223> OTHER INFORMATION: /replace=" "
<220> FEATURE:
<221> NAME/KEY: SITE
<222> LOCATION: (1)..(184)
<223> OTHER INFORMATION: /note="Variant residues given in the sequence
      have no preference with respect to those in the annotations
```

```
          for variant positions"

<400> SEQUENCE: 5

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Asn Asn Leu Glu Asp Pro Ala Ser
65                  70                  75                  80

Arg Asp Leu Val Val Asn Tyr Val Asn Thr Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
            115                 120                 125

Pro Ala Tyr Arg Pro Pro Asn Ala Pro Ile Leu Ser Thr Leu Pro Glu
    130                 135                 140

Thr Thr Val Val Arg Arg Arg Asp Arg Gly Arg Ser Pro Arg Arg Arg
145                 150                 155                 160

Thr Pro Ser Pro Arg Arg Arg Arg Ser Gln Ser Pro Arg Arg Arg Arg
            165                 170                 175

Ser Gln Ser Arg Glu Ser Gln Cys
            180

<210> SEQ ID NO 6
<211> LENGTH: 184
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Asp Ile Asp Pro Tyr Lys Glu Phe Gly Ala Thr Val Glu Leu Leu Ser
1               5                   10                  15

Phe Leu Pro Ser Asp Phe Phe Pro Ser Ile Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Ser Asn Leu Glu Asp Pro Ala Ser
65                  70                  75                  80

Arg Glu Leu Val Val Ser Tyr Val Asn Val Asn Met Gly Leu Lys Ile
                85                  90                  95

Arg Gln Leu Leu Trp Phe His Ile Ser Cys Leu Thr Phe Gly Arg Glu
            100                 105                 110

Thr Val Ile Glu Tyr Leu Val Ser Phe Gly Val Trp Ile Arg Thr Pro
            115                 120                 125

Pro Ala Tyr Arg Pro Pro Asn Ala Pro Ile Leu Ser Thr Leu Pro Glu
    130                 135                 140
```

-continued

```
Thr Thr Val Val Arg Arg Arg Asp Arg Gly Arg Ser Pro Arg Arg Arg
145                 150                 155                 160

Thr Pro Ser Pro Arg Arg Arg Arg Ser Gln Ser Pro Arg Arg Arg Arg
                165                 170                 175

Ser Gln Ser Arg Glu Ser Gln Cys
            180
```

```
<210> SEQ ID NO 7
<211> LENGTH: 552
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
gacatcgacc cctacaagga gttcggcgcc accgtggagc tgctgagctt cctgcccagc      60
gacttcttcc ccagcatcag ggacctgctg gacaccgcca gcgccctgta cagggaggcc     120
ctggagagcc ccgagcactg cagcccccac cacaccgccc tgaggcaggc catcctgtgc     180
tggggcgagc tgatgaccct ggccacctgg gtgggcagca acctggagga ccccgccagc     240
agggagctgg tggtgagcta cgtgaacgtg aacatgggcc tgaagatcag gcagctgctg     300
tggttccaca tcagctgcct gaccttcggc agggagaccg tgatcgagta cctggtgagc     360
ttcggcgtgt ggatcaggac cccccccgcc tacaggcccc caacgccccc catcctgagc     420
accctgcccg agaccaccgt ggtgaggagg agggacaggg gcaggagccc caggaggagg     480 accccccagcc ccaggaggag gaggagccag agccccagga ggaggaggag ccagagcagg     540
gagagccagt gc                                                       552
```

```
<210> SEQ ID NO 8
<211> LENGTH: 305
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Pro Leu Ser Tyr Gln His Phe Arg Lys Leu Leu Leu Leu Asp Glu Glu
1               5                   10                  15

Ala Gly Pro Leu Glu Glu Glu Leu Pro Arg Leu Ala Asp Glu Gly Leu
            20                  25                  30

Asn Arg Arg Val Ala Glu Asp Leu Asn Leu Gly Asn Leu Asn Val Ser
            35                  40                  45

Ile Pro Trp Thr His Lys Val Gly Asn Phe Thr Gly Leu Tyr Ser Ser
    50                  55                  60

Thr Val Pro Val Phe Asn Pro Glu Trp Gln Thr Pro Ser Phe Pro Lys
65                  70                  75                  80

Ile His Leu Gln Glu Asp Ile Val Asp Arg Cys Lys Gln Phe Val Gly
                85                  90                  95

Pro Leu Thr Val Asn Glu Lys Arg Arg Leu Lys Leu Ile Met Pro Ala
            100                 105                 110

Arg Phe Tyr Pro Asn Val Thr Lys Tyr Leu Pro Leu Asp Lys Gly Ile
        115                 120                 125

Lys Pro Tyr Tyr Pro Glu His Ala Val Asn His Tyr Phe Gln Thr Arg
    130                 135                 140
```

His Tyr Leu His Thr Leu Trp Lys Ala Gly Ile Leu Tyr Lys Arg Glu
145                 150                 155                 160

Thr Thr Arg Ser Ala Ser Phe Cys Gly Ser Pro Tyr Ser Trp Glu Gln
                165                 170                 175

Glu Leu Gln His Gly Ser Cys Trp Trp Leu Gln Phe Arg Asn Ser Lys
            180                 185                 190

Pro Cys Ser Glu Tyr Cys Leu Thr His Leu Val Asn Leu Leu Glu Asp
        195                 200                 205

Trp Gly Pro Cys Asp Glu His Gly Glu His His Ile Arg Ile Pro Arg
    210                 215                 220

Thr Pro Ala Arg Val Thr Gly Gly Val Phe Leu Val Asp Lys Asn Pro
225                 230                 235                 240

His Asn Thr Ala Glu Ser Arg Leu Val Val Asp Phe Ser Gln Phe Ser
                245                 250                 255

Arg Gly Ile Thr Arg Val Ser Trp Pro Lys Phe Ala Val Pro Asn Leu
                260                 265                 270

Gln Ser Leu Thr Asn Leu Leu Ser Ser Asn Leu Ser Trp Leu Ser Leu
        275                 280                 285

Asp Val Ser Ala Ala Phe Tyr His Ile Pro Leu His Pro Ala Ala Met
    290                 295                 300

Pro
305

<210> SEQ ID NO 9
<211> LENGTH: 915
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
cccctgagct accagcactt caggaagctg ctgctgctgg acgaggaggc cggccccctg        60
gaggaggagc tgcccaggct ggccgacgag ggcctgaaca ggagggtggc cgaggacctg       120
aacctgggca acctgaacgt gagcatcccc tggacccaca aggtgggcaa cttcaccggc       180
ctgtacagca gcaccgtgcc cgtgttcaac cccgagtggc agaccccag cttccccaag        240 atccacctgc aggaggacat cgtggacagg tgcaagcagt cgtgggccc cctgaccgtg        300 aacgagaaga ggaggctgaa gctgatcatg cccgccaggt ctaccccaa cgtgaccaag        360 tacctgcccc tggacaaggg catcaagccc tactaccccg agcacgccgt gaaccactac       420
ttccagacca ggcactacct gcacaccctg tggaaggccg gcatcctgta caagagggag       480
accaccagga gcgccagctt ctgcggcagc ccctacagct gggagcagga gctgcagcac       540
ggcagctgct ggtggctgca gttcaggaac agcaagccct gcagcgagta ctgcctgacc       600
cacctggtga acctgctgga ggactggggc ccctgcgacg agcacggcga gcaccacatc       660
aggatcccca ggaccccgc cagggtgacc ggcggcgtgt tcctggtgga caagaacccc        720
cacaacaccg ccgagagcag gctggtggtg gacttcagcc agttcagcag gggcatcacc       780
agggtgagct ggcccaagtt cgccgtgccc aacctgcaga gcctgaccaa cctgctgagc       840
agcaacctga gctggctgag cctggacgtg agcgccgcct tctaccacat ccccctgcac       900
cccgccgcca tgccc                                                        915

<210> SEQ ID NO 10
<211> LENGTH: 303
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

His Leu Leu Val Gly Ser Ser Gly Leu Ser Arg Tyr Val Ala Arg Leu
1               5                   10                  15

Ser Ser Asn Ser Arg Ile Ile Asn His Gln His Gly Thr Met Gln Asn
            20                  25                  30

Leu His Asp Ser Cys Ser Arg Asn Leu Tyr Val Ser Leu Leu Leu Leu
        35                  40                  45

Tyr Lys Thr Phe Gly Arg Lys Leu His Leu Tyr Ser His Pro Ile Ile
    50                  55                  60

Leu Lys Thr Lys Arg Trp Gly Tyr Ser Leu Asn Phe Met Gly Tyr Val
65                  70                  75                  80

Ile Gly Ser Trp Gly Ser Leu Pro Gln Asp His Ile Ile Gln Lys Ile
                85                  90                  95

Lys Glu Cys Phe Arg Lys Leu Pro Val Asn Arg Pro Ile Asp Trp Lys
            100                 105                 110

Val Cys Gln Arg Ile Val Gly Leu Leu Gly Phe Ala Ala Pro Phe Thr
            115                 120                 125

Gln Cys Gly Tyr Pro Ala Leu Met Pro Leu Tyr Ala Cys Ile Gln Ser
    130                 135                 140

Lys Gln Ala Phe Thr Phe Ser Pro Thr Tyr Lys Ala Phe Leu Ser Lys
145                 150                 155                 160

Gln Tyr Leu Asn Leu Tyr Pro Val Ala Arg Gln Arg Pro Gly Leu Cys
                165                 170                 175

Gln Val Phe Ala Asp Ala Thr Pro Thr Gly Trp Gly Leu Ala Met Gly
            180                 185                 190

His Gln Arg Met Arg Gly Thr Phe Val Ala Pro Leu Pro Ile His Thr
            195                 200                 205

Ala Glu Leu Leu Ala Ala Cys Phe Ala Arg Ser Arg Ser Gly Ala Lys
    210                 215                 220

Ile Leu Gly Thr Asp Asn Ser Val Val Leu Ser Arg Lys Tyr Thr Ser
225                 230                 235                 240

Phe Pro Trp Leu Leu Gly Cys Ala Ala Asn Trp Ile Leu Arg Gly Thr
                245                 250                 255

Ser Phe Val Tyr Val Pro Ser Ala Leu Asn Pro Ala Asp Asp Pro Ser
            260                 265                 270

Arg Gly Arg Leu Gly Leu Ser Arg Pro Leu Leu Arg Leu Pro Phe Arg
            275                 280                 285

Pro Thr Thr Gly Arg Thr Ser Leu Tyr Ala Val Ser Pro Ser Val
    290                 295                 300

<210> SEQ ID NO 11
<211> LENGTH: 909
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

-continued

```
cacctgctgg tgggcagcag cggcctgagc aggtacgtgg ccaggctgag cagcaacagc        60
aggatcatca accaccagca cggcaccatg cagaacctgc acgacagctg cagcaggaac       120
ctgtacgtga gcctgctgct gctgtacaag accttcggca ggaagctgca cctgtacagc       180
caccccatca tcctgaagac caagaggtgg ggctacagcc tgaacttcat gggctacgtg       240
atcggcagct ggggcagcct gccccaggac cacatcatcc agaagatcaa ggagtgcttc       300
aggaagctgc ccgtgaacag gcccatcgac tggaaggtgt gccagaggat cgtgggcctg       360
ctgggcttcg ccgcccctt cacccagtgc ggctaccccg ccctgatgcc cctgtacgcc       420
tgcatccaga gcaagcaggc cttcaccttc agccccacct acaaggcctt cctgagcaag       480
cagtacctga acctgtaccc cgtggccagg cagaggcccg gcctgtgcca ggtgttcgcc       540
gacgccaccc ccaccggctg gggcctggcc atgggccacc agaggatgag gggcaccttc       600 gtggccccc tgcccatcca caccgccgag ctgctggccg cctgcttcgc caggagcagg       660
agcggcgcca agatcctggg caccgacaac agcgtggtgc tgagcaggaa gtacaccagc       720 ttccctggc tgctgggctg cgccgccaac tggatcctga ggggcaccag cttcgtgtac       780
gtgcccagcg ccctgaaccc cgccgacgac cccagcaggg gcaggctggg cctgagcagg       840
cccctgctga ggctgccctt caggcccacc accggcagga ccagcctgta cgccgtgagc       900
cccagcgtg                                                                909
```

```
<210> SEQ ID NO 12
<211> LENGTH: 269
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
```

-continued

```
                180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro
                260                 265

<210> SEQ ID NO 13
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Pro Lys Ala Pro Tyr Thr Ser Thr Leu Leu Pro Pro Glu Leu Ser
1               5                   10                  15

Glu Thr Pro Asn Ala Thr Gln Pro Glu Leu Ala Pro Glu Asp Pro Glu
                20                  25                  30

Asp Ser Ala Leu Leu Glu Asp Pro Val Gly Thr Val Ala Pro Gln Ile
            35                  40                  45

Pro Pro Asn Trp His Ile Pro Ser Ile Gln Asp Ala Ala Thr Pro Tyr
        50                  55                  60

His Pro Pro Ala Thr Pro Asn Asn Met Gly Leu Ile Ala Gly Ala Val
65                  70                  75                  80

Gly Gly Ser Leu Leu Ala Ala Leu Val Ile Cys Gly Ile Val Tyr Trp
                85                  90                  95

Met His Arg Arg Thr Arg Lys Ala Pro Lys Arg Ile Arg Leu Pro His
            100                 105                 110

Ile Arg Glu Asp Asp Gln Pro Ser Ser His Gln Pro Leu Phe Tyr
        115                 120                 125

<210> SEQ ID NO 14
<211> LENGTH: 580
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
            35                  40                  45

Val Leu Asp Gln Leu Thr Asp Pro Pro Gly Val Arg Arg Val Tyr His
        50                  55                  60

Ile Gln Ala Gly Leu Pro Asp Pro Phe Gln Pro Pro Ser Leu Pro Ile
65                  70                  75                  80
```

-continued

```
Thr Val Tyr Tyr Ala Val Leu Glu Arg Ala Cys Arg Ser Val Leu Leu
            85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
            115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
            195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Asp Ile Asp
                260                 265                 270

Pro Tyr Lys Glu Phe Gly Ala Thr Val Glu Leu Leu Ser Phe Leu Pro
            275                 280                 285

Ser Asp Phe Phe Pro Ser Ile Arg Asp Leu Leu Asp Thr Ala Ser Ala
    290                 295                 300

Leu Tyr Arg Glu Ala Leu Glu Ser Pro Glu His Cys Ser Pro His His
305                 310                 315                 320

Thr Ala Leu Arg Gln Ala Ile Leu Cys Trp Gly Glu Leu Met Thr Leu
                325                 330                 335

Ala Thr Trp Val Gly Ser Asn Leu Glu Asp Pro Ala Ser Arg Glu Leu
            340                 345                 350

Val Val Ser Tyr Val Asn Val Asn Met Gly Leu Lys Ile Arg Gln Leu
            355                 360                 365

Leu Trp Phe His Ile Ser Cys Leu Thr Phe Gly Arg Glu Thr Val Ile
    370                 375                 380

Glu Tyr Leu Val Ser Phe Gly Val Trp Ile Arg Thr Pro Pro Ala Tyr
385                 390                 395                 400

Arg Pro Pro Asn Ala Pro Ile Leu Ser Thr Leu Pro Glu Thr Thr Val
            405                 410                 415

Val Arg Arg Arg Asp Arg Gly Arg Ser Pro Arg Arg Arg Thr Pro Ser
            420                 425                 430

Pro Arg Arg Arg Arg Ser Gln Ser Pro Arg Arg Arg Arg Ser Gln Ser
    435                 440                 445

Arg Glu Ser Gln Cys Gly Pro Lys Ala Pro Tyr Thr Ser Thr Leu Leu
    450                 455                 460

Pro Pro Glu Leu Ser Glu Thr Pro Asn Ala Thr Gln Pro Glu Leu Ala
465                 470                 475                 480

Pro Glu Asp Pro Glu Asp Ser Ala Leu Leu Glu Asp Pro Val Gly Thr
                485                 490                 495
```

-continued

```
Val Ala Pro Gln Ile Pro Pro Asn Trp His Ile Pro Ser Ile Gln Asp
        500                 505                 510

Ala Ala Thr Pro Tyr His Pro Pro Ala Thr Pro Asn Asn Met Gly Leu
        515                 520                 525

Ile Ala Gly Ala Val Gly Gly Ser Leu Leu Ala Ala Leu Val Ile Cys
        530                 535                 540

Gly Ile Val Tyr Trp Met His Arg Arg Thr Arg Lys Ala Pro Lys Arg
545                 550                 555                 560

Ile Arg Leu Pro His Ile Arg Glu Asp Asp Gln Pro Ser Ser His Gln
                565                 570                 575

Pro Leu Phe Tyr
        580
```

```
<210> SEQ ID NO 15
<211> LENGTH: 1743
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15 atggggggg ctgccgccag gttggggggcc gtgattttgt ttgtcgtcat agtgggcctc      60 catgggtcc gcggcaaata tgccttggcg gatgcctctc tcaagatggc cgaccccaat     120
cgctttcgcg gcaaagacct tccggtcctg gaccagctga ccgaccctcc gggggtccgg     180
cgcgtgtacc acatccaggc gggcctaccg gacccgttcc agcccccccag cctcccgatc     240 acggtttact acgccgtgtt ggagcgcgcc tgccgcagcg tgctcctaaa cgcaccgtcg     300 gaggccccc agattgtccg cggggcctcc aagacgtcc ggaaacaacc ctacaacctg     360
accatcgctt ggtttcggat gggaggcaac tgtgctatcc ccatcacggt catggagtac     420
accgaatgct cctacaacaa gtctctgggg gcctgtccca tccgaacgca gccccgctgg     480
aactactatg acagcttcag cgccgtcagc gaggataacc tggggttcct gatgcacgcc     540
cccgcgtttg agaccgccgg cacgtacctg cggctcgtga agataaacga ctggacggag     600
attacacagt ttatcctgga gcaccgagcc aagggctcct gtaagtacgc cctcccgctg     660
cgcatccccc cgtcagcctg cctctccccc caggcctacc agcaggggt gacggtggac     720 agcatcggga tgctgccccg cttcatcccc gagaaccagc gcaccgtcgc cgtatacagc     780
ttgaagatcg ccgggtggca cgggcccgac atcgacccct acaaggagtt cggcgccacc     840
gtggagctgc tgagcttcct gcccagcgac ttcttcccca gcatcaggga cctgctggac     900
accgccagcg ccctgtacag ggaggccctg gagagcccg agcactgcag ccccaccac     960 accgccctga ggcaggccat cctgtgctgg ggcgagctga tgaccctggc cacctgggtg    1020
ggcagcaacc tggaggaccc cgccagcagg gagctggtgg tgagctacgt gaacgtgaac    1080
atgggcctga agatcaggca gctgctgtgg ttccacatca gctgcctgac cttcggcagg    1140
gagaccgtga tcgagtacct ggtgagcttc ggcgtgtgga tcaggacccc ccccgcctac    1200 aggccccca acgcccccat cctgagcacc ctgcccgaga ccaccgtggt gaggaggagg    1260
gacaggggca ggagccccag gaggaggacc cccagcccca ggaggaggag gagccagagc    1320
cccaggagga ggaggagcca gagcagggag agccagtgcg gcccaaggc cccatacacg    1380 agcaccctgc tgccccggga gctgtccgag accccaacg ccacgcagcc agaactcgcc    1440
ccggaagacc ccgaggattc ggccctcttg gaggaccccg tggggacggt ggcgccgcaa    1500
```

-continued atcccaccaa actggcacat cccgtcgatc caggacgccg cgacgcctta ccatcccccg      1560
gccaccccga acaacatggg cctgatcgcc ggcgcggtgg gcggcagtct cctggcagcc      1620
ctggtcattt gcggaattgt gtactggatg caccgccgca ctcggaaagc cccaaagcgc      1680
atacgcctcc cccacatccg ggaagacgac cagccgtcct cgcaccagcc cttgtttac      1740 tag                                                                    1743

<210> SEQ ID NO 16
<211> LENGTH: 701
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Pro Leu Ser
            260                 265                 270

Tyr Gln His Phe Arg Lys Leu Leu Leu Leu Asp Glu Glu Ala Gly Pro
        275                 280                 285

Leu Glu Glu Glu Leu Pro Arg Leu Ala Asp Glu Gly Leu Asn Arg Arg
    290                 295                 300

```
Val Ala Glu Asp Leu Asn Leu Gly Asn Leu Asn Val Ser Ile Pro Trp
305                 310                 315                 320

Thr His Lys Val Gly Asn Phe Thr Gly Leu Tyr Ser Ser Thr Val Pro
                325                 330                 335

Val Phe Asn Pro Glu Trp Gln Thr Pro Ser Phe Pro Lys Ile His Leu
            340                 345                 350

Gln Glu Asp Ile Val Asp Arg Cys Lys Gln Phe Val Gly Pro Leu Thr
            355                 360                 365

Val Asn Glu Lys Arg Arg Leu Lys Leu Ile Met Pro Ala Arg Phe Tyr
        370                 375                 380

Pro Asn Val Thr Lys Tyr Leu Pro Leu Asp Lys Gly Ile Lys Pro Tyr
385                 390                 395                 400

Tyr Pro Glu His Ala Val Asn His Tyr Phe Gln Thr Arg His Tyr Leu
                405                 410                 415

His Thr Leu Trp Lys Ala Gly Ile Leu Tyr Lys Arg Glu Thr Thr Arg
            420                 425                 430

Ser Ala Ser Phe Cys Gly Ser Pro Tyr Ser Trp Glu Gln Glu Leu Gln
        435                 440                 445

His Gly Ser Cys Trp Trp Leu Gln Phe Arg Asn Ser Lys Pro Cys Ser
        450                 455                 460

Glu Tyr Cys Leu Thr His Leu Val Asn Leu Leu Glu Asp Trp Gly Pro
465                 470                 475                 480

Cys Asp Glu His Gly Glu His His Ile Arg Ile Pro Arg Thr Pro Ala
            485                 490                 495

Arg Val Thr Gly Gly Val Phe Leu Val Asp Lys Asn Pro His Asn Thr
            500                 505                 510

Ala Glu Ser Arg Leu Val Val Asp Phe Ser Gln Phe Ser Arg Gly Ile
        515                 520                 525

Thr Arg Val Ser Trp Pro Lys Phe Ala Val Pro Asn Leu Gln Ser Leu
    530                 535                 540

Thr Asn Leu Leu Ser Ser Asn Leu Ser Trp Leu Ser Leu Asp Val Ser
545                 550                 555                 560

Ala Ala Phe Tyr His Ile Pro Leu His Pro Ala Ala Met Pro Gly Pro
            565                 570                 575

Lys Ala Pro Tyr Thr Ser Thr Leu Leu Pro Pro Glu Leu Ser Glu Thr
            580                 585                 590

Pro Asn Ala Thr Gln Pro Glu Leu Ala Pro Glu Asp Pro Glu Asp Ser
        595                 600                 605

Ala Leu Leu Glu Asp Pro Val Gly Thr Val Ala Pro Gln Ile Pro Pro
    610                 615                 620

Asn Trp His Ile Pro Ser Ile Gln Asp Ala Ala Thr Pro Tyr His Pro
625                 630                 635                 640

Pro Ala Thr Pro Asn Asn Met Gly Leu Ile Ala Gly Ala Val Gly Gly
                645                 650                 655

Ser Leu Leu Ala Ala Leu Val Ile Cys Gly Ile Val Tyr Trp Met His
        660                 665                 670

Arg Arg Thr Arg Lys Ala Pro Lys Arg Ile Arg Leu Pro His Ile Arg
        675                 680                 685

Glu Asp Asp Gln Pro Ser Ser His Gln Pro Leu Phe Tyr
    690                 695                 700
```

<210> SEQ ID NO 17
<211> LENGTH: 2106

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17 atggggggggg ctgccgccag gttgggggcc gtgattttgt ttgtcgtcat agtgggcctc      60 catgggggtcc gcggcaaata tgccttggcg gatgcctctc tcaagatggc cgaccccaat     120
cgctttcgcg gcaaagacct tccggtcctg gaccagctga ccgaccctcc gggggtccgg     180
cgcgtgtacc acatccaggc gggcctaccg gacccgttcc agccccccag cctcccgatc     240
acggtttact acgccgtgtt ggagcgcgcc tgccgcagcg tgctcctaaa cgcaccgtcg     300
gaggcccccc agattgtccg cggggcctcc aagacgtcc ggaaacaacc ctacaacctg      360
accatcgctt ggtttcggat gggaggcaac tgtgctatcc ccatcacggt catggagtac     420
accgaatgct cctacaacaa gtctctgggg gcctgtccca tccgaacgca gccccgctgg     480
aactactatg acagcttcag cgccgtcagc gaggataacc tggggttcct gatgcacgcc     540
cccgcgtttg agaccgccgg cacgtacctg cggctcgtga agataaacga ctggacggag     600
attacacagt ttatcctgga gcaccgagcc aagggctcct gtaagtacgc cctcccgctg     660
cgcatccccc cgtcagcctg cctctcccccc caggcctacc agcaggggggt gacggtggac     720 agcatcggga tgctgccccg cttcatcccc gagaaccagc gcaccgtcgc cgtatacagc     780
ttgaagatcg ccgggtggca cgggcccccc ctgagctacc agcacttcag gaagctgctg     840
ctgctggacg aggaggccgg cccccctggag gaggagctgc ccaggctggc cgacgagggc     900
ctgaacagga gggtggccga ggacctgaac ctgggcaacc tgaacgtgag catcccctgg     960
acccacaagg tgggcaactt caccggcctg tacagcagca ccgtgccccgt gttcaacccc    1020 gagtggcaga ccccccagctt ccccaagatc cacctgcagg aggacatcgt ggacaggtgc    1080
aagcagttcg tgggtcccct gaccgtgaac gagaagagga ggctgaagct gatcatgccc    1140
gccaggttct accccaacgt gaccaagtac ctgcccctgg acaagggcat caagccctac    1200
taccccgagc acgccgtgaa ccactacttc cagaccagc actacctgca caccctgtgg    1260
aaggccggca tcctgtacaa gagggagacc accaggagcg ccagcttctg cggcagcccc    1320
tacagctggg agcaggagct gcagcacggc agctgctggt ggctgcagtt caggaacagc    1380
aagccctgca gcgagtactg cctgacccac ctggtgaacc tgctggagga ctgggggtccc    1440 tgcgacgagc acgccgagca ccacatcagg atccccagga cccccgccag ggtgaccggc    1500
ggcgtgttcc tggtggacaa gaacccccac aacaccgccg agagcaggct ggtggtggac    1560
ttcagccagt tcagcagggg catcaccagg gtgagctggc ccaagttcgc cgtgcccaac    1620
ctgcagagcc tgaccaacct gctgagcagc aacctgagct ggctgagcct ggacgtgagc    1680
gccgccttct accacatccc cctgcacccc gccgccatgc ccgggcccaa ggccccatac    1740
acgagcaccc tgctgccccc ggagctgtcc gagacccccca acgccacgca gccagaactc    1800
gccccggaag accccgagga ttcggccctc ttggaggacc ccgtggggac ggtggcgccg    1860
caaatcccac aaaactggca catcccgtcg atccaggacg ccgcgacgcc ttaccatccc    1920
ccggccaccc cgaacaacat gggcctgatc gccggcgcgg tgggcggcag tctcctggca    1980
gccctggtca tttgcggaat tgtgtactgg atgcaccgcc gcactcggaa agccccaaag    2040
cgcatacgcc tccccacat ccgggaagac gaccagccgt cctcgcacca gcccttgttt    2100
```

-continued tactag                                                                                      2106

<210> SEQ ID NO 18
<211> LENGTH: 699
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
        130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro His Leu Leu
            260                 265                 270

Val Gly Ser Ser Gly Leu Ser Arg Tyr Val Ala Arg Leu Ser Ser Asn
        275                 280                 285

Ser Arg Ile Ile Asn His Gln His Gly Thr Met Gln Asn Leu His Asp
    290                 295                 300

Ser Cys Ser Arg Asn Leu Tyr Val Ser Leu Leu Leu Leu Tyr Lys Thr
305                 310                 315                 320

Phe Gly Arg Lys Leu His Leu Tyr Ser His Pro Ile Ile Leu Lys Thr
                325                 330                 335

Lys Arg Trp Gly Tyr Ser Leu Asn Phe Met Gly Tyr Val Ile Gly Ser
            340                 345                 350

-continued

```
Trp Gly Ser Leu Pro Gln Asp His Ile Ile Gln Lys Ile Lys Glu Cys
    355                 360                 365

Phe Arg Lys Leu Pro Val Asn Arg Pro Ile Asp Trp Lys Val Cys Gln
    370                 375                 380

Arg Ile Val Gly Leu Leu Gly Phe Ala Ala Pro Phe Thr Gln Cys Gly
385                 390                 395                 400

Tyr Pro Ala Leu Met Pro Leu Tyr Ala Cys Ile Gln Ser Lys Gln Ala
                405                 410                 415

Phe Thr Phe Ser Pro Thr Tyr Lys Ala Phe Leu Ser Lys Gln Tyr Leu
                420                 425                 430

Asn Leu Tyr Pro Val Ala Arg Gln Arg Pro Gly Leu Cys Gln Val Phe
                435                 440                 445

Ala Asp Ala Thr Pro Thr Gly Trp Gly Leu Ala Met Gly His Gln Arg
    450                 455                 460

Met Arg Gly Thr Phe Val Ala Pro Leu Pro Ile His Thr Ala Glu Leu
465                 470                 475                 480

Leu Ala Ala Cys Phe Ala Arg Ser Arg Ser Gly Ala Lys Ile Leu Gly
                485                 490                 495

Thr Asp Asn Ser Val Val Leu Ser Arg Lys Tyr Thr Ser Phe Pro Trp
                500                 505                 510

Leu Leu Gly Cys Ala Ala Asn Trp Ile Leu Arg Gly Thr Ser Phe Val
                515                 520                 525

Tyr Val Pro Ser Ala Leu Asn Pro Ala Asp Asp Pro Ser Arg Gly Arg
    530                 535                 540

Leu Gly Leu Ser Arg Pro Leu Leu Arg Leu Pro Phe Arg Pro Thr Thr
545                 550                 555                 560

Gly Arg Thr Ser Leu Tyr Ala Val Ser Pro Ser Val Gly Pro Lys Ala
                565                 570                 575

Pro Tyr Thr Ser Thr Leu Leu Pro Pro Glu Leu Ser Glu Thr Pro Asn
                580                 585                 590

Ala Thr Gln Pro Glu Leu Ala Pro Glu Asp Pro Glu Asp Ser Ala Leu
                595                 600                 605

Leu Glu Asp Pro Val Gly Thr Val Ala Pro Gln Ile Pro Pro Asn Trp
    610                 615                 620

His Ile Pro Ser Ile Gln Asp Ala Ala Thr Pro Tyr His Pro Pro Ala
625                 630                 635                 640

Thr Pro Asn Asn Met Gly Leu Ile Ala Gly Ala Val Gly Gly Ser Leu
                645                 650                 655

Leu Ala Ala Leu Val Ile Cys Gly Ile Val Tyr Trp Met His Arg Arg
                660                 665                 670

Thr Arg Lys Ala Pro Lys Arg Ile Arg Leu Pro His Ile Arg Glu Asp
                675                 680                 685

Asp Gln Pro Ser Ser His Gln Pro Leu Phe Tyr
    690                 695
```

<210> SEQ ID NO 19
<211> LENGTH: 2100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

-continued

```
atgggggggg ctgccgccag gttggggggcc gtgattttgt ttgtcgtcat agtgggcctc          60 catgggggtcc gcggcaaata tgccttggcg gatgcctctc tcaagatggc cgacccccaat         120 cgctttcgcg gcaaagacct tccggtcctg gaccagctga ccgaccctcc gggggtccgg          180
cgcgtgtacc acatccaggc gggcctaccg gacccgttcc agcccccag cctccccgatc          240 acggtttact acgccgtgtt ggagcgcgcc tgccgcagcg tgctcctaaa cgcaccgtcg          300
gaggcccccc agattgtccg cgggggcctcc gaagacgtcc ggaaacaacc ctacaacctg         360
accatcgctt ggtttcggat gggaggcaac tgtgctatcc ccatcacggt catggagtac         420
accgaatgct cctacaacaa gtctctgggg gcctgtccca tccgaacgca gccccgctgg          480
aactactatg acagcttcag cgccgtcagc gaggataacc tggggttcct gatgcacgcc          540
cccgcgtttg agaccgccgg cacgtacctg cggctcgtga agataaacga ctggacggag          600
attacacagt ttatcctgga gcaccgagcc aagggctcct gtaagtacgc cctcccgctg          660
cgcatccccc cgtcagcctg cctctccccc caggcctacc agcaggggggt gacggtggac          720 agcatcggga tgctgccccg cttcatcccc gagaaccagc gcaccgtcgc cgtatacagc          780
ttgaagatcg ccgggtggca cgggccccac ctgctggtgg cagcagcgg cctgagcagg          840 tacgtggcca ggctgagcag caacagcagg atcatcaacc accagcacgg caccatgcag          900
aacctgcacg acagctgcag caggaacctg tacgtgagcc tgctgctgct gtacaagacc          960
ttcggcagga agctgcacct gtacagccac cccatcatcc tgaagaccaa gaggtgggggc         1020 tacagcctga acttcatggg ctacgtgatc ggcagctggg gcagcctgcc ccaggaccac          1080
atcatccaga agatcaagga gtgcttcagg aagctgcccg tgaacaggcc catcgactgg          1140
aaggtgtgcc agaggatcgt gggcctgctg ggcttcgccg ccccccttcac ccagtgcggc        1200 tacccccgccc tgatgcccct gtacgcctgc atccagagca agcaggcctt caccttcagc         1260
cccacctaca aggccttcct gagcaagcag tacctgaacc tgtaccccgt ggccaggcag          1320
aggcccggcc tgtgccaggt gttcgccgac gccacccccca ccggctgggg cctggccatg        1380
ggccaccaga ggatgagggg caccttcgtg gcccccctgc ccatccacac cgccgagctg         1440
ctggccgcct gcttcgccag gagcaggagc ggcgccaaga tcctgggcac cgacaacagc         1500
gtggtgctga gcaggaagta caccagcttc ccctggctgc tgggctgcgc cgccaactgg          1560
atcctgaggg gcaccagctt cgtgtacgtg cccagcgccc tgaaccccgc cgacgacccc         1620
agcaggggca ggctgggcct gagcaggccc ctgctgaggc tgcccttcag gcccaccacc        1680
ggcaggacca gcctgtacgc cgtgagcccc agcgtggggc ccaaggcccc atacacgagc         1740
accctgctgc ccccggagct gtccgagacc cccaacgcca cgcagccaga actcgccccg         1800
gaagaccccg aggattcggc cctcttggag gaccccgtgg ggacggtggc ccgcaaatc          1860 ccaccaaact ggcacatccc gtcgatccag gacgccgcga cgccttacca tcccccggcc          1920
accccgaaca acatgggcct gatcgccggc gcggtggggcg gcagtctcct ggcagccctg        1980
gtcatttgcg gaattgtgta ctggatgcac cgccgcactc ggaaagcccc aaagcgcata         2040 cgcctcccccc acatccggga agacgaccag ccgtcctcgc accagcccctt gttttactag      2100
```

<210> SEQ ID NO 20
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 20

Asp Ile Asp Pro Tyr Lys Glu Phe Gly Ala Thr Val Glu Leu Leu
1               5                   10                  15

<210> SEQ ID NO 21
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Lys Glu Phe Gly Ala Thr Val Glu Leu Leu Ser Phe Leu Pro Ser
1               5                   10                  15

<210> SEQ ID NO 22
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Thr Val Glu Leu Leu Ser Phe Leu Pro Ser Asp Phe Phe Pro Ser
1               5                   10                  15

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Phe Leu Pro Ser Asp Phe Phe Pro Ser Ile Arg Asp Leu Leu
1               5                   10                  15

<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Phe Phe Pro Ser Ile Arg Asp Leu Leu Asp Thr Ala Ser Ala
1               5                   10                  15

<210> SEQ ID NO 25
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ile Arg Asp Leu Leu Asp Thr Ala Ser Ala Leu Tyr Arg Glu Ala

-continued

```
1               5                   10                  15
```

```
<210> SEQ ID NO 26
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asp Thr Ala Ser Ala Leu Tyr Arg Glu Ala Leu Glu Ser Pro Glu
1               5                   10                  15

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Leu Tyr Arg Glu Ala Leu Glu Ser Pro Glu His Cys Ser Pro His
1               5                   10                  15

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Leu Glu Ser Pro Glu His Cys Ser Pro His His Thr Ala Leu Arg
1               5                   10                  15

<210> SEQ ID NO 29
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

His Cys Ser Pro His His Thr Ala Leu Arg Gln Ala Ile Leu Cys
1               5                   10                  15

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

His Thr Ala Leu Arg Gln Ala Ile Leu Cys Trp Gly Glu Leu Met
1               5                   10                  15

<210> SEQ ID NO 31
```

-continued

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gln Ala Ile Leu Cys Trp Gly Glu Leu Met Thr Leu Ala Thr Trp
1               5                   10                  15

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Trp Gly Glu Leu Met Thr Leu Ala Thr Trp Val Gly Ser Asn Leu
1               5                   10                  15

<210> SEQ ID NO 33
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Thr Leu Ala Thr Trp Val Gly Ser Asn Leu Glu Asp Pro Ala Ser
1               5                   10                  15

<210> SEQ ID NO 34
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Val Gly Ser Asn Leu Glu Asp Pro Ala Ser Arg Glu Leu Val Val
1               5                   10                  15

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Glu Asp Pro Ala Ser Arg Glu Leu Val Val Ser Tyr Val Asn Val
1               5                   10                  15

<210> SEQ ID NO 36
<211> LENGTH: 15
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 36

Arg Glu Leu Val Val Ser Tyr Val Asn Val Asn Met Gly Leu Lys
1               5                   10                  15

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Tyr Val Asn Val Asn Met Gly Leu Lys Ile Arg Gln Leu Leu
1               5                   10                  15

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Asn Met Gly Leu Lys Ile Arg Gln Leu Leu Trp Phe His Ile Ser
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ile Arg Gln Leu Leu Trp Phe His Ile Ser Cys Leu Thr Phe Gly
1               5                   10                  15

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Trp Phe His Ile Ser Cys Leu Thr Phe Gly Arg Glu Thr Val Ile
1               5                   10                  15

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 41

Cys Leu Thr Phe Gly Arg Glu Thr Val Ile Glu Tyr Leu Val Ser
1               5                   10                  15

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Arg Glu Thr Val Ile Glu Tyr Leu Val Ser Phe Gly Val Trp Ile
1               5                   10                  15

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Glu Tyr Leu Val Ser Phe Gly Val Trp Ile Arg Thr Pro Pro Ala
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Phe Gly Val Trp Ile Arg Thr Pro Pro Ala Tyr Arg Pro Pro Asn
1               5                   10                  15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Thr Pro Pro Ala Tyr Arg Pro Pro Asn Ala Pro Ile Leu Ser
1               5                   10                  15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Tyr Arg Pro Pro Asn Ala Pro Ile Leu Ser Thr Leu Pro Glu Thr
1               5                   10                  15
```

```
<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Pro Ile Leu Ser Thr Leu Pro Glu Thr Thr Val Val Arg Arg
1               5                   10                  15

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Thr Leu Pro Glu Thr Thr Val Val Arg Arg Arg Asp Arg Gly Arg
1               5                   10                  15

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Val Val Arg Arg Arg Asp Arg Gly Arg Ser Pro Arg Arg Arg
1               5                   10                  15

<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Arg Asp Arg Gly Arg Ser Pro Arg Arg Arg Thr Pro Ser Pro Arg
1               5                   10                  15

<210> SEQ ID NO 51
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Pro Arg Arg Arg Thr Pro Ser Pro Arg Arg Arg Arg Ser Gln
1               5                   10                  15

<210> SEQ ID NO 52
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Thr Pro Ser Pro Arg Arg Arg Arg Ser Gln Ser Pro Arg Arg Arg
1               5                   10                  15

<210> SEQ ID NO 53
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Arg Arg Arg Ser Gln Ser Pro Arg Arg Arg Arg Ser Gln Ser Arg
1               5                   10                  15

<210> SEQ ID NO 54
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Pro Arg Arg Arg Arg Arg Ser Gln Ser Arg Glu Ser Gln Cys
1               5                   10                  15

<210> SEQ ID NO 55
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Pro Leu Ser Tyr Gln His Phe Arg Lys Leu Leu Leu Leu Asp Glu
1               5                   10                  15

<210> SEQ ID NO 56
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

His Phe Arg Lys Leu Leu Leu Leu Asp Glu Glu Ala Gly Pro Leu
1               5                   10                  15

<210> SEQ ID NO 57
<211> LENGTH: 15
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 57

Leu Leu Leu Asp Glu Glu Ala Gly Pro Leu Glu Glu Glu Leu Pro
1               5                   10                  15

<210> SEQ ID NO 58
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Glu Ala Gly Pro Leu Glu Glu Glu Leu Pro Arg Leu Ala Asp Glu
1               5                   10                  15

<210> SEQ ID NO 59
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Glu Glu Glu Leu Pro Arg Leu Ala Asp Glu Gly Leu Asn Arg Arg
1               5                   10                  15

<210> SEQ ID NO 60
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Arg Leu Ala Asp Glu Gly Leu Asn Arg Arg Val Ala Glu Asp Leu
1               5                   10                  15

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Leu Asn Arg Arg Val Ala Glu Asp Leu Asn Leu Gly Asn Leu
1               5                   10                  15

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

```
Val Ala Glu Asp Leu Asn Leu Gly Asn Leu Asn Val Ser Ile Pro
1               5                   10                  15

<210> SEQ ID NO 63
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Asn Leu Gly Asn Leu Asn Val Ser Ile Pro Trp Thr His Lys Val
1               5                   10                  15

<210> SEQ ID NO 64
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asn Val Ser Ile Pro Trp Thr His Lys Val Gly Asn Phe Thr Gly
1               5                   10                  15

<210> SEQ ID NO 65
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Trp Thr His Lys Val Gly Asn Phe Thr Gly Leu Tyr Ser Ser Thr
1               5                   10                  15

<210> SEQ ID NO 66
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Asn Phe Thr Gly Leu Tyr Ser Ser Thr Val Pro Val Phe Asn
1               5                   10                  15

<210> SEQ ID NO 67
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Leu Tyr Ser Ser Thr Val Pro Val Phe Asn Pro Glu Trp Gln Thr
1               5                   10                  15
```

```
<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Val Pro Val Phe Asn Pro Glu Trp Gln Thr Pro Ser Phe Pro Lys
1               5                   10                  15

<210> SEQ ID NO 69
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Pro Glu Trp Gln Thr Pro Ser Phe Pro Lys Ile His Lys Leu Gln Glu
1               5                   10                  15

<210> SEQ ID NO 70
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Pro Ser Phe Pro Lys Ile His Lys Leu Gln Glu Asp Ile Val Asp Arg
1               5                   10                  15

<210> SEQ ID NO 71
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ile His Lys Leu Gln Glu Asp Ile Val Asp Arg Cys Lys Gln Phe Val
1               5                   10                  15

<210> SEQ ID NO 72
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Glu Asp Ile Val Asp Arg Cys Lys Gln Phe Val Gly Pro Leu Thr Val
1               5                   10                  15

<210> SEQ ID NO 73
<211> LENGTH: 16
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Arg Cys Lys Gln Phe Val Gly Pro Leu Thr Val Asn Glu Lys Arg Arg
1               5                   10                  15

<210> SEQ ID NO 74
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Val Gly Pro Leu Thr Val Asn Glu Lys Arg Arg Leu Lys Leu Ile Met
1               5                   10                  15

<210> SEQ ID NO 75
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Val Asn Glu Lys Arg Arg Leu Lys Leu Ile Met Pro Ala Arg Phe Tyr
1               5                   10                  15

<210> SEQ ID NO 76
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Arg Leu Lys Leu Ile Met Pro Ala Arg Phe Tyr Pro Asn Val Thr Lys
1               5                   10                  15

<210> SEQ ID NO 77
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Met Pro Ala Arg Phe Tyr Pro Asn Val Thr Lys Tyr Leu Pro Leu Asp
1               5                   10                  15

<210> SEQ ID NO 78
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 78

Tyr Pro Asn Val Thr Lys Tyr Leu Pro Leu Asp Lys Gly Ile Lys Pro
1               5                   10                  15

<210> SEQ ID NO 79
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Lys Tyr Leu Pro Leu Asp Lys Gly Ile Lys Pro Tyr Tyr Pro Glu His
1               5                   10                  15

<210> SEQ ID NO 80
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Asp Lys Gly Ile Lys Pro Tyr Tyr Pro Glu His Ala Val Asn His Tyr
1               5                   10                  15

<210> SEQ ID NO 81
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Pro Tyr Tyr Pro Glu His Ala Val Asn His Tyr Phe Gln Thr Arg His
1               5                   10                  15

<210> SEQ ID NO 82
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

His Ala Val Asn His Tyr Phe Gln Thr Arg His Tyr Leu His Thr Leu
1               5                   10                  15

<210> SEQ ID NO 83
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

-continued

```
Tyr Phe Gln Thr Arg His Tyr Leu His Thr Leu Trp Lys Ala Gly Ile
1               5                   10                  15

<210> SEQ ID NO 84
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

His Tyr Leu His Thr Leu Trp Lys Ala Gly Ile Leu Tyr Lys Arg Glu
1               5                   10                  15

<210> SEQ ID NO 85
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Leu Trp Lys Ala Gly Ile Leu Tyr Lys Arg Glu Thr Thr Arg Ser Ala
1               5                   10                  15

<210> SEQ ID NO 86
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Ile Leu Tyr Lys Arg Glu Thr Thr Arg Ser Ala Ser Phe Cys Gly Ser
1               5                   10                  15

<210> SEQ ID NO 87
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Glu Thr Thr Arg Ser Ala Ser Phe Cys Gly Ser Pro Tyr Ser Trp Glu
1               5                   10                  15

<210> SEQ ID NO 88
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Ala Ser Phe Cys Gly Ser Pro Tyr Ser Trp Glu Gln Glu Leu Gln His
1               5                   10                  15
```

```
<210> SEQ ID NO 89
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ser Pro Tyr Ser Trp Glu Gln Glu Leu Gln His Gly Ser Cys Trp Trp
1               5                   10                  15

<210> SEQ ID NO 90
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Glu Gln Glu Leu Gln His Gly Ser Cys Trp Trp Leu Gln Phe Arg Asn
1               5                   10                  15

<210> SEQ ID NO 91
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

His Gly Ser Cys Trp Trp Leu Gln Phe Arg Asn Ser Lys Pro Cys Ser
1               5                   10                  15

<210> SEQ ID NO 92
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Trp Leu Gln Phe Arg Asn Ser Lys Pro Cys Ser Glu Tyr Cys Leu Thr
1               5                   10                  15

<210> SEQ ID NO 93
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Asn Ser Lys Pro Cys Ser Glu Tyr Cys Leu Thr His Leu Val Asn Leu
1               5                   10                  15

<210> SEQ ID NO 94
<211> LENGTH: 16
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 94

Ser Glu Tyr Cys Leu Thr His Leu Val Asn Leu Leu Glu Asp Trp Gly
1               5                   10                  15

<210> SEQ ID NO 95
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Thr His Leu Val Asn Leu Leu Glu Asp Trp Gly Pro Cys Asp Glu His
1               5                   10                  15

<210> SEQ ID NO 96
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Leu Leu Glu Asp Trp Gly Pro Cys Asp Glu His Gly Glu His His Ile
1               5                   10                  15

<210> SEQ ID NO 97
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Pro Cys Asp Glu His Gly Glu His His Ile Arg Ile Pro Arg Thr
1               5                   10                  15

<210> SEQ ID NO 98
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

His Gly Glu His His Ile Arg Ile Pro Arg Thr Pro Ala Arg Val Thr
1               5                   10                  15

<210> SEQ ID NO 99
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 99

Ile Arg Ile Pro Arg Thr Pro Ala Arg Val Thr Gly Gly Val Phe Leu
1               5                   10                  15

<210> SEQ ID NO 100
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Thr Pro Ala Arg Val Thr Gly Gly Val Phe Leu Val Asp Lys Asn Pro
1               5                   10                  15

<210> SEQ ID NO 101
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Thr Gly Gly Val Phe Leu Val Asp Lys Asn Pro His Asn Thr Ala Glu
1               5                   10                  15

<210> SEQ ID NO 102
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Leu Val Asp Lys Asn Pro His Asn Thr Ala Glu Ser Arg Leu Val Val
1               5                   10                  15

<210> SEQ ID NO 103
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Pro His Asn Thr Ala Glu Ser Arg Leu Val Val Asp Phe Ser Gln Phe
1               5                   10                  15

<210> SEQ ID NO 104
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Glu Ser Arg Leu Val Val Asp Phe Ser Gln Phe Ser Arg Gly Ile Thr
```

```
1               5               10              15
```

```
<210> SEQ ID NO 105
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Val Asp Phe Ser Gln Phe Ser Arg Gly Ile Thr Arg Val Ser Trp Pro
1               5               10              15

<210> SEQ ID NO 106
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Phe Ser Arg Gly Ile Thr Arg Val Ser Trp Pro Lys Phe Ala Val Pro
1               5               10              15

<210> SEQ ID NO 107
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Thr Arg Val Ser Trp Pro Lys Phe Ala Val Pro Asn Leu Gln Ser Leu
1               5               10              15

<210> SEQ ID NO 108
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Pro Lys Phe Ala Val Pro Asn Leu Gln Ser Leu Thr Asn Leu Leu Ser
1               5               10              15

<210> SEQ ID NO 109
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Pro Asn Leu Gln Ser Leu Thr Asn Leu Leu Ser Ser Asn Leu Ser Trp
1               5               10              15

<210> SEQ ID NO 110
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Leu Thr Asn Leu Leu Ser Ser Asn Leu Ser Trp Leu Ser Leu Asp Val
1               5                   10                  15

<210> SEQ ID NO 111
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Ser Ser Asn Leu Ser Trp Leu Ser Leu Asp Val Ser Ala Ala Phe Tyr
1               5                   10                  15

<210> SEQ ID NO 112
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Trp Leu Ser Leu Asp Val Ser Ala Ala Phe Tyr His Ile Pro Leu His
1               5                   10                  15

<210> SEQ ID NO 113
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Val Ser Ala Ala Phe Tyr His Ile Pro Leu His Pro Ala Ala Met Pro
1               5                   10                  15

<210> SEQ ID NO 114
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

His Leu Leu Val Gly Ser Ser Gly Leu Ser Arg Tyr Val Ala Arg
1               5                   10                  15

<210> SEQ ID NO 115
<211> LENGTH: 16
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 115

Ser Ser Gly Leu Ser Arg Tyr Val Ala Arg Leu Ser Ser Asn Ser Arg
1               5                   10                  15

<210> SEQ ID NO 116
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Arg Tyr Val Ala Arg Leu Ser Ser Asn Ser Arg Ile Ile Asn His Gln
1               5                   10                  15

<210> SEQ ID NO 117
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Leu Ser Ser Asn Ser Arg Ile Ile Asn His Gln His Gly Thr Met Gln
1               5                   10                  15

<210> SEQ ID NO 118
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Arg Ile Ile Asn His Gln His Gly Thr Met Gln Asn Leu His Asp Ser
1               5                   10                  15

<210> SEQ ID NO 119
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Gln His Gly Thr Met Gln Asn Leu His Asp Ser Cys Ser Arg Asn Leu
1               5                   10                  15

<210> SEQ ID NO 120
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 120

Gln Asn Leu His Asp Ser Cys Ser Arg Asn Leu Tyr Val Ser Leu Leu
1               5                   10                  15

<210> SEQ ID NO 121
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ser Cys Ser Arg Asn Leu Tyr Val Ser Leu Leu Leu Tyr Lys Thr
1               5                   10                  15

<210> SEQ ID NO 122
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Leu Tyr Val Ser Leu Leu Leu Leu Tyr Lys Thr Phe Gly Arg Lys Leu
1               5                   10                  15

<210> SEQ ID NO 123
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Leu Leu Leu Tyr Lys Thr Phe Gly Arg Lys Leu His Leu Tyr Ser His
1               5                   10                  15

<210> SEQ ID NO 124
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Thr Phe Gly Arg Lys Leu His Leu Tyr Ser His Pro Ile Ile Leu Lys
1               5                   10                  15

<210> SEQ ID NO 125
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Leu His Leu Tyr Ser His Pro Ile Ile Leu Lys Thr Lys Arg Trp Gly
1               5                   10                  15

<210> SEQ ID NO 126
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 126

His Pro Ile Ile Leu Lys Thr Lys Arg Trp Gly Tyr Ser Leu Asn Phe
1               5                   10                  15

<210> SEQ ID NO 127
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 127

Lys Thr Lys Arg Trp Gly Tyr Ser Leu Asn Phe Met Gly Tyr Val Ile
1               5                   10                  15

<210> SEQ ID NO 128
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 128

Gly Tyr Ser Leu Asn Phe Met Gly Tyr Val Ile Gly Ser Trp Gly Ser
1               5                   10                  15

<210> SEQ ID NO 129
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 129

Phe Met Gly Tyr Val Ile Gly Ser Trp Gly Ser Leu Pro Gln Asp His
1               5                   10                  15

<210> SEQ ID NO 130
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 130

Ile Gly Ser Trp Gly Ser Leu Pro Gln Asp His Ile Ile Gln Lys Ile
1               5                   10                  15

<210> SEQ ID NO 131
<211> LENGTH: 16

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Ser Leu Pro Gln Asp His Ile Ile Gln Lys Ile Lys Glu Cys Phe Arg
1               5                   10                  15

<210> SEQ ID NO 132
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

His Ile Ile Gln Lys Ile Lys Glu Cys Phe Arg Lys Leu Pro Val Asn
1               5                   10                  15

<210> SEQ ID NO 133
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Ile Lys Glu Cys Phe Arg Lys Leu Pro Val Asn Arg Pro Ile Asp Trp
1               5                   10                  15

<210> SEQ ID NO 134
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Arg Lys Leu Pro Val Asn Arg Pro Ile Asp Trp Lys Val Cys Gln Arg
1               5                   10                  15

<210> SEQ ID NO 135
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Asn Arg Pro Ile Asp Trp Lys Val Cys Gln Arg Ile Val Gly Leu Leu
1               5                   10                  15

<210> SEQ ID NO 136
<211> LENGTH: 16
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic peptide"

<400> SEQUENCE: 136

Trp Lys Val Cys Gln Arg Ile Val Gly Leu Leu Gly Phe Ala Ala Pro
1               5                   10                  15

<210> SEQ ID NO 137
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Arg Ile Val Gly Leu Leu Gly Phe Ala Ala Pro Phe Thr Gln Cys Gly
1               5                   10                  15

<210> SEQ ID NO 138
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Leu Gly Phe Ala Ala Pro Phe Thr Gln Cys Gly Tyr Pro Ala Leu Met
1               5                   10                  15

<210> SEQ ID NO 139
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Pro Phe Thr Gln Cys Gly Tyr Pro Ala Leu Met Pro Leu Tyr Ala Cys
1               5                   10                  15

<210> SEQ ID NO 140
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Gly Tyr Pro Ala Leu Met Pro Leu Tyr Ala Cys Ile Gln Ser Lys Gln
1               5                   10                  15

<210> SEQ ID NO 141
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141
```

```
Met Pro Leu Tyr Ala Cys Ile Gln Ser Lys Gln Ala Phe Thr Phe Ser
1               5                   10                  15
```

<210> SEQ ID NO 142
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

```
Cys Ile Gln Ser Lys Gln Ala Phe Thr Phe Ser Pro Thr Tyr Lys Ala
1               5                   10                  15
```

<210> SEQ ID NO 143
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

```
Gln Ala Phe Thr Phe Ser Pro Thr Tyr Lys Ala Phe Leu Ser Lys Gln
1               5                   10                  15
```

<210> SEQ ID NO 144
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

```
Ser Pro Thr Tyr Lys Ala Phe Leu Ser Lys Gln Tyr Leu Asn Leu Tyr
1               5                   10                  15
```

<210> SEQ ID NO 145
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

```
Ala Phe Leu Ser Lys Gln Tyr Leu Asn Leu Tyr Pro Val Ala Arg Gln
1               5                   10                  15
```

<210> SEQ ID NO 146
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

```
Gln Tyr Leu Asn Leu Tyr Pro Val Ala Arg Gln Arg Pro Gly Leu Cys
1               5                   10                  15
```

-continued

```
<210> SEQ ID NO 147
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Tyr Pro Val Ala Arg Gln Arg Pro Gly Leu Cys Gln Val Phe Ala Asp
1               5                   10                  15

<210> SEQ ID NO 148
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Gln Arg Pro Gly Leu Cys Gln Val Phe Ala Asp Ala Thr Pro Thr Gly
1               5                   10                  15

<210> SEQ ID NO 149
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Cys Gln Val Phe Ala Asp Ala Thr Pro Thr Gly Trp Gly Leu Ala Met
1               5                   10                  15

<210> SEQ ID NO 150
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Asp Ala Thr Pro Thr Gly Trp Gly Leu Ala Met Gly His Gln Arg Met
1               5                   10                  15

<210> SEQ ID NO 151
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gly Trp Gly Leu Ala Met Gly His Gln Arg Met Arg Gly Thr Phe Val
1               5                   10                  15

<210> SEQ ID NO 152
<211> LENGTH: 16
<212> TYPE: PRT
```

-continued

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Met Gly His Gln Arg Met Arg Gly Thr Phe Val Ala Pro Leu Pro Ile
1               5                   10                  15

<210> SEQ ID NO 153
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Met Arg Gly Thr Phe Val Ala Pro Leu Pro Ile His Thr Ala Glu Leu
1               5                   10                  15

<210> SEQ ID NO 154
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Val Ala Pro Leu Pro Ile His Thr Ala Glu Leu Leu Ala Ala Cys Phe
1               5                   10                  15

<210> SEQ ID NO 155
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Ile His Thr Ala Glu Leu Leu Ala Ala Cys Phe Ala Arg Ser Arg Ser
1               5                   10                  15

<210> SEQ ID NO 156
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Leu Leu Ala Ala Cys Phe Ala Arg Ser Arg Ser Gly Ala Lys Ile Leu
1               5                   10                  15

<210> SEQ ID NO 157
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 157

Phe Ala Arg Ser Arg Ser Gly Ala Lys Ile Leu Gly Thr Asp Asn Ser
1               5                   10                  15

<210> SEQ ID NO 158
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Ser Gly Ala Lys Ile Leu Gly Thr Asp Asn Ser Val Val Leu Ser Arg
1               5                   10                  15

<210> SEQ ID NO 159
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Leu Gly Thr Asp Asn Ser Val Val Leu Ser Arg Lys Tyr Thr Ser Phe
1               5                   10                  15

<210> SEQ ID NO 160
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Ser Val Val Leu Ser Arg Lys Tyr Thr Ser Phe Pro Trp Leu Leu Gly
1               5                   10                  15

<210> SEQ ID NO 161
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Arg Lys Tyr Thr Ser Phe Pro Trp Leu Leu Gly Cys Ala Ala Asn Trp
1               5                   10                  15

<210> SEQ ID NO 162
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

-continued

```
Phe Pro Trp Leu Leu Gly Cys Ala Ala Asn Trp Ile Leu Arg Gly Thr
1               5                   10                  15
```

<210> SEQ ID NO 163
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

```
Gly Cys Ala Ala Asn Trp Ile Leu Arg Gly Thr Ser Phe Val Tyr Val
1               5                   10                  15
```

<210> SEQ ID NO 164
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

```
Trp Ile Leu Arg Gly Thr Ser Phe Val Tyr Val Pro Ser Ala Leu Asn
1               5                   10                  15
```

<210> SEQ ID NO 165
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

```
Thr Ser Phe Val Tyr Val Pro Ser Ala Leu Asn Pro Ala Asp Asp Pro
1               5                   10                  15
```

<210> SEQ ID NO 166
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

```
Val Pro Ser Ala Leu Asn Pro Ala Asp Asp Pro Ser Arg Gly Arg Leu
1               5                   10                  15
```

<210> SEQ ID NO 167
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

```
Asn Pro Ala Asp Asp Pro Ser Arg Gly Arg Leu Gly Leu Ser Arg Pro
1               5                   10                  15
```

-continued

```
<210> SEQ ID NO 168
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Pro Ser Arg Gly Arg Leu Gly Leu Ser Arg Pro Leu Leu Arg Leu Pro
1               5                   10                  15

<210> SEQ ID NO 169
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Leu Gly Leu Ser Arg Pro Leu Leu Arg Leu Pro Phe Arg Pro Thr Thr
1               5                   10                  15

<210> SEQ ID NO 170
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Pro Leu Leu Arg Leu Pro Phe Arg Pro Thr Thr Gly Arg Thr Ser Leu
1               5                   10                  15

<210> SEQ ID NO 171
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Pro Phe Arg Pro Thr Thr Gly Arg Thr Ser Leu Tyr Ala Val Ser Pro
1               5                   10                  15

<210> SEQ ID NO 172
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Thr Gly Arg Thr Ser Leu Tyr Ala Val Ser Pro Ser Val
1               5                   10

<210> SEQ ID NO 173
<211> LENGTH: 200
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 173

His Phe Arg Lys Leu Leu Leu Leu Asp Glu Glu Ala Gly Pro Leu Glu
1               5                   10                  15

Glu Glu Leu Pro Arg Leu Ala Asp Glu Gly Leu Asn Arg Arg Val Ala
            20                  25                  30

Glu Asp Leu Asn Leu Gly Asn Leu Pro Glu Trp Gln Thr Pro Ser Phe
        35                  40                  45

Pro Lys Ile His Leu Gln Glu Asp Ile Val Asp Arg Cys Lys Gln Phe
    50                  55                  60

Val Gly Pro Leu Thr Val Asn Glu Lys Arg Arg Leu Lys Leu Ile Met
65                  70                  75                  80

Pro Ala Arg Phe Tyr Pro Asn Val Thr Lys Tyr Leu Pro Leu Asp Lys
                85                  90                  95

Gly Ile Lys Pro Tyr Tyr Pro Glu His Ala Val Asn His Tyr Phe Gln
            100                 105                 110

Thr Arg His Tyr Leu His Thr Leu Trp Lys Ala Gly Ile Leu Tyr Lys
            115                 120                 125

Arg Glu Thr Thr Arg Ser Ala Ser Phe Cys Gly Ser Pro Tyr Ser Trp
    130                 135                 140

Glu Gln Glu Leu Gln His Gly Ser Cys Trp Trp Leu Gln Phe Arg Asn
145                 150                 155                 160

Ser Lys Pro Cys Ser Glu Tyr Cys Leu Thr His Leu Val Asn Leu Leu
                165                 170                 175

Glu Asp Trp Gly Pro Cys Asp Glu His Gly Glu His His Ile Arg Ile
            180                 185                 190

Pro Arg Thr Pro Ala Arg Val Thr
        195                 200

<210> SEQ ID NO 174
<211> LENGTH: 380
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Tyr Leu Pro Leu Asp Lys Gly Ile Lys Pro Tyr Tyr Pro Glu His Ala
1               5                   10                  15

Val Asn His Tyr Phe Gln Thr Arg His Tyr Leu His Thr Leu Trp Lys
            20                  25                  30

Ala Gly Ile Leu Tyr Lys Arg Glu Thr Thr Arg Ser Ala Ser Phe Cys
        35                  40                  45

Gly Ser Pro Tyr Ser Trp Glu Gln Glu Leu Gln His Gly Ser Cys Trp
    50                  55                  60

Trp Leu Gln Phe Arg Asn Ser Lys Pro Cys Ser Glu Tyr Cys Leu Thr
65                  70                  75                  80

His Leu Val Asn Leu Leu Glu Asp Trp Gly Pro Cys Asp Glu His Gly
                85                  90                  95

Glu His His Ile Arg Ile Pro Arg Thr Pro Ala Arg Val Thr Gly Gly
            100                 105                 110

-continued

```
Val Phe Leu Val Asp Lys Asn Pro His Asn Thr Ala Glu Ser Arg Leu
        115                 120                 125

Val Val Asp Phe Ser Gln Phe Ser Arg Gly Ile Thr Arg Val Ser Trp
    130                 135                 140

Pro Lys Phe Ala Val Pro Asn Leu Gln Ser Leu Thr Asn Leu Leu Ser
145                 150                 155                 160

Ser Asn Leu Ser Trp Leu Ser Leu Asp Val Gln Ala Phe Thr Phe Ser
                165                 170                 175

Pro Thr Tyr Lys Ala Phe Leu Ser Lys Gln Tyr Leu Asn Leu Tyr Pro
                180                 185                 190

Val Ala Arg Gln Arg Pro Gly Leu Cys Gln Val Phe Ala Asp Ala Thr
                195                 200                 205

Pro Thr Gly Trp Gly Leu Ala Met Gly His Gln Arg Met Arg Gly Thr
        210                 215                 220

Phe Val Ala Pro Leu Pro Ile His Thr Ala Glu Leu Leu Ala Ala Cys
225                 230                 235                 240

Phe Ala Arg Ser Arg Ser Gly Ala Lys Ile Leu Gly Thr Asp Asn Ser
                245                 250                 255

Val Val Leu Ser Arg Lys Tyr Thr Ser Phe Pro Trp Leu Leu Gly Cys
                260                 265                 270

Ala Ala Asn Trp Ile Leu Arg Gly Thr Ser Phe Val Tyr Val Pro Ser
        275                 280                 285

Ala Leu Asn Pro Ala Asp Asp Val Gly Ser Asn Leu Glu Asp Pro Ala
        290                 295                 300

Ser Arg Glu Leu Val Val Ser Tyr Val Asn Val Asn Met Gly Leu Lys
305                 310                 315                 320

Ile Arg Gln Leu Leu Trp Phe His Ile Ser Cys Leu Thr Phe Gly Arg
                325                 330                 335

Glu Thr Val Ile Glu Tyr Leu Val Ser Phe Gly Val Trp Ile Arg Thr
                340                 345                 350

Pro Pro Ala Tyr Arg Pro Pro Asn Ala Pro Ile Leu Ser Thr Leu Pro
        355                 360                 365

Glu Thr Thr Val Val Arg Arg Arg Asp Arg Gly Arg
    370                 375                 380
```

```
<210> SEQ ID NO 175
<211> LENGTH: 410
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175
```

```
His Phe Arg Lys Leu Leu Leu Leu Asp Glu Glu Ala Gly Pro Leu Glu
1               5                   10                  15

Glu Glu Leu Pro Arg Leu Ala Asp Glu Gly Leu Asn Arg Arg Val Ala
        20                  25                  30

Glu Asp Leu Asn Leu Gly Asn Leu Pro Glu Trp Gln Thr Pro Ser Phe
        35                  40                  45

Pro Lys Ile His Leu Gln Glu Asp Ile Val Asp Arg Cys Lys Gln Phe
    50                  55                  60

Val Gly Pro Leu Thr Val Asn Glu Lys Arg Arg Leu Lys Leu Ile Met
65                  70                  75                  80

Pro Ala Arg Phe Tyr Pro Asn Val Thr Lys Tyr Leu Pro Leu Asp Lys
```

```
                85              90              95

Gly Ile Lys Pro Tyr Tyr Pro Glu His Ala Val Asn His Tyr Phe Gln
            100             105             110

Thr Arg His Tyr Leu His Thr Leu Trp Lys Ala Gly Ile Leu Tyr Lys
            115             120             125

Arg Glu Thr Thr Arg Ser Ala Ser Phe Cys Gly Ser Pro Tyr Ser Trp
            130             135             140

Glu Gln Glu Leu Gln His Gly Ser Cys Trp Trp Leu Gln Phe Arg Asn
145             150             155             160

Ser Lys Pro Cys Ser Glu Tyr Cys Leu Thr His Leu Val Asn Leu Leu
                165             170             175

Glu Asp Trp Gly Pro Cys Asp Glu His Gly Glu His His Ile Arg Ile
            180             185             190

Pro Arg Thr Pro Ala Arg Val Thr Gln Ala Phe Thr Phe Ser Pro Thr
            195             200             205

Tyr Lys Ala Phe Leu Ser Lys Gln Tyr Leu Asn Leu Tyr Pro Val Ala
            210             215             220

Arg Gln Arg Pro Gly Leu Cys Gln Val Phe Ala Asp Ala Thr Pro Thr
225             230             235             240

Gly Trp Gly Leu Ala Met Gly His Gln Arg Met Arg Gly Thr Phe Val
                245             250             255

Ala Pro Leu Pro Ile His Thr Ala Glu Leu Leu Ala Ala Cys Phe Ala
            260             265             270

Arg Ser Arg Ser Gly Ala Lys Ile Leu Gly Thr Asp Asn Ser Val Val
            275             280             285

Leu Ser Arg Lys Tyr Thr Ser Phe Pro Trp Leu Leu Gly Cys Ala Ala
            290             295             300

Asn Trp Ile Leu Arg Gly Thr Ser Phe Val Tyr Val Pro Ser Ala Leu
305             310             315             320

Asn Pro Ala Asp Asp Val Gly Ser Asn Leu Glu Asp Pro Ala Ser Arg
            325             330             335

Glu Leu Val Val Ser Tyr Val Asn Val Asn Met Gly Leu Lys Ile Arg
            340             345             350

Gln Leu Leu Trp Phe His Ile Ser Cys Leu Thr Phe Gly Arg Glu Thr
            355             360             365

Val Ile Glu Tyr Leu Val Ser Phe Gly Val Trp Ile Arg Thr Pro Pro
            370             375             380

Ala Tyr Arg Pro Pro Asn Ala Pro Ile Leu Ser Thr Leu Pro Glu Thr
385             390             395             400

Thr Val Val Arg Arg Arg Asp Arg Gly Arg
                405             410
```

<210> SEQ ID NO 176
<211> LENGTH: 1140
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 176

```
tatctgccgc tggataaagg cattaaaccg tattatccgg aacatgcggt gaaccattat    60
tttcagaccc gccattatct gcataccctg tggaaagcgg gcattctgta taaacgcgaa    120
accacccgca gcgcgagctt ttgcggcagc ccgtatagct gggaacagga actgcagcat    180
```

```
ggcagctgct ggtggctgca gtttcgcaac agcaaaccgt gcagcgaata ttgcctgacc      240
catctggtga acctgctgga agattgggga ccgtgcgatg aacatggcga acatcatatt      300
cgcattccgc gcaccccggc gcgcgtgacc ggcggcgtgt ttctggtgga taaaaacccg      360
cataacaccg cggaaagccg cctggtggtg gattttagcc agtttagccg cggcattacc      420
cgcgtgagct ggccgaaatt tgcggtgccg aacctgcaga gcctgaccaa cctgctgagc      480
agcaacctga gctggctgag cctggatgtg caggcgttta cctttagccc gacctataaa      540
gcgtttctga gcaaacagta tctgaacctg tatccggtgg cgcgccagcg cccgggcctg      600
tgccaggtgt ttgcggatgc gaccccgacc ggctggggcc tggcgatggg ccatcagcgc      660
atgcgcggca cctttgtggc gccgctgccg attcataccg cggaactgct ggcggcgtgc      720
tttgcgcgca gccgcagcgg cgcgaaaatt ctgggcaccg ataacagcgt ggtgctgagc      780
cgcaaatata ccagctttcc gtggctgctg ggctgcgcgg cgaactggat tctgcgcggc      840
accagctttg tgtatgtgcc gagcgcgctg aacccggcgg atgatgtggg cagcaacctg      900
gaagatccgg cgagccgcga actggtggtg agctatgtga acgtgaacat gggcctgaaa      960
attcgccagc tgctgtggtt tcatattagc tgcctgacct ttggccgcga aaccgtgatt      1020
gaatatctgg tgagctttgg cgtgtggatt cgcaccccgc cggcgtatcg cccgccgaac      1080
gcgccgattc tgagcaccct gccggaaacc accgtggtgc ccgccgcgcga tcggggccgc      1140
```

<210> SEQ ID NO 177
<211> LENGTH: 1230
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 177

```
cattttcgca aactgctgct gctggatgaa gaagcgggac cgctggaaga agaactgccg      60
cgcctggcgg atgaaggcct gaaccgccgc gtggcggaag atctgaacct gggcaacctg      120
ccggaatggc agaccccgag ctttccgaaa attcatctgc aggaagatat tgtggatcgc      180
tgcaaacagt ttgtgggacc gctgaccgtg aacgaaaaac gccgcctgaa actgattatg      240
ccggcgcgct tttatccgaa cgtgaccaaa tatctgccgc tggataaagg cattaaaccg      300
tattatccgg aacatgcggt gaaccattat tttcagaccc gccattatct gcataccctg      360
tggaaagcgg gcattctgta taaacgcgaa accacccgca gcgcgagctt ttgcggcagc      420
ccgtatagct gggaacagga actgcagcat ggcagctgct ggtggctgca gtttcgcaac      480
agcaaaccgt gcagcgaata ttgcctgacc catctggtga acctgctgga agattgggga      540
ccgtgcgatg aacatggcga acatcatatt cgcattccgc gcaccccggc gcgcgtgacc      600
caggcgttta cctttagccc gacctataaa gcgtttctga gcaaacagta tctgaacctg      660
tatccggtgg cgcgccagcg cccgggcctg tgccaggtgt ttgcggatgc gaccccgacc      720
ggctggggcc tggcgatggg ccatcagcgc atgcgcggca cctttgtggc gccgctgccg      780
attcataccg cggaactgct ggcggcgtgc tttgcgcgca gccgcagcgg cgcgaaaatt      840
ctgggcaccg ataacagcgt ggtgctgagc cgcaaatata ccagctttcc gtggctgctg      900
ggctgcgcgg cgaactggat tctgcgcggc accagctttg tgtatgtgcc gagcgcgctg      960
aacccggcgg atgatgtggg cagcaacctg gaagatccgg cgagccgcga actggtggtg      1020
```

-continued

```
agctatgtga acgtgaacat gggcctgaaa attcgccagc tgctgtggtt tcatattagc    1080
tgcctgacct ttggccgcga aaccgtgatt gaatatctgg tgagctttgg cgtgtggatt    1140 cgcacccgc cggcgtatcg cccgccgaac gcgccgattc tgagcaccct gccggaaacc     1200
accgtggtgc gccgccgaga tcgaggccgc                                    1230
```

<210> SEQ ID NO 178
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 178

Tyr Leu Pro Leu Asp Lys Gly Ile Lys Pro Tyr Tyr Pro Glu His Ala
1               5                   10                  15

Val Asn His Tyr Phe Gln Thr Arg His Tyr Leu His Thr Leu Trp Lys
            20                  25                  30

Ala Gly Ile Leu Tyr Lys Arg Glu Thr Thr Arg Ser Ala Ser Phe Cys
        35                  40                  45

Gly Ser Pro Tyr Ser Trp Glu Gln Glu Leu Gln His Gly Ser Cys Trp
    50                  55                  60

Trp Leu Gln Phe Arg Asn Ser Lys Pro Cys Ser Glu Tyr Cys Leu Thr
65                  70                  75                  80

His Leu Val Asn Leu Leu Glu Asp Trp Gly Pro Cys Asp Glu His Gly
                85                  90                  95

Glu His His Ile Arg Ile Pro Arg Thr Pro Ala Arg Val Thr Gly Gly
            100                 105                 110

Val Phe Leu Val Asp Lys Asn Pro His Asn Thr Ala Glu Ser Arg Leu
        115                 120                 125

Val Val Asp Phe Ser Gln Phe Ser Arg Gly Ile Thr Arg Val Ser Trp
    130                 135                 140

Pro Lys Phe Ala Val Pro Asn Leu Gln Ser Leu Thr Asn Leu Leu Ser
145                 150                 155                 160

Ser Asn Leu Ser Trp Leu Ser Leu Asp Val
            165                 170

<210> SEQ ID NO 179
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 179

Gln Ala Phe Thr Phe Ser Pro Thr Tyr Lys Ala Phe Leu Ser Lys Gln
1               5                   10                  15

Tyr Leu Asn Leu Tyr Pro Val Ala Arg Gln Arg Pro Gly Leu Cys Gln
            20                  25                  30

Val Phe Ala Asp Ala Thr Pro Thr Gly Trp Gly Leu Ala Met Gly His
        35                  40                  45

Gln Arg Met Arg Gly Thr Phe Val Ala Pro Leu Pro Ile His Thr Ala
    50                  55                  60

Glu Leu Leu Ala Ala Cys Phe Ala Arg Ser Arg Ser Gly Ala Lys Ile
65                  70                  75                  80

```
Leu Gly Thr Asp Asn Ser Val Val Leu Ser Arg Lys Tyr Thr Ser Phe
                85                  90                  95

Pro Trp Leu Leu Gly Cys Ala Ala Asn Trp Ile Leu Arg Gly Thr Ser
            100                 105                 110

Phe Val Tyr Val Pro Ser Ala Leu Asn Pro Ala Asp Asp
        115                 120                 125

<210> SEQ ID NO 180
<211> LENGTH: 85
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Val Gly Ser Asn Leu Glu Asp Pro Ala Ser Arg Glu Leu Val Val Ser
1               5                   10                  15

Tyr Val Asn Val Asn Met Gly Leu Lys Ile Arg Gln Leu Leu Trp Phe
                20                  25                  30

His Ile Ser Cys Leu Thr Phe Gly Arg Glu Thr Val Ile Glu Tyr Leu
            35                  40                  45

Val Ser Phe Gly Val Trp Ile Arg Thr Pro Pro Ala Tyr Arg Pro Pro
        50                  55                  60

Asn Ala Pro Ile Leu Ser Thr Leu Pro Glu Thr Thr Val Val Arg Arg
65                  70                  75                  80

Arg Asp Arg Gly Arg
                85

<210> SEQ ID NO 181
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

His Phe Arg Lys Leu Leu Leu Leu Asp Glu Glu Ala Gly Pro Leu Glu
1               5                   10                  15

Glu Glu Leu Pro Arg Leu Ala Asp Glu Gly Leu Asn Arg Arg Val Ala
            20                  25                  30

Glu Asp Leu Asn Leu Gly Asn Leu Pro Glu Trp Gln Thr Pro Ser Phe
        35                  40                  45

Pro Lys Ile His Leu Gln Glu Asp Ile Val Asp Arg Cys Lys Gln Phe
        50                  55                  60

Val Gly Pro Leu Thr Val Asn Glu Lys Arg Arg Leu Lys Leu Ile Met
65                  70                  75                  80

Pro Ala Arg Phe Tyr Pro Asn Val Thr Lys Tyr Leu Pro Leu Asp Lys
                85                  90                  95

Gly Ile Lys Pro Tyr Tyr Pro Glu His Ala Val Asn His Tyr Phe Gln
            100                 105                 110

Thr Arg His Tyr Leu His Thr Leu Trp Lys Ala Gly Ile Leu Tyr Lys
            115                 120                 125

Arg Glu Thr Thr Arg Ser Ala Ser Phe Cys Gly Ser Pro Tyr Ser Trp
        130                 135                 140
```

-continued

```
Glu Gln Glu Leu Gln His Gly Ser Cys Trp Trp Leu Gln Phe Arg Asn
145                 150                 155                 160

Ser Lys Pro Cys Ser Glu Tyr Cys Leu Thr His Leu Val Asn Leu Leu
                165                 170                 175

Glu Asp Trp Gly Pro Cys Asp Glu His Gly Glu His His Ile Arg Ile
            180                 185                 190

Pro Arg Thr Pro Ala Arg Val Thr
        195                 200
```

<210> SEQ ID NO 182
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

```
Gln Ala Phe Thr Phe Ser Pro Thr Tyr Lys Ala Phe Leu Ser Lys Gln
1                   5                   10                  15

Tyr Leu Asn Leu Tyr Pro Val Ala Arg Gln Arg Pro Gly Leu Cys Gln
                20                  25                  30

Val Phe Ala Asp Ala Thr Pro Thr Gly Trp Gly Leu Ala Met Gly His
            35                  40                  45

Gln Arg Met Arg Gly Thr Phe Val Ala Pro Leu Pro Ile His Thr Ala
        50                  55                  60

Glu Leu Leu Ala Ala Cys Phe Ala Arg Ser Arg Ser Gly Ala Lys Ile
65                  70                  75                  80

Leu Gly Thr Asp Asn Ser Val Val Leu Ser Arg Lys Tyr Thr Ser Phe
                85                  90                  95

Pro Trp Leu Leu Gly Cys Ala Ala Asn Trp Ile Leu Arg Gly Thr Ser
            100                 105                 110

Phe Val Tyr Val Pro Ser Ala Leu Asn Pro Ala Asp Asp
        115                 120                 125
```

<210> SEQ ID NO 183
<211> LENGTH: 85
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

```
Val Gly Ser Asn Leu Glu Asp Pro Ala Ser Arg Glu Leu Val Val Ser
1                   5                   10                  15

Tyr Val Asn Val Asn Met Gly Leu Lys Ile Arg Gln Leu Leu Trp Phe
                20                  25                  30

His Ile Ser Cys Leu Thr Phe Gly Arg Glu Thr Val Ile Glu Tyr Leu
            35                  40                  45

Val Ser Phe Gly Val Trp Ile Arg Thr Pro Pro Ala Tyr Arg Pro Pro
        50                  55                  60

Asn Ala Pro Ile Leu Ser Thr Leu Pro Glu Thr Thr Val Val Arg Arg
65                  70                  75                  80

Arg Asp Arg Gly Arg
            85
```

<210> SEQ ID NO 184
<211> LENGTH: 2331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184 atggggggg ctgccgccag gttgggggcc gtgattttgt ttgtcgtcat agtgggcctc      60
catggggtcc gcggcaaata tgccttggcg gatgcctctc tcaagatggc cgaccccaat     120
cgctttcgcg gcaaagacct tccggtcctg gaccagctga ccgaccctcc gggggtccgg     180
cgcgtgtacc acatccaggc gggcctaccg gacccgttcc agcccccccag cctcccgatc     240 acggtttact acgccgtgtt ggagcgcgcc tgccgcagcg tgctcctaaa cgcaccgtcg     300 gaggccccc agattgtccg cggggcctcc gaagacgtcc ggaaacaacc ctacaacctg     360
accatcgctt ggtttcggat gggaggcaac tgtgctatcc ccatcacggt catggagtac     420
accgaatgct cctacaacaa gtctctgggg gcctgtccca tccgaacgca gccccgctgg     480
aactactatg acagcttcag cgccgtcagc gaggataacc tggggttcct gatgcacgcc     540
cccgcgtttg agaccgccgg cacgtacctg cggctcgtga agataaacga ctggacggag     600
attacacagt ttatcctgga gcaccgagcc aagggctcct gtaagtacgc cctcccgctg     660
cgcatccccc cgtcagcctg cctctccccc caggcctacc agcaggggt gacggtggac     720 agcatcggga tgctgccccg cttcatcccc gagaaccagc gcaccgtcgc cgtatacagc     780
ttgaagatcg ccgggtggca cgggccctat ctgccgctgg ataaaggcat taaaccgtat     840
tatccggaac atgcggtgaa ccattatttt cagacccgcc attatctgca taccctgtgg     900
aaagcgggca ttctgtataa acgcgaaacc acccgcagcg cgagcttttg cggcagcccg     960
tatagctggg aacaggaact gcagcatggc agctgctggt ggctgcagtt cgcaacagc     1020 aaaccgtgca gcgaatattg cctgacccat ctggtgaacc tgctggaaga ttggggaccg     1080
tgcgatgaac atggcgaaca tcatattcgc attccgcgca ccccggcgcg cgtgaccggc     1140
ggcgtgtttc tggtggataa aaacccgcat aacaccgcgg aaagccgcct ggtggtggat     1200
tttagccagt ttagccgcgg cattacccgc gtgagctggc cgaaatttgc ggtgccgaac     1260
ctgcagagcc tgaccaacct gctgagcagc aacctgagct ggctgagcct ggatgtgcag     1320
gcgtttacct ttagcccgac ctataaagcg tttctgagca aacagtatct gaacctgtat     1380
ccggtggcgc gccagcgccc gggcctgtgc caggtgtttg cggatgcgac cccgaccggc     1440
tggggcctgg cgatgggcca tcagcgcatg cgcggcacct tgtggcgcc gctgccgatt     1500 cataccgcga aactgctggc ggcgtgcttt gcgcgcagcc gcagcggcgc gaaaattctg     1560
ggcaccgata acagcgtggt gctgagccgc aaatatacca gctttccgtg gctgctgggc     1620
tgcgcggcga actggattct gcgcggcacc agctttgtgt atgtgccgag cgcgctgaac     1680
ccggcggatg atgtgggcag caacctggaa gatccggcga ccgcgaact ggtggtgagc     1740 tatgtgaacg tgaacatggg cctgaaaatt cgccagctgc tgtggtttca tattagctgc     1800
ctgacctttg ccgcgaaac cgtgattgaa tatctggtga gctttggcgt gtggattcgc     1860
accccgccgg cgtatcgccc gccgaacgcg ccgattctga gcaccctgcc ggaaaccacc     1920
gtggtgcgcc gccgcgatcg gggccgcggg cccaaggccc catacacgag caccctgctg     1980
cccccggagc tgtccgagac ccccaacgcc acgcagccag aactcgcccc ggaagacccc     2040

-continued

```
gaggattcgg ccctcttgga ggaccccgtg gggacggtgg cgccgcaaat cccaccaaac    2100
tggcacatcc cgtcgatcca ggacgccgcg acgccttacc atccccggc accccgaac      2160 aacatgggcc tgatcgccgg cgcggtgggc ggcagtctcc tggcagccct ggtcatttgc    2220
ggaattgtgt actggatgca ccgccgcact cggaaagccc caaagcgcat acgcctcccc    2280
cacatccggg aagacgacca gccgtcctcg caccagccct tgttttacta g            2331
```

<210> SEQ ID NO 185
<211> LENGTH: 776
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Tyr Leu Pro
            260                 265                 270

Leu Asp Lys Gly Ile Lys Pro Tyr Tyr Pro Glu His Ala Val Asn His
        275                 280                 285

Tyr Phe Gln Thr Arg His Tyr Leu His Thr Leu Trp Lys Ala Gly Ile
    290                 295                 300
```

-continued

```
Leu Tyr Lys Arg Glu Thr Thr Arg Ser Ala Ser Phe Cys Gly Ser Pro
305             310             315             320

Tyr Ser Trp Glu Gln Glu Leu Gln His Gly Ser Cys Trp Trp Leu Gln
            325             330             335

Phe Arg Asn Ser Lys Pro Cys Ser Glu Tyr Cys Leu Thr His Leu Val
            340             345             350

Asn Leu Leu Glu Asp Trp Gly Pro Cys Asp Glu His Gly Glu His His
            355             360             365

Ile Arg Ile Pro Arg Thr Pro Ala Arg Val Thr Gly Gly Val Phe Leu
    370             375             380

Val Asp Lys Asn Pro His Asn Thr Ala Glu Ser Arg Leu Val Val Asp
385             390             395             400

Phe Ser Gln Phe Ser Arg Gly Ile Thr Arg Val Ser Trp Pro Lys Phe
            405             410             415

Ala Val Pro Asn Leu Gln Ser Leu Thr Asn Leu Leu Ser Ser Asn Leu
            420             425             430

Ser Trp Leu Ser Leu Asp Val Gln Ala Phe Thr Phe Ser Pro Thr Tyr
            435             440             445

Lys Ala Phe Leu Ser Lys Gln Tyr Leu Asn Leu Tyr Pro Val Ala Arg
    450             455             460

Gln Arg Pro Gly Leu Cys Gln Val Phe Ala Asp Ala Thr Pro Thr Gly
465             470             475             480

Trp Gly Leu Ala Met Gly His Gln Arg Met Arg Gly Thr Phe Val Ala
            485             490             495

Pro Leu Pro Ile His Thr Ala Glu Leu Leu Ala Ala Cys Phe Ala Arg
            500             505             510

Ser Arg Ser Gly Ala Lys Ile Leu Gly Thr Asp Asn Ser Val Val Leu
            515             520             525

Ser Arg Lys Tyr Thr Ser Phe Pro Trp Leu Leu Gly Cys Ala Ala Asn
            530             535             540

Trp Ile Leu Arg Gly Thr Ser Phe Val Tyr Val Pro Ser Ala Leu Asn
545             550             555             560

Pro Ala Asp Asp Val Gly Ser Asn Leu Glu Asp Pro Ala Ser Arg Glu
            565             570             575

Leu Val Val Ser Tyr Val Asn Val Asn Met Gly Leu Lys Ile Arg Gln
            580             585             590

Leu Leu Trp Phe His Ile Ser Cys Leu Thr Phe Gly Arg Glu Thr Val
            595             600             605

Ile Glu Tyr Leu Val Ser Phe Gly Val Trp Ile Arg Thr Pro Pro Ala
    610             615             620

Tyr Arg Pro Pro Asn Ala Pro Ile Leu Ser Thr Leu Pro Glu Thr Thr
625             630             635             640

Val Val Arg Arg Arg Asp Arg Gly Arg Gly Pro Lys Ala Pro Tyr Thr
            645             650             655

Ser Thr Leu Leu Pro Pro Glu Leu Ser Glu Thr Pro Asn Ala Thr Gln
            660             665             670

Pro Glu Leu Ala Pro Glu Asp Pro Glu Asp Ser Ala Leu Leu Glu Asp
            675             680             685

Pro Val Gly Thr Val Ala Pro Gln Ile Pro Pro Asn Trp His Ile Pro
            690             695             700

Ser Ile Gln Asp Ala Ala Thr Pro Tyr His Pro Pro Ala Thr Pro Asn
705             710             715             720

Asn Met Gly Leu Ile Ala Gly Ala Val Gly Gly Ser Leu Leu Ala Ala
```

-continued

```
              725              730              735
Leu Val Ile Cys Gly Ile Val Tyr Trp Met His Arg Arg Thr Arg Lys
              740              745              750

Ala Pro Lys Arg Ile Arg Leu Pro His Ile Arg Glu Asp Asp Gln Pro
       755              760              765

Ser Ser His Gln Pro Leu Phe Tyr
     770              775
```

```
<210> SEQ ID NO 186
<211> LENGTH: 2421
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 186 atggggggg ctgccgccag gttggggggcc gtgattttgt ttgtcgtcat agtgggcctc      60
catggggtcc gcggcaaata tgccttggcg gatgcctctc tcaagatggc cgaccccaat     120
cgctttcgcg gcaaagacct tccggtcctg accagctga ccgaccctcc gggggtccgg      180
cgcgtgtacc acatccaggc gggcctaccg gacccgttcc agcccccag cctcccgatc      240 acggtttact acgccgtgtt ggagcgcgcc tgccgcagcg tgctcctaaa cgcaccgtcg      300 gaggccccc agattgtccg cggggcctcc gaagacgtcc ggaaacaacc ctacaacctg      360
accatcgctt ggtttcggat gggaggcaac tgtgctatcc ccatcacggt catggagtac     420
accgaatgct cctacaacaa gtctctgggg gcctgtccca tccgaacgca gccccgctgg     480
aactactatg acagcttcag cgccgtcagc gaggataacc tggggttcct gatgcacgcc     540
cccgcgtttg agaccgccgg cacgtacctg cggctcgtga agataaacga ctggacggag     600
attacacagt ttatcctgga gcaccgagcc aagggctcct gtaagtacgc cctcccgctg     660
cgcatccccc cgtcagcctg cctctccccc caggcctacc agcaggggggt gacggtggac     720 agcatcggga tgctgccccg cttcatcccc gagaaccagc gcaccgtcgc cgtatacagc     780
ttgaagatcg ccgggtggca cgggccccat tttcgcaaac tgctgctgct ggatgaagaa     840
gcgggaccgc tggaagaaga actgccgcgc ctggcggatg aaggcctgaa ccgccgcgtg     900
gcggaagatc tgaacctggg caacctgccg gaatggcaga ccccgagctt tccgaaaatt     960
catctgcagg aagatattgt ggatcgctgc aaacagtttg tgggaccgct gaccgtgaac    1020
gaaaaacgcc gcctgaaact gattatgccg gcgcgctttt atccgaacgt gaccaaatat    1080
ctgccgctgg ataaaggcat taaaccgtat tatccggaac atgcggtgaa ccattatttt    1140
cagaccccgc cattatctgca taccctgtgg aaagcgggca ttctgtataa acgcgaaacc    1200
acccgcagcg cgagcttttg cggcagcccg tatagctggg aacaggaact gcagcatggc    1260
agctgctggt ggctgcagtt tcgcaacagc aaaccgtgca gcgaatattg cctgaccccat    1320 ctggtgaacc tgctggaaga ttggggaccg tgcgatgaac atggcgaaca tcatattcgc    1380
attccgcgca ccccggcgcg cgtgacccag gcgtttacct ttagcccgac ctataaagcg    1440
tttctgagca aacagtatct gaacctgtat ccggtggcgc gccagcgccc gggcctgtgc    1500
caggtgtttg cggatgcgac cccgaccggc tggggcctgg cgatgggcca tcagcgcatg    1560
cgcggcacct ttgtggcgcc gctgccgatt cataccgcgg aactgctggc ggcgtgcttt    1620
gcgcgcagcc gcagcggcgc gaaaattctg ggcaccgata acagcgtggt gctgagccgc    1680
```

-continued

```
aaatatacca gctttccgtg gctgctgggc tgcgcggcga actggattct gcgcggcacc      1740
agctttgtgt atgtgccgag cgcgctgaac ccggcggatg atgtgggcag caacctggaa      1800
gatccggcga gccgcgaact ggtggtgagc tatgtgaacg tgaacatggg cctgaaaatt      1860
cgccagctgc tgtggtttca tattagctgc ctgacctttg gccgcgaaac cgtgattgaa      1920
tatctggtga gctttggcgt gtggattcgc accccgccgg cgtatcgccc gccgaacgcg      1980
ccgattctga gcaccctgcc ggaaaccacc gtggtgcgcc gccgagatcg aggccgcggg      2040
cccaaggccc catacacgag caccctgctg cccccggagc tgtccgagac ccccaacgcc      2100
acgcagccag aactcgcccc ggaagacccc gaggattcgg ccctcttgga ggaccccgtg      2160
gggacggtgg cgccgcaaat cccaccaaac tggcacatcc cgtcgatcca ggacgccgcg      2220
acgccttacc atcccccggc caccccgaac aacatgggcc tgatcgccgg cgcggtgggc      2280
ggcagtctcc tggcagccct ggtcatttgc ggaattgtgt actggatgca ccgccgcact      2340
cggaaagccc caaagcgcat acgcctcccc cacatccggg aagacgacca gccgtcctcg      2400
caccagccct tgtttactta g                                               2421
```

```
<210> SEQ ID NO 187
<211> LENGTH: 806
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
        130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
        210                 215                 220
```

```
Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
            245                 250                 255

Ala Val Tyr Ser Leu Lys Ile Ala Gly Trp His Gly Pro His Phe Arg
            260                 265                 270

Lys Leu Leu Leu Leu Asp Glu Glu Ala Gly Pro Leu Glu Glu Glu Leu
            275                 280                 285

Pro Arg Leu Ala Asp Glu Gly Leu Asn Arg Arg Val Ala Glu Asp Leu
        290                 295                 300

Asn Leu Gly Asn Leu Pro Glu Trp Gln Thr Pro Ser Phe Pro Lys Ile
305                 310                 315                 320

His Leu Gln Glu Asp Ile Val Asp Arg Cys Lys Gln Phe Val Gly Pro
                325                 330                 335

Leu Thr Val Asn Glu Lys Arg Arg Leu Lys Leu Ile Met Pro Ala Arg
                340                 345                 350

Phe Tyr Pro Asn Val Thr Lys Tyr Leu Pro Leu Asp Lys Gly Ile Lys
            355                 360                 365

Pro Tyr Tyr Pro Glu His Ala Val Asn His Tyr Phe Gln Thr Arg His
        370                 375                 380

Tyr Leu His Thr Leu Trp Lys Ala Gly Ile Leu Tyr Lys Arg Glu Thr
385                 390                 395                 400

Thr Arg Ser Ala Ser Phe Cys Gly Ser Pro Tyr Ser Trp Glu Gln Glu
                405                 410                 415

Leu Gln His Gly Ser Cys Trp Trp Leu Gln Phe Arg Asn Ser Lys Pro
            420                 425                 430

Cys Ser Glu Tyr Cys Leu Thr His Leu Val Asn Leu Leu Glu Asp Trp
            435                 440                 445

Gly Pro Cys Asp Glu His Gly Glu His His Ile Arg Ile Pro Arg Thr
        450                 455                 460

Pro Ala Arg Val Thr Gln Ala Phe Thr Phe Ser Pro Thr Tyr Lys Ala
465                 470                 475                 480

Phe Leu Ser Lys Gln Tyr Leu Asn Leu Tyr Pro Val Ala Arg Gln Arg
                485                 490                 495

Pro Gly Leu Cys Gln Val Phe Ala Asp Ala Thr Pro Thr Gly Trp Gly
            500                 505                 510

Leu Ala Met Gly His Gln Arg Met Arg Gly Thr Phe Val Ala Pro Leu
            515                 520                 525

Pro Ile His Thr Ala Glu Leu Leu Ala Ala Cys Phe Ala Arg Ser Arg
        530                 535                 540

Ser Gly Ala Lys Ile Leu Gly Thr Asp Asn Ser Val Val Leu Ser Arg
545                 550                 555                 560

Lys Tyr Thr Ser Phe Pro Trp Leu Leu Gly Cys Ala Ala Asn Trp Ile
                565                 570                 575

Leu Arg Gly Thr Ser Phe Val Tyr Val Pro Ser Ala Leu Asn Pro Ala
            580                 585                 590

Asp Asp Val Gly Ser Asn Leu Glu Asp Pro Ala Ser Arg Glu Leu Val
            595                 600                 605

Val Ser Tyr Val Asn Val Asn Met Gly Leu Lys Ile Arg Gln Leu Leu
        610                 615                 620

Trp Phe His Ile Ser Cys Leu Thr Phe Gly Arg Glu Thr Val Ile Glu
625                 630                 635                 640
```

-continued

```
Tyr Leu Val Ser Phe Gly Val Trp Ile Arg Thr Pro Pro Ala Tyr Arg
                645             650             655

Pro Pro Asn Ala Pro Ile Leu Ser Thr Leu Pro Glu Thr Thr Val Val
            660             665             670

Arg Arg Arg Asp Arg Gly Arg Gly Pro Lys Ala Pro Tyr Thr Ser Thr
        675             680             685

Leu Leu Pro Pro Glu Leu Ser Glu Thr Pro Asn Ala Thr Gln Pro Glu
    690             695             700

Leu Ala Pro Glu Asp Pro Glu Asp Ser Ala Leu Leu Glu Asp Pro Val
705             710             715             720

Gly Thr Val Ala Pro Gln Ile Pro Pro Asn Trp His Ile Pro Ser Ile
            725             730             735

Gln Asp Ala Ala Thr Pro Tyr His Pro Pro Ala Thr Pro Asn Asn Met
            740             745             750

Gly Leu Ile Ala Gly Ala Val Gly Gly Ser Leu Leu Ala Ala Leu Val
        755             760             765

Ile Cys Gly Ile Val Tyr Trp Met His Arg Arg Thr Arg Lys Ala Pro
    770             775             780

Lys Arg Ile Arg Leu Pro His Ile Arg Glu Asp Asp Gln Pro Ser Ser
785             790             795             800

His Gln Pro Leu Phe Tyr
                805

<210> SEQ ID NO 188
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Phe Ala Val Pro Asn Leu Gln Ser Leu
1               5

<210> SEQ ID NO 189
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Pro Glu Trp Gln Thr Pro Ser Phe Pro Lys Ile His Leu Gln Glu
1               5                   10                  15

<210> SEQ ID NO 190
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Pro Ser Phe Pro Lys Ile His Leu Gln Glu Asp Ile Val Asp Arg
1               5                   10                  15
```

-continued

```
<210> SEQ ID NO 191
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Ile His Leu Gln Glu Asp Ile Val Asp Arg Cys Lys Gln Phe Val
1               5                   10                  15

<210> SEQ ID NO 192
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Asp Ile Val Asp Arg Cys Lys Gln Phe Val Gly Pro Leu Thr Val
1               5                   10                  15

<210> SEQ ID NO 193
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Cys Lys Gln Phe Val Gly Pro Leu Thr Val Asn Glu Lys Arg Arg
1               5                   10                  15

<210> SEQ ID NO 194
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Gly Pro Leu Thr Val Asn Glu Lys Arg Arg Leu Lys Leu Ile Met
1               5                   10                  15

<210> SEQ ID NO 195
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Asn Glu Lys Arg Arg Leu Lys Leu Ile Met Pro Ala Arg Phe Tyr
1               5                   10                  15

<210> SEQ ID NO 196
<211> LENGTH: 15
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 196

Leu Lys Leu Ile Met Pro Ala Arg Phe Tyr Pro Asn Val Thr Lys
1               5                   10                  15

<210> SEQ ID NO 197
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Pro Ala Arg Phe Tyr Pro Asn Val Thr Lys Tyr Leu Pro Leu Asp
1               5                   10                  15

<210> SEQ ID NO 198
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Pro Asn Val Thr Lys Tyr Leu Pro Leu Asp Lys Gly Ile Lys Pro
1               5                   10                  15

<210> SEQ ID NO 199
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Tyr Leu Pro Leu Asp Lys Gly Ile Lys Pro Tyr Tyr Pro Glu His
1               5                   10                  15

<210> SEQ ID NO 200
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Lys Gly Ile Lys Pro Tyr Tyr Pro Glu His Ala Val Asn His Tyr
1               5                   10                  15

<210> SEQ ID NO 201
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 201

Tyr Tyr Pro Glu His Ala Val Asn His Tyr Phe Gln Thr Arg His
1               5                   10                  15

<210> SEQ ID NO 202
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Ala Val Asn His Tyr Phe Gln Thr Arg His Tyr Leu His Thr Leu
1               5                   10                  15

<210> SEQ ID NO 203
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Phe Gln Thr Arg His Tyr Leu His Thr Leu Trp Lys Ala Gly Ile
1               5                   10                  15

<210> SEQ ID NO 204
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Tyr Leu His Thr Leu Trp Lys Ala Gly Ile Leu Tyr Lys Arg Glu
1               5                   10                  15

<210> SEQ ID NO 205
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Trp Lys Ala Gly Ile Leu Tyr Lys Arg Glu Thr Thr Arg Ser Ala
1               5                   10                  15

<210> SEQ ID NO 206
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Leu Tyr Lys Arg Glu Thr Thr Arg Ser Ala Ser Phe Cys Gly Ser
```

-continued

```
1               5                    10                   15
```

<210> SEQ ID NO 207
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

```
Thr Thr Arg Ser Ala Ser Phe Cys Gly Ser Pro Tyr Ser Trp Glu
1               5                    10                   15
```

<210> SEQ ID NO 208
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

```
Ser Phe Cys Gly Ser Pro Tyr Ser Trp Glu Gln Glu Leu Gln His
1               5                    10                   15
```

<210> SEQ ID NO 209
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

```
Pro Tyr Ser Trp Glu Gln Glu Leu Gln His Gly Ser Cys Trp Trp
1               5                    10                   15
```

<210> SEQ ID NO 210
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

```
Gln Glu Leu Gln His Gly Ser Cys Trp Trp Leu Gln Phe Arg Asn
1               5                    10                   15
```

<210> SEQ ID NO 211
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

```
Gly Ser Cys Trp Trp Leu Gln Phe Arg Asn Ser Lys Pro Cys Ser
1               5                    10                   15
```

<210> SEQ ID NO 212

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Leu Gln Phe Arg Asn Ser Lys Pro Cys Ser Glu Tyr Cys Leu Thr
1               5                   10                  15

<210> SEQ ID NO 213
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Ser Lys Pro Cys Ser Glu Tyr Cys Leu Thr His Leu Val Asn Leu
1               5                   10                  15

<210> SEQ ID NO 214
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Glu Tyr Cys Leu Thr His Leu Val Asn Leu Leu Glu Asp Trp Gly
1               5                   10                  15

<210> SEQ ID NO 215
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

His Leu Val Asn Leu Leu Glu Asp Trp Gly Pro Cys Asp Glu His
1               5                   10                  15

<210> SEQ ID NO 216
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Leu Glu Asp Trp Gly Pro Cys Asp Glu His Gly Glu His His Ile
1               5                   10                  15

<210> SEQ ID NO 217
<211> LENGTH: 15
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 217

Pro Cys Asp Glu His Gly Glu His His Ile Arg Ile Pro Arg Thr
1               5                   10                  15

<210> SEQ ID NO 218
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Gly Glu His His Ile Arg Ile Pro Arg Thr Pro Ala Arg Val Thr
1               5                   10                  15

<210> SEQ ID NO 219
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Arg Ile Pro Arg Thr Pro Ala Arg Val Thr Gly Gly Val Phe Leu
1               5                   10                  15

<210> SEQ ID NO 220
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Pro Ala Arg Val Thr Gly Gly Val Phe Leu Val Asp Lys Asn Pro
1               5                   10                  15

<210> SEQ ID NO 221
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Gly Gly Val Phe Leu Val Asp Lys Asn Pro His Asn Thr Ala Glu
1               5                   10                  15

<210> SEQ ID NO 222
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 222

Val Asp Lys Asn Pro His Asn Thr Ala Glu Ser Arg Leu Val Val
1               5                   10                  15

<210> SEQ ID NO 223
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

His Asn Thr Ala Glu Ser Arg Leu Val Val Asp Phe Ser Gln Phe
1               5                   10                  15

<210> SEQ ID NO 224
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Ser Arg Leu Val Val Asp Phe Ser Gln Phe Ser Arg Gly Ile Thr
1               5                   10                  15

<210> SEQ ID NO 225
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Asp Phe Ser Gln Phe Ser Arg Gly Ile Thr Arg Val Ser Trp Pro
1               5                   10                  15

<210> SEQ ID NO 226
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Ser Arg Gly Ile Thr Arg Val Ser Trp Pro Lys Phe Ala Val Pro
1               5                   10                  15

<210> SEQ ID NO 227
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Arg Val Ser Trp Pro Lys Phe Ala Val Pro Asn Leu Gln Ser Leu
1               5                   10                  15
```

-continued

```
<210> SEQ ID NO 228
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Lys Phe Ala Val Pro Asn Leu Gln Ser Leu Thr Asn Leu Leu Ser
1               5                   10                  15

<210> SEQ ID NO 229
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Asn Leu Gln Ser Leu Thr Asn Leu Leu Ser Ser Asn Leu Ser Trp
1               5                   10                  15

<210> SEQ ID NO 230
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Thr Asn Leu Leu Ser Ser Asn Leu Ser Trp Leu Ser Leu Asp Val
1               5                   10                  15

<210> SEQ ID NO 231
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Ser Asn Leu Ser Trp Leu Ser Leu Asp Val Ser Ala Ala Phe Tyr
1               5                   10                  15

<210> SEQ ID NO 232
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Leu Ser Leu Asp Val Ser Ala Ala Phe Tyr His Ile Pro Leu His
1               5                   10                  15

<210> SEQ ID NO 233
<211> LENGTH: 15
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Ser Ala Ala Phe Tyr His Ile Pro Leu His Pro Ala Ala Met Pro
1               5                   10                  15
```

ADENOVIRAL VECTORS ENCODING HEPATITIS B VIRAL ANTIGENS FUSED TO HERPES VIRUS GLYCOPROTEIN D AND METHODS OF USING THE SAME

CROSS REFERENCE TO RELATED APPLICATIONS

This application is the National Stage of International Patent Application No. PCT/US2021/012630, filed Jan. 8, 2021, which claims priority to U.S. Provisional Application No. 62/958,809, filed Jan. 9, 2020, U.S. Provisional Application No. 62/958,827, filed Jan. 9, 2020, U.S. Provisional Application No. 62/967,242, filed Jan. 29, 2020, U.S. Provisional Application No. 62/967,104, filed Jan. 29, 2020, U.S. Provisional Application No. 63/064,506, filed Aug. 12, 2020, U.S. Provisional Application No. 63/064,571, filed Aug. 12, 2020, U.S. Provisional Application No. 63/112,202, filed Nov. 11, 2020, and U.S. Provisional Application No. 63/112,219, filed Nov. 11, 2020, the disclosure of each application is hereby incorporated by reference in their entirety.

SEQUENCE LISTING

The instant application contains a Sequence Listing which has been submitted electronically in ASCII format and is hereby incorporated by reference in its entirety. The ASCII copy, created on Jun. 30, 2022, is named 111876_000067_SL.txt and is 151,446 bytes in size.

FIELD OF THE INVENTION

Disclosed herein are non-naturally occurring variants of the hepatitis B virus (HBV) Core protein, the HBV polymerase N-terminal domain, and the HBV polymerase C-terminal domain, as well as immunogenic fragments thereof and fusion proteins comprising the same.

BACKGROUND OF THE INVENTION

The World Health Organization estimates that, in 2015, 257 million people were living with chronic hepatitis B infection (defined as hepatitis B surface antigen positive) and that hepatitis B resulted in an estimated 887,000 deaths, mostly from cirrhosis and hepatocellular carcinoma (i.e., primary liver cancer). Assuming that women of reproductive age constitute 25.3% of the world's population (United Nations data), adults chronically infected may include 65 million women of childbearing age who can potentially transmit HBV to their babies (WHO Global Hepatitis Report 2017. Available at: apps_who_int/iris/bitstream/handle/10665/255016/9789241565455-eng.pdf;
jsessionid=D78616700ED7322D4109CA4541FB94EA?
sequence=1). The overall incidence rate in 2016 was 1.0 case per 100,000 population (Centers for Disease Control and Prevention. Viral Hepatitis Surveillance—United States, 2017. Atlanta: US Department of Health and Human Services, Centers for Disease Control and Prevention; 2019. Available at: www_cdc_gov/hepatitis/statistics/2017surveillance/index.htm.). In 2017 alone, a total of 3,407 cases of acute hepatitis B were reported to the Centers for Disease Control and Prevention (CDC).

Despite the availability of a prophylactic HBV vaccine, the burden of chronic HBV infection continues to be a significant unmet worldwide medical problem, due to suboptimal treatment options and sustained rates of new infections in most parts of the developing world.

SUMMARY OF THE INVENTION

Provided herein is a hepatitis B virus (HBV) Core protein comprising the amino acid sequence of SEQ ID NO: 6 or an immunogenic fragment thereof.

Also provided is an HBV polymerase N-terminal domain comprising the amino acid sequence of SEQ ID NO: 8 or an immunogenic fragment thereof.

An HBV polymerase C-terminal domain comprising the amino acid sequence of SEQ ID NO: 10 or an immunogenic fragment thereof is also disclosed.

Fusion proteins comprising: an N-terminal herpes simplex virus (HSV) glycoprotein (gD) sequence or a variant thereof, the disclosed HBV Core protein, HBV polymerase N-terminal domain, HBV polymerase C-terminal domain, or immunogenic fragments thereof, and a C-terminal HSV gD sequence or a variant thereof are also provided.

Also provided herein are fusion proteins comprising: an N-terminal herpes simplex virus (HSV) glycoprotein (gD) sequence or a variant thereof, combinations of the disclosed HBV Core protein, HBV polymerase N-terminal domain, HBV polymerase C-terminal domain, and/or immunogenic fragments thereof, and a C-terminal HSV gD sequence or a variant thereof.

Nucleic acid molecules encoding the disclosed proteins or fusion proteins, vectors comprising the nucleic acid molecules, and vaccines comprising the disclosed vectors are disclosed herein.

Also provided herein are methods of inducing an immune response to HBV in a subject, the method comprising providing to the subject an effective amount of any of the disclosed fusion proteins, nucleic acid molecules, vectors, or vaccines to thereby induce an immune response to HBV.

BRIEF DESCRIPTION OF THE DRAWINGS

The summary, as well as the following detailed description, is further understood when read in conjunction with the appended drawings. For the purpose of illustrating the disclosed proteins, vaccines, and methods, there are shown in the drawings exemplary embodiments of the proteins, vaccines, and methods; however, the proteins, vaccines, and methods are not limited to the specific embodiments disclosed. In the drawings:

FIG. 2A-2C show insert-specific CD8+ T cell frequency; FIG. 2D-2F show insert-specific CD4+ T cell frequency.

T cell responses are shown for HLA-A2 tg mice which carry a human MHC class I molecule but mouse MHC class II molecules. T cells were gated on activated CD44+ cells. Each consecutively numbered "peptide" consists of 15 amino acids beginning on the $1^{st}$, $6^{th}$, $11^{th}$, etc. amino acid of the Core, PolN, or PolC sequence. Thus, for example, peptide 1 of Core corresponds to amino acids 1-15 of SEQ ID NO: 6 (i.e. the epitope-optimized Core amino acid sequence), peptide 2 of Core corresponds to amino acids 6-20 of SEQ ID NO: 6, peptide 3 of Core corresponds to amino acids 11-25 of SEQ ID NO: 6, etc. Similarly, peptide 1 of PolN corresponds to amino acids 1-15 of SEQ ID NO: 8 (i.e. the epitope-optimized PolN amino acid sequence), peptide 2 of PolN corresponds to amino acids 6-20 of SEQ ID NO: 8, peptide 3 of PolN corresponds to amino acids 11-25 of SEQ ID NO: 8, etc. Likewise, peptide 1 of PolC corresponds to amino acids 1-15 of SEQ ID NO: 10 (i.e. the epitope-optimized PolC amino acid sequence), peptide 2 of PolC corresponds to amino acids 6-20 of SEQ ID NO: 10, peptide 3 of PolC corresponds to amino acids 11-25 of SEQ ID NO: 10, etc.

Figure 6:
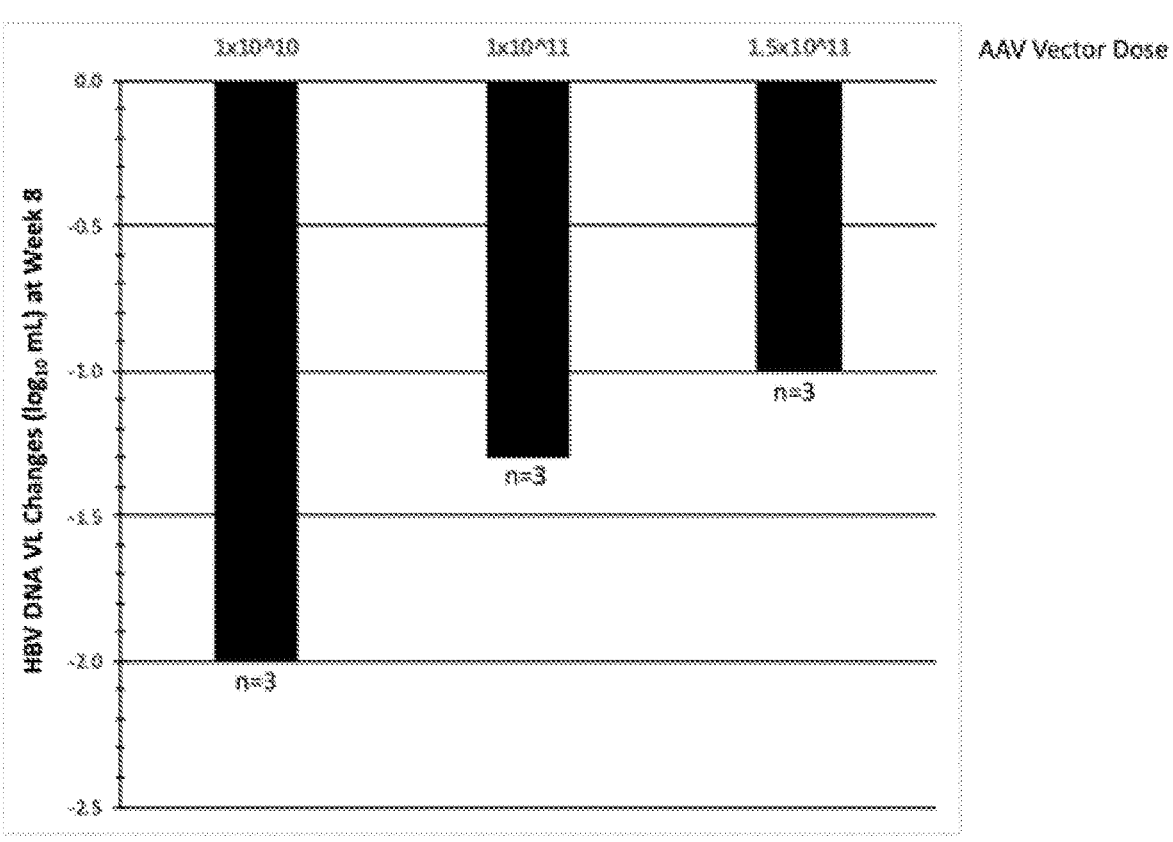

FIG. 6 illustrates the effect of vaccination on HBV genome copy numbers in serum upon AAV-1.3HBV challenge. A group of 3 mice were challenged with $1\times10^{10}$, $1\times10^{11}$ or $1.5\times10^{11}$ virus genomes (vg) of an adeno-associated virus 8 (AAV8)-1.3HBV vector and 8 weeks later were vaccinated with AdC6-gDPolN. Viral titers were tested 8 weeks after vaccination and compared to pre-vaccination titers. Viral changes from baseline for each treatment group are shown.

FIG. 7A, FIG. 7B, FIG. 7C, FIG. 7D, and FIG. 7E illustrate exemplary HBV epitope shifting experiments. FIG. 7A—mice were immunized with the AdC6-gDPolN vaccine. Four weeks later splenocytes were tested by intracellular cytokine staining for IFN-γ responses to peptide pools representing the PolN sequence. T cells after stimulation were stained for T cell markers. FIG. 7B—results obtained with the same assay using splenocytes from mice that were challenged with $1\times10^{10}$ vg of AAV8-1.3-HBV. Mice were vaccinated 4 weeks later and T cell responses were tested from spleens 10 weeks later. FIG. 7C—results obtained with the same assay using splenocytes from mice that had been challenged with $1.5\times10^{11}$ vg of AAV8-1.3-HBV. Mice were vaccinated 4 weeks later and T cell responses were tested from spleen 10 weeks later. FIGS. 7A, 7B, and 7C show the frequencies of IFN-γ producing CD44+ CD8+ T cells over all CD44+CD8+ T cells. Background responses obtained by splenocytes incubated without peptide pools were subtracted. FIG. 7D—peptide pools. FIG. 7E—individual peptide sequences. FIG. 7E discloses SEQ ID NOs: 55-68 and 189-233, respectively, in order of appearance.

Figure 8A:
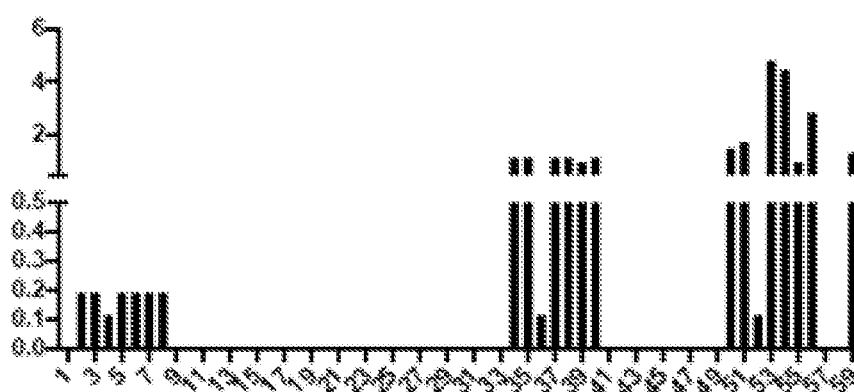
Figure 8B:
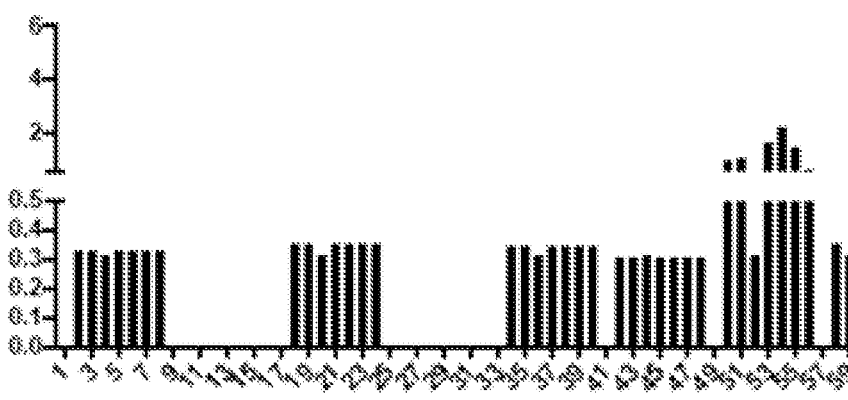
Figure 8C:
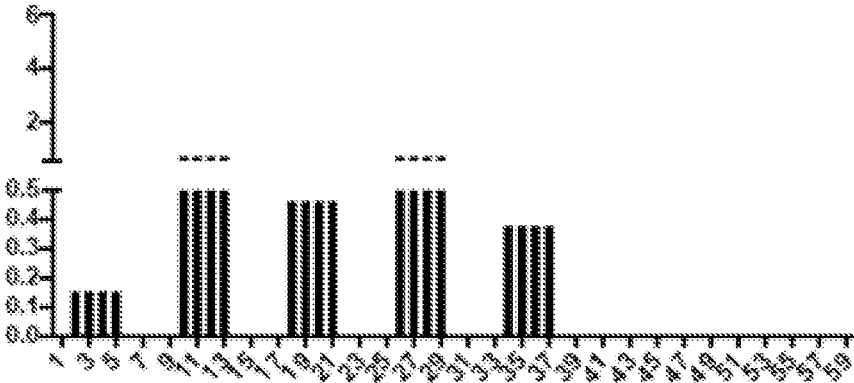

FIG. 8A, FIG. 8B, and FIG. 8C show data from the same experiment described above in FIG. 7. Based on the responses to the peptide pools, it was determined which individual peptides (both pools and peptides shown in FIG. 7) were positive. The graphs show responses to all of the peptides. Each peptide was present in two pools and therefore two values for frequencies were obtained for each peptide; only the lower data points are shown in this figure.

Figures 9A, 9B, 9C:
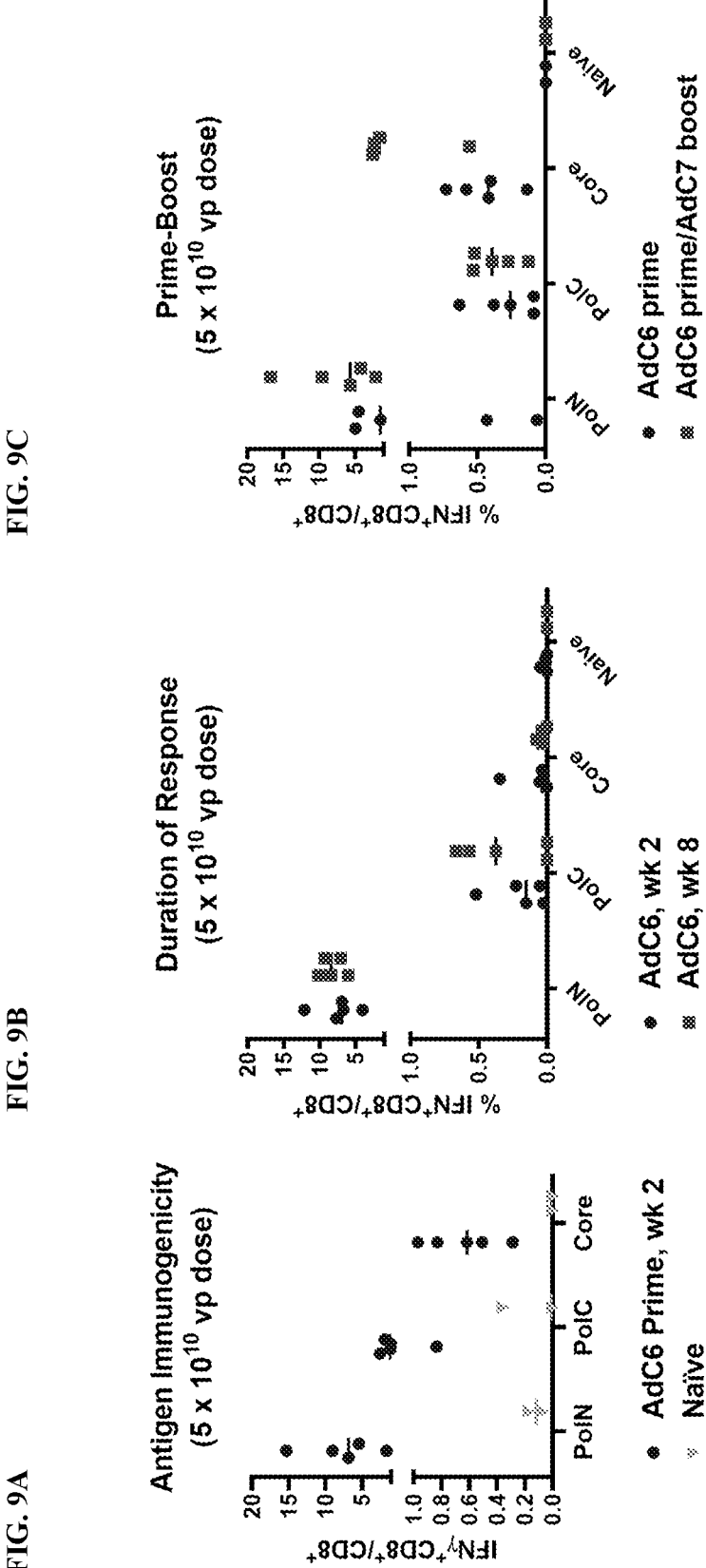

FIG. 9A, FIG. 9B, and FIG. 9C illustrate the results from exemplary immunogenicity experiments performed on C57B1/6 mice (n=5 per group) injected with various doses of exemplary AdC6-gDCore, AdC6-gDPolN, or AdC6-gD-PolC vectors and boosted with AdC7 vectors containing the same insert (i.e. AdC7-gDCore, AdC7-gDPolN, or AdC7-gDPolC vectors) two months after the first injection. FIG.

9A illustrates antigen immunogenicity, FIG. 9B illustrates the duration of response, and FIG. 9C illustrates the prime-boost response.

Figure 10:
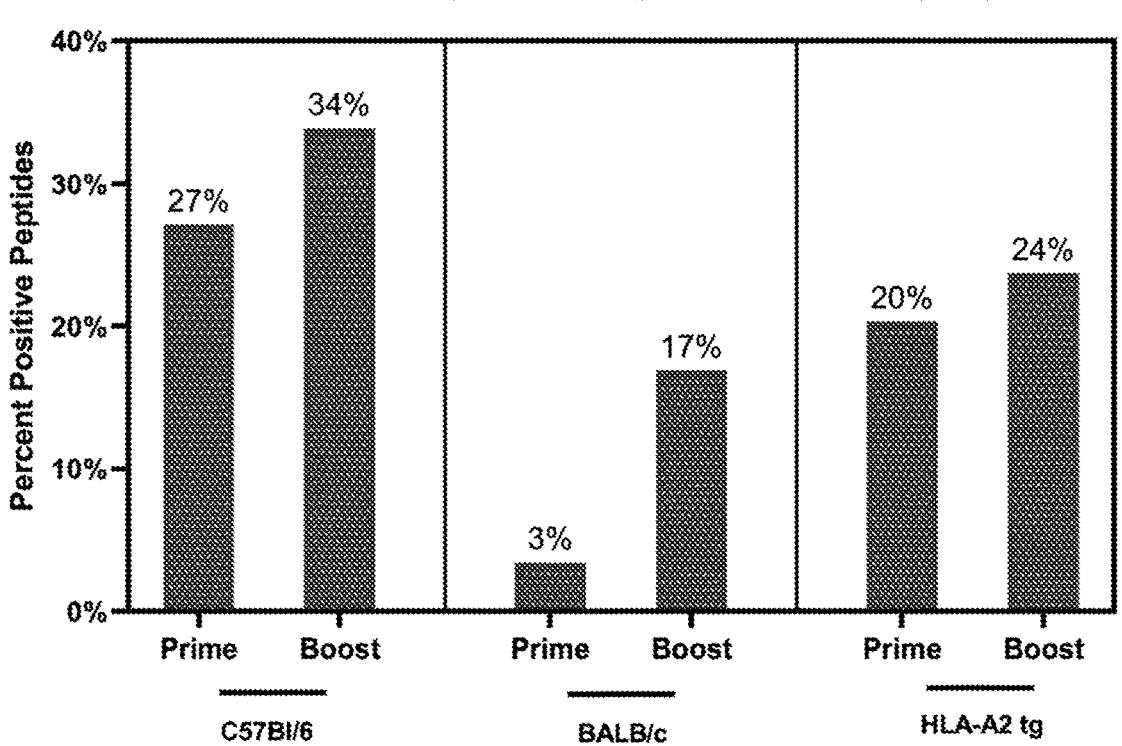

FIG. 10 illustrates the CD8+ T cell peptide recognition of PolN epitopes in BALB/c, C57B1/6, and HLA-A2 transgenic mice after vaccination with a prime of AdC6-gDPolN and a boost of AdC7-gDPolN. CD8+ T cell peptide recognition was calculated as the fraction of positive peptides recognized two weeks after either the prime or the boost by the total number of overlapping 8 peptides from PolN (59 peptides total).

Figure 11B:
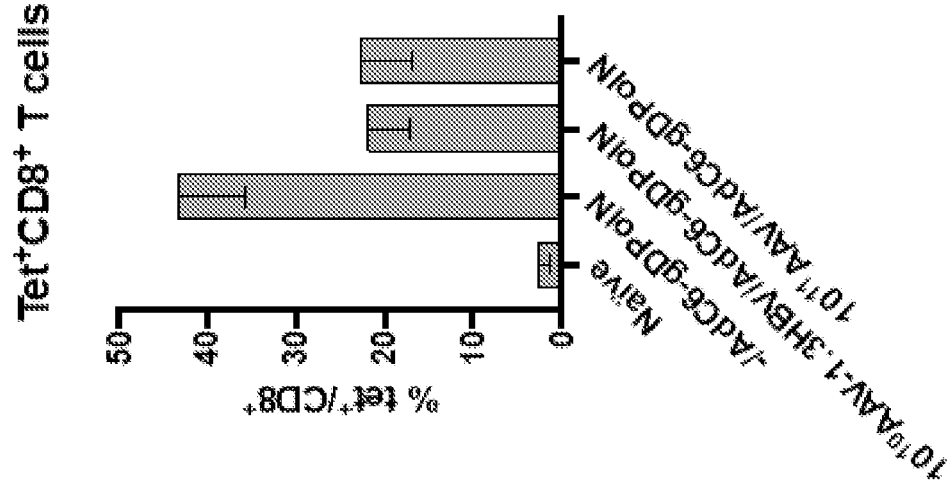
Figure 11A:
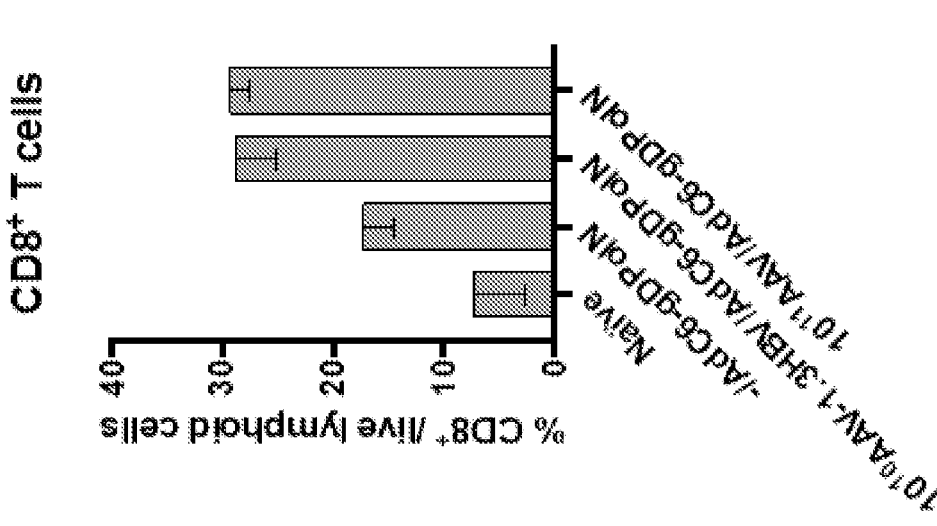
Figures 12A, 12B, 12C, 12D, 12E, 12F:
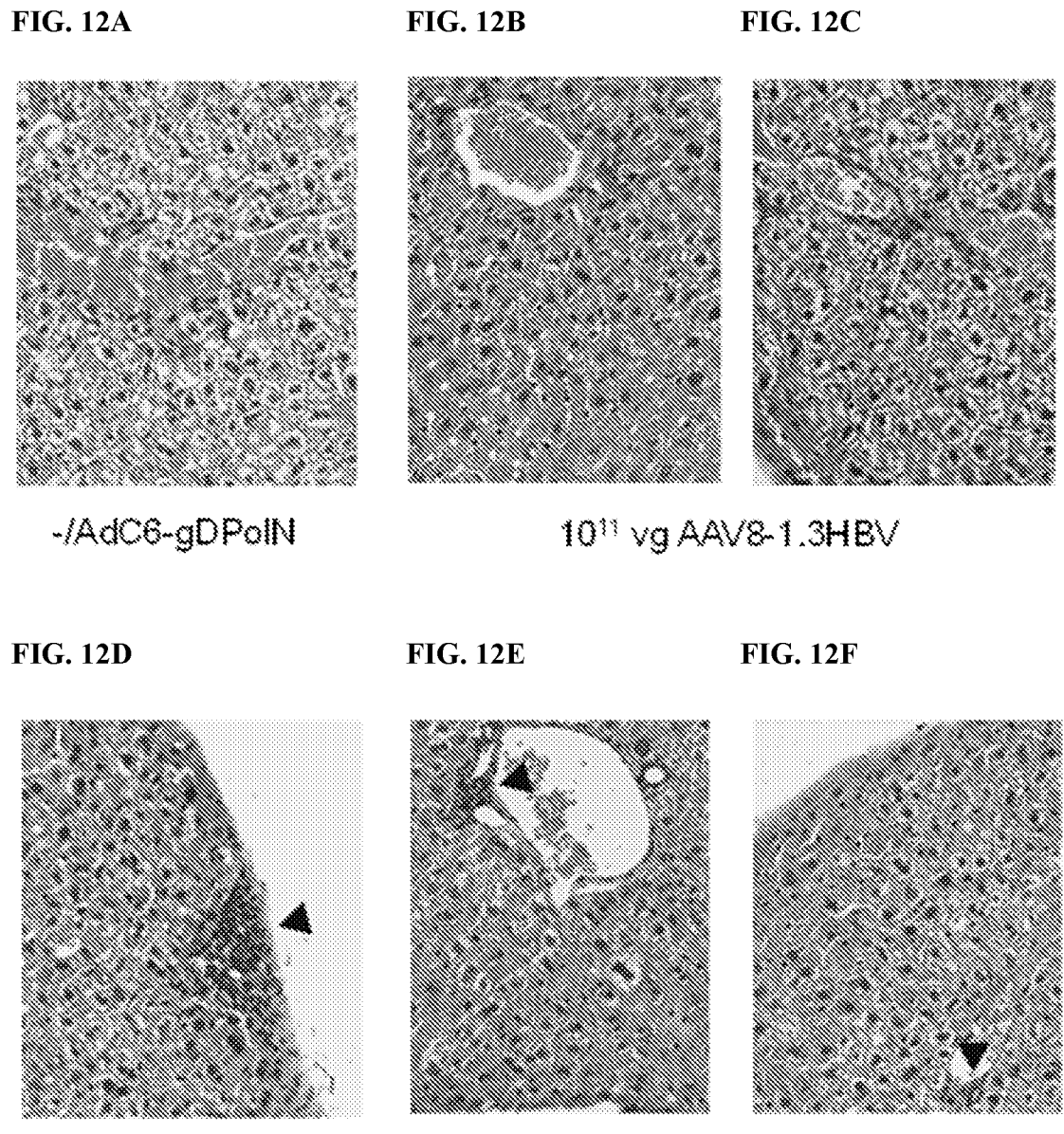

FIG. 11A and FIG. 11B illustrate vaccine-induced HBV-specific CD8+ T cell response in the liver of C57B1/6 mice injected with the indicated vectors. *p-value between 0.01-0.05; ***p-value between 0.0001-0.001; via 1-way ANOVA.

FIG. 12A, FIG. 12B, FIG. 12C, FIG. 12D, FIG. 12E, and FIG. 12F illustrate hematoxylin & eosin staining of liver samples from C57B1/6 mice injected with the indicated vectors. 20× magnification. Arrows indicate areas of lymphocytic infiltrates.

FIG. 13A and FIG. 13B illustrate vaccine-induced markers of CD8+ T cell activation/exhaustion in the liver of C57B1/6 mice injected with the indicated vectors. p-value between 0.001-0.01; *p-value between 0.0001-0.001; via 1-way ANOVA.

FIG. 14A and FIG. 14B illustrate HBV viral dynamics in C57B1/6 mice injected with an exemplary AdC6-gDPolN vector. The median HBV DNA VL/ml at week 4-7.3 $\log_{10}$ cps/mL are provided. n=7; one mouse excluded for missing data.

FIG. 15A and FIG. 15B illustrate the impact of AAV-induced HBV on CD8+ T cell responses in C57B1/6 mice first injected with $10^{10}$ or $10^{11}$ vg of AAV-1.3HBV and then four weeks later boosted with $10^{10}$ vp of an exemplary AdC6-gDPolN vector. In FIG. 15B, each slice represents an individual epitope with size showing the proportion of the total; only responses>0.1% were included. Pullouts represent epitopes only recognized in AAV8-1.3HBV infected mice.

Figure 16:
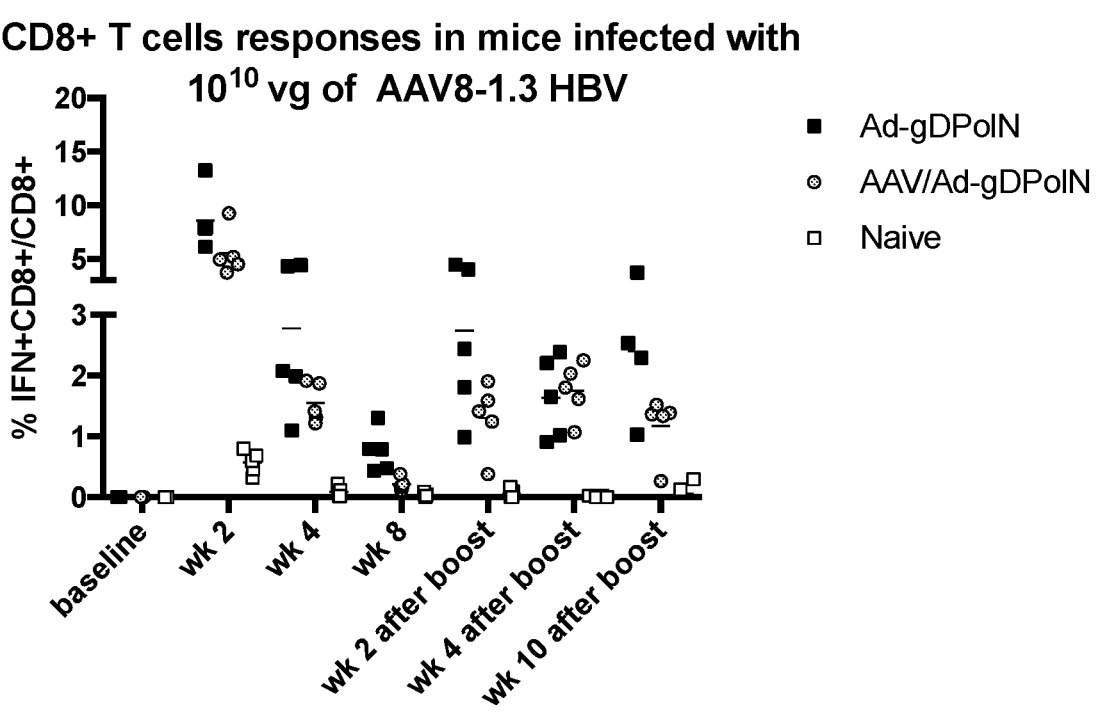

FIG. 16 illustrates the frequencies of IFN-γ-producing CD8+ T cells for individual C57B1/6 mice that were injected i.v. with the $10^{10}$ vg of the AAV8-1.3HBV vectors, vaccinated 4 weeks later with $5 \times 10^9$ vp of the AdC6-gDPolN vector, and boosted 2 months later with the same dose of the AdC7-gDPolN vaccine. Control mice only received the vaccine. Naïve mice served as additional controls.

Figure 17A:
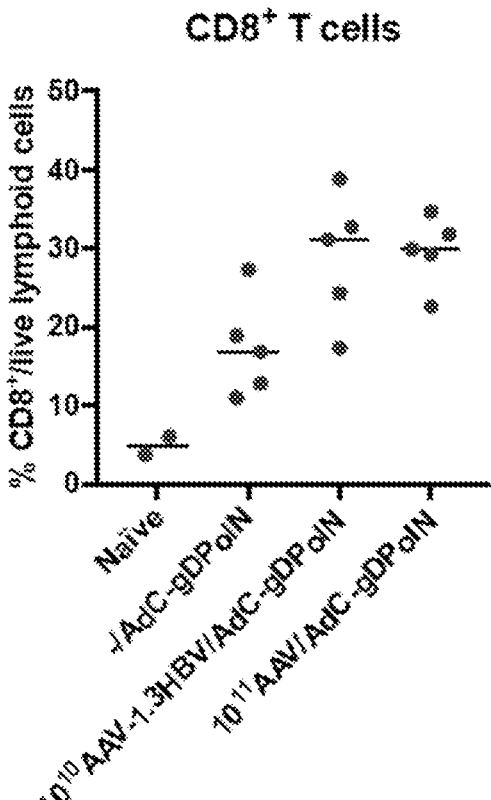
Figure 17B:
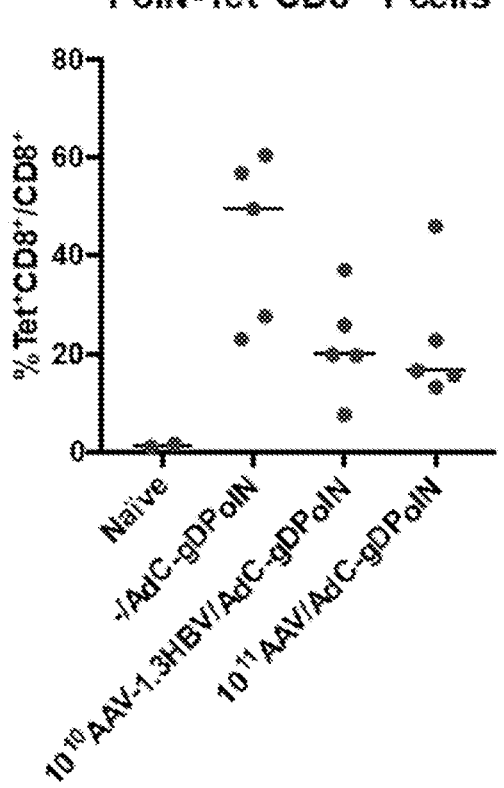
Figures 18A, 18B, 18C, 18D, 18E, 18F:
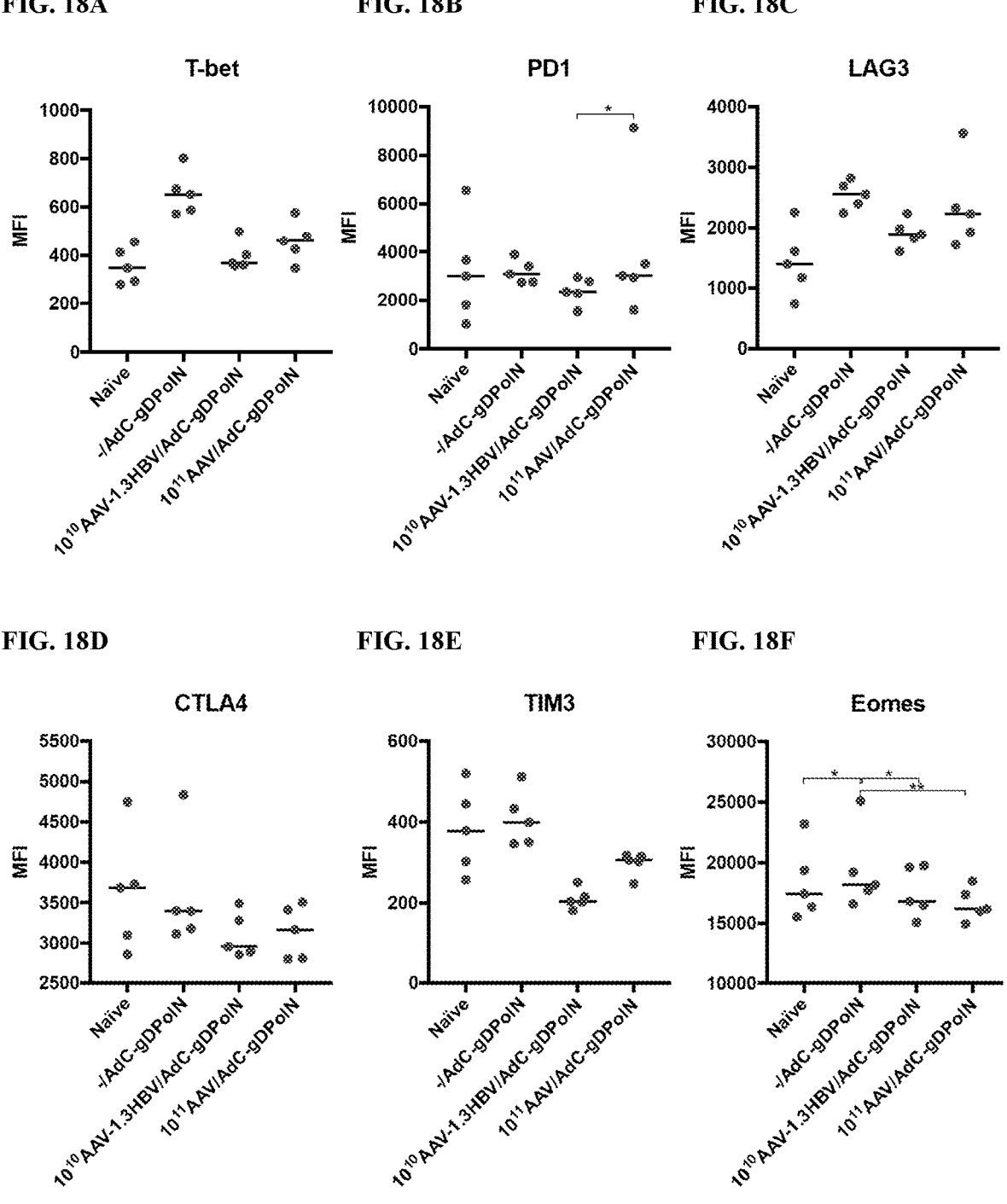
Figures 19A, 19B, 19C, 19D, 19E, 19F:
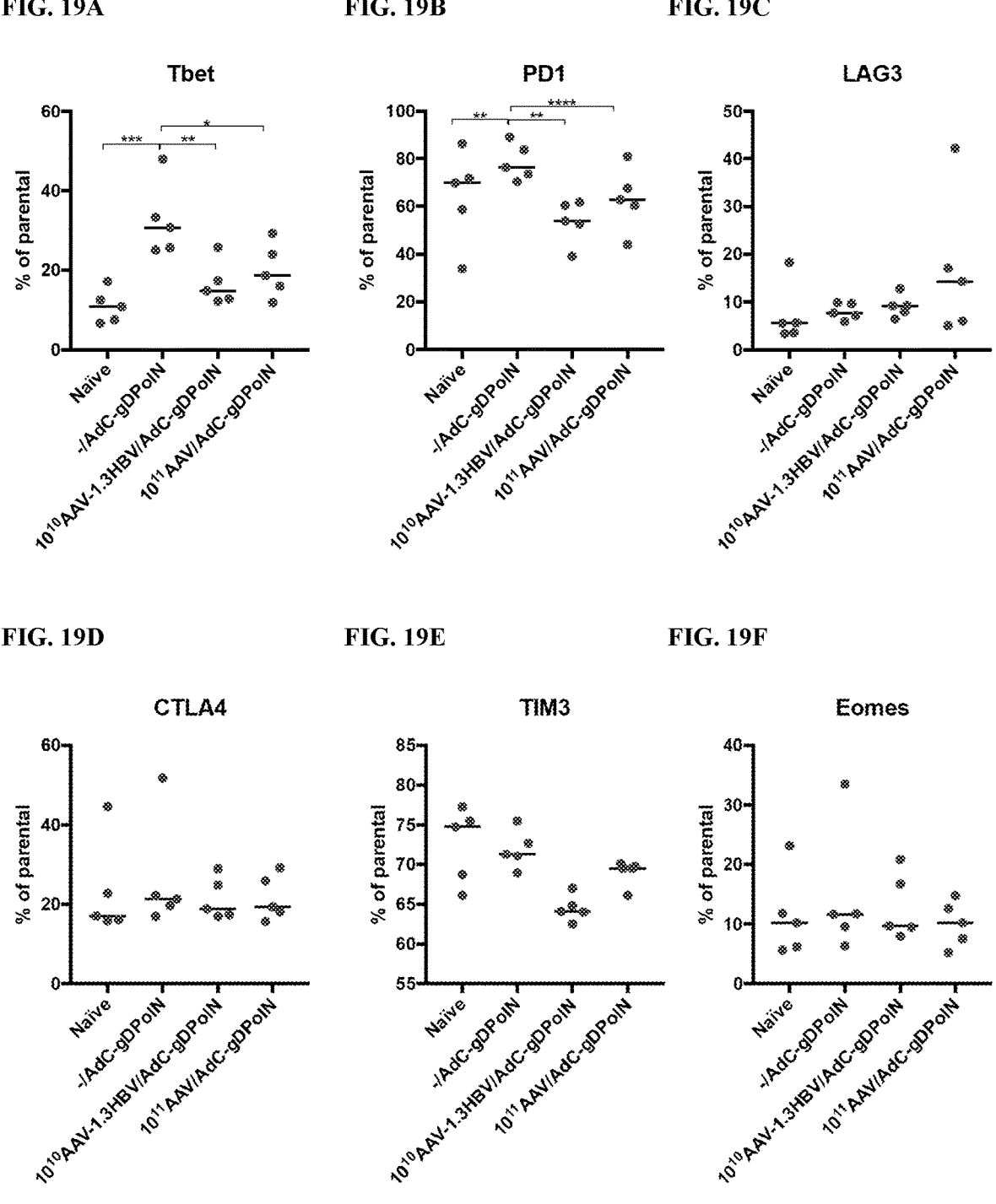

FIG. 17A and FIG. 17B illustrate: A) % of CD8+ T cells within the lymphatic infiltrates of livers of individual mice; and B) the frequencies of PolN-tetramer+CD8+ T cells within the same infiltrates. C57B1/6 mice were injected i.v. with the $10^{10}$ or $10^{11}$ vg of the AAV8-1.3HBV vector, were vaccinated 4 weeks later with $5 \times 10^9$ vp of the AdC6-gDPolN vector, and were boosted 2 months later with the same dose of the AdC7-gDPolN vaccine. Control mice only received the vaccine. Naïve mice served as additional controls.

FIG. 18A, FIG. 18B, FIG. 18C, FIG. 18D, FIG. 18E, and FIG. 18F illustrate the phenotypes of the infiltrating tetramer+CD8+ T cells in comparison to naïve (i.e., tetramer CD44-CD8+) T cells analyzed with the mean fluorescent intensity (MFI) of the indicated markers. Lines with stars above indicate significant differences by multiple t-test. (*) p≤0.05-0.01, () p≤0.01-0.001, (*) p≤0.001-0.0001, (****) p≤0.0001.

FIG. 19A, FIG. 19B, FIG. 19C, FIG. 19D, FIG. 19E, and FIG. 19F illustrate the percentage of Tet+ or naïve CD8+ T cells positive for the indicated markers. Lines with stars above indicate significant differences by multiple t-test. (*) p≤0.05-0.01, () p≤0.01-0.001, (*) p≤0.001-0.0001, (****) p≤0.0001.

Figure 20A:
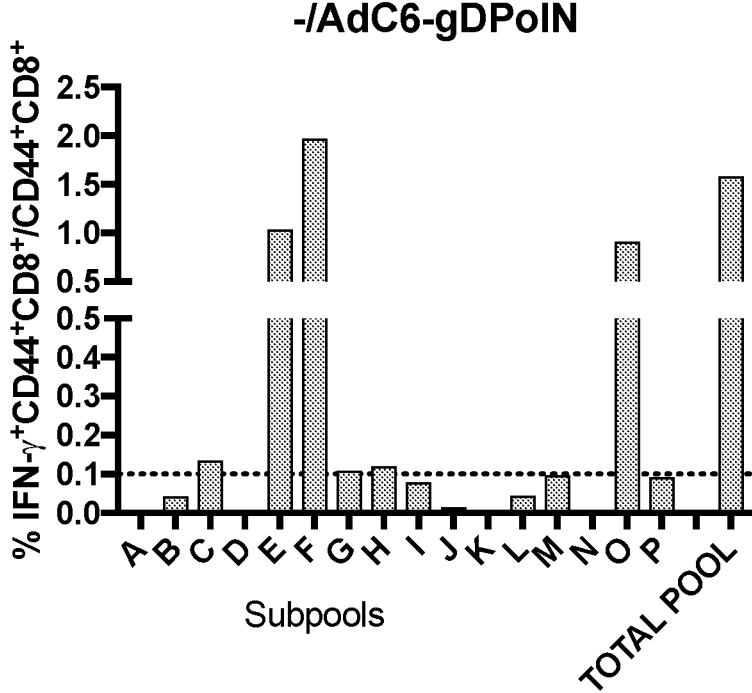
Figure 20B:
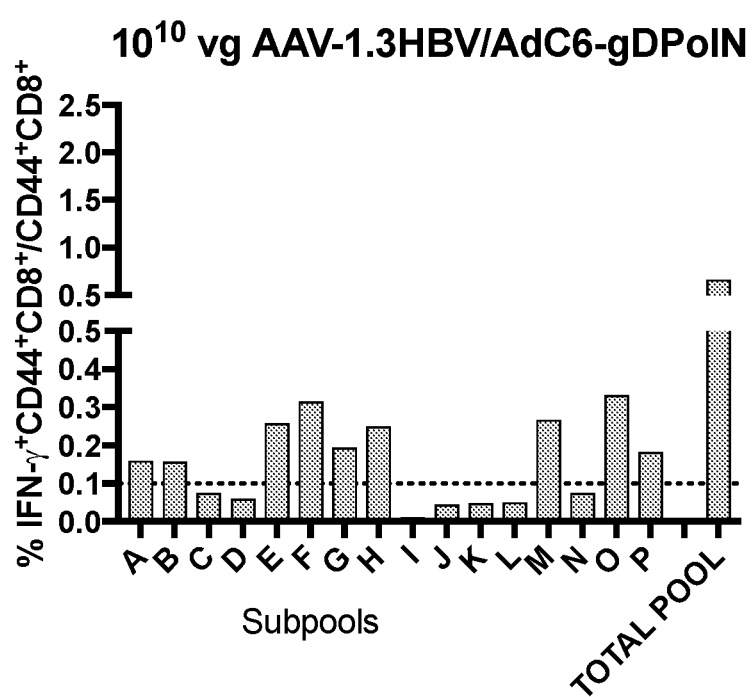
Figure 20C:
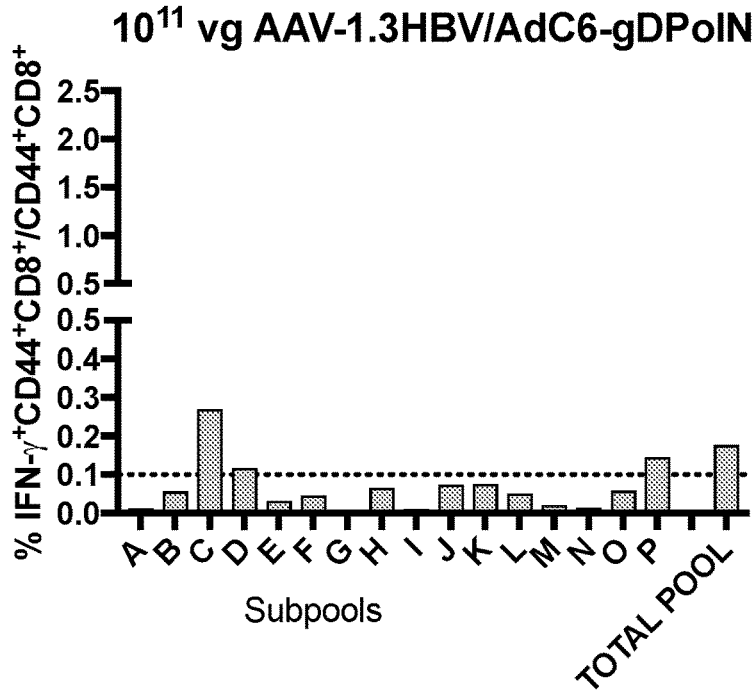
Figure 20D:
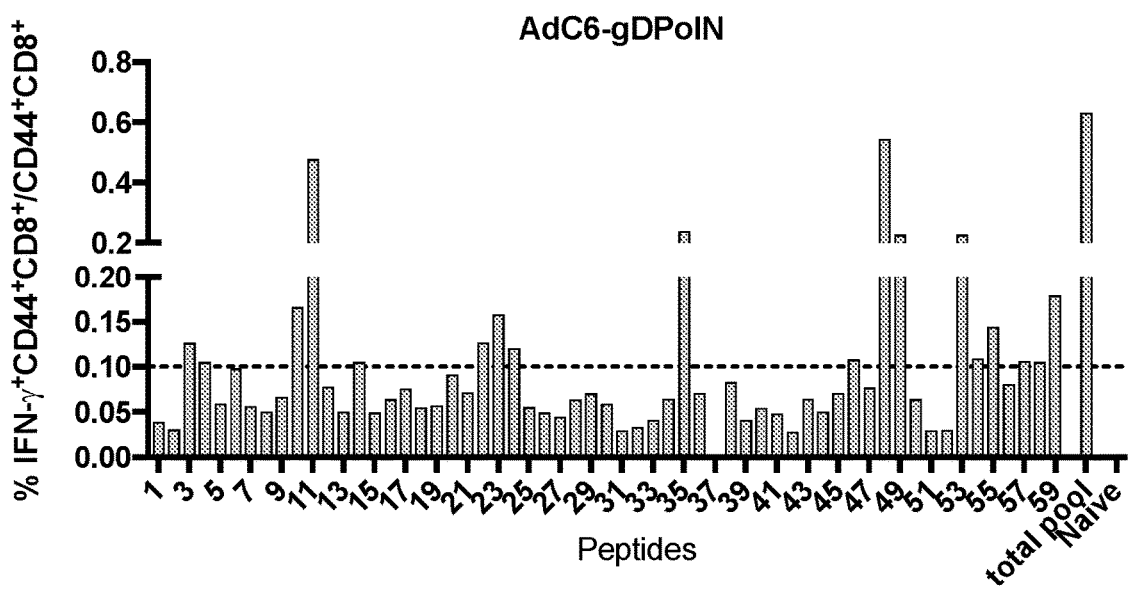
Figure 20E:
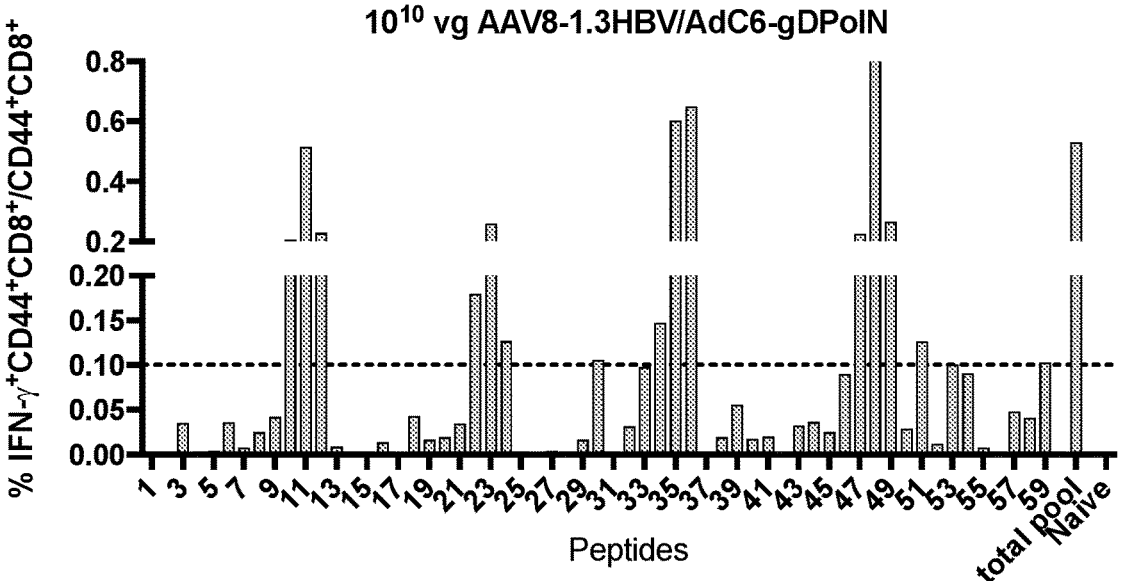

FIG. 20A, FIG. 20B, FIG. 20C, FIG. 20D, FIG. 20E, and FIG. 20F illustrate the CD8+ T cell response to individual peptides spanning the PolN sequence. Total pool-response to mixtures of all PolN peptides; Naïve—response of naïve mice to mixtures of all PolN peptides. FIG. 20A and FIG. 20D show CD8+ T cell responses of mice that received just the AdC6-gDPolN vaccine. FIG. 20B and FIG. 20E show CD8+ T cell responses of mice that were injected with $10^{10}$ vg of AAV8-1.3HBV 4 weeks prior to vaccination with AdC6-gDPolN.

Figure 20F:
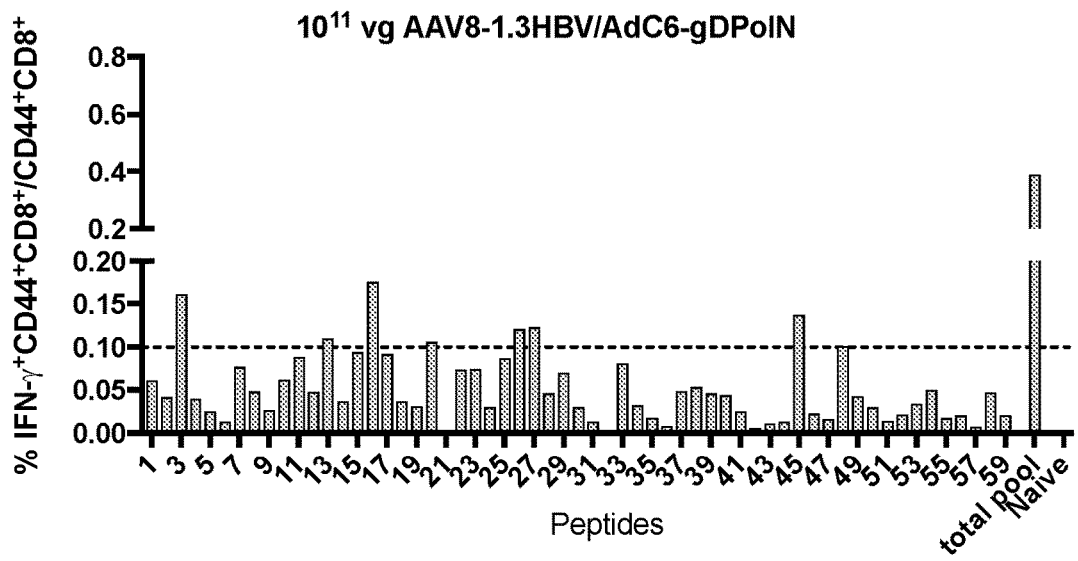

FIG. 20C and FIG. 20F show CD8+ T cell responses of mice that were injected with $10^{11}$vg of AAV8-1.3HBV 4 weeks prior to vaccination with AdC6-gDPolN. FIGS. 20A, 20B and 20C can be used to calculate the breadth of the immune response by individual epitopes using the peptide pools shown in FIG. 7D and the individual peptide sequences recognized using FIG. 7E.

Figure 21A:
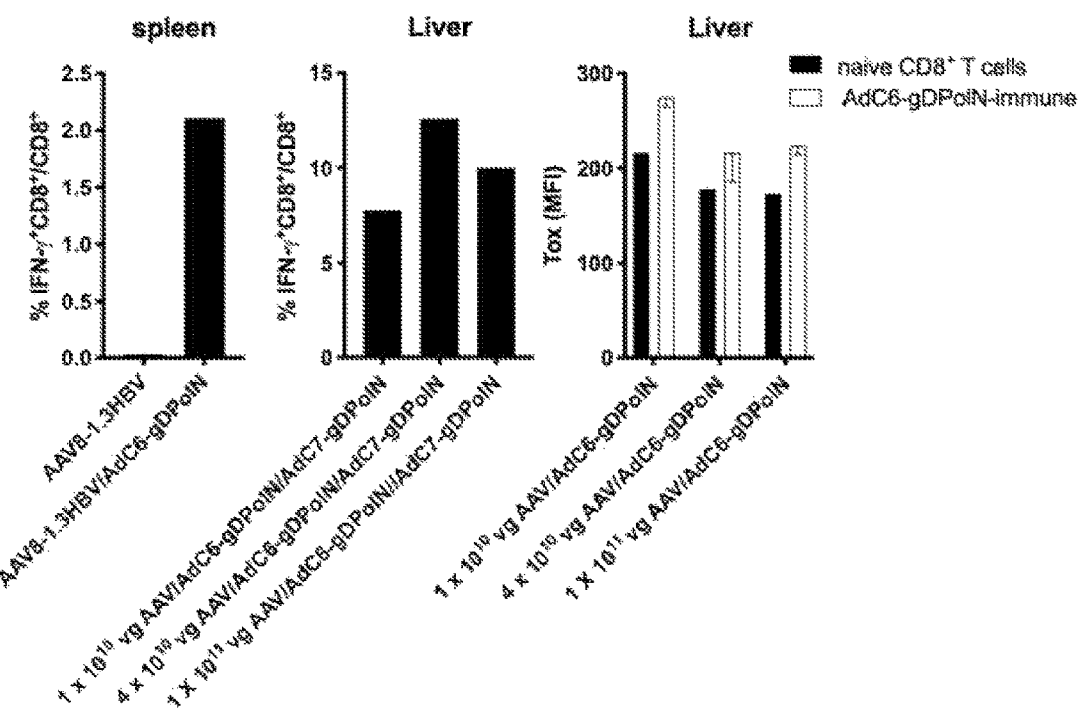
Figure 21B:
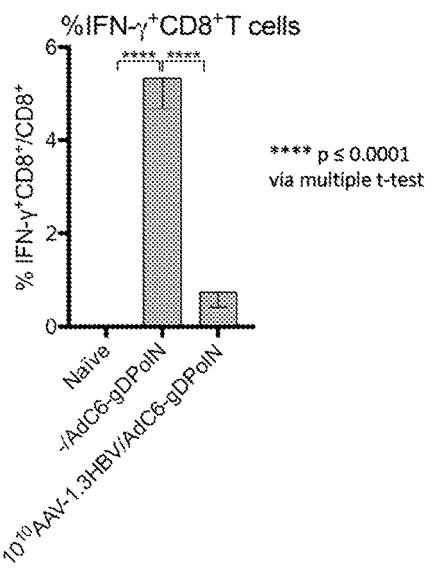

FIG. 21A and FIG. 21B illustrate the PolN-specific CD8+ T cells in the spleen or liver of mice. FIG. 21A left panel shows CD8+ T cell responses in spleen of AAV8-1.3HBV injected mice that did or did not receive the AdC6-gDPolN vaccine at $5 \times 10^{10}$ vp subsequently. FIG. 21A middle panel shows CD8+ T cell frequencies in livers of mice that were treated with different doses of AAV8-1.3HBV and then received vaccines in a prime boost regimen. FIG. 21A right panel shows the levels of Tox-1 expression in PolN-specific CD8+ T cells or naïve CD8+ T cells from the same experiment. FIG. 21B illustrates % IFN-γ+ CD8+ T cells.

Figure 22A:
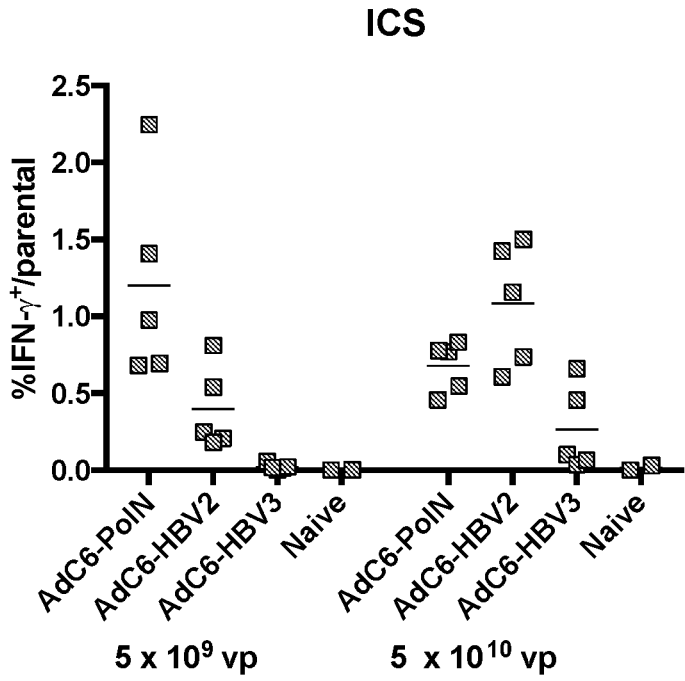
Figure 22B:
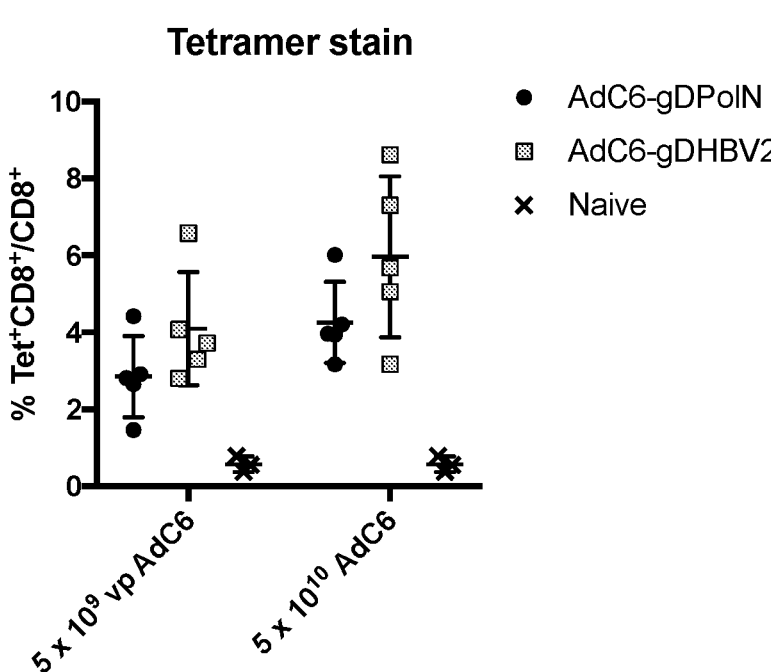

FIG. 22A and FIG. 22B illustrate A) CD8+ T cell frequencies in the blood of mice injected with the indicated AdC6 vectors; and B) frequencies of tetramer+CD8+ T cells.

Figure 23:
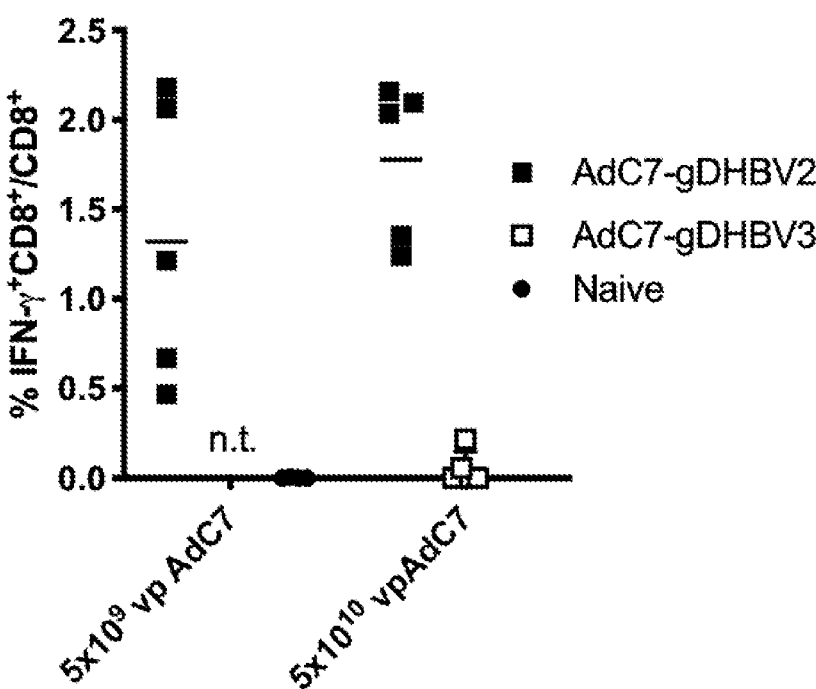
Figure 24A:
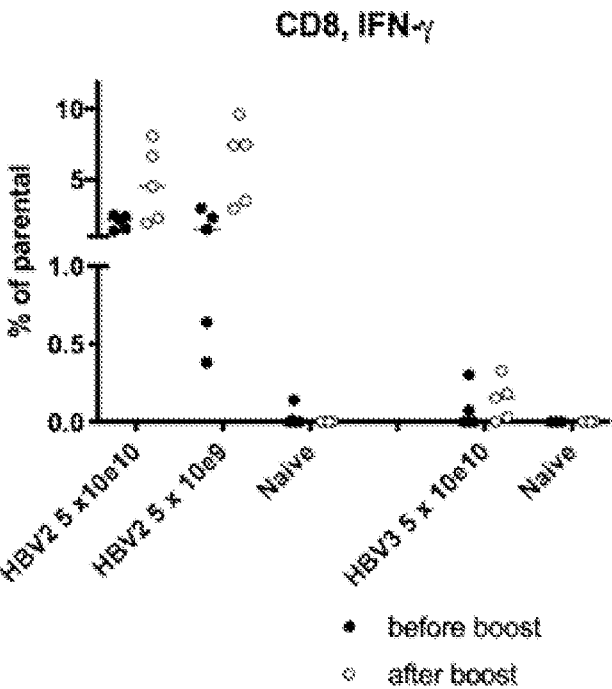
Figure 24B:
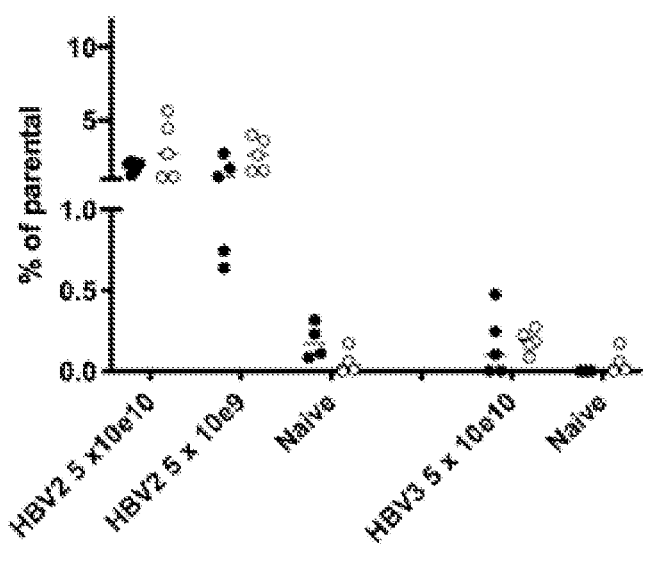
Figure 24C:
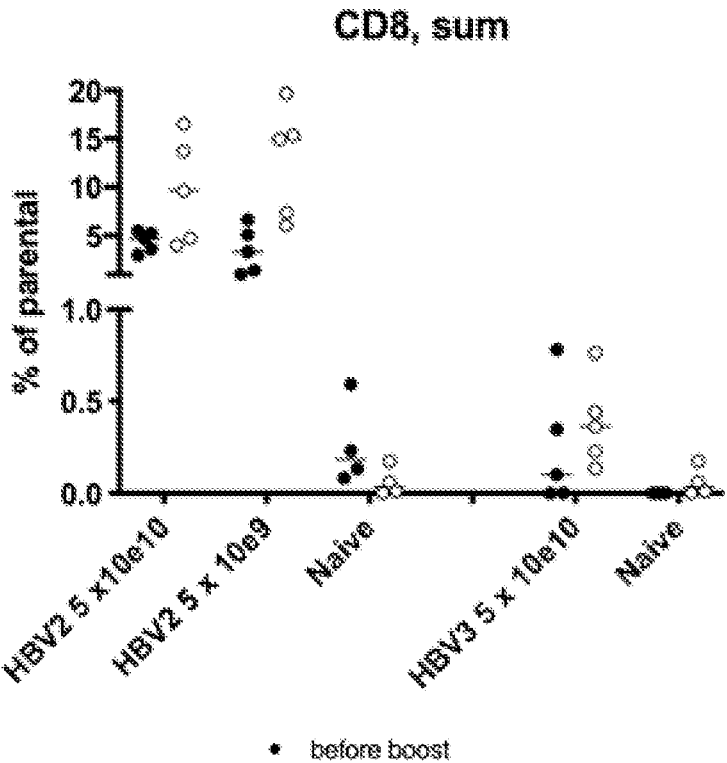
Figure 24D:
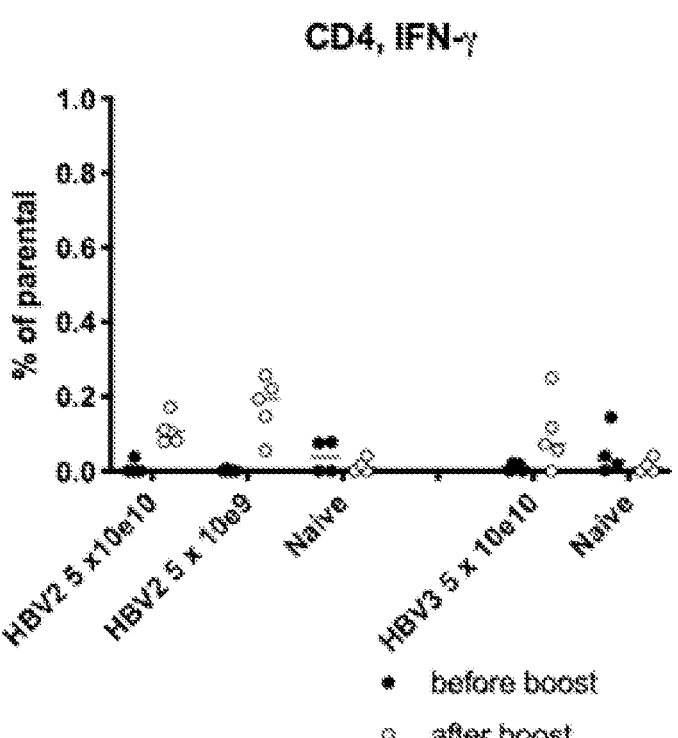
Figure 24E:
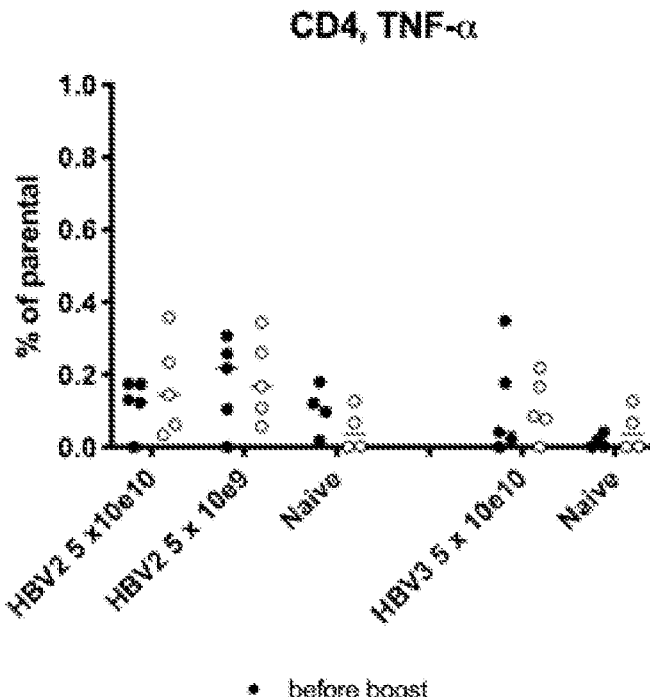
Figure 24F:
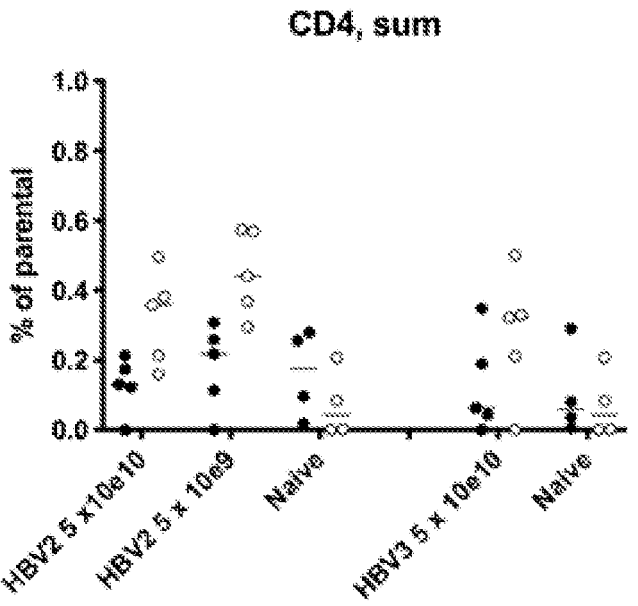

FIG. 23 illustrates CD8+ T cell frequencies in the blood of mice injected with the indicated AdC7 vectors.

FIG. 24A, FIG. 24B, FIG. 24C, FIG. 24D, FIG. 24E, and FIG. 24F illustrate CD8+ (FIG. 24A-FIG. 24C) and CD4+ (FIG. 24D-FIG. 24F) T cell frequencies to the gDHBV2 and gDHBV3 inserts in blood of mice injected with the indicated AdC7 vectors ("after prime") and then boosted with the corresponding AdC6 vectors ("after boost"). Graphs show frequencies of T cells producing IFN-γ, frequencies of T cells producing TNF-α, and the sum of frequencies of T cells producing either cytokine.

Figure 25A:
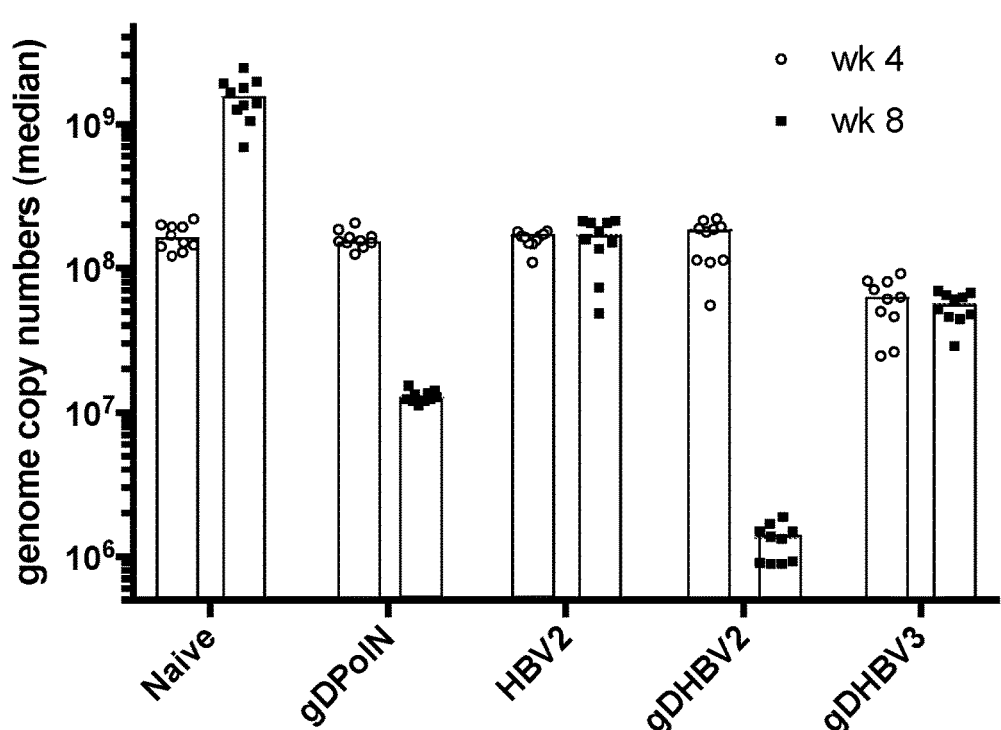
Figure 25B:
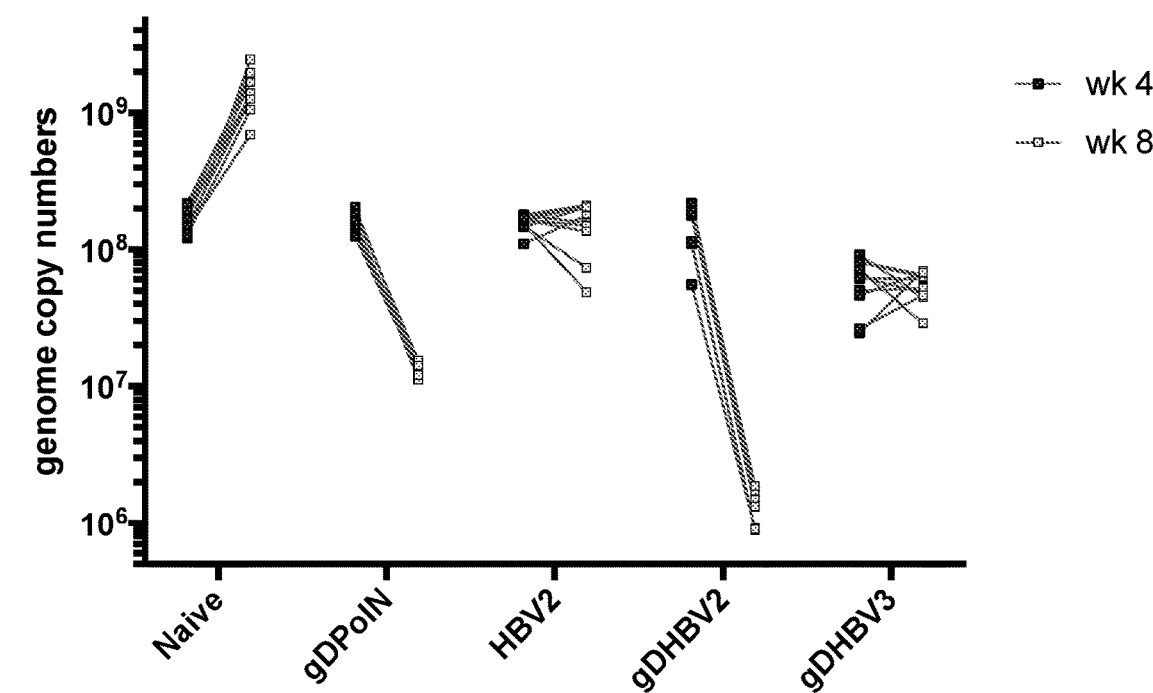

FIG. 25A and FIG. 25B illustrate the HBV DNA viral titer in C57B1/6 mice that were challenged with $1 \times 10^9$ vg of AAV8-1.3HBV and were vaccinated 4 weeks later with $1 \times 10^{10}$ vp of AdC6-gDPolN ("gDPolN"), AdC6-gDHBV2 ("gDHBV2"), AdC6-gDHBV3 ("gDHBV3"), or AdC6-HBV2 without gD ("HBV2"); AAV-infected, non-vaccinated animals ("naïve"), and non-AAV-infected, non-vaccinated animals (data not shown) served as controls. FIG. 25A illustrates the viral titer for each group at weeks 4 and 8 after AAV challenge; FIG. 25B illustrates the results of the individual mice at weeks 4 and 8 after AAV challenge.

FIG. 26A, FIG. 26B, FIG. 26C, and FIG. 26D illustrate the percent of parental IFN-γ and/or TNF-α producing CD8+ T cells (FIG. 26A), CD44+CD8+ T cells (FIG. 26B), CD4+ T cells (FIG. 26C) or CD44+CD4+ T cells (FIG. 26D) two and eight weeks after prime and two and four weeks after the boost (as the mean) using the indicated construct.

Figures 27A, 27B, 27C:
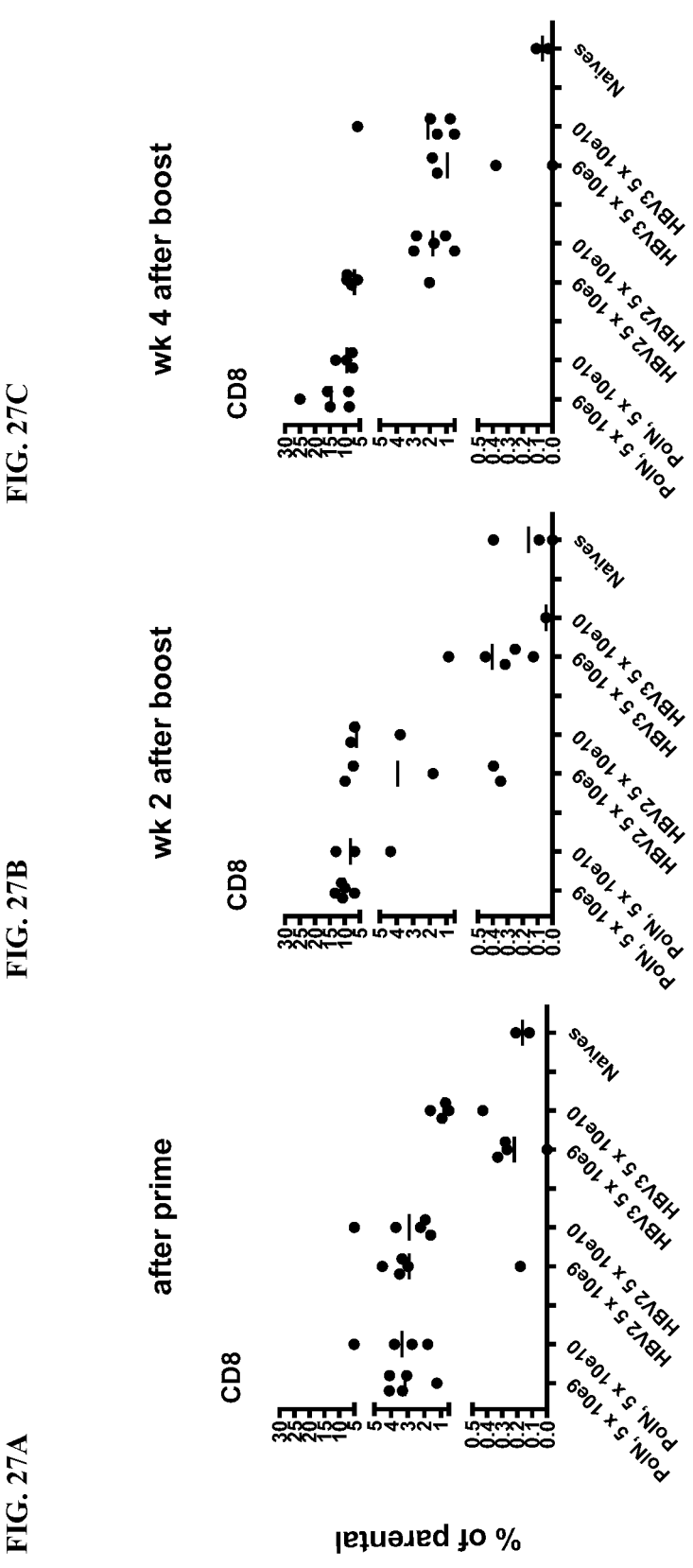

FIG. 27A, FIG. 27B, and FIG. 27C illustrate CD8+ T cells at multiple time points: four weeks after prime (FIG. 27A);

two weeks after the boost (FIG. 27B); and four weeks after the boost (FIG. 27C) with the indicated constructs (PolN=gDPolN; HBV2=gDHBV2; HBV3=gDHBV3). The graph shows the overall frequencies of CD8$^+$ T cells producing IFN-γ$^+$ as assessed by ICS.

Figures 28A, 28B, 28C:
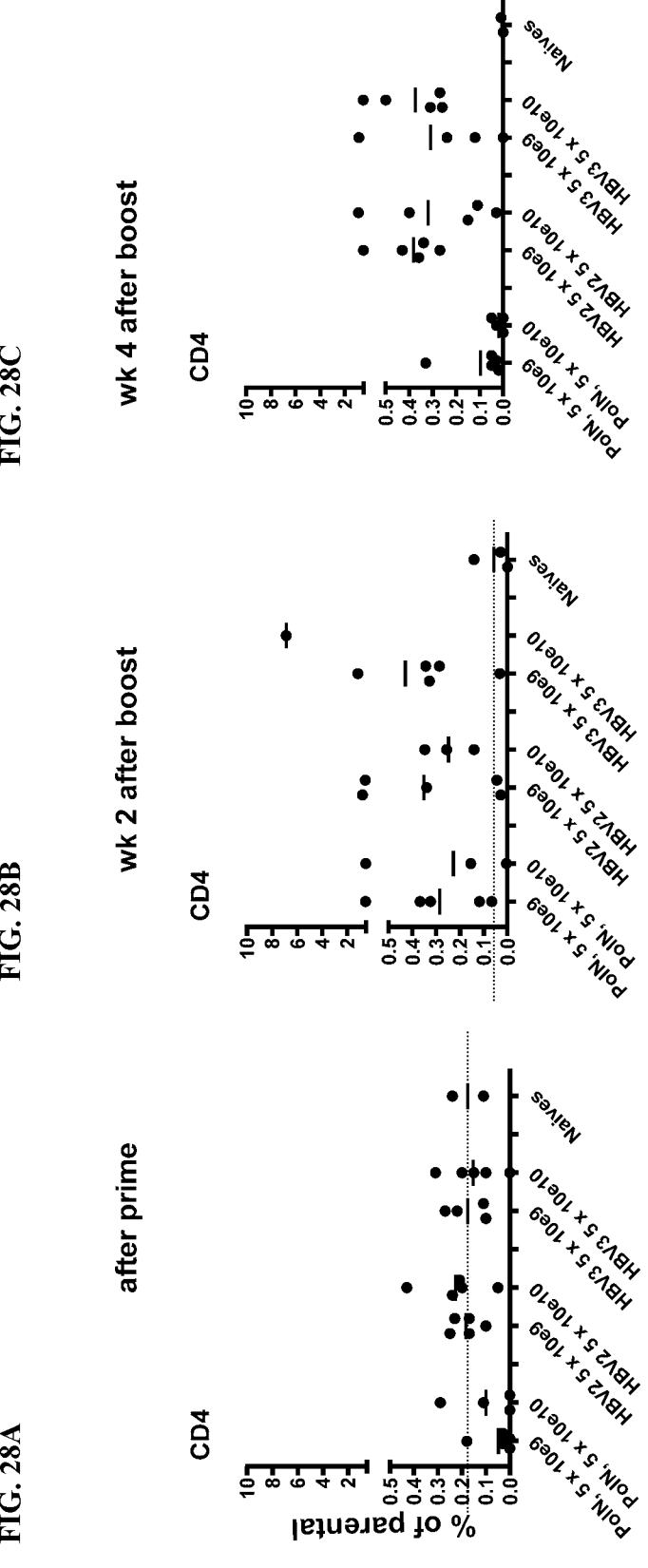

FIG. 28A, FIG. 28B, and FIG. 28C illustrate cytokine-producing CD4$^+$ T cells at multiple time points: four weeks after prime (FIG. 28A); two weeks after the boost (FIG. 28B); and four weeks after the boost (FIG. 28C) with the indicated constructs (PolN=gDPolN; HBV2=gDHBV2; HBV3=gDHBV3) as assessed by ICS. The dashed line indicates the cut-off for positive responses, based on the results from the naïve mice.

Figure 29A:
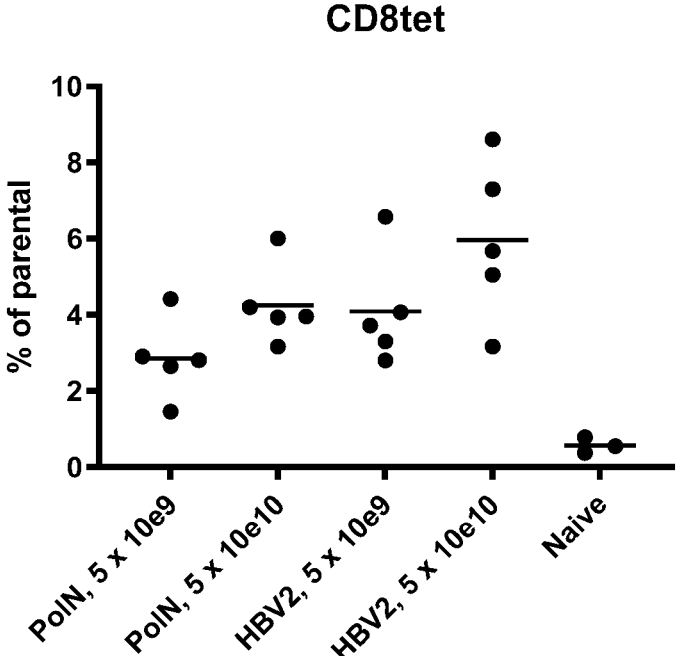
Figure 29B:
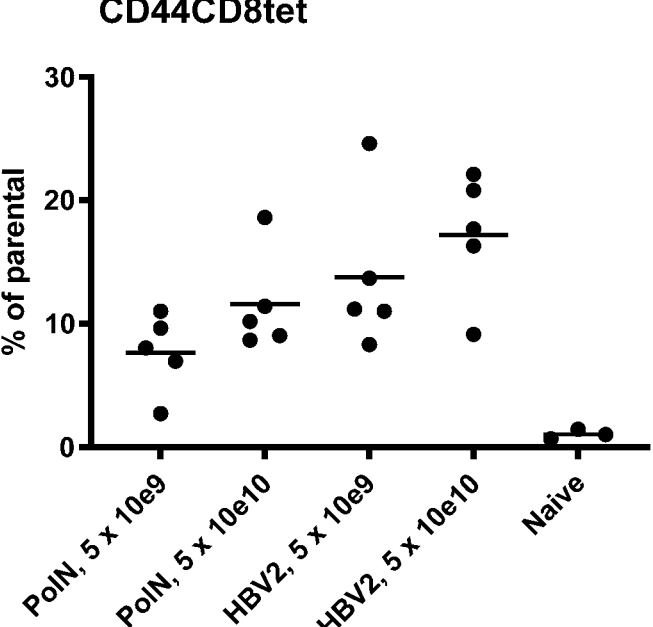

FIG. 29A and FIG. 29B illustrate the results of tetramer staining gated on either CD8+ T cells (FIG. 29A) or CD44+ CD8+ T cells (FIG. 29B) at four weeks after the prime with the indicated construct (PolN=gDPolN; HBV2=gDHBV2).

Figures 30A, 30B, 30C:
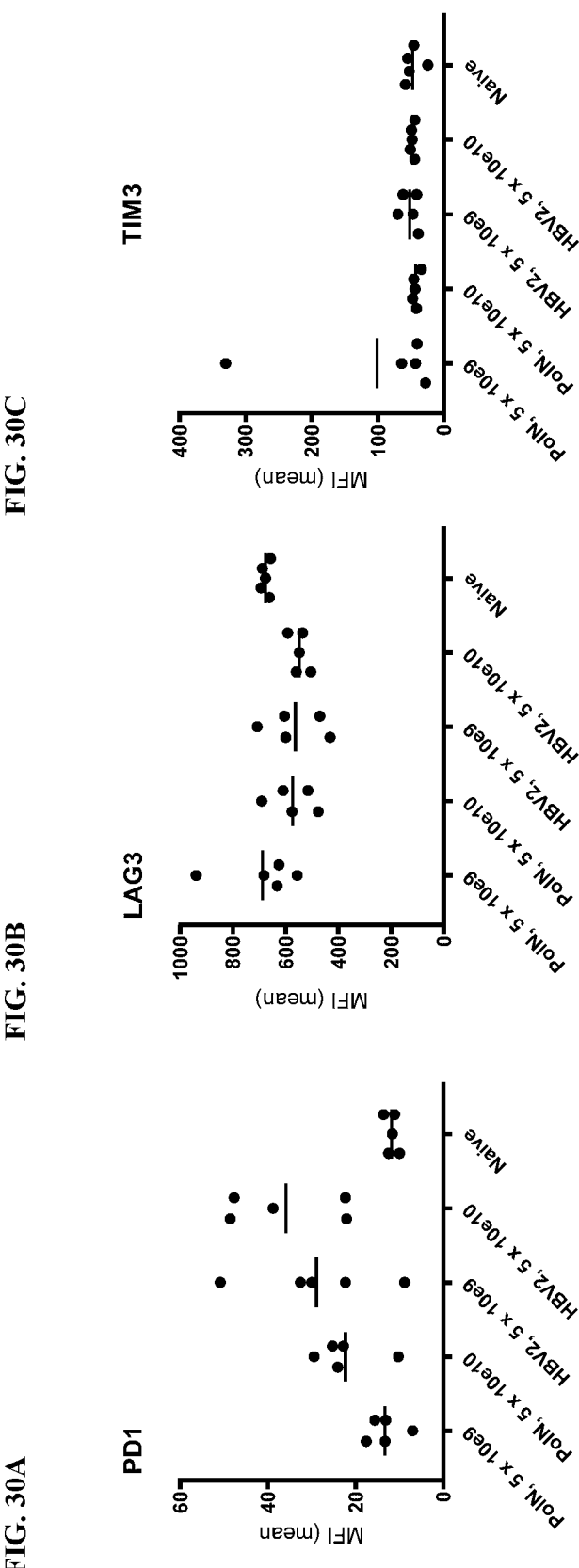
Figures 30D, 30E, 30F:
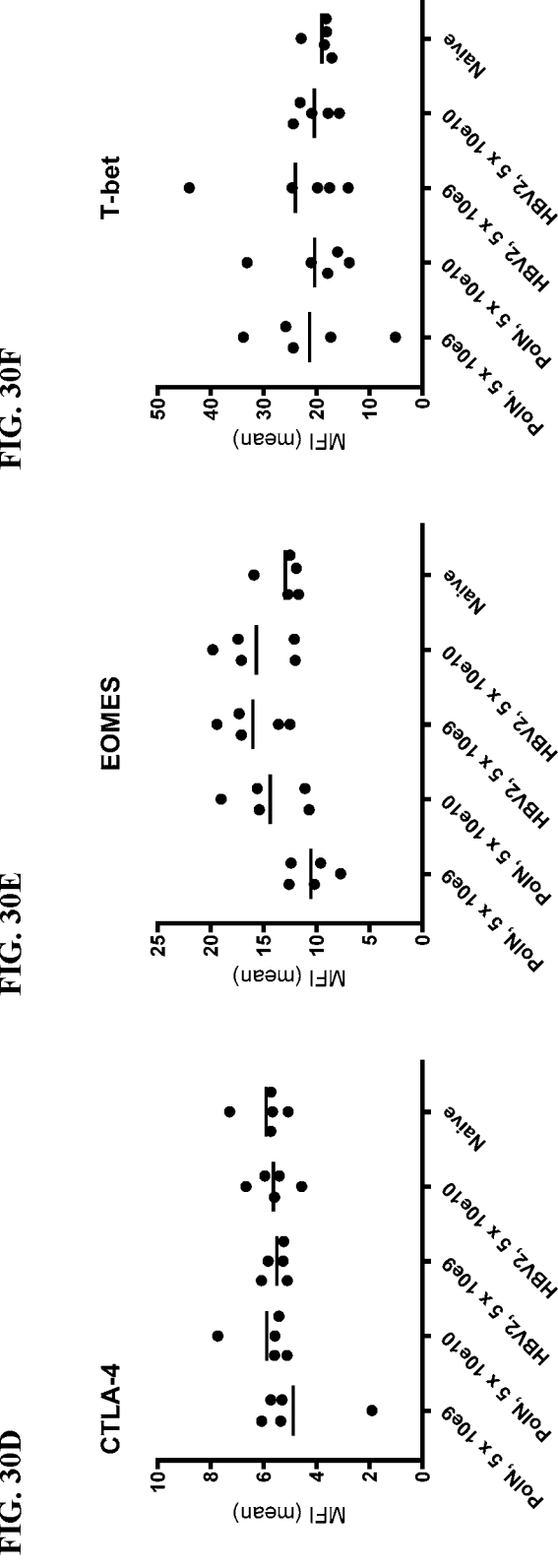

FIG. 30A, FIG. 30B, FIG. 30C, FIG. 30D, FIG. 30E, and FIG. 30F illustrates the phenotypes of the tetramer+CD8+ T cells shown as the mean fluorescent intensity of a dye linked to the indicated antibody: FIG. 30A—anti-PD1 antibody conjugated to BV605; FIG. 30B—anti-LAG3 antibody conjugated to BV650; FIG. 30C—anti-TIM3 antibody conjugated to Pe-Cy7-A; FIG. 30D—anti-CTLA4 antibody conjugated to PE-A; FIG. 30E—anti-EOMES antibody conjugated to AF488; and FIG. 30F—anti-T-bet antibody conjugated to BV786.

Figure 31:
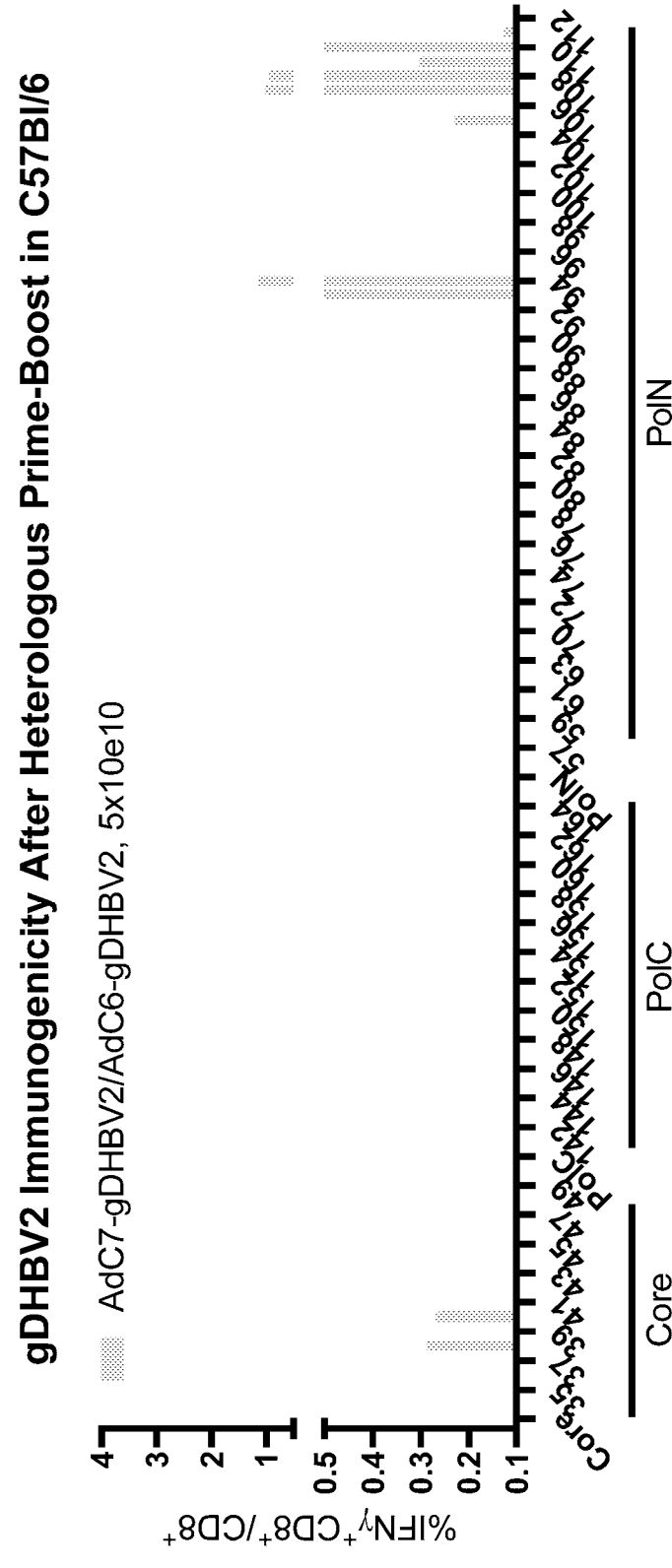

FIG. 31 illustrates the CD8$^+$ T cell responses after a prime vaccination of 5×10$^{10}$ vp AdC7-gDHBV2 followed two months later by vaccination with 5×10$^{10}$ vp AdC6-gDHBV2. Numbers on the X axis correspond to the SEQ ID NO as provided herein.

Figure 32:
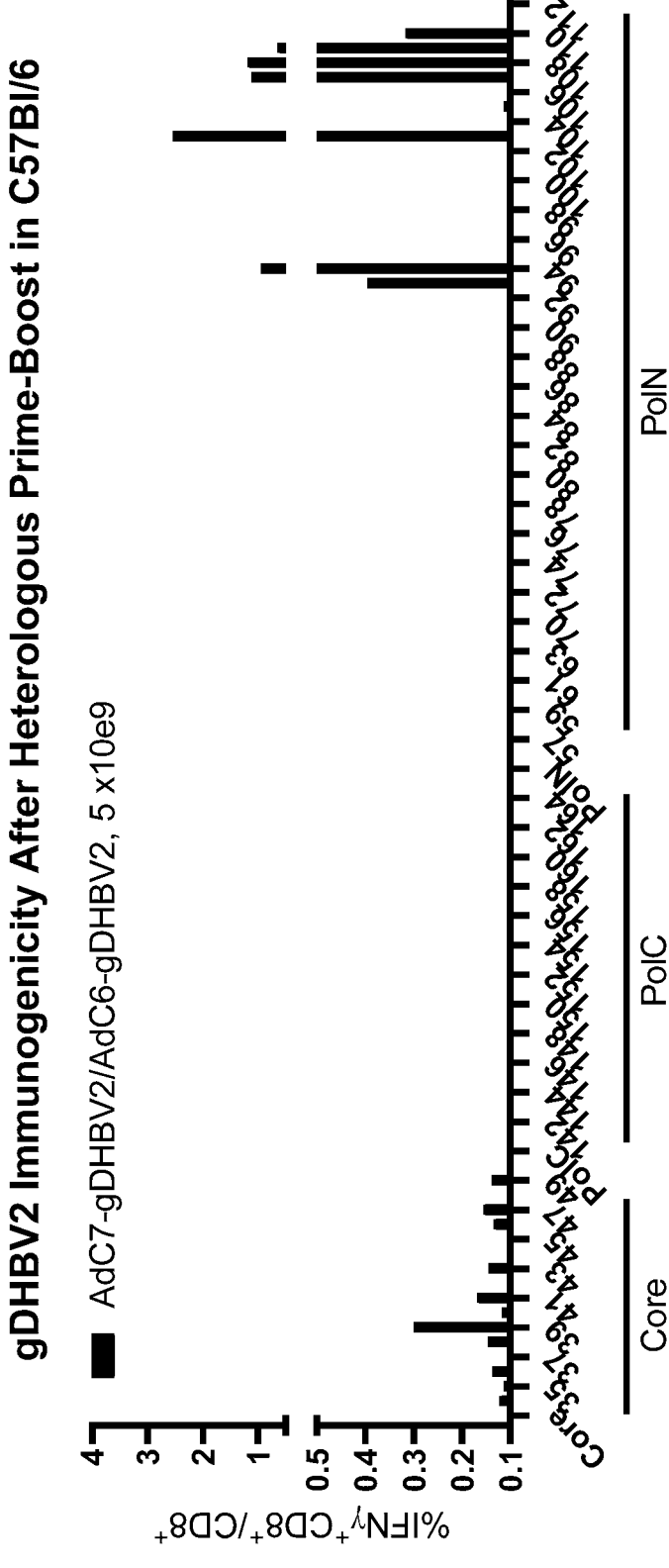

FIG. 32 illustrates the CD8+ T cell responses after a prime vaccination with 5×10$^9$ vp AdC7-gDHBV2 followed two months later by vaccination with 5×10$^9$ vp AdC6-gDHBV2. Numbers on the X axis correspond to the SEQ ID NO as provided herein.

Figure 33:
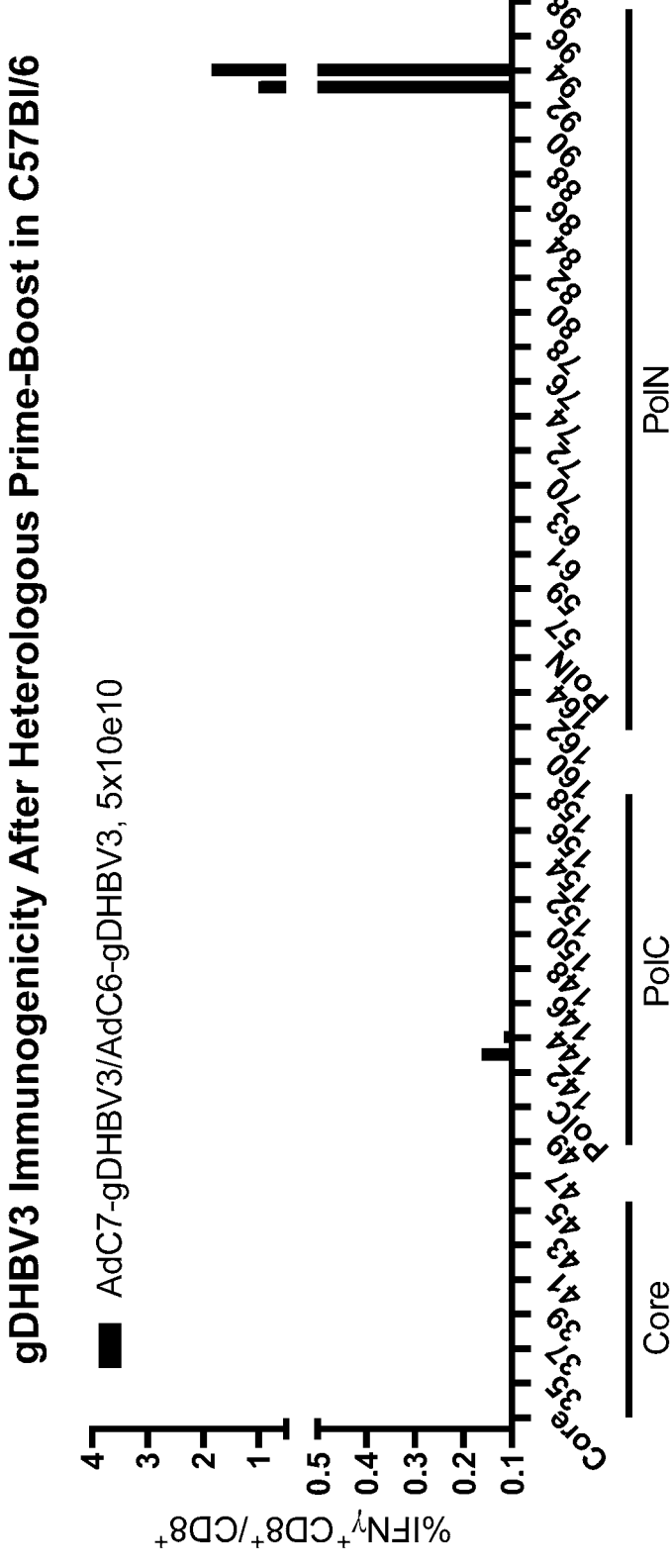

FIG. 33 shows the immunogenicity after a prime vaccination with 5×10$^{10}$ vp AdC7-gDHBV3 followed two months later by vaccination with 5×10$^{10}$ vp AdC6-gDHBV3. Numbers on the X axis correspond to the SEQ ID NO as provided herein.

Figure 34:
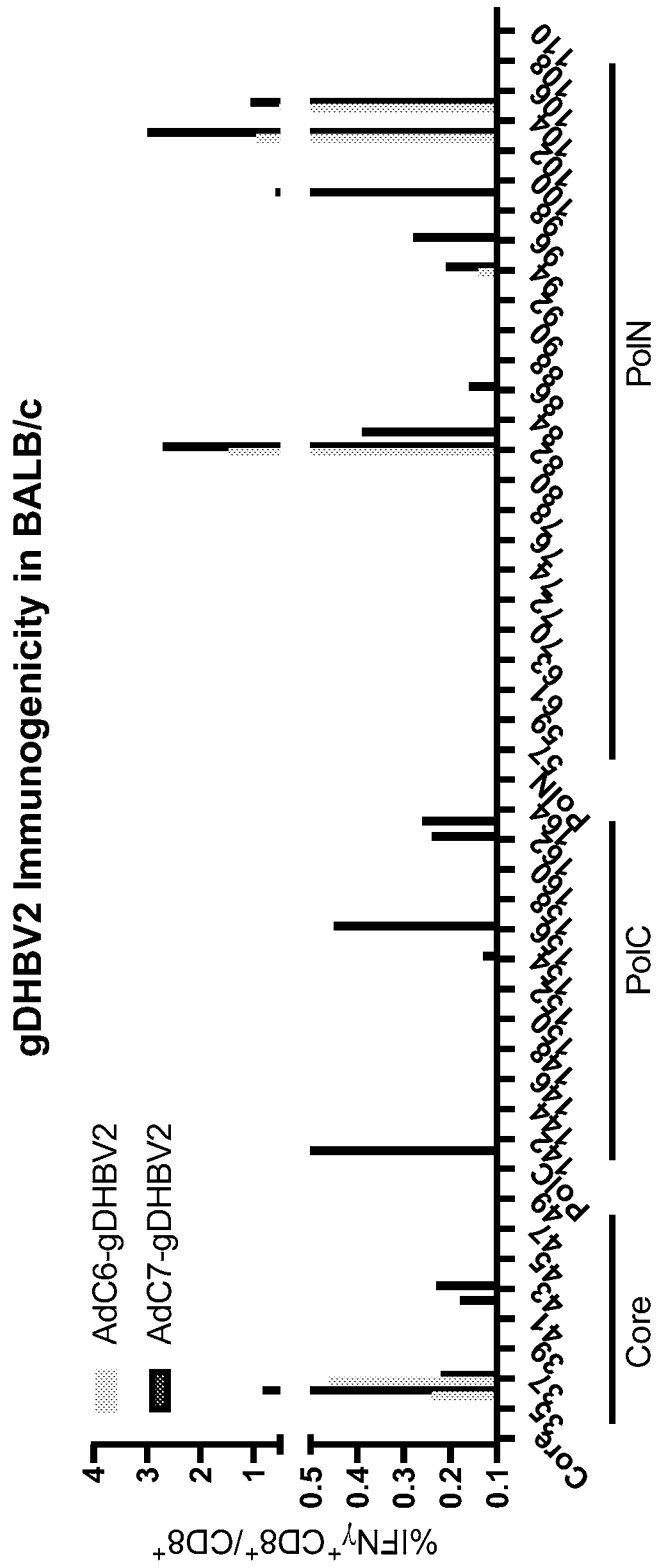

FIG. 34 illustrates the immunogenicity of the AdC6-gDHBV2 and AdC7-gDHBV2 vaccines corresponding to the SEQ ID NO (X axis) as provided herein. Core, PolC, and PolN regions in both HBV2 constructs were immunogenic.

Figure 35:
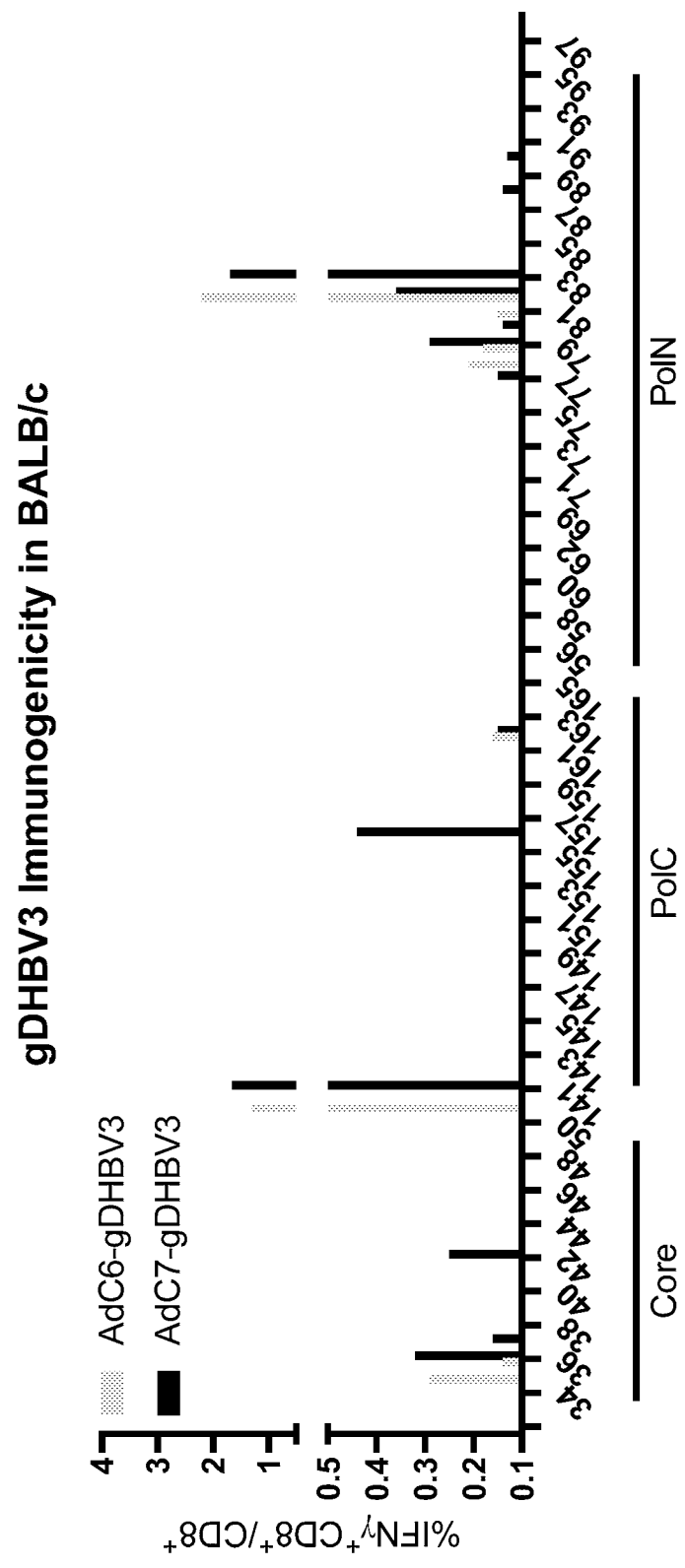

FIG. 35 illustrates the immunogenicity of the AdC6-gDHBV3 and AdC7-gDHBV3 vaccines corresponding to the SEQ ID NO (X axis) as provided herein. Core, PolC, and PolN regions in both HBV3 constructs were immunogenic.

DETAILED DESCRIPTION OF ILLUSTRATIVE EMBODIMENTS

The disclosed proteins, vaccines, and methods may be understood more readily by reference to the following detailed description taken in connection with the accompanying figures, which form a part of this disclosure. It is to be understood that the disclosed proteins, vaccines, and methods are not limited to the specific proteins, vaccines, and methods described and/or shown herein, and that the terminology used herein is for the purpose of describing particular embodiments by way of example only and is not intended to be limiting of the claimed proteins, vaccines, and methods.

Unless specifically stated otherwise, any description as to a possible mechanism or mode of action or reason for improvement is meant to be illustrative only, and the disclosed proteins, vaccines, and methods are not to be constrained by the correctness or incorrectness of any such suggested mechanism or mode of action or reason for improvement.

Throughout this text, the descriptions refer to proteins and methods of using said proteins. Where the disclosure describes or claims a feature or embodiment associated with a proteins, such a feature or embodiment is equally applicable to the methods of using said proteins. Likewise, where the disclosure describes or claims a feature or embodiment associated with a method of using the proteins, such a feature or embodiment is equally applicable to the proteins.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed proteins, vaccines, and methods which are, for clarity, described herein in the context of separate embodiments, may also be provided in combination in a single embodiment. Conversely, various features of the disclosed proteins, vaccines, and methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, "immunogenic fragment thereof" refers to a portion of the disclosed HBV Core (Core), HBV polymerase N-terminal domain (PolN), or HBV polymerase C-terminal domain (PolC) that can produce an immune response in a subject.

As used herein, "providing to the subject" and similar terms indicate a procedure by which the fusion proteins, nucleic acid molecules, vectors, or vaccines are delivered to a subject such that target cells, tissues, or segments of the body of the subject are contacted with the fusion proteins, nucleic acid molecules, vectors, or vaccines. "Providing to the subject" includes parenteral and non-parenteral routes of administration.

The term "biosimilar" (of an approved reference product/ biological drug, i.e., reference listed drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is to be expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extent the mechanisms are known for the reference product. The condition or conditions of use prescribed, recommended, or suggested in the labeling proposed for the biosimilar have been previously approved for the reference product. The route of administration, the dosage form, and/or the strength of the biosimilar are the same as those of the reference product and the biosimilar is manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance. Biosimilars of the disclosed proteins and fusion proteins are included within the scope of this disclosure.

The term "subject" as used herein is intended to mean any animal, in particular, mammals. Although induction of an immune response in mice is exemplified herein, any type of mammal can be treated using the disclosed methods. Thus, the methods are applicable to human and nonhuman animals, although preferably used with mice and humans, and most preferably with humans.

The term "comprising" is intended to include examples encompassed by the terms "consisting essentially of" and "consisting of"; similarly, the term "consisting essentially of" is intended to include examples encompassed by the term "consisting of."

The following abbreviations are used herein: hepatitis B virus (HBV); adenovirus (Ad); herpes simplex virus (HSV); glycoprotein (gD); and virus genomes (vg).

Provided herein is a non-naturally occurring variant of the hepatitis B virus (HBV) Core protein. The disclosed HBV Core protein can comprise the amino acid sequence of SEQ ID NO: 6 or an immunogenic fragment thereof. Exemplary immunogenic fragments of SEQ ID NO: 6 include SEQ ID NOs: 20-54 provided in Table 3, below. In some embodiments, the immunogenic fragment of the HBV Core protein comprises the amino acid sequence of SEQ ID NO: 180. In some embodiments, the immunogenic fragment of the HBV Core protein comprises the amino acid sequence of SEQ ID NO: 183.

Nucleic acid molecules encoding the HBV Core protein or an immunogenic fragment thereof are also provided. The nucleic acid molecule can encode the HBV Core protein comprising the amino acid sequence of SEQ ID NO: 6. In some embodiments, the nucleic acid molecule comprises the nucleotide sequence of SEQ ID NO: 7. The nucleic acid molecules can encode the Core fragments provided in Table 3. In some embodiments, the nucleic acid molecule encodes the amino acid sequence of SEQ ID NO: 180. In some embodiments, the nucleic acid molecule encodes the amino acid sequence of SEQ ID NO: 183.

Vectors comprising the nucleic acid molecules encoding the HBV Core protein or an immunogenic fragment thereof are also provided. Suitable vectors include viral vectors, such as lentiviral vectors, retroviral vectors, adenoviral vectors, adeno-associated viral vectors, alphavirus replicons, herpes virus vectors, pox virus vectors, and rhabdovirus vectors. In some embodiments, the viral vector is an adenoviral vector. The adenoviral vector can be a chimpanzee-derived adenoviral vector. In some aspects, the vector is an AdC68 vector as described in Farina S F, Gao G P, Xiang Z Q, Rux J J, Burnett R M, Alvira M R, Marsh J, Ertl H C, Wilson J M. "Replication-defective vector based on a chimpanzee adenovirus." J Virol. 2001 December; 75(23):11603-13. In some aspects, the vector is an AdC7 vector as described in Reyes-Sandoval A, Fitzgerald J C, Grant R, Roy S, Xiang Z Q, Li Y, Gao G P, Wilson J M, Ertl H C. "Human immunodeficiency virus type 1-specific immune responses in primates upon sequential immunization with adenoviral vaccine carriers of human and simian serotypes" J Virol. 2004 July; 78(14):7392-9. In some aspects, the vector is an AdC6 vector as described in Pinto A R, Fitzgerald J C, Giles-Davis W, Gao G P, Wilson J M, Ertl H C. "Induction of CD8$^+$ T cells to an HIV-1 antigen through a prime boost regimen with heterologous E1-deleted adenoviral vaccine carriers" J Immunol. 2003 Dec. 15; 171(12): 6774-9.

In some embodiments, the vector comprises the nucleic acid molecule comprising the nucleotide sequence of SEQ ID NO: 7. In some embodiments, the vector is an AdC6 vector comprising the nucleic acid molecule comprising the nucleotide sequence of SEQ ID NO: 7. In some embodiments, the vector is an AdC7 vector comprising the nucleic acid molecule comprising the nucleotide sequence of SEQ ID NO: 7.

In some embodiments, the vector comprises the nucleic acid molecule that encodes the amino acid sequence of SEQ ID NO: 180. In some aspects, the vector is an AdC6 vector. In some aspects, the vector is an AdC7 vector. In some embodiments, the vector comprises the nucleic acid molecule that encodes the amino acid sequence of SEQ ID NO: 183. In some aspects, the vector is an AdC6 vector. In some aspects, the vector is an AdC7 vector.

Vaccines comprising the vectors comprising the nucleic acid molecules encoding the HBV Core protein or an immunogenic fragment thereof are also disclosed. In some embodiments, the vaccine comprises a vector comprising the nucleic acid molecule comprising the nucleotide sequence of SEQ ID NO: 7. In some embodiments, the vaccine comprises an AdC6 vector comprising the nucleic acid molecule comprising the nucleotide sequence of SEQ ID NO: 7. In some embodiments, the vaccine comprises an AdC7 vector comprising the nucleic acid molecule comprising the nucleotide sequence of SEQ ID NO: 7. In some embodiments, the vaccine comprises an AdC6 vector comprising the nucleic acid molecule that encodes the amino acid sequence of SEQ ID NO: 180. In some embodiments, the vaccine comprises an AdC7 vector comprising the nucleic acid molecule that encodes the amino acid sequence of SEQ ID NO: 180. In some embodiments, the vaccine comprises an AdC6 vector that comprises the nucleic acid molecule that encodes the amino acid sequence of SEQ ID NO: 183. In some embodiments, the vaccine comprises an AdC7 vector that comprises the nucleic acid molecule that encodes the amino acid sequence of SEQ ID NO: 183.

The vaccine can further comprise a pharmaceutically acceptable carrier or pharmaceutical acceptable excipient. As used herein, "pharmaceutically acceptable carrier" or "pharmaceutical acceptable excipient" includes any material which, when combined with the disclosed fusion proteins, nucleic acids, or vectors, allows the fusion proteins, nucleic acids, or vectors to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Also disclosed herein are non-naturally occurring variants of the HBV polymerase N-terminal domain (PolN) and the HBV polymerase C-terminal domain (PolC). The disclosed HBV polymerase N-terminal domain can comprise the amino acid sequence of SEQ ID NO: 8 or an immunogenic fragment thereof. Exemplary immunogenic fragments of SEQ ID NO: 8 include SEQ ID NOs: 55-113 provided in Table 4, below. In some embodiments, the immunogenic fragment of the HBV PolN comprises the amino acid sequence of SEQ ID NO: 178. In some embodiments, the immunogenic fragment of the HBV PolN comprises the amino acid sequence of SEQ ID NO: 181. The disclosed HBV polymerase C-terminal domain can comprise the amino acid sequence of SEQ ID NO: 10 or an immunogenic fragment thereof. Exemplary immunogenic fragments of SEQ ID NO: 10 include SEQ ID NOs: 114-172 provided in Table 5, below. In some embodiments, the immunogenic fragment of the HBV PolC comprises the amino acid sequence of SEQ ID NO: 179. In some embodiments, the immunogenic fragment of the HBV PolC comprises the amino acid sequence of SEQ ID NO: 182.

Nucleic acid molecules encoding the HBV polymerase N-terminal domain or an immunogenic fragment thereof, or the HBV polymerase C-terminal domain or an immunogenic fragment thereof, are also provided. The nucleic acid molecule can encode the HBV polymerase N-terminal domain comprising the amino acid sequence of SEQ ID NO: 8. In some embodiments, the nucleic acid molecule encoding the HBV polymerase N-terminal domain comprises the nucleotide sequence of SEQ ID NO: 9. The nucleic acid molecules can encode the HBV polymerase N-terminal domain fragments provided in Table 4. The nucleic acid molecule can encode the HBV polymerase C-terminal domain comprising the amino acid sequence of SEQ ID NO: 10. In some embodiments, the nucleic acid molecule encoding the HBV polymerase C-terminal domain comprises the nucleotide sequence of SEQ ID NO: 11. The nucleic acid molecules can encode the HBV polymerase C-terminal domain fragments provided in Table 5. In some embodiments, the nucleic acid molecule encodes the amino acid sequence of SEQ ID NO: 178. In some embodiments, the nucleic acid molecule encodes the amino acid sequence of SEQ ID NO: 181. In some embodiments, the nucleic acid molecule encodes the amino acid sequence of SEQ ID NO: 179. In some embodiments, the nucleic acid molecule encodes the amino acid sequence of SEQ ID NO: 182.

Vectors comprising the nucleic acid molecules encoding the HBV polymerase N-terminal domain or an immunogenic fragment thereof or C-terminal domain or an immunogenic fragment thereof are also provided. Suitable vectors include those described above. In some embodiments, the vector comprises the nucleic acid molecule comprising the nucleotide sequence of SEQ ID NO: 9. In some embodiments, the vector comprises the nucleic acid molecule comprising the nucleotide sequence of SEQ ID NO: 11. In some aspects, the vector is an adenoviral vector. Suitable adenoviral vectors include, for example, an AdC6 vector or AdC7 vector. In some embodiments, the vector is an AdC6 vector comprising the nucleic acid molecule comprising the nucleotide sequence of SEQ ID NO: 9. In some embodiments, the vector is an AdC7 vector comprising the nucleic acid molecule comprising the nucleotide sequence of SEQ ID NO: 9. In some embodiments, the vector is an AdC6 vector comprising the nucleic acid molecule comprising the nucleotide sequence of SEQ ID NO: 11. In some embodiments, the vector is an AdC7 vector comprising the nucleic acid molecule comprising the nucleotide sequence of SEQ ID NO: 11. In some embodiments, the vector comprises the nucleic acid molecule that encodes the amino acid sequence of SEQ ID NO: 178. In some aspects, the vector is an AdC6 vector. In some aspects, the vector is an AdC7 vector. In some embodiments, the vector comprises the nucleic acid molecule that encodes the amino acid sequence of SEQ ID NO: 181. In some aspects, the vector is an AdC6 vector. In some aspects, the vector is an AdC7 vector. In some embodiments, the vector comprises the nucleic acid molecule that encodes the amino acid sequence of SEQ ID NO: 179. In some aspects, the vector is an AdC6 vector. In some aspects, the vector is an AdC7 vector. In some embodiments, the vector comprises the nucleic acid molecule that encodes the amino acid sequence of SEQ ID NO: 182. In some aspects, the vector is an AdC6 vector. In some aspects, the vector is an AdC7 vector.

Vaccines comprising the vectors comprising the nucleic acid molecules encoding the HBV polymerase N-terminal domain or an immunogenic fragment thereof or HBV polymerase C-terminal domain or an immunogenic fragment thereof are also disclosed. In some embodiments, the vaccine comprises a vector comprising the nucleic acid molecule comprising the nucleotide sequence of SEQ ID NO: 9. The vaccine can comprise an AdC6 vector comprising the nucleic acid molecule comprising the nucleotide sequence of SEQ ID NO: 9. The vaccine can comprise an AdC7 vector comprising the nucleic acid molecule comprising the nucleotide sequence of SEQ ID NO: 9. In some embodiments, the vaccine comprises a vector comprising the nucleic acid molecule comprising the nucleotide sequence of SEQ ID NO: 11. The vaccine can comprise an AdC6 vector comprising the nucleic acid molecule comprising the nucleotide sequence of SEQ ID NO: 11. The vaccine can comprise an AdC7 vector comprising the nucleic acid molecule comprising the nucleotide sequence of SEQ ID NO: 11. The vaccine can further comprise a pharmaceutically acceptable carrier or pharmaceutical acceptable excipient as disclosed above. In some embodiments, the vaccine comprises a vector comprising the nucleic acid molecule that encodes the amino acid sequence of SEQ ID NO: 178. In some aspects, the vector is an AdC6 vector. In some aspects, the vector is an AdC7 vector. In some embodiments, the vaccine comprises a vector comprising the nucleic acid molecule that encodes the amino acid sequence of SEQ ID NO: 181. In some aspects, the vector is an AdC6 vector. In some aspects, the vector is an AdC7 vector. In some embodiments, the vaccine comprises a vector comprising the nucleic acid molecule that encodes the amino acid sequence of SEQ ID NO: 179. In some aspects, the vector is an AdC6 vector. In some aspects, the vector is an AdC7 vector. In some embodiments, the vaccine comprises a vector comprising the nucleic acid molecule that encodes the amino acid sequence of SEQ ID NO: 182. In some aspects, the vector is an AdC6 vector. In some aspects, the vector is an AdC7 vector.

Fusion proteins comprising combinations of the disclosed HBV Core protein or immunogenic fragments thereof, the HBV polymerase N-terminal domain or immunogenic fragments thereof, and/or the HBV polymerase C-terminal domain or immunogenic fragments thereof are also provided herein. For example, the fusion protein can comprise:

(1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;

(2) one or more immunogenic fragments of the HBV Core protein comprising the amino acid sequence of SEQ ID NO: 6 and one or more immunogenic fragments of the HBV polymerase N-terminal domain comprising the amino acid sequence of SEQ ID NO: 8. For example, one or more of SEQ ID NOs: 20-54 provided in Table 3 (immunogenic fragments of SEQ ID NO: 6) and one or more of SEQ ID NOs: 55-113 provided in Table 4 (immunogenic fragments of SEQ ID NO: 8);

(3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;

(4) one or more immunogenic fragments of the HBV Core protein comprising the amino acid sequence of SEQ ID NO: 6 and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6) and one or more of SEQ ID NOs: 114-172 provided in Table 5 (immunogenic fragments of SEQ ID NO: 10);

(5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;

(6) one or more immunogenic fragments of the HBV polymerase N-terminal domain comprising the amino acid sequence of SEQ ID NO: 8 and one or more immunogenic fragments of the HBV polymerase C-terminal domain comprising the amino acid sequence of SEQ ID NO: 10. For example, one or more of SEQ ID NOs: 55-113 provided in Table 4 (immunogenic fragments of SEQ ID NO: 8) and one or more of SEQ ID NOs: 114-172 provided in Table 5 (immunogenic fragments of SEQ ID NO: 10);

(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof, (8) one or more immunogenic fragments of the HBV Core protein comprising the amino acid sequence of SEQ ID NO: 6, one or more immunogenic fragments of the HBV polymerase N-terminal domain comprising the amino acid sequence of SEQ ID NO: 8, and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6), one or more of SEQ ID NOs: 55-113 provided in Table 4 (immunogenic fragments of SEQ ID NO: 8), and one or more of SEQ ID NOs: 114-172 provided in Table 5 (immunogenic fragments of SEQ ID NO: 10);

(9) An HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof, or

(10) An HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof.

The fusion protein can comprise an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof. In some embodiments, the fusion protein comprises the amino acid sequence of SEQ ID NO: 174.

The fusion protein can comprise an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof. In some embodiments, the fusion protein comprises the amino acid sequence of SEQ ID NO: 175.

Also provided herein are fusion proteins comprising a herpes simplex virus (HSV) glycoprotein (gD) sequence and the disclosed HBV Core protein, the HBV polymerase N-terminal domain, the HBV polymerase C-terminal domain, or various combinations thereof.

The HSV gD is a receptor-binding glycoprotein of HSV. The gD ectodomain is organized in two structurally and functionally differentiated regions: the amino-terminus, which includes the signal sequence and receptor-binding sites; and the carboxy-terminus, which includes the pro-fusion domain and the transmembrane domain. gD interacts with the herpesvirus entry mediator (HVEM) receptor and the nectin receptors. Interaction of gD with the receptors results in the down-regulation of the HVEM receptors binding to BTLA or CD160, which are immunoinhibitory molecules that are expressed on T cells. In some embodiments, the disclosed fusion proteins comprising gD and the disclosed HBV Core protein, the HBV polymerase N-terminal domain, the HBV polymerase C-terminal domain (referred to as "gDCore," "gDPolN" or "gDPolC," respectively), or combinations thereof are expected to enhance a subject's immune response against HBV to a greater extent compared to the HBV Core and/or polymerase antigens alone (i.e. without gD).

Suitable HSV gD proteins for use in the disclosed fusion proteins include wild-type or mutant gD that retains the ability to: 1) augment stimulation of a CD8$^+$ T cell response to an antigen; and/or 2) disrupt an HVEM-BTLA pathway activity.

The fusion proteins can comprise the HBV Core protein or an immunogenic fragment thereof, HBV polymerase N-terminal domain or an immunogenic fragment thereof, HBV polymerase C-terminal domain or an immunogenic fragment thereof disclosed herein, or any combination thereof, an N-terminal HSV gD protein sequence, and a C-terminal HSV gD protein sequence. The HBV Core protein, HBV polymerase N-terminal domain, and HBV polymerase C-terminal domain can be those provided in Table 9 or the immunogenic fragments provided in Tables 3-5. The HBV Core protein, HBV polymerase N-terminal domain, HBV polymerase C-terminal domain, or immunogenic fragments thereof can be inserted between the N-terminal HSV gD protein sequence and the C-terminal HSV gD protein sequence. In some aspects, the N-terminal HSV gD protein sequence comprises the amino acid sequence of SEQ ID NO: 12 and the C-terminal HSV gD protein sequence comprises the amino acid sequence of SEQ ID NO: 13. In some embodiments, the N-terminal HSV gD protein sequence comprises amino acid residues 26-269 of SEQ ID NO: 12.

The fusion protein can comprise:
an N-terminal HSV gD sequence or a variant thereof;
an HBV Core protein comprising the amino acid sequence of SEQ ID NO: 6 or an immunogenic fragment thereof; and
a C-terminal HSV gD sequence or a variant thereof.

The immunogenic fragment of the HBV Core protein can comprise any one of SEQ ID NOs: 20-54, 180, or 183.

The fusion protein can comprise:
an N-terminal HSV gD sequence or a variant thereof;
an HBV Core protein comprising the amino acid sequence of SEQ ID NO: 180 or SEQ ID NO: 183; and
a C-terminal HSV gD sequence or a variant thereof.

The fusion protein can comprise:
an N-terminal HSV gD sequence or a variant thereof;
an HBV polymerase N-terminal domain comprising the amino acid sequence of SEQ ID NO: 8 or an immunogenic fragment thereof; and
a C-terminal HSV gD protein sequence or a variant thereof.

The immunogenic fragment of the HBV polymerase N-terminal domain can comprise any one of SEQ ID NOs: 55-113, 178, or 181.

The fusion protein can comprise:
an N-terminal HSV gD sequence or a variant thereof;
an HBV polymerase N-terminal domain comprising the amino acid sequence of SEQ ID NO: 178 or SEQ ID NO: 181; and
a C-terminal HSV gD protein sequence or a variant thereof.

The fusion protein can comprise:
an N-terminal HSV gD sequence or a variant thereof;
an HBV polymerase C-terminal domain comprising the amino acid sequence of SEQ ID NO: 10 or an immunogenic fragment thereof; and
a C-terminal HSV gD protein sequence or a variant thereof.

The immunogenic fragment of the HBV polymerase C-terminal domain can comprise any one of SEQ ID NOs: 114-172, 179, or 182.

The fusion protein can comprise:
an N-terminal HSV gD sequence or a variant thereof;
an HBV polymerase C-terminal domain comprising the amino acid sequence of SEQ ID NO: 179 or SEQ ID NO: 182; and
a C-terminal HSV gD protein sequence or a variant thereof.

The fusion protein can comprise:
an N-terminal HSV gD sequence or a variant thereof;
an HBV sequence comprising:
(1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;
(2) one or more immunogenic fragments of the HBV Core protein comprising the amino acid sequence of SEQ ID NO: 6 and one or more immunogenic fragments of the HBV polymerase N-terminal domain comprising the amino acid sequence of SEQ ID NO: 8. For example, one or more of SEQ ID NOs: 20-54 provided in Table 3 (immunogenic fragments of SEQ ID NO: 6) and one or more of SEQ ID NOs: 55-113 provided in Table 4 (immunogenic fragments of SEQ ID NO: 8);
(3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;
(4) one or more immunogenic fragments of the HBV Core protein comprising the amino acid sequence of SEQ ID NO: 6 and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6) and one or more of SEQ ID NOs: 114-172 provided in Table 5 (immunogenic fragments of SEQ ID NO: 10);
(5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;
(6) one or more immunogenic fragments of the HBV polymerase N-terminal domain comprising the amino acid sequence of SEQ ID NO: 8 and one or more immunogenic fragments of the HBV polymerase C-terminal domain comprising the amino acid sequence of SEQ ID NO: 10. For example, one or more of SEQ ID NOs: 55-113 provided in Table 4 (immunogenic fragments of SEQ ID NO: 8) and one or more of SEQ ID NOs: 114-172 provided in Table 5 (immunogenic fragments of SEQ ID NO: 10);

(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof; or (8) one or more immunogenic fragments of the HBV Core protein comprising the amino acid sequence of SEQ ID NO: 6, one or more immunogenic fragments of the HBV polymerase N-terminal domain comprising the amino acid sequence of SEQ ID NO: 8, and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6), one or more of SEQ ID NOs: 55-113 provided in Table 4 (immunogenic fragments of SEQ ID NO: 8), and one or more of SEQ ID NOs: 114-172 provided in Table 5 (immunogenic fragments of SEQ ID NO: 10);

(9) an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof; or

(10) an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof and a C-terminal HSV gD protein sequence or a variant thereof.

In some embodiments, the N-terminal HSV gD sequence can comprise at least amino acids 1-269 of HSV gD. The N-terminal HSV gD sequence, for example, can comprise the amino acid sequence of SEQ ID NO: 12. In some embodiments, the N-terminal HSV gD sequence comprises amino acid residues 26-269 of SEQ ID NO: 12.

In some embodiments, the C-terminal HSV gD sequence comprises the transmembrane domain of the HSV gD. The C-terminal HSV gD sequence, for example, can comprise the amino acid sequence of SEQ ID NO: 13.

The fusion protein can comprise the amino acid sequence of SEQ ID NO: 14 (corresponding to gDCore) or an immunogenic fragment thereof. The fusion protein can comprise the amino acid sequence of SEQ ID NO: 16 (corresponding to gDPolN) or an immunogenic fragment thereof. The fusion protein can comprise the amino acid sequence of SEQ ID NO: 18 (corresponding to gDPolC) or an immunogenic fragment thereof. In some embodiments, the amino acid sequence of any one of SEQ ID NOs: 14, 16, or 18, or the immunogenic fragment thereof, does not contain the N-terminal 25 amino acid signal peptide.

The fusion protein can comprise the amino acid sequence of SEQ ID NO: 185 (gDHBV2). The fusion protein can comprise the amino acid sequence of SEQ ID NO: 187 (gDHBV3).

Nucleic acid molecules encoding any of the disclosed fusion proteins are also provided. In some embodiments, the nucleic acid molecule comprises the nucleotide sequence of SEQ ID NO: 15 (corresponding to gDCore). In some embodiments, the nucleic acid molecule comprises the nucleotide sequence of SEQ ID NO: 17 (corresponding to gDPolN). In some embodiments, the nucleic acid molecule comprises the nucleotide sequence of SEQ ID NO: 19 (corresponding to gDPolC).

The nucleic acid molecule can comprise the nucleotide sequence of SEQ ID NO: 184 (gDHBV2). The nucleic acid molecule can comprise the nucleotide sequence of SEQ ID NO: 186 (gDHBV3).

Vectors comprising the nucleic acid molecules encoding the fusion proteins are also disclosed. Suitable vectors include those described above including, for example, an adenoviral vector. In some embodiments, the adenoviral vector is an AdC6 vector. In some embodiments, the adenoviral vector is an AdC7 vector. The vector can comprise the nucleotide sequence of SEQ ID NO: 184 (gDHBV2). In some aspects, the vector is an AdC6 vector that comprises the nucleotide sequence of SEQ ID NO: 184 (gDHBV2). In some aspects, the vector is an AdC7 vector that comprises the nucleotide sequence of SEQ ID NO: 184 (gDHBV2). The vector can comprise the nucleotide sequence of SEQ ID NO: 186 (gDHBV3). In some aspects, the vector is an AdC6 vector that comprises the nucleotide sequence of SEQ ID NO: 186 (gDHBV3). In some aspects, the vector is an AdC7 vector that comprises the nucleotide sequence of SEQ ID NO: 186 (gDHBV3).

Vaccines comprising any of the disclosed vectors are also provided. The vaccine can further comprise a pharmaceutically acceptable carrier or pharmaceutical acceptable excipient as disclosed above. The vaccine can comprise a vector comprising the nucleotide sequence of SEQ ID NO: 184 (gDHBV2). In some aspects, the vaccine comprises an AdC6 vector that comprises the nucleotide sequence of SEQ ID NO: 184 (gDHBV2). In some aspects, the vaccine comprises an AdC7 vector that comprises the nucleotide sequence of SEQ ID NO: 184 (gDHBV2). The vaccine can comprise a vector that comprises the nucleotide sequence of SEQ ID NO: 186 (gDHBV3). In some aspects, the vaccine comprises an AdC6 vector that comprises the nucleotide sequence of SEQ ID NO: 186 (gDHBV3). In some aspects, the vaccine comprises an AdC7 vector that comprises the nucleotide sequence of SEQ ID NO: 186 (gDHBV3).

Provided herein are methods of inducing an immune response to HBV in a subject, the methods comprising providing to the subject an effective amount of any of the disclosed fusion proteins, any of the disclosed nucleic acid molecules, any of the disclosed vectors, or any of the disclosed vaccines to thereby induce an immune response to HBV. In some embodiments, the methods comprise providing to the subject an effective amount of any of the disclosed fusion proteins to thereby induce an immune response to HBV. In some embodiments, the methods comprise providing to the subject an effective amount of any of the disclosed nucleic acid molecules to thereby induce an immune response to HBV. In some embodiments, the methods comprise providing to the subject an effective amount of any of the disclosed vectors to thereby induce an immune response to HBV. In some embodiments, the methods comprise providing to the subject an effective amount of any of the disclosed vaccines to thereby induce an immune response to HBV.

The methods can comprise providing to the subject an effective amount of a vaccine comprising an AdC6 vector, wherein the AdC6 vector comprises a fusion protein comprising the amino acid sequence of any one of SEQ ID NOs: 14, 16, or 18, or an immunogenic fragment thereof. In some embodiments, the methods further comprise providing to the subject, subsequent to providing the vaccine comprising the AdC6 vector, a vaccine comprising an AdC7 vector comprising a fusion protein comprising the amino acid sequence of any one of SEQ ID NOs: 14, 16, or 18, or an immunogenic fragment thereof. Such prime-boost methods can comprise:

Providing to the subject a vaccine comprising an AdC6 vector comprising a fusion protein comprising the amino acid sequence of SEQ ID NO: 14, or an immunogenic fragment thereof, and subsequently providing to the subject a vaccine comprising an AdC7 vector comprising a fusion protein comprising the amino acid sequence of SEQ ID NO: 14, or an immunogenic fragment thereof. In some embodiments, the amino acid sequence of SEQ ID NO: 14, or an immunogenic fragment thereof, does not contain the N-terminal 25 amino acid signal peptide;

Providing to the subject a vaccine comprising an AdC6 vector comprising a fusion protein comprising the amino acid sequence of SEQ ID NO: 16, or an immunogenic fragment thereof, and subsequently providing to the subject a vaccine comprising an AdC7 vector comprising a fusion protein comprising the amino acid sequence of SEQ ID NO: 16, or an immunogenic fragment thereof. In some embodiments, the amino acid sequence of SEQ ID NO: 16, or an immunogenic fragment thereof, does not contain the N-terminal 25 amino acid signal peptide; or Providing to the subject a vaccine comprising an AdC6 vector comprising a fusion protein comprising the amino acid sequence of SEQ ID NO: 18, or an immunogenic fragment thereof, and subsequently providing to the subject a vaccine comprising an AdC7 vector comprising a fusion protein comprising the amino acid sequence of SEQ ID NO: 18, or an immunogenic fragment thereof. In some embodiments, the amino acid sequence of SEQ ID NO: 18, or an immunogenic fragment thereof, does not contain the N-terminal 25 amino acid signal peptide.

The methods can comprise providing to the subject an effective amount of a vaccine comprising an AdC7 vector, wherein the AdC7 vector comprises a fusion protein comprising the amino acid sequence of any one of SEQ ID NOs: 14, 16, or 18, or an immunogenic fragment thereof. In some embodiments, the methods further comprise providing to the subject, subsequent to providing the vaccine comprising the AdC7 vector, a vaccine comprising an AdC6 vector comprising a fusion protein comprising the amino acid sequence of any one of SEQ ID NOs: 14, 16, or 18, or an immunogenic fragment thereof. Such prime-boost methods can comprise:

Providing to the subject a vaccine comprising an AdC7 vector comprising a fusion protein comprising the amino acid sequence of SEQ ID NO: 14, or an immunogenic fragment thereof, and subsequently providing to the subject a vaccine comprising an AdC6 vector comprising a fusion protein comprising the amino acid sequence of SEQ ID NO: 14, or an immunogenic fragment thereof. In some embodiments, the amino acid sequence of SEQ ID NO: 14, or an immunogenic fragment thereof, does not contain the N-terminal 25 amino acid signal peptide;

Providing to the subject a vaccine comprising an AdC7 vector comprising a fusion protein comprising the amino acid sequence of SEQ ID NO: 16, or an immunogenic fragment thereof, and subsequently providing to the subject a vaccine comprising an AdC6 vector comprising a fusion protein comprising the amino acid sequence of SEQ ID NO: 16, or an immunogenic fragment thereof. In some embodiments, the amino acid sequence of SEQ ID NO: 16, or an immunogenic fragment thereof, does not contain the N-terminal 25 amino acid signal peptide; or Providing to the subject a vaccine comprising an AdC7 vector comprising a fusion protein comprising the amino acid sequence of SEQ ID NO: 18, or an immunogenic fragment thereof, and subsequently providing to the subject a vaccine comprising an AdC6 vector comprising a fusion protein comprising the amino acid sequence of SEQ ID NO: 18, or an immunogenic fragment thereof. In some embodiments, the amino acid sequence of SEQ ID NO: 18, or an immunogenic fragment thereof, does not contain the N-terminal 25 amino acid signal peptide.

The methods can comprise providing to the subject an effective amount of a vaccine comprising an AdC6 vector, wherein the AdC6 vector comprises a fusion protein comprising the amino acid sequence of SEQ ID NO: 185 or 187, or an immunogenic fragment thereof. In some embodiments, the methods further comprise providing to the subject, subsequent to providing the vaccine comprising the AdC6 vector, a vaccine comprising an AdC7 vector comprising a fusion protein comprising the amino acid sequence of SEQ ID NO: 185 or 187, or an immunogenic fragment thereof. Such prime-boost methods can comprise:

Providing to the subject a vaccine comprising an AdC6 vector comprising a fusion protein comprising the amino acid sequence of SEQ ID NO: 185, or an immunogenic fragment thereof, and subsequently providing to the subject a vaccine comprising an AdC7 vector comprising a fusion protein comprising the amino acid sequence of SEQ ID NO: 185, or an immunogenic fragment thereof. In some embodiments, the amino acid sequence of SEQ ID NO: 185, or an immunogenic fragment thereof, does not contain the N-terminal 25 amino acid signal peptide; or Providing to the subject a vaccine comprising an AdC6 vector comprising a fusion protein comprising the amino acid sequence of SEQ ID NO: 187, or an immunogenic fragment thereof, and subsequently providing to the subject a vaccine comprising an AdC7 vector comprising a fusion protein comprising the amino acid sequence of SEQ ID NO: 187, or an immunogenic fragment thereof. In some embodiments, the amino acid sequence of SEQ ID NO: 187, or an immunogenic fragment thereof, does not contain the N-terminal 25 amino acid signal peptide.

The methods can comprise providing to the subject an effective amount of a vaccine comprising an AdC7 vector, wherein the AdC7 vector comprises a fusion protein comprising the amino acid sequence of SEQ ID NO: 185 or 187, or an immunogenic fragment thereof. In some embodiments, the methods further comprise providing to the subject, subsequent to providing the vaccine comprising the AdC7 vector, a vaccine comprising an AdC6 vector comprising a fusion protein comprising the amino acid sequence of SEQ ID NO: 185 or 187, or an immunogenic fragment thereof. Such prime-boost methods can comprise:

Providing to the subject a vaccine comprising an AdC7 vector comprising a fusion protein comprising the amino acid sequence of SEQ ID NO: 185, or an immunogenic fragment thereof, and subsequently providing to the subject a vaccine comprising an AdC6 vector comprising a fusion protein comprising the amino acid sequence of SEQ ID NO: 185, or an immunogenic fragment thereof. In some embodiments, the amino acid sequence of SEQ ID NO: 185, or an immunogenic fragment thereof, does not contain the N-terminal 25 amino acid signal peptide; or Providing to the subject a vaccine comprising an AdC7 vector comprising a fusion protein comprising the amino acid sequence of SEQ ID NO: 187, or an immunogenic fragment thereof, and subsequently providing to the subject a vaccine comprising an AdC6 vector comprising a fusion protein comprising the amino acid sequence of SEQ ID NO: 187, or an immunogenic fragment thereof. In some embodiments, the amino acid sequence of SEQ ID NO: 187, or an immunogenic fragment thereof, does not contain the N-terminal 25 amino acid signal peptide.

The immune response induced by the disclosed methods include, but is not limited to, T cell responses, B cell responses, or both (i.e. cellular and/or humoral immune responses). The immune response can be a primary immune response or a secondary immune response. The disclosed methods can induce a subject's immune response against HBV to a greater extent compared to the HBV Core or polymerase antigens alone (i.e. without gD).

The disclosed methods can be used for both therapeutic treatment and prophylactic or preventative measures and can reduce the severity and/or frequency of symptoms, eliminate symptoms and/or the underlying cause of the symptoms, reduce the frequency or likelihood of symptoms and/or their underlying cause, and improve or remediate damage caused, directly or indirectly, by HBV. Treatment also includes prolonging survival as compared to the expected survival of a subject not receiving treatment. Subjects to be treated include those that have HBV as well as those prone to have HBV or those in which HBV is to be prevented.

The amount of the disclosed fusion proteins, nucleic acid molecules, vectors, or vaccines needed to thereby induce an immune response to HBV (e.g. a "effective amount") may vary according to factors such as the disease state, age, sex, and weight of the subject, and the ability of the fusion proteins, nucleic acid molecules, vectors, or vaccines to cause a desired response in the subject. Exemplary indicators of an effective amount include, for example, improved well-being of the subject and reduction, elimination, or prevention of HBV symptoms.

Also provided is the use of any of the disclosed fusion proteins, nucleic acid molecules, vectors, or vaccines in the manufacture of a medicament for inducing an immune response to HBV in a subject.

The disclosed fusion proteins, nucleic acid molecules, vectors, or vaccines for use in inducing an immune response to HBV in a subject is also provided.

EXAMPLES

The following examples are provided to further describe some of the embodiments disclosed herein. The examples are intended to illustrate, not to limit, the disclosed embodiments.

Generation of an Epitope-Optimized Core Sequence

Hepatitis B virus (HBV) can be grouped into several genotypes, based on phylogenic clustering. To assist in the development of an antigen insert for a multi-genotype HBV vaccine for patients with chronic infections, a preliminary bioinformatics evaluation of the genes encoding the HBV Core and HBV polymerase across genotypes A, B, C and D was conducted.

The Core amino acid sequences from the four major HBV clades were downloaded as aligned ClustalW sequences from Hepatitis B Virus database (HBVdb) (release version 45.0; last updated on Aug. 2, 2018). The amino acid sequences represented thousands of HBV genomes inputted from users across Europe, as summarized in the following table.

TABLE 1

| Number of unique Core genomes analyzed | | |
|---|---|---|
| Genotype | HBV Gene | Unique Genomes Analyzed |
| HBV genotype A | Core | 1,482 |
| HBV genotype B | | 2,800 |
| HBV genotype C | | 2,768 |
| HBV genotype D | | 1,579 |

"Consensus" Core sequences were first identified for each genotype using the Shannon Entropy tool hosted by the Los Alamos National Laboratory (www.hiv.1anl.gov/content/sequence/ENTROPY/entropy), which calculated the variation and frequency at each amino acid position. These calculations were repeated for each genotype, generating four "consensus" Core sequences, one for each genotype analyzed (SEQ ID NOs: 1-4):

```
Genotype A Consensus
                                      (SEQ ID NO: 1)
MDIDPYKEFGATVELLSFLPSDFFPSVRDLLDTASALYREALESPEHCSP HHTALRQAILCWGELMTLATWVGNNLeDPASRDLWNYVNTNMGLKIRQLL

WFHISCLTFGRETVLEYLVSFGVWIRTPPAYRPPNAPILSTLPETTVVRR

RDRGRSPRRRTPSPRRRRSQSPRRRRSQSRESQC-

Genotype B Consensus
                                      (SEQ ID NO: 2)
MDIDpYKEFGASvELLSFLPSDFFPSiRDLLDTAsALYREALESPEHCSP HHTALRQAIlCWGELMNLATWVGSNLeDPASRELVVsYVNVNMGLKiRQL LWFHISCLTFGRETVLEYLVSFGVWIRTPpAYRPpNAPILSTLPETTVVR RRGRSPRRRTPSPRRRRSQSPRRRRSQSREsQC- Genotype C Consensus
                                      (SEQ ID NO: 3)
MDIDpYKEFGASVELLSFLPSDFFPSIRDLLDTASALYREALESPEHCSP HHTALRQAILCWGELMNLATWVGSNLEDPASRELVVsYVNVNMGLKiRQl LWFHISCLTFGRETVLEYLVSFGVWIRTPpAYRPPNAPILSTLPETTVVR

RRGRSPRRRTPSPRRRRSQSPRRRSQSRESQC -
```

-continued

Genotype D Consensus (SEQ ID NO: 4)

MDIDPYKEFGAtVELLSFLPsDFFPSVRDLLDTASALYReALESPEHCSP

HHTALRQAILCWGeLMtLATWVGgNLEDPaSRDLVVSYVNTNmGLKFRQL

LWFHISCLTFGReTViEYLVSFGVWIRTPpAYRPPNAPILSTLPETTVvR

RRGRSPRRRTPSPRRRRSQSPRRRRSQSRESQC- (Bold, underlined residues represent amino acids having less than 90% frequency).

The above "consensus" Core sequences were combined to generate an epitope-optimized Core sequence. Conserved amino acids were identified at each amino acid residue of the Core protein from each genotype (A, B, C and D) and the frequency and variation within a given sample of genotype genomes was determined. To select amino acids at sites of variation, each variation was tested using epitope prediction algorithms across multiple HLA types and the most immunogenic sequence was selected. Specifically:

(1) Each residue across the four genotypes that was identical were maintained. The genome weighted frequency was also calculated to inform the variability with spacer added, where applicable, to align the sequences for diversity.

(2) Residues that were not identical across the four genotypes were identified and the amino acid diversity was recorded (see Table 2). The initial Core sequence (SEQ ID NO: 5) is provided below, with the residues that were not identical across the four genotypes labeled as Xi-Xii and the residues having less than 90% frequency in bold, underlined font:

MDIDPYKEFGAX₁VELLSELPSDFEPSX₂DLLDTASALYREALESPEHCS

PHHTALRQAILCWGELMX₃LATWVGX₄NLeDPASRX₅LVVX₆YVNX₇NMG

LKX₈RQLLWFHISCLTFGRETVX₉EYLVSFGVWIRTPPAYRPPNAPILST

LPETTVVRRRX₁₀X₁₁GRSPRRRTPSPRRRRSQSPRRRRSQSRESQC (3) To determine the final amino acid at these positions, epitope prediction algorithms were used to select the appropriate amino acid. For amino acids that showed variability between the genotypes, amino acids that were present in 3 of the genotypes were selected or an MHC class I epitope prediction software was used to select the most immunogenic amino acids. This approach maximized the potential immunogenicity across the greatest number of HLA types. The epitope-optimized Core sequence across all genotypes and within genotypes is shown below (SEQ ID NO: 6):

DIDPYKEFGATVELLSFLPSDFFPSIRDLLDTASALYREALESPEHCSPH

HTALRQAILCWGELMTLATWVGSNLEDPASRELVVSYVNVNMGLKIRQLL

WFHISCLTFGRETVIEYLVSFGVWIRTPPAYRPPNAPILSTLPETTVVRR

RDRGRSPRRRTPSPRRRRSQSPRRRRSQSRESQC

Figure 1:
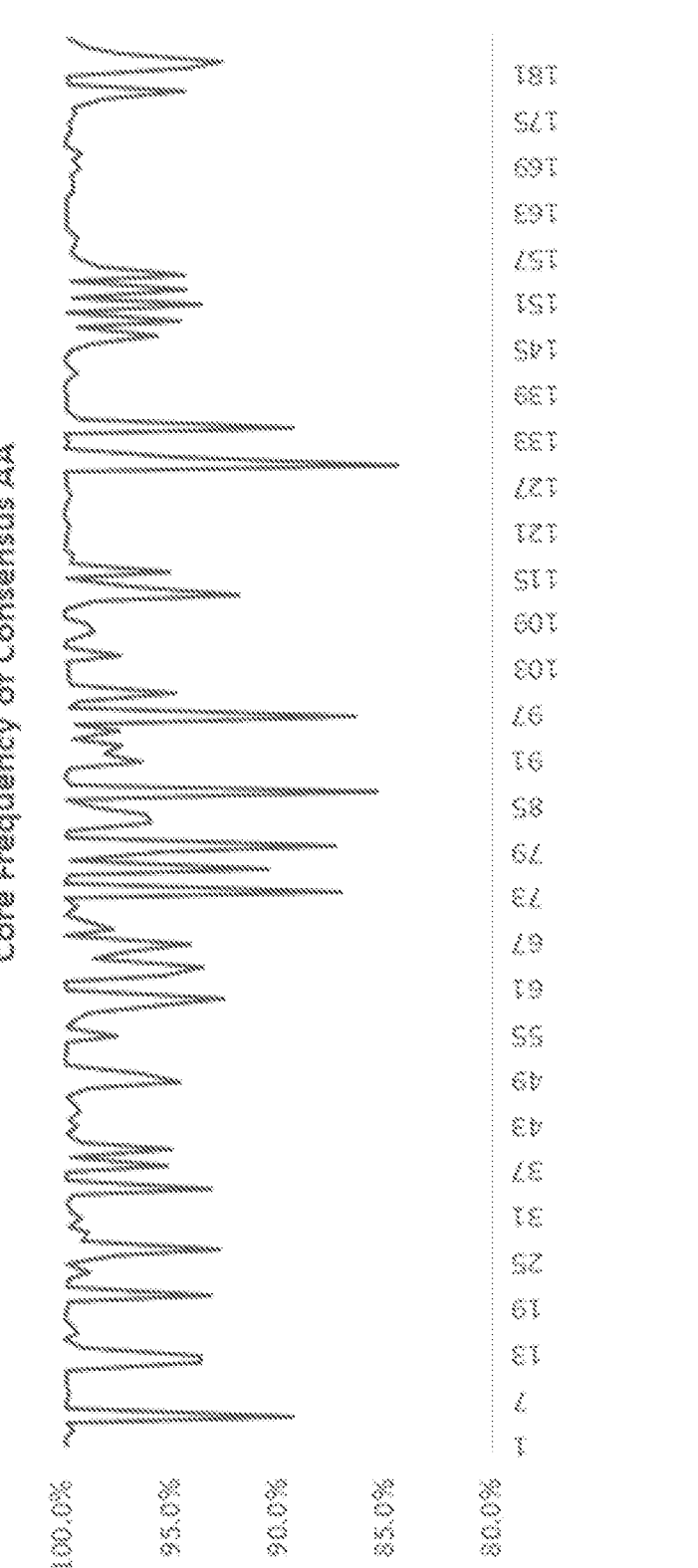
FIG. 1 illustrates the frequency of epitope-optimized Core amino acids. Amino acid residues are indicated on the X-axis; percent sequence similarity across all genomes analyzed is indicated on the Y-axis.
Figures 2A, 2B, 2C:
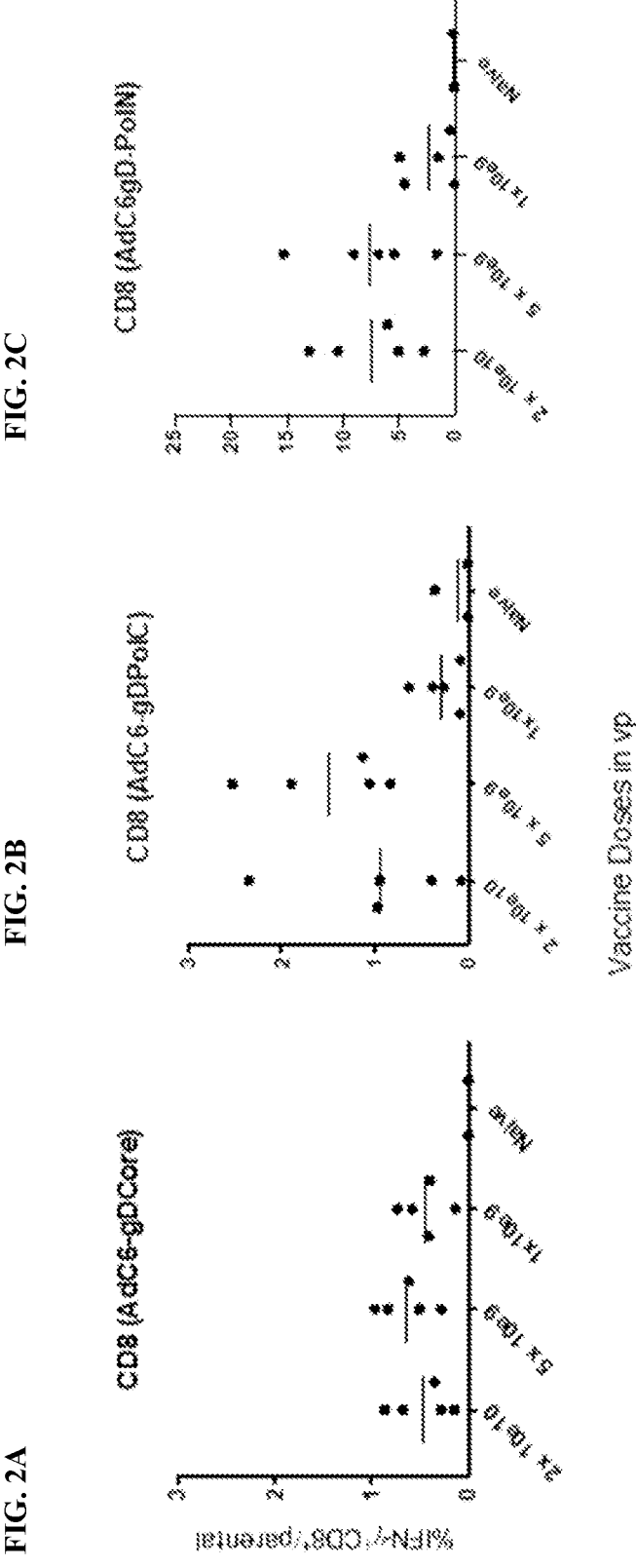
FIG. 2A, FIG. 2B, FIG. 2C, FIG. 2D, FIG. 2E, and FIG. 2F illustrate vaccine insert-specific T cell frequencies in C57B1/6 mice following intramuscular (i.m.) injection with the indicated doses of: replication-defective adenovirus vector of chimpanzee serotype 6 (AdC6) containing the epitope-optimized Core sequence genetically fused into gD (SEQ ID NO: 15) (AdC6-gDCore) (FIG. 2A and FIG. 2D); AdC6 containing the epitope-optimized polymerase C-terminal domain sequence genetically fused into gD (SEQ ID NO: 19) (AdC6-gDPolC) (FIG. 2B and FIG. 2E); and AdC6 containing the epitope-optimized polymerase N-terminal domain sequence genetically fused into gD (SEQ ID NO: 17) (AdC6-gDPolN) (FIG. 2C and FIG. 2F). Mice were bled 14 days after the injection and T cell frequencies to the various HBV inserts were analyzed by intracellular cytokine staining (ICS) for interferon (IFN)-γ upon stimulation of cells with overlapping peptides representing the HBV sequences. Control cells were cultured without peptides. Graphs show results for individual mice with medians indicated by the lines.
Figures 2D, 2E, 2F:
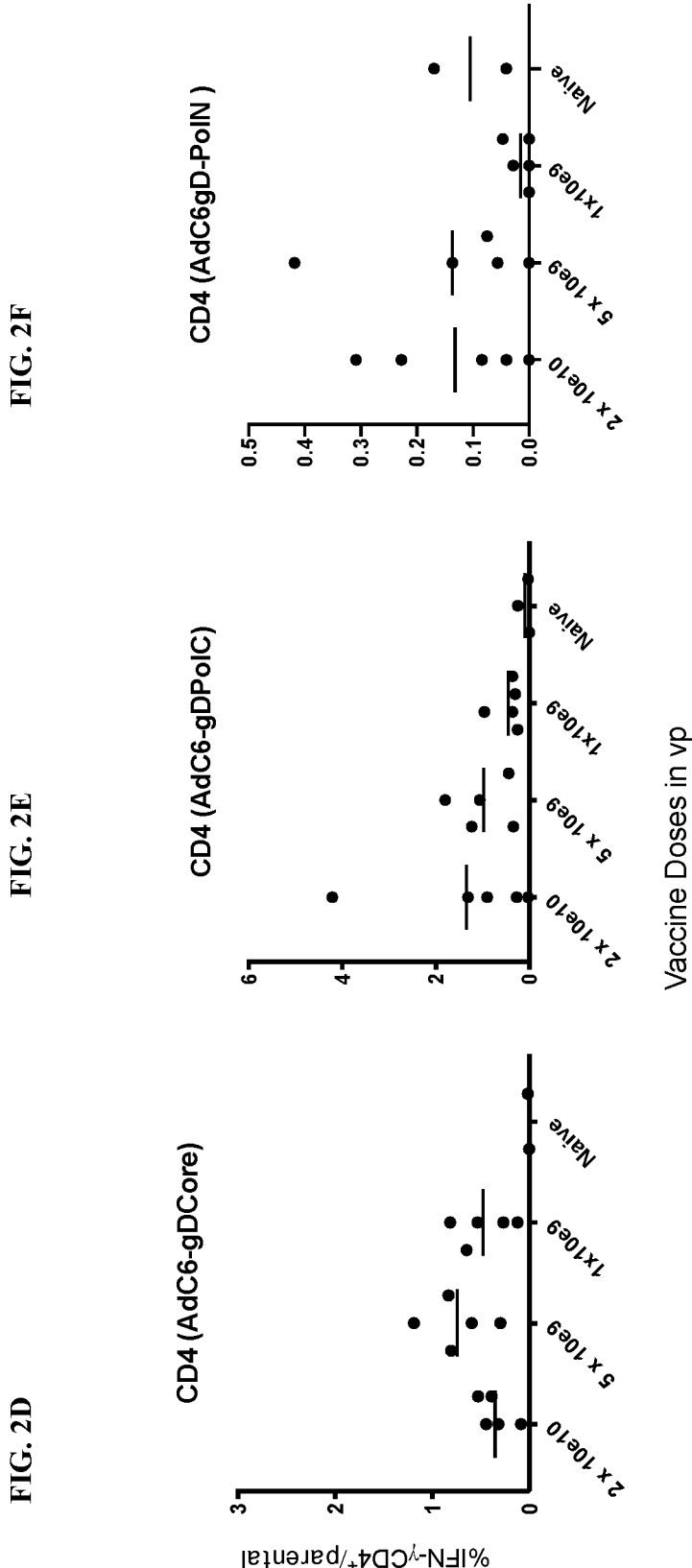

The average variation at each site across all genomes, weighted by the number of clade-specific genomes analyzed, was calculated and showed areas and residues of higher and greater conservation. FIG. 1.

Generation of Epitope-Optimized Polymerase Sequences

An epitope-optimized polymerase sequence was generated from the four major HBV clades as discussed above for the Core sequence. Because the polymerase is long, two fragments—an N-terminal fragment (from which a highly variable segment between the genotypes was removed) and a C-terminal fragment—were generated. Both fragments are approximately 300 amino acids in length. The epitope-optimized polymerase amino acid sequences are shown below and in Table 9:

Epitope-optimized HBV polymerase N-terminal amino acid sequence (SEQ ID NO: 8):

PLSYQHFRKLLLLDEEAGPLEEELPRLADEGLNRRVAEDLNLGNLNVSIP

WTHKVGNFTGLYSSTVPVFNPEWQTPSFPKIHLQEDIVDRCKQFVGPLTV

NEKRRLKLIMPARFYPNVTKYLPLDKGIKPYYPEHAVNHYFQTRHYLHTL

WKAGILYKRETTRSASFCGSPYSWEQELQHGSCWWLQFRNSKPCSEYCLT

TABLE 2

| | | | | Residues that were not identical across the four genotypes | | | | | | | |
|---|---|---|---|---|---|---|---|---|---|---|---|
| Residue # | X₁ | X₂ | X₃ | X₄ | X₅ | X₆ | X₇ | X₈ | X₉ | X₁₀ | X₁₁ |
| Genotype A Consensus | T | V | T | N | D | N | T | I | L | D | R |
| A-Consensus Frequency | 95.4% | 98.2% | 96.0% | 94.0% | 99.5% | 98.9% | 98.3% | 98.8% | 98.2% | 95.8% | 99.5% |
| Genotype B Consensus | S | i | N | S | E | s | V | i | L | — | — |
| B-Consensus Frequency | 97.1% | 89.7% | 93.5% | 90.1% | 91.5% | 75.2% | 93.6% | 80.1% | 99.4% | — | — |
| Genotype C Consensus | S | I | N | S | E | s | V | i | L | — | — |
| C-Consensus Frequency | 99.4% | 90.3% | 97.3% | 96.3% | 97.0% | 83.7% | 97.8% | 78.7% | 98.8% | — | — |
| Genotype D Consensus | t | V | t | g | D | S | T | F | i | — | — |
| D-Consensus Frequency | 75.7% | 97.0% | 87.5% | 58.7% | 98.4% | 93.7% | 96.5% | 99.1% | 77.8% | — | — |

-continued

HLVNLLEDWGPCDEHGEHHIRIPRTPARVTGGVFLVDKNPHNTAESRLVV

DFSQFSRGITRVSWPKFAVPNLQSLTNLLSSNLSWLSLDVSAAFYHIPLH

PAAMP

Epitope-optimized HBV polymerase C-terminal amino
acid sequence (SEQ ID NO: 10):
HLLVGSSGLSRYVARLSSNSRIINHQHGTMQNLHDSCSRNLYVSLLLLYK

TFGRKLHLYSHPIILKTKRWGYSLNFMGYVIGSWGSLPQDHIIQKIKECF

RKLPVNRPIDWKVCQRIVGLLGFAAPFTQCGYPALMPLYACIQSKQAFTF

SPTYKAFLSKQYLNLYPVARQRPGLCQVFADATPTGWGLAMGHQRMRGTF

VAPLPIHTAELLAACFARSRSGAKILGTDNSVVLSRKYTSFPWLLGCAAN

WILRGTSFVYVPSALNPADDPSRGRLGLSRPLLRLPFRPTTGRTSLYAVS

PSV

Generation of AdC6 and AdC7 Vectors Expressing the Epitope-Optimized Core and Polymerase Sequences The genes encoding the epitope-optimized Core or polymerase amino acid sequences were cloned into transfer vectors that contained the herpes simplex virus (HSV) glycoprotein D (gD) sequence under the control of the CMV promoter. The genes were then cloned into the E1-deleted, E3 ORF 3, 4, 5, 6, and 7-deleted replication deficient adenoviral vector (as described in PCT/US2017/043315) to generate the following vectors:

AdC6 containing the epitope-optimized Core sequence fused to gD (AdC6-gDCore);

AdC6 containing the epitope-optimized polymerase N-terminal sequence fused to gD (AdC6-gDPolN);

AdC6 containing the epitope-optimized polymerase C-terminal sequence fused to gD (AdC6-gDPolC);

AdC7 containing the epitope-optimized Core sequence fused to gD (AdC7-gDCore);

AdC7 containing the epitope-optimized polymerase N-terminal sequence fused to gD (AdC7-gDPolN); and AdC7 containing the epitope-optimized polymerase C-terminal sequence fused to gD (AdC7-gDPolC).

Correct clones were identified by restriction enzyme digest and the cloning sites were sequenced. Vectors were rescued and expanded in HEK 293 cells, purified by cesium chloride (CsCl) gradient centrifugation, and the vector concentration (vp) was determined by spectrophotometry. Vectors were titrated for infectious units upon their expansion in serial dilutions in HEK 293 cells, followed by isolation and reverse transcription of RNA and a nested hexon-specific PCR reaction. Genetic integrity of the vectors was determined by restriction enzyme digest followed by gel electrophoresis of purified viral DNA. Protein expression was determined by Western blotting using gD-specific antibodies. Genetic stability was determined by serial passages (12-15) of the vectors in HEK 293 cells followed by restriction enzyme digest of purified viral DNA and gel electrophoresis.

Testing of Immunogenicity of Vaccines in Mice

C57B1/6, BALB/c, and HLA-A2 tg mice (n=5 per group) were injected with various concentrations of each of the above vectors. Naïve mice served as controls. Mice were bled at different times after the injection and frequencies of insert-specific CD8+ and CD4+ T cells were determined by intracellular cytokine staining (ICS) for IFN-γ. Two months after the first injection, AdC6-immune mice were boosted with the heterologous vector (AdC7) expressing the same insert. Frequencies of HBV-specific T cells were tested again. Results after priming are shown in FIGS. 2A-2F and FIG. 3A (C57B1/6 mice), FIG. 3B (BALB/c mice) and FIG. 3C (HLA-A2 mice). Results after the boost are shown in FIGS. 4A-4C and 5A-5B.

Figure 3A:
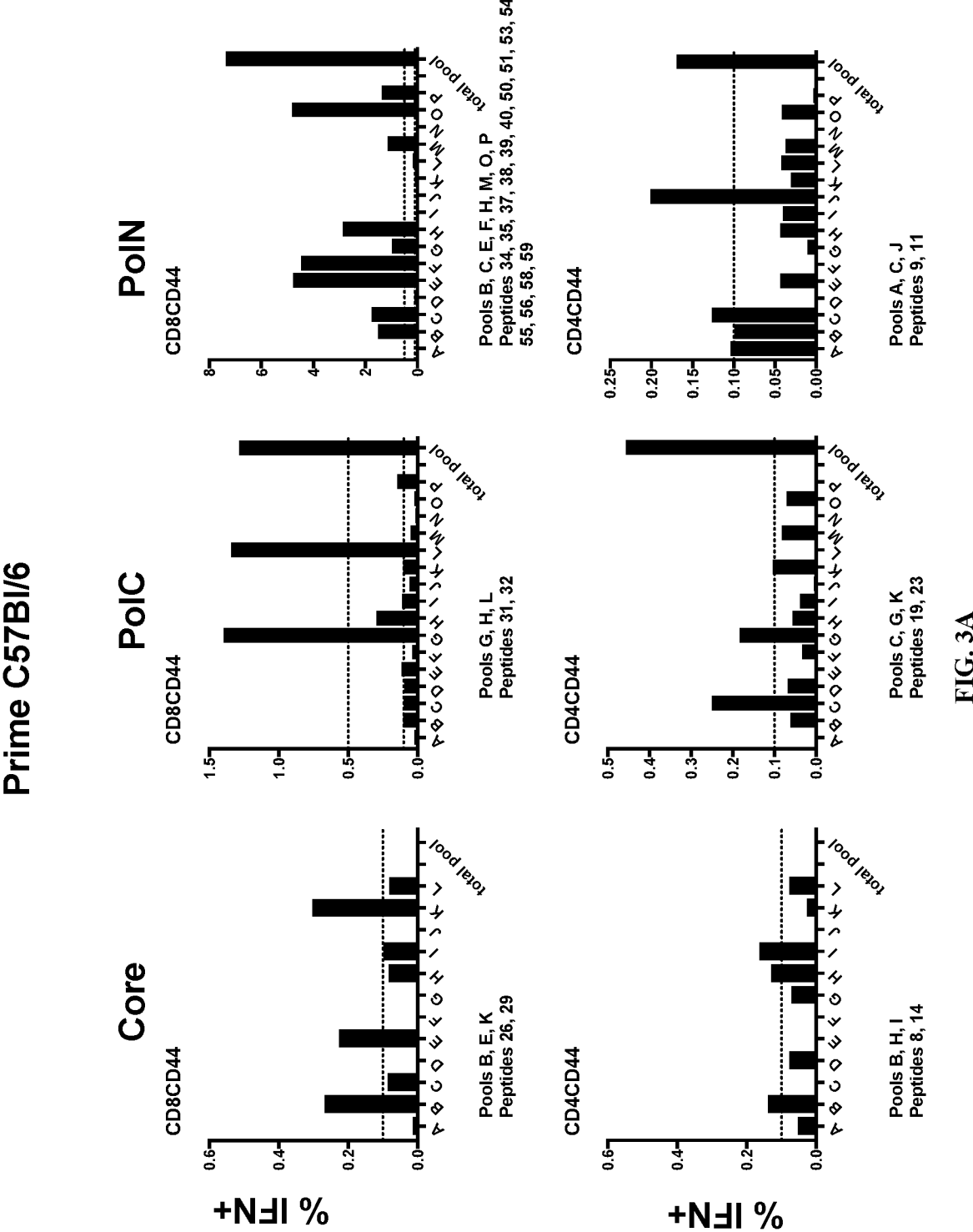
FIG. 3A, FIG. 3B, and FIG. 3C illustrate T cell frequencies in different mouse strains (A: C57B1/6 mice; B: BALB/c mice; C: HLA-A2 transgenic (tg) mice) to pools of peptides representing the indicated HBV sequence. Results were obtained with splenocytes harvested 4 weeks after immunization and tested by ICS for IFN-γ. Peptides were arranged in matrices so that recognition of 2 pools identified one peptide. The graphs show responses to the different pools; responses to a pool containing all peptides are shown to the right. Background frequencies obtained without the peptides were subtracted. Pools that were deemed to elicit a response and peptides identified in response to different pools are listed at the bottom of each figure. CD8+ T cell and CD4+ T cell responses are shown for BALB/c mice; CD8+ T cell responses are shown for HLA-A2 tg mice, which carry a human MHC class I molecule but mouse MHC class II molecules. T cells were gated on activated CD44+ cells. Each consecutively numbered "peptide" consists of 15 amino acids beginning on the $1^{st}$, $6^{th}$, $11^{th}$, etc. amino acid of the Core, PolN, or PolC sequence. Thus, for example, peptide 1 of Core corresponds to amino acids 1-15 of SEQ ID NO: 6 (i.e. the epitope-optimized Core amino acid sequence), peptide 2 of Core corresponds to amino acids 6-20 of SEQ ID NO: 6, peptide 3 of Core corresponds to amino acids 11-25 of SEQ ID NO: 6, etc. Similarly, peptide 1 of PolN corresponds to amino acids 1-15 of SEQ ID NO: 8 (ie. the epitope-optimized PolN amino acid sequence), peptide 2 of PolN corresponds to amino acids 6-20 of SEQ ID NO: 8, peptide 3 of PolN corresponds to amino acids 11-25 of SEQ ID NO: 8, etc. Likewise, peptide 1 of PolC corresponds to amino acids 1-15 of SEQ ID NO: 10 (i.e. the epitope-optimized PolC amino acid sequence), peptide 2 of PolC corresponds to amino acids 6-20 of SEQ ID NO: 10, peptide 3 of PolC corresponds to amino acids 11-25 of SEQ ID NO: 10, etc.
Figure 3B:
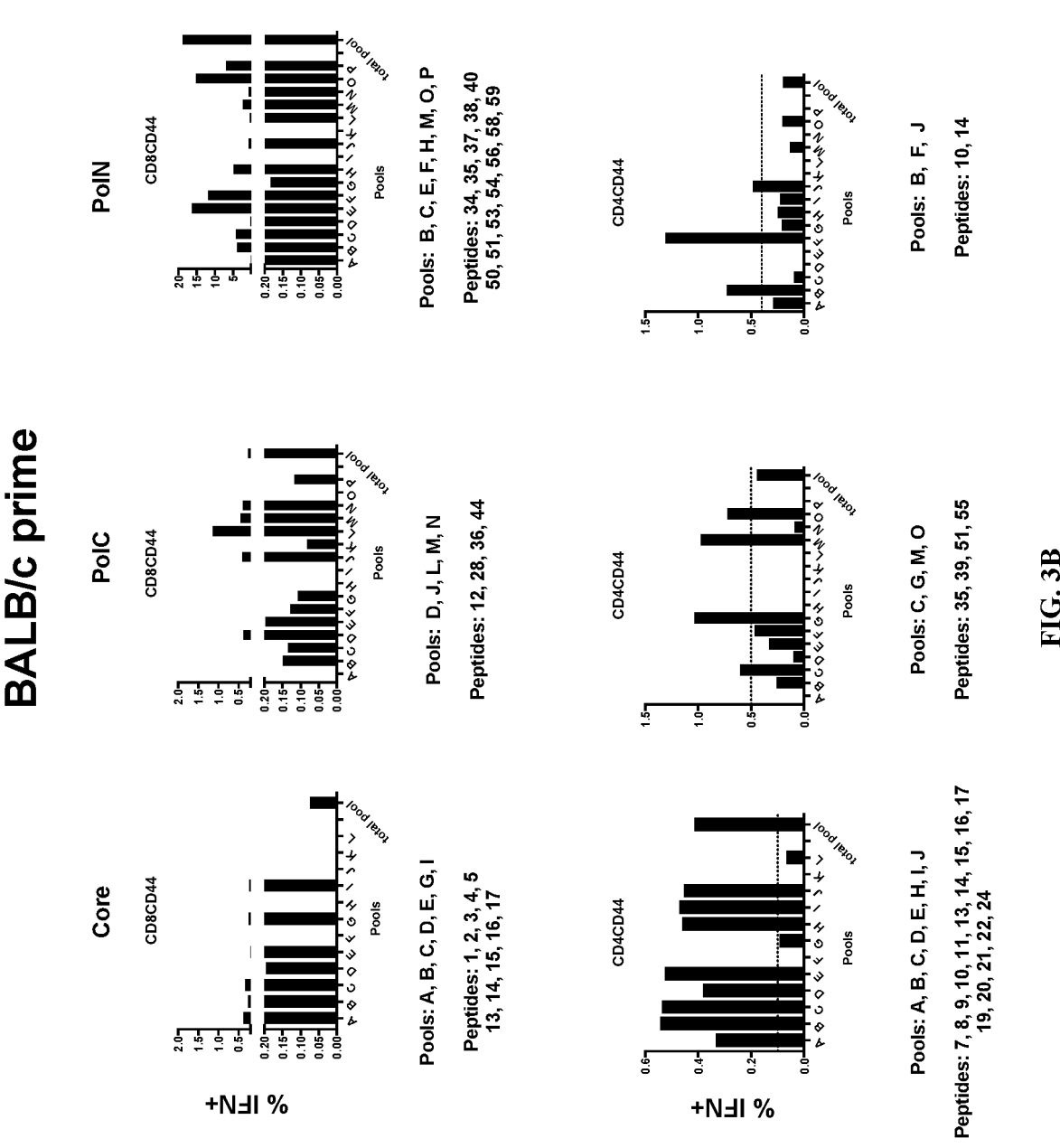
Figure 3C:
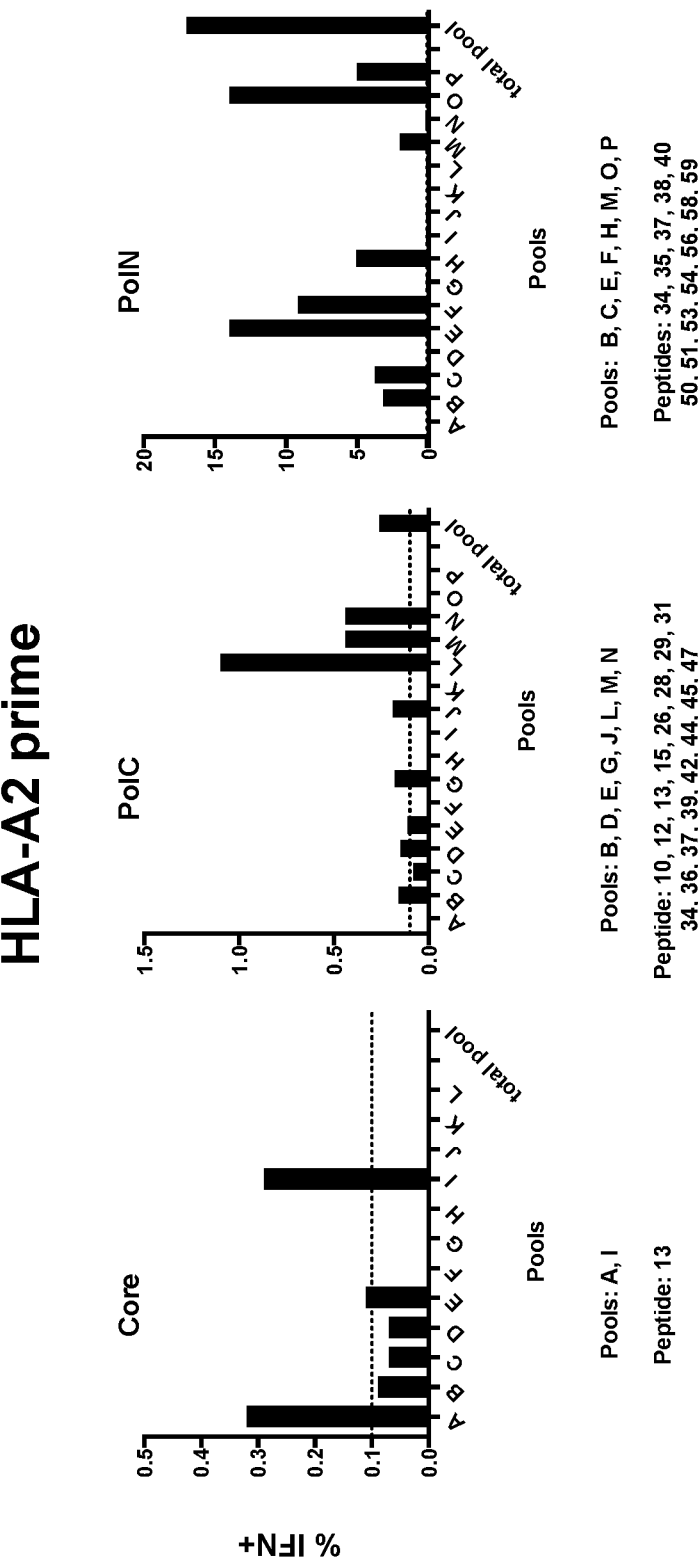

C57B1/6 mice showed a very robust CD8+ T cell response to the epitope-optimized polymerase N-terminal sequence and lower responses to the epitope-optimized polymerase C-terminal sequence and the epitope-optimized Core sequence, while CD4+ responses were better against the epitope-optimized Core sequence and the epitope-optimized polymerase C-terminal sequence (FIG. 2A-FIG. 2F). Epitope mapping in C57B1/6 mice showed higher and broader responses to PolN than PolC (FIG. 3A). Within PolN a total of 14 peptides were recognized by CD8+ T cells while within PolC only two adjacent peptides, which most likely reflect one epitope, were recognized. CD4+ T cells failed to respond to PolN or PolC. This pattern was largely mirrored in BALB/c mice, where CD8+ T cell responses were highest against PolN with recognition of 12 peptides followed by PolC with recognition of 4 peptides (FIG. 3B). Responses to Core were low but surprisingly broad with recognition of 10 peptides (FIG. 3B). BALB/c CD4+ T cells responded best to Core with recognition of 15 peptides with lower recognition of PolC (4 peptides) or PolN (2 peptides). CD8+ T cell responses were also tested in HLA-A2 tg mice where PolN again triggered the highest response involving 12 peptides (FIG. 3C). The response to PolC was lower but broader (16 peptides) while only one peptide of Core was detected (FIG. 3C). The sequences of the peptides tested in the priming experiments are provided in Table 3 (Core peptides), Table 4 (PolN peptides), and Table 5 (PolC peptides). The peptide composition of the peptide pools from the priming experiments are provided in Tables 6-8. Overall these data show that the inserts elicited detectable T cell responses that in most cases were directed against multiple epitopes within each sequence.

TABLE 3

| Epitope-Optimized Core Peptides | | | |
|---|---|---|---|
| Peptide | Amino Acid Sequence | SEQ ID NO: | Prime |
| 1 | DIDPYKEFGATVELL | 20 | CD8 (B/c) |
| 2 | KEFGATVELLSFLPS | 21 | CD8 (B/c) |
| 3 | TVELLSFLPSDFFPS | 22 | CD8 (B/c) |
| 4 | SFLPSDFFPSIRDLL | 23 | CD8 (B/c) |
| 5 | DFFPSIRDLLDTASA | 24 | CD8 (B/c) |
| 6 | IRDLLDTASALYREA | 25 | |
| 7 | DTASALYREALESPE | 26 | CD4 (B/c) |
| 8 | LYREALESPEHCSPH | 27 | CD4 (B1/6); CD4 (B/c) |
| 9 | LESPEHCSPHHTALR | 28 | CD4 (B/c) |
| 10 | HCSPHHTALRQAILC | 29 | CD4 (B/c) |
| 11 | HTALRQAILCWGELM | 30 | CD4 (B/c) |
| 12 | QAILCWGELMTLATW | 31 | |
| 13 | WGELMTLATWVGSNL | 32 | CD8 (B/c); CD4 (B/c); CD8 (HLA) |
| 14 | TLATWVGSNLEDPAS | 33 | CD8 (B/c); CD4 (B/c) |

TABLE 3-continued

Epitope-Optimized Core Peptides

| Peptide | Amino Acid Sequence | SEQ ID NO: | Prime |
|---|---|---|---|
| 15 | VGSNLEDPASRELVV | 34 | CD8 (B/c); CD4 (B/c) |
| 16 | EDPASRELVVSYVNV | 35 | CD8 (B/c); CD4 (B/c) |
| 17 | RELVVSYVNVNMGLK | 36 | CD8 (B/c); CD4 (B/c) |
| 18 | SYVNVNMGLKIRQLL | 37 | |
| 19 | NMGLKIRQLLWFHIS | 38 | CD4 (B/c) |
| 20 | IRQLLWFHISCLTFG | 39 | CD4 (B/c) |
| 21 | WFHISCLTFGRETVI | 40 | CD4 (B/c) |
| 22 | CLTFGRETVIEYLVS | 41 | CD4 (B/c) |
| 23 | RETVIEYLVSFGVWI | 42 | CD4 (B/c) |
| 24 | EYLVSFGVWIRTPPA | 43 | |
| 25 | FGVWIRTPPAYRPPN | 44 | |
| 26 | RTPPAYRPPNAPILS | 45 | CD8 (B1/6) |
| 27 | YRPPNAPILSTLPET | 46 | |
| 28 | APILSTLPETTVVRR | 47 | CD4 (B1/6) |
| 29 | TLPETTVVRRRDRGR | 48 | CD8 (B1/6) |
| 30 | TVVRRRDRGRSPRRR | 49 | |
| 31 | RDRGRSPRRRTPSPR | 50 | |
| 32 | SPRRRTPSPRRRRSQ | 51 | |
| 33 | TPSPRRRRSQSPRRR | 52 | |
| 34 | RRRSQSPRRRRRSQSR | 53 | |
| 35 | SPRRRRRSQSRESQC | 54 | |

B/c = BALB/c; B1/6 = C57B1/6; HLA = HLA-A2

TABLE 4

Epitope-Optimized PolN Peptides

| Peptide | Amino Acid Sequence | SEQ ID NO: | Prime |
|---|---|---|---|
| 1 | PLSYQHFRKLLLLDE | 55 | |
| 2 | HFRKLLLLDEEAGPL | 56 | |
| 3 | LLLDEEAGPLEEELP | 57 | |
| 4 | EAGPLEEELPRLADE | 58 | |
| 5 | EEELPRLADEGLNRR | 59 | |
| 6 | RLADEGLNRRVAEDL | 60 | |
| 7 | GLNRRVAEDLNLGNL | 61 | |
| 8 | VAEDLNLGNLNVSIP | 62 | |
| 9 | NLGNLNVSIPWTHKV | 63 | |
| 10 | NVSIPWTHKVGNFTG | 64 | CD4 (B/c) |

TABLE 4-continued

Epitope-Optimized PolN Peptides

| Peptide | Amino Acid Sequence | SEQ ID NO: | Prime |
|---|---|---|---|
| 11 | WTHKVGNFTGLYSST | 65 | |
| 12 | GNFTGLYSSTVPVFN | 66 | |
| 13 | LYSSTVPVFNPEWQT | 67 | |
| 14 | VPVFNPEWQTPSFPK | 68 | CD4 (B/c) |
| 15 | PEWQTPSFPKIHKLQE | 69 | |
| 16 | PSFPKIHKLQEDIVDR | 70 | |
| 17 | IHKLQEDIVDRCKQFV | 71 | |
| 18 | EDIVDRCKQFVGPLTV | 72 | |
| 19 | RCKQFVGPLTVNEKRR | 73 | |
| 20 | VGPLTVNEKRRLKLIM | 74 | |
| 21 | VNEKRRLKLIMPARFY | 75 | |
| 22 | RLKLIMPARFYPNVTK | 76 | |
| 23 | MPARFYPNVTKYLPLD | 77 | |
| 24 | YPNVTKYLPLDKGIKP | 78 | |
| 25 | KYLPLDKGIKPYYPEH | 79 | |
| 26 | DKGIKPYYPEHAVNHY | 80 | |
| 27 | PYYPEHAVNHYFQTRH | 81 | |
| 28 | HAVNHYFQTRHYLHTL | 82 | |
| 29 | YFQTRHYLHTLWKAGI | 83 | |
| 30 | HYLHTLWKAGILYKRE | 84 | |
| 31 | LWKAGILYKRETTRSA | 85 | |
| 32 | ILYKRETTRSASFCGS | 86 | |
| 33 | ETTRSASFCGSPYSWE | 87 | |
| 34 | ASFCGSPYSWEQELQH | 88 | CD8 (B1/6); CD8 (B/c); CD8 (HLA) |
| 35 | SPYSWEQELQHGSCWW | 89 | CD8 (B1/6); CD8 (B/c); CD8 (HLA) |
| 36 | EQELQHGSCWWLQFRN | 90 | |
| 37 | HGSCWWLQFRNSKPCS | 91 | CD8 (B1/6); CD8 (B/c); CD8 (HLA) |
| 38 | WLQFRNSKPCSEYCLT | 92 | CD8 (B1/6); CD8 (B/c); CD8 (HLA) |
| 39 | NSKPCSEYCLTHLVNL | 93 | CD8 (B1/6) |
| 40 | SEYCLTHLVNLLEDWG | 94 | CD8 (B1/6); CD8 (B/c); CD8 (HLA) |
| 41 | THLVNLLEDWGPCDEH | 95 | |
| 42 | LLEDWGPCDEHGEHHI | 96 | |
| 43 | GPCDEHGEHHIRIPRT | 97 | |
| 44 | HGEHHIRIPRTPARVT | 98 | |

TABLE 4-continued

Epitope-Optimized PolN Peptides

| Peptide | Amino Acid Sequence | SEQ ID NO: | Prime |
|---------|---------------------|------------|-------|
| 45 | IRIPRTPARVTGGVFL | 99 | |
| 46 | TPARVTGGVFLVDKNP | 100 | |
| 47 | TGGVFLVDKNPHNTAE | 101 | |
| 48 | LVDKNPHNTAESRLVV | 102 | |
| 49 | PHNTAESRLVVDFSQF | 103 | |
| 50 | ESRLVVDFSQFSRGIT | 104 | CD8 (B1/6); CD8 (B/c); CD8 (HLA) |
| 51 | VDFSQFSRGITRVSWP | 105 | CD8 (B1/6); CD8 (B/c); CD8 (HLA) |
| 52 | FSRGITRVSWPKFAVP | 106 | |
| 53 | TRVSWPKFAVPNLQSL | 107 | CD8 (B1/6); CD8 (B/c); CD8 (HLA) |
| 54 | PKFAVPNLQSLTNLLS | 108 | CD8 (B1/6); CD8 (B/c); CD8 (HLA) |
| 55 | PNLQSLTNLLSSNLSW | 109 | CD8 (B1/6) |
| 56 | LTNLLSSNLSWLSLDV | 110 | CD8 (B1/6); CD8 (B/c); CD8 (HLA) |
| 57 | SSNLSWLSLDVSAAFY | 111 | |
| 58 | WLSLDVSAAFYHIPLH | 112 | CD8 (B1/6); CD8 (B/c); CD8 (HLA) |
| 59 | VSAAFYHIPLHPAAMP | 113 | CD8 (B1/6); CD8 (B/c); CD8 (HLA) |

B/c = BALB/c; B1/6 = C57B1/6; HLA = HLA-A2

TABLE 5

Epitope-Optimized PolC Peptides

| Peptide | Amino Acid Sequence | SEQ ID NO: | Prime |
|---------|---------------------|------------|-------|
| 1 | HLLVGSSGLSRYVAR | 114 | |
| 2 | SSGLSRYVARLSSNSR | 115 | |
| 3 | RYVARLSSNSRIINHQ | 116 | |
| 4 | LSSNSRIINHQHGTMQ | 117 | |
| 5 | RIINHQHGTMQNLHDS | 118 | |
| 6 | QHGTMQNLHDSCSRNL | 119 | |
| 7 | QNLHDSCSRNLYVSLL | 120 | |
| 8 | SCSRNLYVSLLLLYKT | 121 | |
| 9 | LYVSLLLLYKTFGRKL | 122 | |
| 10 | LLLYKTFGRKLHLYSH | 123 | CD8 (HLA) |
| 11 | TFGRKLHLYSHPIILK | 124 | |
| 12 | LHLYSHPIILKTKRWG | 125 | CD8 (B/c); CD8 (HLA) |
| 13 | HPIILKTKRWGYSLNF | 126 | CD8 (HLA) |

TABLE 5-continued

Epitope-Optimized PolC Peptides

| Peptide | Amino Acid Sequence | SEQ ID NO: | Prime |
|---------|---------------------|------------|-------|
| 14 | KTKRWGYSLNFMGYVI | 127 | |
| 15 | GYSLNFMGYVIGSWGS | 128 | CD8 (HLA) |
| 16 | FMGYVIGSWGSLPQDH | 129 | |
| 17 | IGSWGSLPQDHIIQKI | 130 | |
| 18 | SLPQDHIIQKIKECFR | 131 | |
| 19 | HIIQKIKECFRKLPVN | 132 | |
| 20 | IKECFRKLPVNRPIDW | 133 | |
| 21 | RKLPVNRPIDWKVCQR | 134 | |
| 22 | NRPIDWKVCQRIVGLL | 135 | |
| 23 | WKVCQRIVGLLGFAAP | 136 | |
| 24 | RIVGLLGFAAPFTQCG | 137 | |
| 25 | LGFAAPFTQCGYPALM | 138 | |
| 26 | PFTQCGYPALMPLYAC | 139 | CD8 (HLA) |
| 27 | GYPALMPLYACIQSKQ | 140 | |
| 28 | MPLYACIQSKQAFTFS | 141 | CD8 (B/c); CD8 (HLA) |
| 29 | CIQSKQAFTFSPTYKA | 142 | CD8 (HLA) |
| 30 | QAFTFSPTYKAFLSKQ | 143 | |
| 31 | SPTYKAFLSKQYLNLY | 144 | CD8 (B1/6); CD8 (HLA) |
| 32 | AFLSKQYLNLYPVARQ | 145 | CD8 (B1/6) |
| 33 | QYLNLYPVARQRPGLC | 146 | |
| 34 | YPVARQRPGLCQVFAD | 147 | CD8 (HLA) |
| 35 | QRPGLCQVFADATPTG | 148 | CD4 (B/c) |
| 36 | CQVFADATPTGWGLAM | 149 | CD8 (B/c); CD8 (HLA) |
| 37 | DATPTGWGLAMGHQRM | 150 | CD8 (HLA) |
| 38 | GWGLAMGHQRMRGTFV | 151 | |
| 39 | MGHQRMRGTFVAPLPI | 152 | CD4 (B/c); CD8 (HLA) |
| 40 | MRGTFVAPLPIHTAEL | 153 | |
| 41 | VAPLPIHTAELLAACF | 154 | |
| 42 | IHTAELLAACFARSRS | 155 | CD8 (HLA) |
| 43 | LLAACFARSRSGAKIL | 156 | |
| 44 | FARSRSGAKILGTDNS | 157 | CD8 (B/c); CD8 (HLA) |
| 45 | SGAKILGTDNSVVLSR | 158 | CD8 (HLA) |
| 46 | LGTDNSVVLSRKYTSF | 159 | |
| 47 | SVVLSRKYTSFPWLLG | 160 | |
| 48 | RKYTSFPWLLGCAANW | 161 | CD8 (HLA) |
| 49 | FPWLLGCAANWILRGT | 162 | |
| 50 | GCAANWILRGTSFVYV | 163 | |

TABLE 5-continued

| | Epitope-Optimized PolC Peptides | | |
|---|---|---|---|
| Peptide | Amino Acid Sequence | SEQ ID NO: | Prime |
| 51 | WILRGTSFVYVPSALN | 164 | CD4 (B/c) |
| 52 | TSFVYVPSALNPADDP | 165 | |
| 53 | VPSALNPADDPSRGRL | 166 | |
| 54 | NPADDPSRGRLGLSRP | 167 | |
| 55 | PSRGRLGLSRPLLRLP | 168 | CD4 (B/c) |
| 56 | LGLSRPLLRLPFRPTT | 169 | |
| 57 | PLLRLPFRPTTGRTSL | 170 | |
| 58 | PFRPTTGRTSLYAVSP | 171 | |
| 59 | TGRTSLYAVSPSV | 172 | |

B/c = BALB/c; B1/6 = C57Bl/6; HLA = HLA-A2

TABLE 6

| | Epitope-Optimized Core Pool | | | | | |
|---|---|---|---|---|---|---|
| Core Matrix | A | B | C | D | E | F |
| G | 1 | 2 | 3 | 4 | 5 | 6 |
| H | 7 | 8 | 9 | 10 | 11 | 12 |
| I | 13 | 14 | 15 | 16 | 17 | 18 |
| J | 19 | 20 | 21 | 22 | 23 | 24 |
| K | 25 | 26 | 27 | 28 | 29 | 30 |
| L | 31 | 32 | 33 | 34 | 35 | |

TABLE 7

| | Epitope-Optimized PolN Pool | | | | | | | |
|---|---|---|---|---|---|---|---|---|
| Pol N Matrix | A | B | C | D | E | F | G | H |
| I | 1 | 2 | 3 | 4 | 5 | 6 | 7 | 8 |
| J | 9 | 10 | 11 | 12 | 13 | 14 | 15 | 16 |
| K | 17 | 18 | 19 | 20 | 21 | 22 | 23 | 24 |
| L | 25 | 26 | 27 | 28 | 29 | 30 | 31 | 32 |
| M | 33 | 34 | 35 | 36 | 37 | 38 | 39 | 40 |
| N | 41 | 42 | 43 | 44 | 45 | 46 | 47 | 48 |
| O | 49 | 50 | 51 | 52 | 53 | 54 | 55 | 56 |
| P | 57 | 58 | 59 | | | | | |

TABLE 8

| | Epitope-Optimized PolC Pool | | | | | | | |
|---|---|---|---|---|---|---|---|---|
| Pol C Matrix | A | B | C | D | E | F | G | H |
| I | 1 | 2 | 3 | 4 | 5 | 6 | 7 | 8 |
| J | 9 | 10 | 11 | 12 | 13 | 14 | 15 | 16 |
| K | 17 | 18 | 19 | 20 | 21 | 22 | 23 | 24 |
| L | 25 | 26 | 27 | 28 | 29 | 30 | 31 | 32 |
| M | 33 | 34 | 35 | 36 | 37 | 38 | 39 | 40 |
| N | 41 | 42 | 43 | 44 | 45 | 46 | 47 | 48 |
| O | 49 | 50 | 51 | 52 | 53 | 54 | 55 | 56 |
| P | 57 | 58 | | | | | | |

Figure 4A:
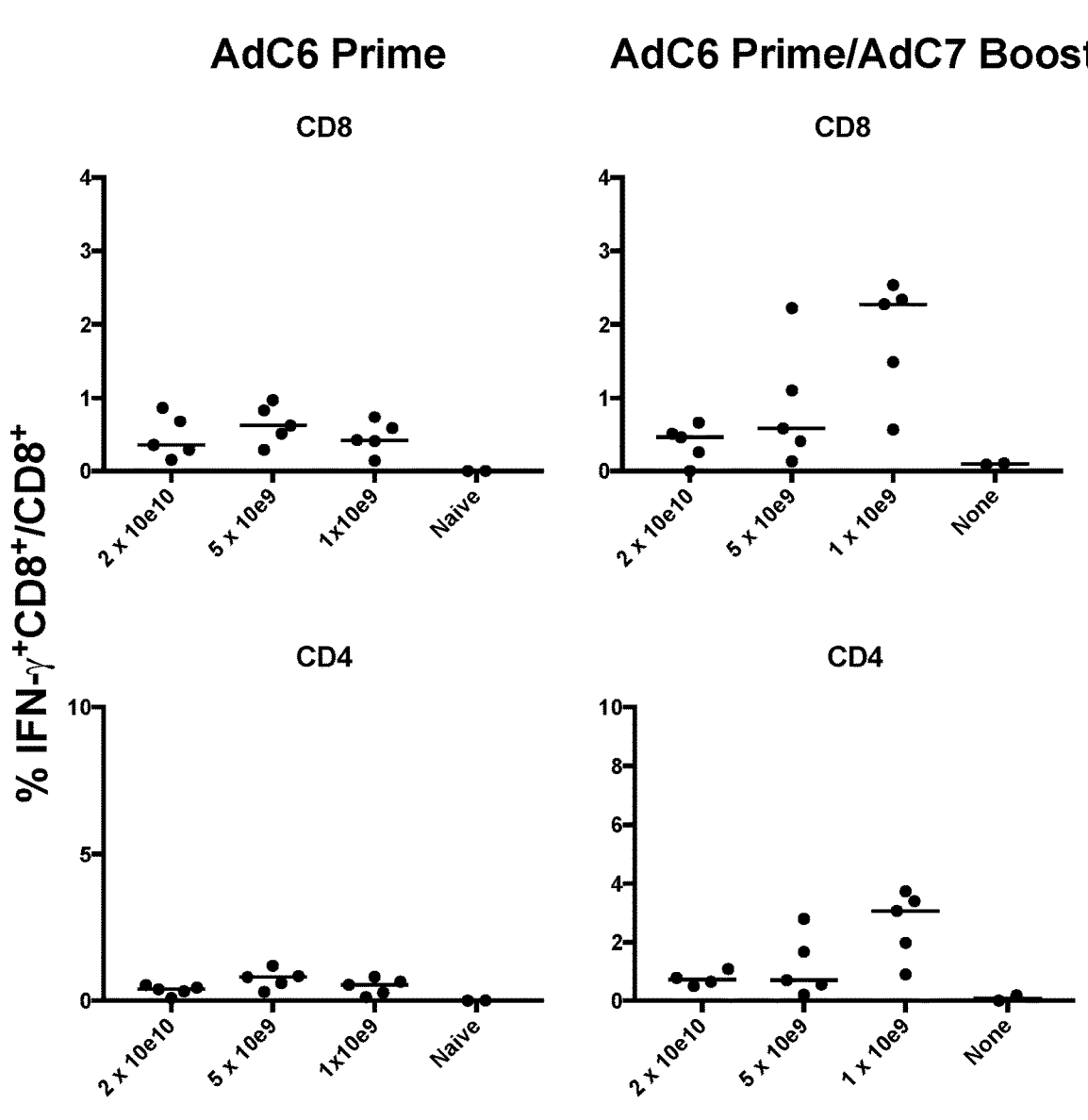
FIG. 4A, FIG. 4B and FIG. 4C show the IFN-γ response upon boosting with AdC6-gDCore (A), AdC6-gDPolC (B), and AdC6-gDPolN (C) in C57B1/6 mice immunized with various doses of the indicated vectors. The left graphs show responses tested from blood 2 weeks after priming with AdC6 vector. Mice were boosted 8 weeks later with the same doses of AdC7 vectors expressing the same inserts. The right graphs show responses at 2 weeks after the boost in blood.
Figure 4B:
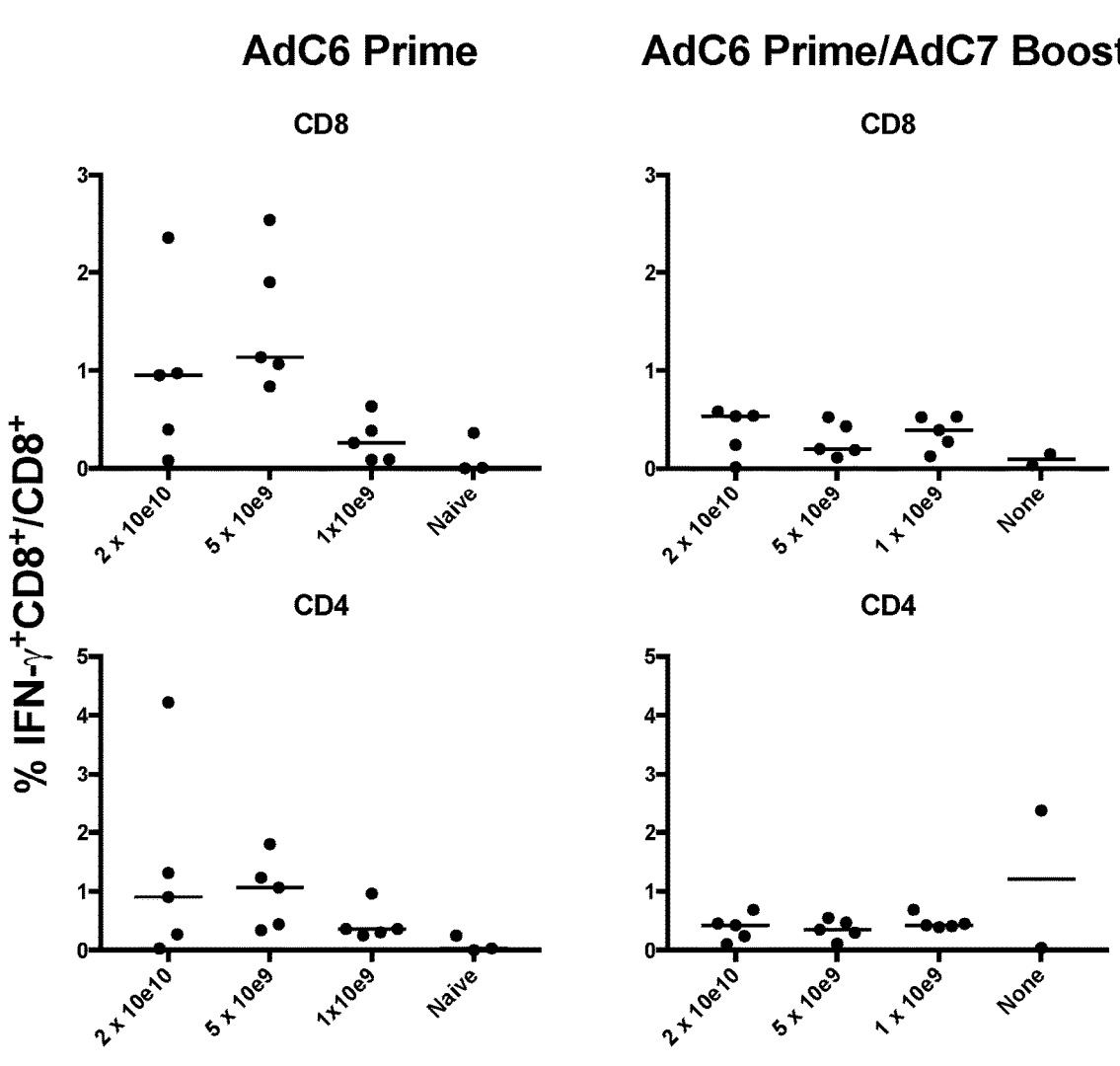
Figure 4C:
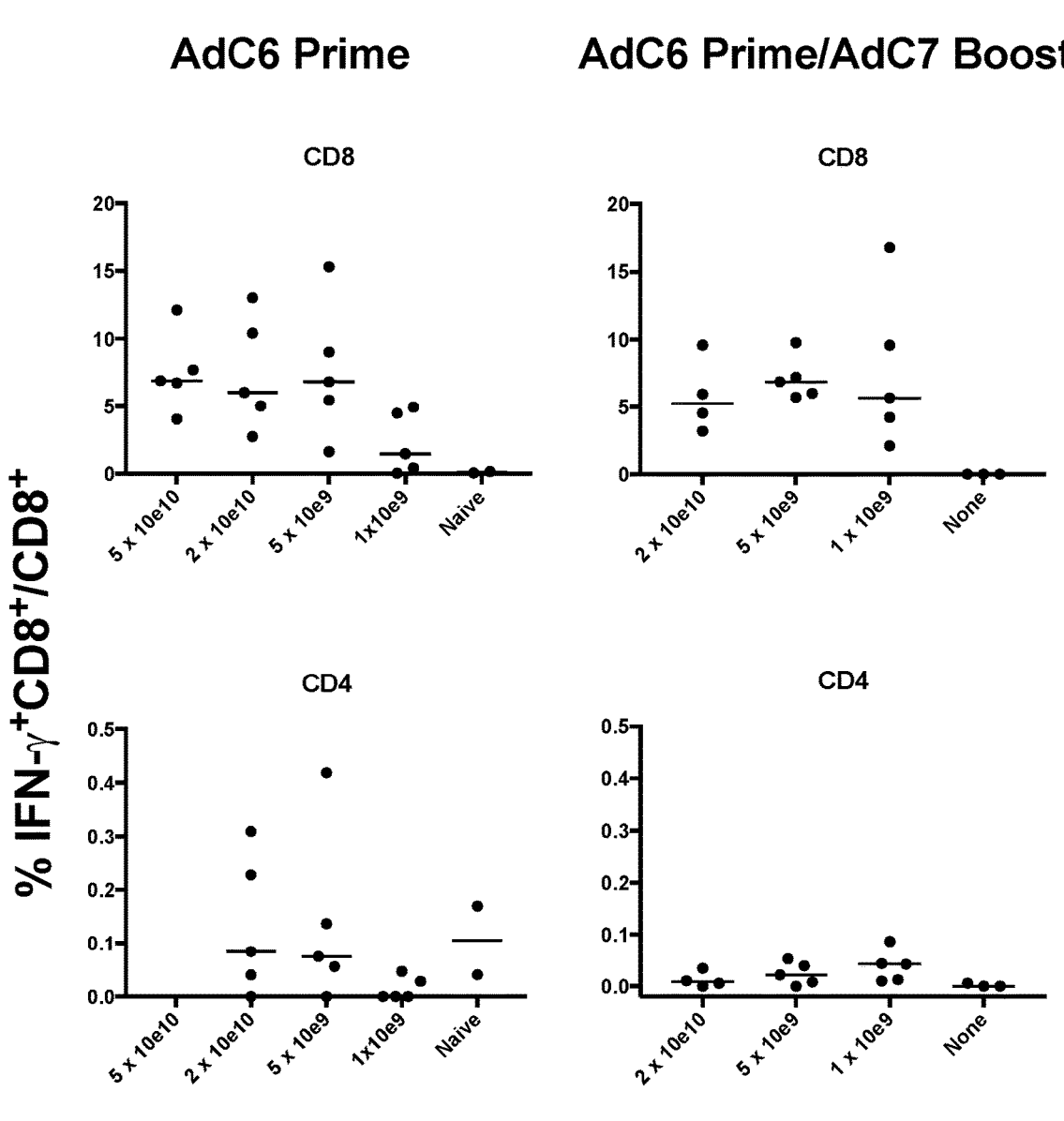
Figure 5A:
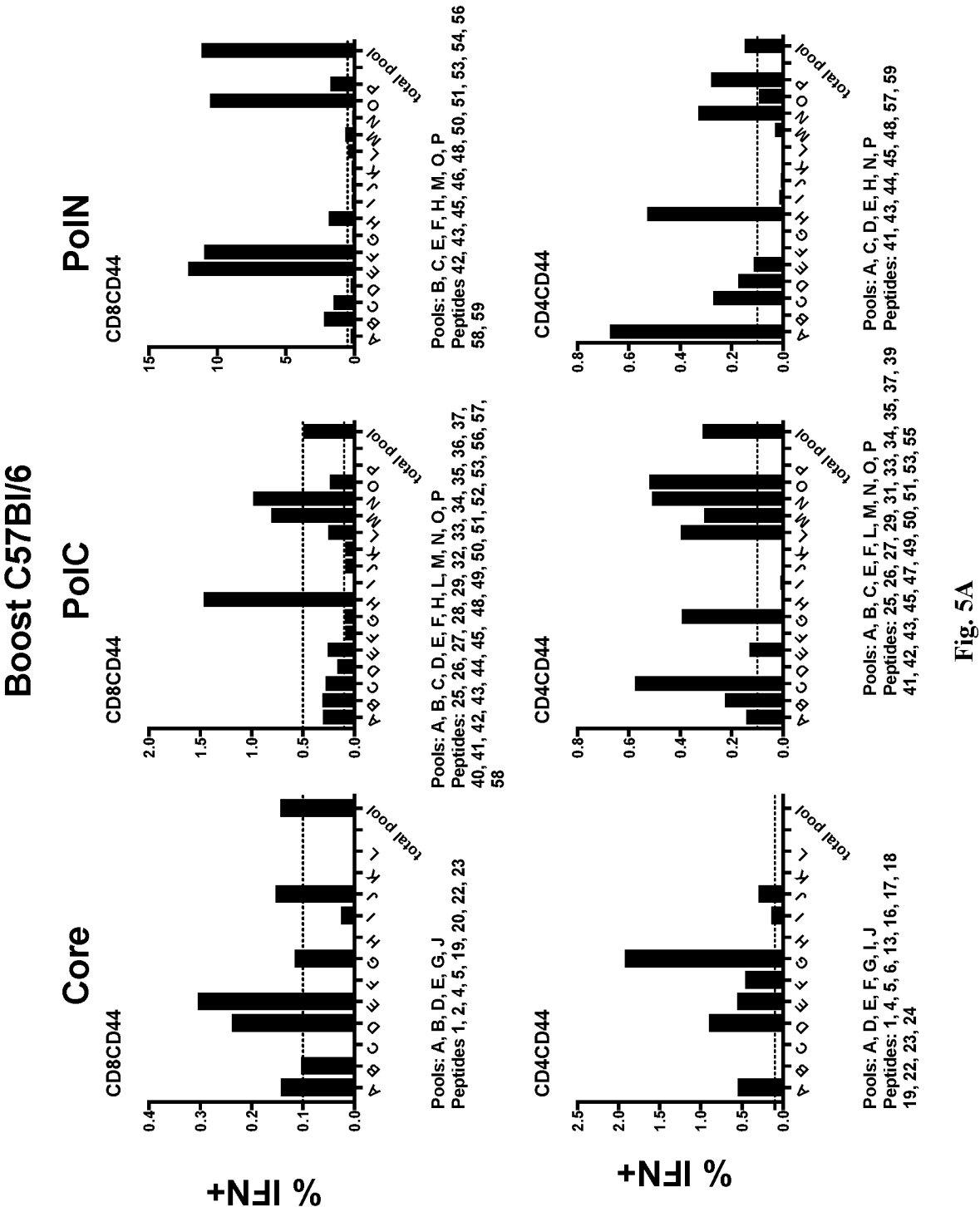
FIG. 5A, FIG. 5B, and FIG. 5C illustrate T cell frequencies in different mouse strains (A: C57B1/6 mice; B: BALB/c mice; C: HLA-A2 tg mice) to pools of peptides representing the indicated HBV sequence. Mice were primed with AdC6 vectors expressing either of the 3 inserts (i.e., Core, PolC, or PolN) and were boosted 8 weeks later with AdC7 vectors expressing the same inserts. Results were obtained with splenocytes harvested 4 weeks after the immunization and tested by ICS for IFN-γ. Peptides were arranged in matrices so that recognition of 2 pools identified one peptide. The graphs show responses to the different pools; responses to a pool containing all peptides are shown to the right. Background frequencies obtained without the peptides were subtracted. Pools that were deemed to elicit a response and peptides identified in response to different pools are listed at the bottom of each figure. CD8+ T cell and CD4+ T cell responses are shown for BALB/c mice; CD8+
Figure 5B:
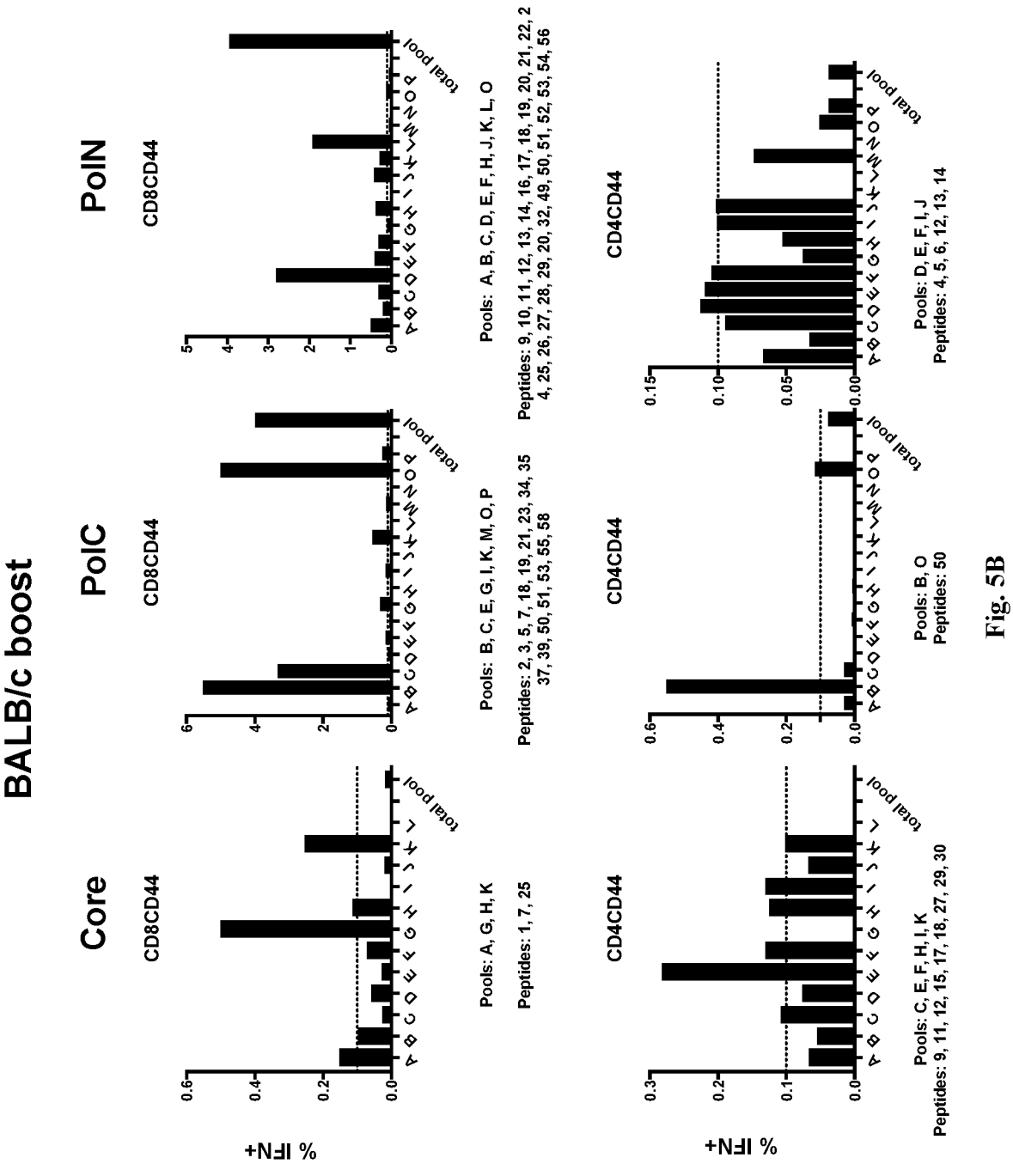
Figure 5C:
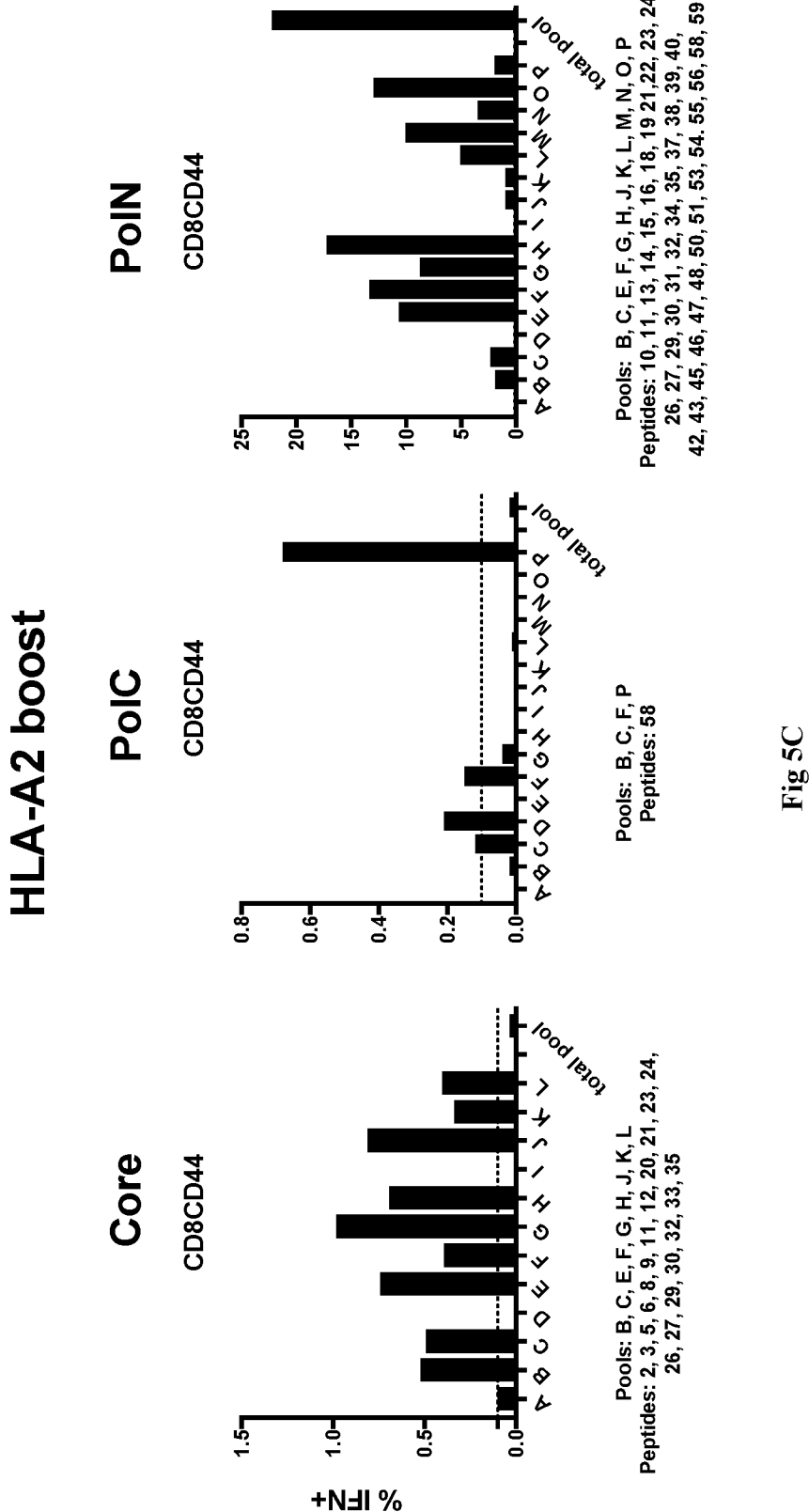

After the boost, which was tested in C571B1/6, BALB/c and HLA-A2 tg mice, increases in responses were mainly seen for inserts and at vector doses that upon priming induced suboptimal responses, i.e., for Core tested at the $1 \times 10^9$ vp vector dose (FIG. 4A-4C). Although booster immunization failed to increase the response to PolN or PolC when vectors were injected at high doses, the boost nevertheless broadened the T cell responses (FIG. 5A-5C)

Immunogenicity Summary

The above results illustrate that:

The vaccines are immunogenic: PolN>PolC>Core for CD8⁺ T cells; Core>PolC>PolN for CD4⁺ T cell responses;

Immune responses can be boosted by a heterologous vaccine carrier;

Immune responses are broad; and

The breadth of the T cell responses increases after the boost.

Effect of Vaccination on HBV Titers Low Dose AAV-1.3HBV Challenge

A group of 3 mice were challenged with $1 \times 10^{10}$, $1 \times 10^{11}$ or $1.5 \times 10^{11}$ vg of AAV-1.3HBV and were vaccinated with AdC6-gDPolN 8 weeks later. Viral titers were tested 8 weeks after vaccination and compared to pre-vaccination titers. FIG. 6 shows viral changes from baseline for each treatment group.

Epitope Shifting

CD8+ T cells to HBV antigens become exhausted during chronic HBV infections. Progression towards exhaustion is more rapid and pronounced for CD8+ T cells to dominant, as compared to subdominant, epitopes. The underlying reason is that exhaustion is driven by overwhelming antigen-driven stimulation through the T cell receptor; dominant epitopes are presented at higher levels on MHC class I antigens expressed by antigen presenting cells than sub-dominant epitopes with lower avidity to their restricting elements. Typical vaccine approaches primarily induce immune responses to dominant epitopes. Therapeutic vaccines should take into account loss of T cells to dominant epitopes during chronic virus infections and should be designed to favor expansion of CD8+ T cells to subdominant epitopes, which have a higher likelihood of resisting disease-driven exhaustion, translating to superior disease control.

The epitope profile in naïve mice immunized with an adenovirus vector comprising a nucleic acid sequence encoding the HBV polymerase N-terminal domain (PolN) fused to the herpes simplex virus glycoprotein D ("AdC6-gDPolN", wherein the amino acid sequence of gDPolN is SEQ ID NO: 16) was determined. Responses in mice that had not been pre-treated with the AAV8-1.3HBV vector were compared to those obtained in mice infected with an AAV8 vector expressing the 1.3HBV genome prior to vaccination with the AdC6-gDPolN. The AAV8-1.3HBV vector induced high titers of HBV in serum, which could drive CD8+ T cell exhaustion.

In the first series of experiments a peptide pool matrix was used to identify epitopes in mice vaccinated with the AdC6-gDPolN vector, but not challenged with an AAV-1.3HBV vector. A number of regions in these naïve mice were identified that elicited potent responses (e.g. greater than 1% IFN-γ production CD8+CD44+ T cells. FIG. 7A and FIG. 8A. In the second experiment, mice were challenged with $1 \times 10^{10}$ virus genomes (vg) of the AAV-1.3HBV vector, were vaccinated 4 weeks later with an AdC6 vector expressing the same HBV polymerase sequence (gDPolN) as in the initial experiment in non-challenged mice, and ten weeks thereafter the HBV PolN-specific CD8+ T cell epitope profile was determined using peptide pool matrices on splenocytes from the mice that had been challenged prior to vaccination. FIG.

7B and FIG. 8B. The experiment was repeated using more stringent conditions by challenging mice with a $1.5 \times 10^{11}$ vg dose of the AAV8-1.3HBV vector. Mice were again vaccinated 4 weeks later and were tested approximately 10 weeks after vaccination for CD8$^+$ T cell responses to the peptide pool matrices. FIG. 7C and FIG. 8C. In both experiments, compared to the results obtained from unvaccinated mice, a shift was observed in the epitope profile in AAV8-1.3HBV infected mice, which at the time of vaccination had high viral loads between $10^7$-$10^9$ vg per ml of serum. The effect was more pronounced in mice that had been challenged with a high dose of the AAV8-1.3HBV vector. In both experiments a reduction in responses were observed. Furthermore, especially in mice challenged with the high dose of AAV8-1.3HBV, the results showed a loss of CD8+ T cells to many of the epitopes that showed immunodominance in uninfected vaccinated mice (e.g. within region represented by peptides 50 to 59, FIG. 8), a better preservation of epitopes that were subdominant (such as those within the region represented by peptides 2 to 8) as well as new epitopes, such as in the region presented by peptides 10 to 29. These data confirm a shift from recognition of dominant to recognition of subdominant epitopes.

Based on these data, a new HBV polymerase N-terminal domain insert (HBV PolN v2) was generated (SEQ ID NO: 173):

HFRKLLLLDEEAGPLEEELPRLADEGLNRRVAEDLNLGNLPEWQTPSFPK

IHLQEDIVDRCKQFVGPLTVNEKRRLKLIMPARFYPNVTKYLPLDKGIKP

YYPEHAVNHYFQTRHYLHTLWKAGILYKRETTRSASFCGSPYSWEQELQH

GSCWWLQFRNSKPCSEYCLTHLVNLLEDWGPCDEHGEHHIRIPRTPARVT

This insert induced CD8+ T cell responses mainly to subdominant epitopes to which responses remain intact in mice with high HBV viral loads.

Immunogenicity and Efficacy of gDCore, gDPolN, and gDPolC Vaccines

The immunogenicity and efficacy the AdC6-gDCore, AdC6-gDPolN, AdC6-gDPolC, AdC7-gDCore, AdC7-gD-PolN, and AdC7-gDPolC vaccines in an AAV8-HBV mouse model were analyzed.

Methods—Immunogenicity

C57B1/6 mice (n=5 per group) were injected with various doses of: AdC6-gDCore (gDCore nucleic acid sequence corresponding to SEQ ID NO: 15); AdC6-gDPolN (gDPolN nucleic acid sequence corresponding to SEQ ID NO: 17); or AdC6-gDPolC (gDPolC nucleic acid sequence corresponding to SEQ ID NO: 19). Two months after the first injection, AdC6 vector-immunized mice were boosted with AdC7 vectors containing the same insert (e.g. AdC7-gDCore, AdC7-gDPolN, or AdC7-gDPolC). Mice were bled at 14 days and 56 days after the injection and T cell frequencies to the various HBV inserts were analyzed by intracellular cytokine staining (ICS) for interferon (IFN)-γ upon stimulation of cells with overlapping peptides representing the HBV sequences. Control cells were cultured without peptides. Frequencies and phenotype of CD8+ T cells to one immunodominant epitope within PolN were tested for by staining with an MHC I tetramer. The breadth and specificity of CD8+ T cell responses to individual peptides within a target sequence was performed via epitope mapping of splenocytes (CD8+ T cells tested by ICS for IFN-γ).

To assess CD8$^+$ T cells in the liver, C57B1/6 mice (n=8 per group) received intravenous administration of $1 \times 10^{10}$ viral genomes (vg) of AAV8-1.3HBV, $1 \times 10^{11}$ vg of AAV8-1.3HBV, or nothing via their tail vein, and 4 weeks later received a single IM injection of $5 \times 10^9$ viral particles (vp) of AdC6-gDPolN. Eight weeks after the IM injection, mice were sacrificed, livers were removed, and lymphocytes were isolated and stained with T cell markers and a tetramer recognizing the T cell receptor to an immunodominant epitope present in the PolN sequence.

In a separate experiment, three groups of C57B1/6 mice (n=4 per group) received a single IM injection of $5 \times 10^9$ vp of AdC6-gDPolN at four weeks (−) or received either intravenous administration of $1 \times 10^{11}$ viral genomes (vg) of AAV8-1.3HBV via their tail vein with or without a single IM injection of $5 \times 10^9$ vp of AdC6-gDPolN four weeks later. Approximately 2 months after administration of AAV8-1.3HBV, mice were sacrificed, livers were removed and liver slices were prepared from each of the three groups, stained with hematoxylin and eosin and evaluated for lymphocytic infiltrates. From the same experiment, cells were stained with a specific tetramer and fluorochrome labeled antibodies to T-bet (clone 4B10, BV785 stain) or antibodies to PD-1 (clone 29F.1A12, BF605 stain), TIM-3 (clone RMT3-23, Pe/Cy7 stain), CTLA-4 (clone UC10-4B9, PE stain), or LAG-3 (clone C9B7W, BV650 stain). Cells were analyzed by flow cytometry and gated on CD44+CD8 tetramer positive cells, which were then gated on the markers. Percent marker positive cells were identified from histograms in comparison to naïve T cells.

Methods—Efficacy

AAV8-1.3HBV Vector Studies—To assess the impact of AdC6-gDPolN on chronic HBV virus exposure, C57B1/6 mice (n=8 per group) were challenged intravenously via their tail vein with $1 \times 10^{10}$ vg of AAV8-1.3HBV and four weeks later immunized with a single IM injection of $5 \times 10^9$ vp of AdC6-gDPolN. HBV DNA viral titers were evaluated by qPCR; pre- and post-vaccination changes from baseline ($\log_{10}$ copies/mL) were reported. Viral genome copy numbers were assessed at four, six, eight, ten, and twelve weeks after AAV8 challenge. Viral dynamics were assessed by PCR over time and the change in log 10 in HBV copies per mL were assessed. The number of mice showing a one, two or three log reductions at different points after treatment was assessed.

Impact of chronic HBV virus exposure on CD8$^+$ T cell antigen recognition over time—The effect of AAV8-1.3HBV on vaccine-induced hepatic CD8$^+$ T cells was assessed. The epitope profile in splenocytes of naïve mice immunized with a single IM injection of $5 \times 10^9$ vp of AdC6-gDPolN was determined 4 weeks after vaccination. Mice challenged with $1 \times 10^{10}$ and $1.5 \times 10^{11}$ vg of AAV8-1.3HBV and subsequently vaccinated with $5 \times 10^9$ vp of AdC6-gDPolN 4 weeks later had CD8+ T cell epitope profiles in splenocytes performed 10 weeks after vaccination (14 weeks after AAV injection). Epitope profiles between AAV-naïve and AAV-treated vaccinated animals were compared. PolN-specific CD8$^+$ T cells from liver were analyzed for differentiation markers.

Results

Immunogenicity—Vaccination induced robust and sustained CD8+ T cell responses to PolN (median frequencies over all circulating CD8+ T cells: 6.0%) and lower responses to PolC and core (median frequencies: 1.0% & 0.4%, respectively; FIG. 9A and FIG. 9B). Boosting at 8 weeks increased responses to all regions with significant changes being observed for core (p=0.007) (FIG. 9C). FIGS. 9A-9C show % CD8+ T cells over all CD8+ T cells for individual mice with medians indicated by the lines. Vaccination induced broad epitope recognition by CD8+ T cells that was further enhanced after boosting (27% to 34%; FIG. 10).

At week 12 following AdC6-gDPolN vaccination, AAV8-1.3HBV-infected vaccinated mice showed a preferential increase in hepatic CD8+ infiltrates (FIGS. 11A-11B and FIG. 12A-12F), a decreased presence of vaccine-induced HBV-specific CD8+ T cells (FIG. 11A and FIG. 11B) and slightly reduced levels of T-bet (suggestive of loss of effector functions) (FIG. 13A-13B). FIG. 11A shows the % CD8+ T cells over all recovered lymphocytes from individual livers. FIG. 11B shows percent tetramer positive CD8+ cells, which were identified from histograms in comparison to naïve T cells. No clear pattern of cellular markers suggestive of T cell differentiation to an exhaustion phenotype was observed, however, between vaccinated AAV1.3HBV-infected and -uninfected mice (FIG. 13A-13B).

Efficacy—Following a single IM injection of the AdC6-gDPolN vector, AAV8-1.3HBV-infected mice had multi-log HBV DNA declines in serum that persisted throughout the 8-week post vaccination period (FIG. 14). Post vaccination, median declines in serum HBV DNA viral load levels at four and eight weeks were 0.86 and 2.69 $\log_{10}$ cps/mL, respectively (FIG. 14A). At week 8, all animals had a >1 $\log_{10}$ cps/mL, 6/7 (86%) had >2 $\log_{10}$ cps/mL, and 2/7 (29%) had >3 $\log_{10}$ cps/mL declines from baseline (FIG. 14B).

Following a single AdC6-gDPolN vector injection, distinct CD8+ T cell recognition patterns to PolN peptides in splenocytes were observed when AAV-HBV-infected and naïve mice were compared. FIG. 15A and FIG. 15B illustrate the results from experiments in which mice were first injected with AAV-1.3HBV and then four weeks later boosted with $10^{10}$ vp of the AdC6-gDPolN vector, splenocytes were harvested 8 weeks after the immunization and tested by ICS for IFN-γ upon a short in vitro stimulation with individual peptides spanning the sequence of PolN. Background frequencies obtained without peptide were subtracted. FIG. 15A shows the peptide recognition profile of mice that received the AdC6-gDPolN vaccine only followed by those that were first injected with the indicated doses of the AAV8-1.3HBV vector. The pie graphs in FIG. 15B show the corresponding responses to peptides that reached the threshold of 0.1% of all CD44+CD8+ cells (data correspond to those in FIG. 15A). Each slice/color represents the frequency of the response to an individual peptide with size showing the proportion of the total; only responses greater than 0.1% were included. Pullouts indicate epitopes only recognized in AAV8-1.3HBV infected mice. It was found that pre-treatment with AAV reduced both the number of epitopes recognized after a single IM prime and the magnitude of the immune response as the sum total of IFN-γ producing CD8+ T cells over the pool of CD8+ T cells. AAV pre-treatment shifted the T cell recognition to new epitopes, which represent roughly a third of the detectable CD8+ T cell response. The percentage of functional HBV-specific CD8+ T cell responses were highest in naïve mice (4.4%, FIG. 15B) but decreased in the presence of low and high dose AAV8-1.3HBV (2.0% & 0.6%; respectively, FIG. 15B). AAV8-1.3HBV-uninfected animals showed strong CD8+ T cell responses to a number of epitopes, which were decreased and shifted in AAV-HBV-infected animals to include T cell recognition of new epitopes.

Discussion

An HBV therapeutic vaccine that targets early CD8+ T cell activation using gD as a genetically encoded checkpoint inhibitor was generated and was shown to:

Induce potent and durable CD8+ T cell responses to key HBV antigens (FIG. 9);

Stimulate very broad CD8+ T cell responses (FIG. 10) that included sub-dominant epitope recognition (FIG. 15); and Achieve sustained multi-log HBV DNA viral load reductions in an AAV mouse model (FIG. 14) with preferential trafficking of functional CD8+ T cells to the liver (FIGS. 11 and 12).

In the disclosed AAV studies, AAV-induced HBV infection caused loss of CD8+ T cell recognition to dominant epitopes of PolN following vaccination with AdC6-gDPolN (FIG. 15). Without intending to be bound by theory, it is believed that it is the breadth of the CD8+ T cells induced by gD and their ability to recognize subdominant epitopes that led to a sustained immune response and multi-log suppression of HBV.

Immunogenicity of AdC6/7-gDPolN in Blood and Liver Following Vaccination in AAV-Induced HBV-Infected Animals The following studies were performed to evaluate CD8+ T cell responses to the AdC6-gDPolN vaccine in blood, spleens, and livers of animals in the presence of pre-existing AAV-induced HBV infection.

Experiment #1—CD8+ T Cell Responses in AAV8-1.3HBV Infected Mice: Response Kinetics in Blood Purpose—To assess the effect of sustained titers of HBV antigen on CD8+ T cell responses to the gDPolN antigen as expressed within the AdC6 vector.

Methods—C57B1/6 mice were injected i.v. with the $10^{10}$ of the AAV8-1.3HBV vector. Four weeks later they were vaccinated with $5\times10^9$ vp of the AdC6-gDPolN vector. Control mice received only the AdC6-gDPolN vector. Naïve mice served as additional controls. Mice were boosted 2 months later with the same dose of the AdC7-gDPolN vaccine. Blood was collected at various times after the prime and the boost and PBMCs were tested for IFN-γ-producing CD8+ T cells.

Results—As shown in FIG. 16, mice mounted a vigorous PolN-specific CD8+ T cell response 2 weeks after vaccination, which gradually declined by week 8 and then increased again after the boost. The CD8+ T cell response was more stable after the boost than after the prime. At most time points tested responses were lower in mice that had been injected with the AAV8-1.3HBV vector than in the controls that had not been injected with an AAV vector.

Experiment #2—CD8+ T Cell Responses in AAV8-1.3HBV Infected Mice: Responses in Liver Purpose—To assess CD8+ T cell responses including markers indicative of T cell exhaustion in livers of AAV8-1.3HBV-infected, vaccinated mice.

Methods—C57B1/6 mice were injected i.v. with the $10^{10}$ or $10^{11}$ vg of the AAV8-1.3HBV vectors. Four weeks later they were vaccinated with $5\times10^9$ vp of the AdC6-gDPolN vector. Control mice received only the AdC6-gDPolN vector. Naïve mice served as additional controls. Mice were boosted 2 months later with the same dose of the AdC7-gDPolN vaccine.

To obtain hepatic lymphocytes, livers were cut into small fragments and treated with 2 mg/ml Collagenase P, 1 mg/ml DNase I (all from Roche, Basel Switzerland) and 2% FBS (Tissue Culture Biologicals, Tulare, CA) in L15 under agitation for 1 hour. Liver fragments were homogenized, filtrated through 70 μm strainers and lymphocytes were purified by Percoll-gradient centrifugation and washed with DMEM supplemented with 10% FBS. Lymphocytes were stained with a violet live/dead dye (Thermo Fisher Scientific), anti-CD8-APC (clone 53-6.7, BioLegend), anti-CD44-Alexa Flour 700 (clone IM7, BioLegend), anti-EOMES-Alexa Fluor 488 (clone Dan11mag, eBioscience), anti-PD1-BV605 (clone 29F.1A12, BioLegend), anti-LAG3-BV650 (clone C9B7W, BioLegend), anti-T-bet-BV786 (clone 4B10, BioLegend), anti-CTLA-4-PE-A (clone UC10-4B9, BioLegend), anti-TIM-3-Pe-Cy7-A (clone RMT3-23, BioLegend), and an APC-labeled MHC class I tetramer (NIH tetramer Facility, Emory University, Atlanta GA) corresponding to amino acids 396-404 FAVPNLQSL (SEQ ID NO: 188) (peptide 55) of the HBV polymerase at +4° C. for 30 min in the dark. Cells were washed and were analyzed by a BD FACS Celesta (BD Biosciences, San Jose, CA) and DiVa software. Post-acquisition analyses were performed with FlowJo (TreeStar, Ashland, OR).

Results—The frequencies of CD8$^+$ T cells within the lymphocytic liver infiltrates were analyzed. Frequencies of CD8$^+$ T cells within the lymphocytic liver infiltrates were increased in vaccinated mice as compared to naïve mice, and further increases were seen in mice that prior to vaccination had been injected with the AAV8-1.3HBV vector (FIG. 17A). Frequencies of PolN-specific CD8$^+$ T cells identified by staining with a tetramer specific for an epitope present in the PolN insert were reduced in AAV-1.3HBV-injected mice (FIG. 17B).

The phenotypes of the infiltrating tetramer$^+$CD8$^+$ T cells in comparison to naïve (i.e., tetramer$^-$CD44$^-$CD8$^+$ T cells) were assessed by determining the mean fluorescent intensity of a dye linked to a given antibody (FIG. 18A-FIG. 18F) and by assessing the percentages (FIG. 19A-FIG. 19F) of CD8$^+$ T cells that were positive for the indicated markers.

T-bet which controls a number of CD8$^+$ T cell functions, was reduced on hepatic CD8$^+$ T cells from mice that had been injected with AAV8-1.3HBV prior to vaccination in comparison the vaccine only group. Exhaustion markers were not increased in AAV8-1.3HBV-pre-treated groups suggesting that the observed loss of PolN-specific CD8$^+$ T cells in presence of HBV was unlikely to be caused by classical CD8$^+$ T cell exhaustion (FIG. 18A-FIG. 18F and FIG. 19A-FIG. 19F).

Experiment #3—Breadth of the PolN-Specific CD8+ T Cell Response in AAV8-1.3HBV Infected Mice Purpose—To assess if the presence of HBV affects the breadth of the CD8$^+$ T cell response to PolN expressed within gD by the AdC vaccines.

Methods—Mice were injected i.v. with the $10^{10}$ or $10^{11}$ vg of the AAV8-1.3HBV vectors and were boosted 2 months later with the corresponding AdC7 vectors. Control mice received only the AdC6-gDPolN vector. Mice were euthanized 10 weeks later and the pooled splenocytes were tested against pools of peptides in the non-AAV infected animal study. Results are provided in FIG. 20A-FIG. 20C.

In a second experiment, mice were injected i.v. with the $10^{10}$ or $10^{11}$ vg of the AAV8-1.3HBV vectors. Four weeks later they were vaccinated with $5 \times 10^{10}$vp of the AdC6-gDPolN vector. Control mice received only the AdC6-gDPolN vector. Naïve mice served as additional controls. Splenocytes were analyzed 6 weeks later for IFN-γ-producing CD8$^+$ T cells in response to individual peptides spanning the PolN sequence. Results are provided in FIG. 20D-FIG. 20F.

Results—The presence of HBV, especially high titers of HBV such as after injection with the $10^{11}$ vg dose of AAV8-HBV1.3, not only reduced overall CD8$^+$ T cell responses to the PolN sequence as presented by the AdC6-gDPolN vaccine but also caused a shift in the epitope recognition profile.

Experiment #4—Functions of Hepatic PolN-Specific CD8$^+$ T Cells in AAV8-1.3HBV Infected Mice Purpose—To evaluate if liver-infiltrating PolN-specific CD8$^+$ T cells remain functional in AAV8-1.3HBV infected mice.

Methods—In the first experiment, C57BL/6 mice were injected i.v. with $3 \times 10^{11}$ vg of AAV8-1.3HBV. One group was vaccinated 8 weeks later with $5 \times 10^{10}$ vp of AdC6-gDPolN vector. The other group was left unvaccinated. Mice were euthanized 4.5 months later and splenocytes were tested for frequencies of CD8$^+$ T cells producing IFN-γ in response to the PolN peptide pool.

In the second experiment, mice were injected with graded concentrations of AAV8-1.3HBV ($1 \times 10^{10}$, $4 \times 10^{10}$, or $1 \times 10^{11}$). All mice were vaccinated 4 weeks later with $5 \times 10^{10}$ vp of the AdC6-gDPolN vector. The mice were boosted 2 months later with the same dose of the AdC7-gDPolN vector. Mice were euthanized 2 months later and lymphocytes were isolated from livers and tested for CD8$^+$ T cells producing IFN-γ in response to the PolN peptide pool. Cells were also stained with an antibody to Tox, a transcription factor that increases in exhausted T cells.

Results—As shown in FIG. 21, vaccine-induced CD8$^+$ T cells remained functional in mice that had been injected with the AAV8-1.3HBV vector.

Experiment #5—Effect of Vaccination of AAV8-1.3HBV Infected Mice on Liver Histology Purpose—To assess if AdC6/7-gDPolN vaccination of AAV.8-1.3HBV-vaccinated mice causes sustained liver damage.

Methods—Mice were injected with $10^{10}$ vg of the AAV8-1.3HPV given i.v. One month later they were vaccinated with $5 \times 10^9$ vp of the AdC6-gDPolN vector. The mice were boosted 2 months later with the same dose of the AdC7-gDPolN vector given at the same dose. The mice were euthanized ~2 months later. Liver sections were collected and fixed in 10% formaldehyde. Sections (~3 μm in thickness) were prepared and stained with Hematoxylin Eosin (H&E). They were reviewed under a light microscope at 20× magnification.

Results—One out of 33 sections from mice that had received both the AAV vector and the vaccine showed a small lymphocytic infiltrate that was at the margin of the liver section.

As shown in FIG. 21B, following a single gDPolN vaccination in HLA-A2-tg mice, frequencies of IFN-γ producing hepatic CD8$^+$ T cells were reduced in mice receiving AAV as compared to those that had only been vaccinated.

Conclusions

CD8$^+$ T cell responses to PolN were reduced in AAV8-1.3HBV infected mice. Nevertheless, they remained detectable.

Exhaustion markers were not increased in AAV8-1.3HBV pre-treated animals suggesting that the observed loss of PolN-specific CD8$^+$ T cells in the presence of HBV was unlikely to be caused by classical CD8$^+$ T cell exhaustion.

AAV-induced HBV-infection caused a shift in the epitope recognition profile of CD8$^+$ T cell responses to PolN.

Vaccine-induced CD8$^+$ T cells remained functional in mice that had been previously infected with the AAV8-1.3HBV vector.

The vaccine used in a prime boost regimen did not cause overt liver damage in HBV positive mice.

Generation of HBV PolN-PolC-Core Constructs

Two multi-antigen inserts (second generation PolN-PolC-Core and third generation PolN-PolC-Core) were generated. The sequences of these inserts are shown below:

2$^{nd}$ generation HBV vaccine insert ("HBV2")(Pol N talics)-Pol C (underlined)-Core)

(SEQ ID NO: 174)

YLPLDKGIKPYYPEHAVNHYFQTRHYLHTLWKAGILYKRETTRSASFCGS

PYSWEQELQHGSCWWLQFRNSKPCSEYCLTHLVNLLEDWGPCDEHGEHHI

RIPRTPARVTGGVFLVDKNPHNTAESRLVVDFSQFSRGITRVSWPKFAVP

NLQSLTNLLSSNLSWLSLDVQAFTFSPTYKAFLSKQYLNLYPVARQRPGL

CQVFADATPTGWGLAMGHQRMRGTFVAPLPIHTAELLAACFARSRSGAKI

LGTDNSVVLSRKYTSFPWLLGCAANWILRGTSFVYVPSALNPADDVGSNL

EDPASRELVVSYVNVNMGLKIRQLLWFHISCLTFGRETVIEYLVSFGVWI

RTPPAYRPPNAPILSTLPETTVVRRRDRGR

3$^{rd}$ generation HBV vaccine insert ("HBV3")(Pol N (italics)-Pol C (underlined)-Core)

(SEQ ID NO: 175)

HFRKLLLLLDEEAGPLEEELPRLADEGLNRRVAEDLNLGNLPEWQTPSFPK

IHLQEDIVDRCKQFVGPLTVNEKRRLKLIMPARFYPNVTKYLPLDKGIKP

YYPEHAVNHYFQTRHYLHTLWKAGILYKRETTRSASFCGSPYSWEQELQH

GSCWWLQFRNSKPCSEYCLTHLVNLLEDWGPCDEHGEHHIRIPRTPARVT

QAFTFSPTYKAFLSKQYLNLYPVARQRPGLCQVFADATPTGWGLAMGHQR

MRGTFVAPLPIHTAELLAACFARSRSGAKILGTDNSVVLSRKYTSFPWLL

GCAANWILRGTSFVYVPSALNPADDVGSNLEDPASRELVVSYVNVNMGLK

IRQLLWFHISCLTFGRETVIEYLVSFGVWIRTPPAYRPPNAPILSTLPET

TVVRRRDRGR

The second generation HBV ("HBV2") insert includes immuno-dominant PolN epitopes identified from mice that had not been infected with the AAV8-1.3HBV vector prior to vaccination. Many of these epitopes were found to be lost in a mouse model of chronic HBV infection brought about by pre-administering an AAV8-1.3HBV vector (as defined in "Epitope Shifting" above). The third generation HBV ("HBV3") insert selects for contiguous regions of PolN that were preferentially recognized by mice with high loads of HBV (see above). Regions of Core and PolC were selected for both constructs using the following general formula: regions with the highest immune responses on either prime (FIG. 3) or boost (FIG. 5) regions in C57B1/6, BALBc and HLA-A2 tg mice, and with the aim of selecting a large contiguous region instead of selecting unique epitopes and inserting spacer sequences between them.

Genetic Integrity and Stability of the 2$^{nd}$ and 3$^{rd}$ Generation HBV Inserts (HBV2 and HBV3)

Western Blot—Purified recombinant viral vector preparations (AdC6-gDHBV2, AdC6-gDHBV3, AdC7-gDHBV2, and AdC7-gDHBV3) were evaluated for their ability to elicit transgene-product expression in vitro. To that end, Western Blot assays were performed to assess the expression of gD protein in cell lysates following cell culture infection with the vector of interest. Adherent HEK293 cell monolayers were infected with known quantities of the purified vector and harvested at 48 hours post-infection, resuspended in lysis and extraction buffer containing protease inhibitors, and lysed by sonication. The total protein extracts were denatured by the use of dithiothreitol as a redox agent and submitted to electrophoresis in a 12% Bis-Tris polyacrylamide gel (PAGE). Subsequent to protein separation by SDS-PAGE, the samples were transferred onto an activated polyvinylidene difluoride membrane by wet electrophoretic transfer. The membrane was immunostained for the detection of gD protein using the primary antibody to gD diluted to 1:1000 in saline (clone PAI-30233, Invitrogen, Carlsbad, CA) for 1 h at room temperature. Membranes were washed with 1×TBS-T prior to incubating with HRP-conjugated goat anti-rabbit secondary IgG (ab6721, Abcam, Cambridge UK) for 1 h at room temperature. This was followed by the addition of a luminol-based chemiluminescent substrate. The stained membrane was exposed to an autoradiography film and signal emission was evaluated after processing by an automated film developer. Following documentation of the gD protein expression in infected HEK293 cell lysates, the membrane was stripped and re-probed for the presence of R-actin in the total protein extract samples. This staining step was employed to evaluate the consistency of the PAGE sample loading step and thus better support the semi-quantitative analysis of the in vitro stimulation of gD protein expression by the recombinant viral vector.

Stability—To ensure the genetic integrity of the viral construct, the genetic stability of each recombinant viral vector lot was assessed through sequential viral passages in adherent HEK293 cell cultures. The recombinant virus pool resulting from each transfection was cultured under standard growing conditions for a total of 12 passages. In the last passage, the virus pool was expanded and the crude harvest purified by cesium chloride gradient. Following vector purification, viral DNA was isolated using the QIAGEN DNeasy Blood & Tissue Kit and evaluated by restriction enzyme digest with Ase I and Bgl II, two restriction enzymes that cleave the DNA template in distinct construct-specific predefined banding patterns. After digestion, samples were submitted to electrophoresis in 1% agarose gel containing ethidium bromide to allow for the visualization of the digested bands, followed by documentation of results using a digital gel imaging system. Viral preparations that exhibited banding patterns identical to those of an early passage virus were considered to have maintained the original molecular clone structure and thus deemed stable at the end of 12 viral passages.

Results—The banding patterns of viral vector DNAs remained stable after 12 passages compared to that after 5 passages indicating the vector genomes were stable (data not shown).

Immunogenicity of the 2$^{nd}$ and 3$^{rd}$ Generation HBV Inserts (HBV2 and HBV3) as Expressed by AdC6 or AdC7 Vectors Purpose—To assess CD8$^+$ T cell responses to the HBV2 and HBV3 inserts expressed by AdC6 vectors or AdC7 vectors.

Methods—Groups of C57B1/6 mice were injected with 5×10$^9$ or 5×10$^{10}$ vp of AdC6-gDHBV2 or AdC6-gDHBV3 vector. Mice injected with the same doses of the AdC6-gDPolN vector served as positive controls; naïve mice served as negative controls. Mice were bled 14 days later and PBMCs were tested for frequencies of CD8$^+$ T cells producing IFN-γ in response to peptide pools corresponding to the HBV inserts. Four weeks later (6 weeks after vaccination) mice were bled again and tested with the PolN-specific tetramer. AdC6-gDHBV3 immunized mice were excluded as this insert lacks the epitope that corresponds to the tetramer.

Groups of C57B1/6 mice were injected with $5\times10^9$ or $5\times10^{10}$ vp of AdC7-gDHBV2 or $5\times10^{10}$ vp of AdC7-gDHBV3 vector. Naïve mice served as negative controls. Mice were bled 14 days later and PBMCs were tested for frequencies of CD8$^+$ T cells producing IFN-γ in response to peptide pools corresponding to the HBV inserts.

Immunogenicity of AdC7 Prime AdC6 Boost

Mice were bled ~4 weeks later and PBMCs were retested by ICS for CD8$^+$ T cells producing IFN-γ and/or TNF-α in response to the peptides for the inserts. Mice were boosted two months after the prime with the same dose of the heterologous vector expressing the same insert. PBMCs were tested by ICS 2 weeks later and pre- and post-boost CD8$^+$ and CD4$^+$ T cell responses were compared. The AdC7-gDHBV2 vector induced robust frequencies of CD8$^+$ T cells producing IFN-γ and/or TNF-α after the prime. Frequencies increased after the AdC6-gDHBV2 boost and this was especially pronounced after the low vector doses and for CD8$^+$ T cells producing IFN-γ. The AdC7-gDHBV3 vector was poorly immunogenic but CD8$^+$ T cell responses became positive after the AdC6-gDHBV3 boost. In the same token CD4+ T cell responses were marginal after the prime but increased after the boost. There was no marked difference in CD4 responses to the HBV2 or HBV3 insert.

Conclusions

Both the AdC6-gDHBV2 and AdC7-gDHBV2 vectors were highly immunogenic (FIG. 22A, FIG. 22B, and FIG. 23) and responses increased after a boost with a heterologous AdC vector expressing the same insert (FIG. 24).

The AdC7-gDHBV2 and AdC7-gDHBV3 vectors displayed borderline immunogenicity consistent with their design as they lack the epitope that corresponds to the tetramer being used (FIG. 22A and FIG. 23).

Boosting AdC7-gDHBV2 with AdC6-gDHBV2 enhances CD8$^+$ T cell responses.

Comparison of HBV DNA Viral Titers in AdC6-gDPolN, AdC6-gDHBV2, AdC6-gDHBV3, or AdC6-HBV2 AAV-Infected Mice Methods Five groups of C57B1/6 mice were challenged with $1\times10^9$ vg of AAV8-1.3HBV and were vaccinated 4 weeks later with $1\times10^{10}$ vp of either AdC6-gDPolN (n=10), AdC6-gDHBV2 (n=10), AdC6-gDHBV3 (n=10), or AdC6-HBV2 without gD (n=10); AAV-infected, non-vaccinated animals ("naïve") (n=10) and non-AAV-infected, non-vaccinated animals (n=2-5) served as controls. Viral titers were tested 4 weeks after AAV injection (before vaccination) and compared to levels 4 weeks after vaccination (week 8 after AAV injection).

Results

At week 8, the median HBV viral titers increased by 0.98 $\log_{10}$ cps/mL in naïve mice, remained unchanged in AdC6-HBV2 vaccinated mice, and declined by −0.04, −1.09 and −2.13 $\log_{10}$ cps/mL in AdC6-gDHBV3, AdC6-gDPolN and AdC6-gDHBV2 vaccinated animals, respectively (FIG. 25A). The results for individual mice are shown in FIG. 25B—all AdC6-gDPolN and AdC6-gDHBV2 vaccinated animals had greater than 1 and 2 $\log_{10}$ copies/mL declines, respectively; in contrast, none of the naïve, AdC6-HBV2, or AdC6-gDHBV3 vaccinated animals had a 1 $\log_{10}$ copies/mL or greater decline at Week 8.

Immunogenicity Studies for gDHBV2 and gDHBV3

The induction of CD8$^+$ T cell responses and their breadth to segments of HBV core and polymerase contained in either gDHBV2 or gDHBV3 following a single prime injection or prime followed by a boost vaccination with a heterologous vector containing the same insert were evaluated.

Experiment 1

Purpose: Assess IFN-γ$^+$ CD8$^+$ T cell responses following prime and boost vaccinations with gD-HBV2 and gD-HBV3 expressed by heterologous chimpanzee adenoviral vectors (AdC6 and AdC7) in C57B1/6 mice.

Methods: Four groups of five C57B1/6 mice were immunized via intramuscular injection as follows: (a) $5\times10^{10}$ vp AdC7-gDHBV2 followed two months later by $5\times10^{10}$ vp AdC6-gDHBV2; (b) $5\times10^9$ vp AdC7-gDHBV2 followed two months later by $5\times10^9$ vp AdC6-gDHBV2; (c) $5\times10^{10}$ vp AdC7-gDHBV3 followed two months later by $5\times10^{10}$ vp AdC6-gDHBV3; or (d) no vaccine. Blood was assessed by ICS for IFN-γ$^+$ CD8$^+$ T cell responses 2 and 6 weeks after the prime, prior to the boost, and then 2 and 4 weeks after the boost.

Figures 26C, 26D:
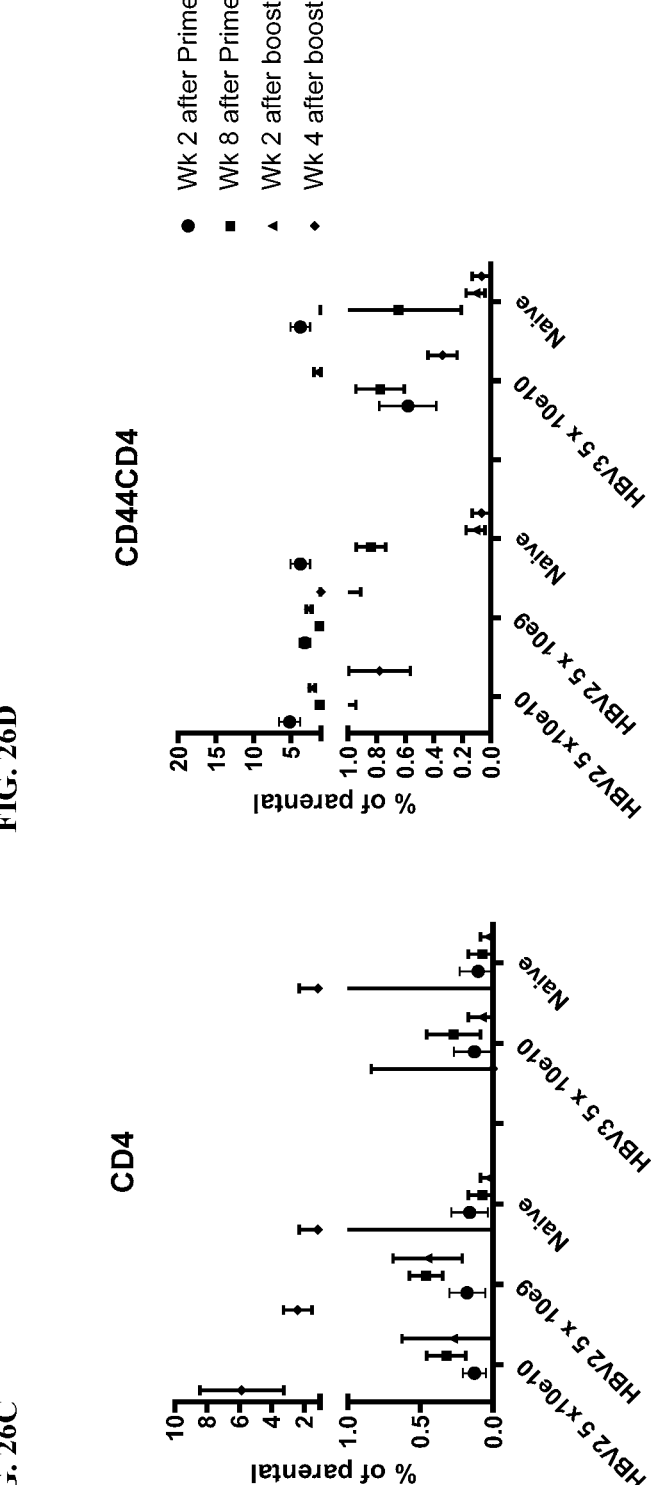

Results: At all time points tested each vaccine construct was found to induce IFN-γ$^+$ CD8$^+$ T cells. FIG. 26 shows the percent of parental IFN-γ and/or TNF-α producing CD8$^+$ T cells (FIG. 26A), CD44+CD8+ T cells (FIG. 26B), CD4+ T cells (FIG. 26C) or CD44+CD4+ T cells (FIG. 26D). Immune responses as assessed by ICS from PBMCs of individual mice are shown two and eight weeks after the prime, as well as two and four weeks after the boost as the mean.

Experiment 2

Purpose: Compare IFN-γ$^+$ CD8$^+$ T cell responses following different doses of prime and boost vaccinations with gD-HBV2 and gD-HBV3 to that with gD-PolN using heterologous chimpanzee adenoviral vectors (AdC6 and AdC7) in C57B1/6 mice.

Methods: Groups of C57B1/6 mice (n=5 mice/group) were immunized as follows:

gDPolN Groups
  (a) $5\times10^9$ vp AdC6-gDPolN followed three months later by $5\times10^9$ vp AdC7-gDPolN; and
  (b) $5\times10^{10}$ vp AdC6-gDPolN followed three months later by $5\times10^{10}$ vp AdC7-gDPolN gDHBV2 Groups
  (c) $5\times10^9$ vp AdC6-gDHBV2 followed three months later by $5\times10^9$ vp AdC7-gDHBV2 and;
  (d) $5\times10^{10}$ vp AdC6-gDHBV2 followed three months later by $5\times10^{10}$ vp AdC7-gDHBV2 gDHBV3 Groups
  (e) $5\times10^9$ vp AdC6-gDHBV3 followed three months later by $5\times10^9$ vp AdC7-gDHBV3 and;
  (f) $5\times10^{10}$ vp AdC6-gDHBV3 followed three months later by $5\times10^{10}$ vp AdC7-gDHBV3

No Treatment Served as Controls

For all treatment groups, immunogenicity CD8$^+$ T cell responses was from blood assessed by ICS for IFN-γ$^+$ at two and six weeks after the prime, prior to the boost, and then two and six weeks after the boost. Immunogenicity was also assessed by tetramer staining using an APC-labeled MHC class I tetramer (NIH tetramer Facility, Emory University, Atlanta GA) corresponding to amino acids 396-404 FAVPNLQSL (peptide 55) of the HBV polymerase at week four after the prime. HBV3 does not contain the FAVPNLQSL peptide.

Results: At all time points, each vaccine tested was found to induce IFN-γ$^+$CD8$^+$ T cells. Results obtained with the gDHBV2 vaccine were similar to those obtained with the gDPolN vaccine; the gDHBV3 vaccine was less immunogenic. Upon tetramer staining, frequencies of the specific CD8$^+$ T cells were comparable between the two vaccines; a number of activation markers tended to be more highly expressed on tetramer+CD8+ T cells from the gDHBV2-immunized groups. FIG. 27 shows CD8$^+$ T cells at multiple time points: four weeks after prime (FIG. 27A); two weeks after the boost (FIG. 27B); and four weeks after the boost (FIG. 27C). The graph shows the overall frequencies of CD8$^+$ T cells producing IFN-$\gamma^+$ as assessed by ICS.

FIG. 28 shows cytokine-producing CD4+ T cells at multiple time points: four weeks after prime (FIG. 28A); two weeks after the boost (FIG. 28B); and four weeks after the boost (FIG. 28C) as assessed by ICS. The dashed line indicates the cut-off for positive responses, based on the results from the naïve mice.

FIG. 29 shows the results of tetramer staining gated on either CD8+ T cells (FIG. 29A) or CD44+CD8+ T cells (FIG. 29B) at four weeks after the prime.

FIG. 30 shows the phenotypes of the tetramer+CD8+ T cells shown as the mean fluorescent intensity of a dye linked to the indicated antibody: FIG. 30A anti-PD1 antibody conjugated to BV605; FIG. 30B anti-LAG3 antibody conjugated to BV650; FIG. 30C anti-TIM3 antibody conjugated to Pe-Cy7-A; FIG. 30D anti-CTLA4 antibody conjugated to PE-A; FIG. 30E anti-EOMES antibody conjugated to AF488; and FIG. 30F anti-T-bet antibody conjugated to BV786.

Experiment 3

The breadth of responses were assessed from pooled splenocytes of vaccinated C57BL/6 mice which were tested by ICS against the individual peptides present in the HBV vaccine inserts.

Methods: Four groups of five C57B1/6 mice were immunized via intramuscular injection as follows: (a) 5×10$^{10}$ vp AdC7-gDHBV2 followed two months later by 5×10$^{10}$ vp AdC6-gDHBV2; (b) 5×10$^9$ vp AdC7-gDHBV2 followed two months later by 5×10$^9$ vp AdC6-gDHBV2; (c) 5×10$^{10}$ vp AdC7-gDHBV3 followed two months later by 5×10$^{10}$ vp AdC6-gDHBV3; or (3) no vaccine. Animals were sacrificed eight weeks after the boost and pooled splenocytes were assessed by ICS for IFN-$\gamma^+$ CD8$^+$ T cell responses to individual HBV2 or HBV3 peptides (cut-off for positive responses set at 0.1%).

Results: Independent of the dose, the prime boost regimen with the gDHBV2 vaccines induced responses to several epitopes within core and polymerase. FIG. 31 shows the CD8$^+$ T cell responses after a prime vaccination of 5×10$^{10}$ vp AdC7-gDHBV2 followed two months later by vaccination with 5×10$^{10}$ vp AdC6-gDHBV2. Numbers on the X axis correspond to the SEQ ID NO as provided herein. FIG. 32 shows the CD8+ T cell responses after a prime vaccination with 5×10$^9$ vp AdC7-gDHBV2 followed two months later by vaccination with 5×10$^9$ vp AdC6-gDHBV2. Numbers on the X axis correspond to the SEQ ID NO as provided herein. FIG. 33 shows the immunogenicity after a prime vaccination with 5×10$^{10}$ vp AdC7-gDHBV3 followed two months later by vaccination with 5×10$^{10}$ vp AdC6-gDHBV3. Numbers on the X axis correspond to the SEQ ID NO as provided herein.

Experiment 4

The breadth of responses were assessed from pooled splenocytes of vaccinated BALB/c mice which were tested by ICS against the individual peptides present in the HBV vaccine inserts.

Methods: Five groups of five BALB/c mice were immunized via intramuscular injection as follows: (a) 5×10$^{10}$ vp AdC6-gDHBV2; (b) 5×10$^{10}$ vp AdC6-gDHBV3; (c) 5×10$^{10}$ vp AdC7-gDHBV2; (d) 5×10$^{10}$ vp AdC7-gDHBV3; or (e) no vaccine. 12 weeks post vaccination animals were sacrificed, spleens were collected and pooled splenocytes were assessed by ICS for IFN-$\gamma^+$ CD8$^+$ T cell responses to individual HBV2 or HBV3 peptides (cut-off for positive responses set at 0.1%).

Results: At week 12, each vaccine construct was found to be immunogenic across multiple regions of the Core and Polymerase genes delivered by the vaccine. FIG. 34 shows the immunogenicity of the AdC6-gDHBV2 and AdC7-gDHBV2 vaccines corresponding to the SEQ ID NO (X axis) as provided herein. Core, PolC, and PolN regions in both HBV2 constructs were immunogenic. FIG. 35 shows the immunogenicity of the AdC6-gDHBV3 and AdC7-gDHBV3 vaccines corresponding to the SEQ ID NO (X axis) as provided herein. Core, PolC, and PolN regions in both HBV3 constructs were immunogenic.

Experiment 5

Methods: Five groups of C57B1/6 mice were challenged with 1×10$^9$ vg of AAV8-1.3HBV and were vaccinated 4 weeks later ("prime vaccination") with 1×10$^{10}$ vp of either AdC6-gDPolN (n=10), AdC6-gDHBV2 (n=10), AdC6-gDHBV3 (n=10), or AdC6-HBV2 without gD (n=10); AAV-infected, non-vaccinated animals (n=10) and non-AAV-infected, non-vaccinated animals (n=2-5) serve as controls. Mice will be bled at various times after the injection and frequencies of insert-specific CD8+ and CD4+ T cells will be determined by intracellular cytokine staining (ICS) for IFN-$\gamma$. PCR will be performed at 2 weeks, 6 weeks, and 8 weeks after the prime vaccination, and a T cell assay will be performed at 4 weeks after the prime vaccination.

At 8 weeks following the prime vaccination, mice will be boosted with AdC7 vectors containing the same antigenic insert used in the prime vaccination ("boost vaccination") and blood and serum will be tested for CD8+/CD4+ T cell as previously described at different time points after vaccination. PCR will be performed at 2 weeks, 6 weeks, and 10 weeks after the boost vaccination, and a T cell assay will be performed at 4 weeks and 12 weeks after the boost vaccination.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in their entirety.

TABLE 9

| Sequences |
| --- |

| | Sequence |
| --- | --- |
| Genotype A Consensus (SEQ ID NO: 1) | MDIDPYKEFGATVELLSFLPSDFFPSVRDLLDTASAL YREALESPEHCSPHHTALRQAILCWGELMTLATWVGN NLeDPASRDLVVNYVNTNMGLKIRQLLWFHISCLTFG RETVLEYLVSFGVWIRTPPAYRPPNAPILSTLPETTV VRRRDRGRSPRRRTPSPRRRRSQSPRRRRSQSRESQC |

TABLE 9-continued

| Sequences |
|---|
| Sequence |

Genotype B
Consensus
(SEQ ID NO: 2)

MDIDpYKEFGASvELLSFLPSDFFPSiRDLLDTAsAL
YREALESPEHCSPHHTALRQAIlCWGELMNLATWVGS
NLeDPASRELVVsYVNVNMGLKiRQLLWFHISCLTFG
RETVLEYLVSFGVWIRTPpAYRPpNAPILSTLPETTV
VRRRGRSPRRRTPSPRRRRSQSPRRRRSQSREsQC

Genotype C
Consensus
(SEQ ID NO: 3)

MDIDpYKEFGASVELLSFLPSDEEPSIRDLLDTASAL
YREALESPEHCSPHHTALRQAILCWGELMNLATWVGS
NLEDPASRELVVsYVNVNMGLKiRQlLWFHISCLTFG
RETVLEYLVSFGVWIRTPpAYRPPNAPILSTLPETTV
VRRRGRSPRRRTPSPRRRRSQSPRRRSQSRESQC

Genotype D
Consensus
(SEQ ID NO: 4)

MDIDPYKEFGAtVELLSFLPsDFFPSVRDLLDTASALYReAL
ESPEHCSPHHTALRQAILCWGeLMtLATWVGgNLEDPaSRDL
VVSYVNTNmGLKFRQLLWFHISCLTFGReTViEYLVSFGVWI
RTPpAYRPPNAPILSTLPETTVvRRRGRSPRRRTPSPRRRRS
QSPRRRRSQSRESQC

Initial Core
sequence
(SEQ ID NO: 5)

MDIDPYKEFGAX$_1$VELLSFLPSDFFPSX$_2$DLLDTASALYREAL
ESPEHCSPHHTALRQAILCWGELMX$_3$LATWVGX$_4$NLeDPASRX$_5$
LVVX$_6$YVNX$_7$NMGLKX$_8$RQLLWFHISCLTFGRETVX$_9$EYLVSF
GVWIRTPPAYRPPNAPILSTLPETTVVRRRX$_{10}$X$_{11}$GRSPRRRT
PSPRRRRSQSPRRRRSQSRESQC

Epitope-
optimized Core
amino acid
sequence
(SEQ ID NO: 6)

DIDPYKEFGATVELLSFLPSDFFPSIRDLLDTASALYREALE
SPEHCSPHHTALRQAILCWGELMTLATWVGSNLEDPASRELV
VSYVNVNMGLKIRQLLWFHISCLTFGRETVIEYLVSFGVWIR
TPPAYRPPNAPILSTLPETTVVRRRDRGRSPRRRTPSPRRRR
SQSPRRRRSQSRESQC

Epitope-
optimized Core
nucleotide
sequence
(SEQ ID NO: 7)

GACATCGACCCCTACAAGGAGTTCGGCGCCACCGTGGAGCTG
CTGAGCTTCCTGCCCAGCGACTTCTTCCCCAGCATCAGGGAC
CTGCTGGACACCGCCAGCGCCCTGTACAGGGAGGCCCTGGAG
AGCCCCGAGCACTGCAGCCCCCACCACACCGCCCTGAGGCAG
GCCATCCTGTGCTGGGGCGAGCTGATGACCCTGGCCACCTGG
GTGGGCAGCAACCTGGAGGACCCCGCCAGCAGGGAGCTGGTG
GTGAGCTACGTGAACGTGAACATGGGCCTGAAGATCAGGCAG
CTGCTGTGGTTCCACATCAGCTGCCTGACCTTCGGCAGGGAG
ACCGTGATCGAGTACCTGGTGAGCTTCGGCGTGTGGATCAGG
ACCCCCCCCGCCTACAGGCCCCCCAACGCCCCCATCCTGAGC
ACCCTGCCCGAGACCACCGTGGTGAGGAGGAGGGACAGGGGC
AGGAGCCCCAGGAGGAGGACCCCCAGCCCCAGGAGGAGGAGG
AGCCAGAGCCCCAGGAGGAGGAGGAGCCAGAGCAGGGAGAGC
CAGTGC

Epitope-
optimized
polymerase N-
terminal amino
acid sequence
(SEQ ID NO: 8)

PLSYQHFRKLLLLLDEEAGPLEEELPRLADEGLNRRVAEDLNL
GNLNVSIPWTHKVGNFTGLYSSTVPVFNPEWQTPSFPKIHLQ
EDIVDRCKQFVGPLTVNEKRRLKLIMPARFYPNVTKYLPLDK
GIKPYYPEHAVNHYFQTRHYLHTLWKAGILYKRETTRSASFC
GSPYSWEQELQHGSCWWLQFRNSKPCSEYCLTHLVNLLEDWG
PCDEHGEHHIRIPRTPARVTGGVFLVDKNPHNTAESRLVVDF
SQFSRGITRVSWPKFAVPNLQSLTNLLSSNLSWLSLDVSAAF
YHIPLHPAAMP

Epitope-
optimized
polymerase N-
terminus
nucleotide
sequence
(SEQ ID NO: 9)

CCCCTGAGCTACCAGCACTTCAGGAAGCTGCTGCTGCTGGAC
GAGGAGGCCGGCCCCCTGGAGGAGGAGCTGCCCAGGCTGGCC
GACGAGGGCCTGAACAGGAGGGTGGCCGAGGACCTGAACCTG
GGCAACCTGAACGTGAGCATCCCCTGGACCCACAAGGTGGGC
AACTTCACCGGCCTGTACAGCAGCACCGTGCCCGTGTTCAAC
CCCGAGTGGCAGACCCCCAGCTTCCCCAAGATCCACCTGCAG
GAGGACATCGTGGACAGGTGCAAGCAGTTCGTGGGCCCCCTG
ACCGTGAACGAGAAGAGGAGGCTGAAGCTGATCATGCCCGCC
AGGTTCTACCCCAACGTGACCAAGTACCTGCCCCCTGGACAAG
GGCATCAAGCCCTACTACCCCGAGCACGCCGTGAACCACTAC
TTCCAGACCAGGCACTACCTGCACACCCTGTGGAAGGCCGGC
ATCCTGTACAAGAGGGAGACCACCAGGAGCGCCAGCTTCTGC
GGCAGCCCCTACAGCTGGGAGCAGGAGCTGCAGCACGGCAGC
TGCTGGTGGCTGCAGTTCAGGAACAGCAAGCCCTGCAGCGAG
TACTGCCTGACCCACCTGGTGAACCTGCTGGAGGACTGGGGC

TABLE 9-continued

| Sequences |
| --- |

| Sequence |
| --- |

CCCTGCGACGAGCACGGCGAGCACCACATCAGGATCCCCAGG
ACCCCCGCCAGGGTGACCGGCGGCGTGTTCCTGGTGGACAAG
AACCCCCACAACACCGCCGAGAGCAGGCTGGTGGTGGACTTC
AGCCAGTTCAGCAGGGGCATCACCAGGGTGAGCTGGCCCAAG
TTCGCCGTGCCCAACCTGCAGAGCCTGACCAACCTGCTGAGC
AGCAACCTGAGCTGGCTGAGCCTGGACGTGAGCGCCGCCTTC
TACCACATCCCCCTG CACCCCGCCGCCATGCCC

Epitope-
optimized
polymerase C-
terminal amino
acid sequence
(SEQ ID NO: 10)

HLLVGSSGLSRYVARLSSNSRIINHQHGTMQNLHDSCSRNLY
VSLLLLYKTFGRKLHLYSHPIILKTKRWGYSLNFMGYVIGSW
GSLPQDHIIQKIKECFRKLPVNRPIDWKVCQRIVGLLGFAAP
FTQCGYPALMPLYACIQSKQAFTFSPTYKAFLSKQYLNLYPV
ARQRPGLCQVFADATPTGWGLAMGHQRMRGTFVAPLPIHTAE
LLAACFARSRSGAKILGTDNSVVLSRKYTSFPWLLGCAANWI
LRGTSFVYVPSALNPADDPSRGRLGLSRPLLRLPFRPTTGRT
SLYAVSPSV

Epitope-
optimized
polymerase C-
terminal
nucleotide
sequence
(SEQ ID NO: 11)

CACCTGCTGGTGGGCAGCAGCGGCCTGAGCAGGTACGTGGCC
AGGCTGAGCAGCAACAGCAGGATCATCAACCACCAGCACGGC
ACCATGCAGAACCTGCACGACAGCTGCAGCAGGAACCTGTAC
GTGAGCCTGCTGCTGCTGTACAAGACCTTCGGCAGGAAGCTG
CACCTGTACAGCCACCCCATCATCCTGAAGACCAAGAGGTGG
GGCTACAGCCTGAACTTCATGGGCTACGTGATCGGCAGCTGG
GGCAGCCTGCCCCAGGACCACATCATCCAGAAGATCAAGGAG
TGCTTCAGGAAGCTGCCCGTGAACAGGCCCATCGACTGGAAG
GTGTGCCAGAGGATCGTGGGCCTGCTGGGCTTCGCCGCCCCC
TTCACCCAGTGCGGCTACCCCGCCCTGATGCCCCTGTACGCC
TGCATCCAGAGCAAGCAGGCCTTCACCTTCAGCCCCACCTAC
AAGGCCTTCCTGAGCAAGCAGTACCTGAACCTGTACCCCGTG
GCCAGGCAGAGGCCCGGCCTGTGCCAGGTGTTCGCCGACGCC
ACCCCCACCGGCTGGGGCCTGGCCATGGGCCACCAGAGGATG
AGGGGCACCTTCGTGGCCCCCCCTGCCCATCCACACCGCCGAG
CTGCTGGCCGCCTGCTTCGCCAGGAGCAGGAGCGGCGCCAAG
ATCCTGGGCACCGACAACAGCGTGGTGCTGAGCAGGAAGTAC
ACCAGCTTCCCCTGGCTGCTGGGCTGCGCCGCCAACTGGATC
CTGAGGGGCACCAGCTTCGTGTACGTGCCCAGCGCCCTGAAC
CCCGCCGACGACCCCAGCAGGGGCAGGCTGGGCCTGAGCAGG
CCCCTGCTGAGGCTGCCCTTCAGGCCCACCACCGGCAGGACC
AGCCTGTACGCCGTGAGCCCCAGCGTG

N-terminal HSV
gD sequence
(SEQ ID NO: 12)
Signal peptide
in italics

*MGGAAARLGAVILFVVIVGLHGVRGK*YALADASLKMADPNRF
RGKDLPVLDQLTDPPGVRRVYHIQAGLPDPFQPPSLPITVYY
AVLERACRSVLLNAPSEAPQIVRGASEDVRKQPYNLTIAWFR
MGGNCAIPITVMEYTECSYNKSLGACPIRTQPRWNYYDSFSA
VSEDNLGFLMHAPAFETAGTYLRLVKINDWTEITQFILEHRA
KGSCKYALPLRIPPSACLSPQAYQQGVTVDSIGMLPRFIPEN
QRTVAVYSLKIAGWHGP

C-terminal HSV
gD sequence
(SEQ ID NO: 13)

GPKAPYTSTLLPPELSETPNATQPELAPEDPEDSALLEDPVG
TVAPQIPPNWHIPSIQDAATPYHPPATPNNMGLIAGAVGGSL
LAALVICGIVYWMHRRTRKAPKRIRLPHIREDDQPSSHQPLF
Y gDCore amino
acid sequence
Core underlined
(SEQ ID NO: 14)
Signal peptide
in italics

*MGGAAARLGAVILFVVIVGLHGVRGK*YALADASLKMADPNRF
RGKDLPVLDQLTDPPGVRRVYHIQAGLPDPFQPPSLPITVYY
AVLERACRSVLLNAPSEAPQIVRGASEDVRKQPYNLTIAWFR
MGGNCAIPITVMEYTECSYNKSLGACPIRTQPRWNYYDSFSA
VSEDNLGFLMHAPAFETAGTYLRLVKINDWTEITQFILEHRA
KGSCKYALPLRIPPSACLSPQAYQQGVTVDSIGMLPRFIPEN
QRTVAVYSLKIAGWHGP<u>DIDPYKEFGATVELLSFLPSDFFPS
IRDLLDTASALYREALESPEHCSPHHTALRQAILCWGELMTL
ATWVGSNLEDPASRELVVSYVNVNMGLKIRQLLWFHISCLTF
GRETVIEYLVSFGVWIRTPPAYRPPNAPILSTLPETTVVRRR
DRGRSPRRRTPSPRRRRSQSPRRRRSQSRESQCGPKAPYTST
LLPPELSETPNATQPELAPEDPEDSALLEDPVG</u>TVAPQIPPN
WHIPSIQDAATPYHPPATPNNMGLIAGAVGGSLLAALVICGI
VYWMHRRTRKAPKRIRLPHIREDDQPSSHQPLFY gDCore nucleic
acid sequence
Core underlined
(SEQ ID NO: 15)

atggggggggctgccgccaggttggggggccgtgattttgtttt
gtcgtcatagtgggcctccatggggtccgcggcaaatatgcc
ttggcggatgcctctctcaagatggccgaccccaatcgcttt
cgcggcaaagaccttccggtcctggaccagctgaccgaccct
ccggggggtccggcgcgtgtaccacatccaggcggggcctaccg
gacccgttccagcccccccagcctcccgatcacggtttactac
gccgtgttggagcgcgcctgccgcagcgtgctcctaaacgca
ccgtcggaggccccccagattgtccgcggggggcctccgaagac TABLE 9-continued

| Sequences |
| --- |

| Sequence |
| --- |

```
gtccggaaacaaccctacaacctgaccatcgcttggtttcgg
atgggaggcaactgtgctatccccatcacggtcatggagtac
accgaatgctcctacaacaagtctctgggggcctgtcccatc
cgaacgcagccccgctggaactactatgacagcttcagcgcc
gtcagcgaggataacctggggttcctgatgcacgcccccgcg
tttgagaccgccggcacgtacctgcggctcgtgaagataaac
gactggacggagattacacagtttatcctggagcaccgagcc
aagggctcctgtaagtacgccctcccgctgcgcatcccccccg
tcagcctgcctctcccccccaggcctaccagcagggggtgacg
gtggacagcatcgggatgctgcccccgcttcatccccgagaac
cagcgcaccgtcgccgtatacagcttgaagatcgccgggtgg
cacgggcccgacatcgacccctacaaggagttcggcgccacc
gtggagctgctgagcttcctgcccagcgacttcttccccagc
atcagggacctgctggacaccgccagcgccctgtacagggag
gccctggagagccccgagcactgcagccccaccacaccgcc
ctgaggcaggccatcctgtgctggggcgagctgatgacccctg
gccacctgggtgggcagcaacctggaggacccccgccagcagg
gagctggtggtgagctacgtgaacgtgaacatgggcctgaag
atcaggcagctgctgtgttccacatcagctgcctgacctttc
ggcagggagaccgtgatcgagtacctggtgagcttcggcgtg
tggatcaggacccccccccgcctacaggcccccaacgcccccc
atcctgagcacccctgcccgagaccaccgtggtgaggaggagg
gacaggggcaggagcccccaggaggaggaccccccagccccagg
aggaggaggagccagagccccaggaggaggaggagccagagc
agggagagccagtgcgggcccaaggcccccatacacgagcacc
ctgctgcccccggagctgtccgagaccccccaacgccacgcag
ccagaactcgccccggaagaccccgaggattcggccctcttg
gaggaccccgtggggacggtggcgccgcaaatcccaccaaac
tggcacatcccgtcgatccaggacgccgcgacgccttaccat
cccccggccaccccgaacaacatgggcctgatcgccggcgcg
gtgggcggcagtctcctggcagccctggtcatttgcggaatt
gtgtactggatgcaccgccgcactcggaaagccccaaagcgc
atacgcctcccccacatccgggaagacgaccagccgtcctcg
caccagcccttgttttactag
```

| gDPolN amino<br>acid sequence<br>PolN underlined<br>(SEQ ID NO: 16)<br>Signal peptide<br>in italics | *MGGAAARLGAVILFVVIVGLHGVRG*KYALADASLKMADPNRF<br>RGKDLPVLDQLTDPPGVRRVYHIQAGLPDPFQPPSLPITVYY<br>AVLERACRSVLLNAPSEAPQIVRGASEDVRKQPYNLTIAWFR<br>MGGNCAIPITVMEYTECSYNKSLGACPIRTQPRWNYYDSFSA<br>VSEDNLGFLMHAPAFETAGTYLRLVKINDWTEITQFILEHRA<br>KGSCKYALPLRIPPSACLSPQAYQQGVTVDSIGMLPRFIPEN<br>QRTVAVYSLKIAGWHGPPLSYQHFRKLLLLDEEAGPLEEELP<br><u>RLADEGLNRRVAEDLNLGNLNVSIPWTHKVGNFTGLYSSTVP</u><br><u>VFNPEWQTPSFPKIHLQEDIVDRCKQFVGPLTVNEKRRLKLI</u><br><u>MPARFYPNVTKYLPLDKGIKPYYPEHAVNHYFQTRHYLHTLW</u><br><u>KAGILYKRETTRSASFCGSPYSWEQELQHGSCWWLQFRNSKP</u><br><u>CSEYCLTHLVNLLEDWGPCDEHGEHHIRIPRTPARVTGGVFL</u><br><u>VDKNPHNTAESRLVVDFSQFSRGITRVSWPKFAVPNLQSLTN</u><br><u>LLSSNLSWLSLDVSAAFYHIPLHPAAMPGPKAPYTSTLLPPE</u><br><u>LSETPNATQPELAPEDPEDSALLEDPVGTVAPQIPPNWHIPS</u><br><u>IQDAATPYHPPATPNNMGLIAGAVGGSLLAALVICGIVYWMH</u><br><u>RRTRKAPKRIRLPHIREDDQPSSHQPLFY</u>* |
| --- | --- |

| gDPolN nucleic<br>acid sequence<br>PolN underlined<br>(SEQ ID NO: 17) | atgggggggggctgccgccaggttgggggccgtgattttgttt<br>gtcgtcatagtgggcctccatggggtccgcggcaaatatgcc<br>ttggcggatgcctctctcaagatggccgaccccaatcgcttt<br>cgcggcaaagaccttccggtcctggaccagctgaccgaccct<br>ccgggggtccggcgcgtgtaccacatccaggcgggcctaccg<br>gacccgttccagcccccagcctcccgatcacggtttactac<br>gccgtgttggagcgcgcctgccgcagcgtgctcctaaacgca<br>ccgtcggaggccccccagattgtccgcggggcctccgaagac<br>gtccggaaacaaccctacaacctgaccatcgcttggtttcgg<br>atgggaggcaactgtgctatccccatcacggtcatggagtac<br>accgaatgctcctacaacaagtctctgggggcctgtcccatc<br>cgaacgcagccccgctggaactactatgacagcttcagcgcc<br>gtcagcgaggataacctggggttcctgatgcacgcccccgcg<br>tttgagaccgccggcacgtacctgcggctcgtgaagataaac<br>gactggacggagattacacagtttatcctggagcaccgagcc<br>aagggctcctgtaagtacgccctcccgctgcgcatcccccccg<br>tcagcctgcctctcccccccaggcctaccagcagggggtgacg<br>gtggacagcatcgggatgctgcccccgcttcatccccgagaac<br>cagcgcaccgtcgccgtatacagcttgaagatcgccgggtgg<br>cacgggcccccccctgagctaccagcacttcaggaagctgctg<br><u>ctgctggacgaggaggccggcccccctggaggaggagctgccc</u><br><u>aggctggccgacgagggcctgaacaggagggtggccgaggac</u><br><u>ctgaacctgggcaacctgaacgtgagcatcccctggacccac</u> |
| --- | --- |

TABLE 9-continued

| Sequences |
| --- |

| Sequence |
| --- |

```
aaggtgggcaacttcaccggcctgtacagcagcaccgtgccc
gtgttcaaccccgagtggcagaccccagcttccccaagatc
cacctgcaggaggacatcgtggacaggtgcaagcagttcgtg
ggtcccctgaccgtgaacgagaagaggaggctgaagctgatc
atgcccgccaggttctaccccaacgtgaccaagtacctgccc
ctggacaagggcatcaagccctactaccccgagcacgccgtg
aaccactacttccagaccaggcactacctgcacaccctgtgg
aaggccggcatcctgtacaagagggagaccaccaggagcgcc
agcttctcgggcagccctacagctgggagcaggagctgcag
cacggcagctgctggtggctgcagttcaggaacagcaagccc
tgcagcgagtactgcctgacccacctggtgaacctgctggag
gactggggtccctgcgacgagcacggcgagcaccacatcagg
atcccaggacccccgccagggtgaccggcggcgtgttcctg
gtggacaagaaccccacaacaccgccgagagcaggctggtg
gtggacttcagccagttcagcaggggcatcaccagggtgagc
tggcccaagttcgccgtgcccaacctgcagagcctgaccaac
ctgctgagcagcaacctgagctggctgagcctggacgtgagc
gccgccttctaccacatcccccctgcaccccgccgccatgccc
gggcccaaggccccatacacgagcaccctgctgcccccggag
ctgtccgagaccccaacgccacgcagccagaactcgccccg
gaagaccccgaggattcggccctcttggaggaccccgtgggg
acggtggcgccgcaaatcccaccaaactggcacatcccgtcg
atccaggacgccgcgacgccttaccatcccccggccaccccg
aacaacatgggcctgatcgccggcgcggtgggcggcagtctc
ctggcagccctggtcatttgcggaattgtgtactggatgcac
cgccgcactcggaaagcccaaagcgcatacgcctccccccac
atccgggaagacgaccagccgtcctcgcaccagcccttgttt
tactag
``` gDPolC amino  
acid sequence  
PolC underlined  
(SEQ ID NO: 18)  
Signal peptide  
in italics

*MGGAAARLGAVILFVVIVGLHGVRG*KYALADASLKMADPNRF  
RGKDLPVLDQLTDPPGVRRVYHIQAGLPDPFQPPSLPITVYY  
AVLERACRSVLLNAPSEAPQIVRGASEDVRKQPYNLTIAWFR  
MGGNCAIPITVMEYTECSYNKSLGACPIRTQPRWNYYDSFSA  
VSEDNLGFLMHAPAFETAGTYLRLVKINDWTEITQFILEHRA  
KGSCKYALPLRIPPSACLSPQAYQQGVTVDSIGMLPRFIPEN  
QRTVAVYSLKIAGWHGPHLLVGSSGLSRYVARLSSNSRIINH  
QHGTMQNLHDSCSRNLYVSLLLLYKTFGRKLHLYSHPIILKT  
KRWGYSLNFMGYVIGSWGSLPQDHIIQKIKECFRKLPVNRPI  
DWKVCQRIVGLLGFAAPFTQCGYPALMPLYACIQSKQAFTFS  
PTYKAFLSKQYLNLYPVARQRPGLCQVFADATPTGWGLAMGH  
QRMRGTFVAPLPIHTAELLAACFARSRSGAKILGTDNSVVLS  
RKYTSFPWLLGCAANWILRGTSFVYVPSALNPADDPSRGRLG  
LSRPLLRLPFRPTTGRTSLYAVSPSVGPKAPYTSTLLPPELS  
ETPNATQPELAPEDPEDSALLEDPVGTVAPQIPPNWHIPSIQ  
DAATPYHPPATPNNMGLIAGAVGGSLLAALVICGIVYWMHRR  
TRKAPKRIRLPHIREDDQPSSHQPLFY gDPolC nucleic  
acid sequence  
PolC underlined  
(SEQ ID NO: 19)

```
atggggggggctgccgccaggttgggggccgtgattttgtttt
gtcgtcatagtgggcctccatggggtccgcggcaaatatgcc
ttggcggatgcctctctcaagatggccgaccccaatcgcttt
cgcggcaaagacttccggtcctggaccagctgaccgaccct
ccgggggtccggcgcgtgtaccacatccaggcgggcctaccg
gacccgttccagcccccccagcctcccgatcacggtttactac
gccgtgttggagcgcgcctgccgcagcgtgctcctaaacgca
ccgtcggaggccccccagattgtccgcggggcctccgaagac
gtccggaaacaaccctacaacctgaccatcgcttggtttcgg
atgggaggcaactgtgctatccccatcacggtcatggagtac
accgaatgctcctacaacaagtctctgggggcctgtcccatc
cgaacgcagccccgctggaactactatgacagcttcagcgcc
gtcagcgaggataacctggggttcctgatgcacgcccccgcg
tttgagaccgccggcacgtacctgcggctcgtgaagataaac
gactggacggagattacacagtttatcctggagcaccgagcc
aagggctcctgtaagtacgccctcccgctgcgcatcccccg
tcagcctgcctctccccccaggcctaccagcagggggtgacg
gtggacagcatcgggatgctgccccgcttcatccccgagaac
cagcgcaccgtcgccgtatacagcttgaagatcgccgggtgg
cacgggccccacctgctggtgggcagcagcgggcctgagcagg
tacgtggccaggctgagcagcaacagcaggatcatcaaccac
cagcacggcaccatgcagaacctgcacgacagctgcagcagg
aacctgtacgtgagcctgctgctgctgtacaagaccttcggc
aggaagctgcacctgtacagccacccccatcatcctgaagacc
aagaggtggggctacagcctgaacttcatgggctacgtgatc
ggcagctgggcagcctgccccaggaccacatcatccagaag
atcaaggagtgcttcaggaagctgcccgtgaacaggcccatc
gactggaaggtgtgccagaggatcgtgggcctgctgggcttc
gccgcccccttcacccagtgcggctaccccgccctgatgccc
```

TABLE 9-continued

Sequences

Sequence

<u>ctgtacgcctgcatccagagcaagcaggccttcaccttcagc</u>
<u>cccacctacaaggccttcctgagcaagcagtacctgaacctg</u>
<u>tacccccgtggccaggcagaggcccggcctgtgccaggtgttc</u>
<u>gccgacgccacccccaccggctggggcctggccatgggccac</u>
<u>cagaggatgagggggcaccttcgtggcccccctgcccatccac</u>
accgccgagctgctggccgcctgcttcgccaggagcaggagc
ggcgccaagatcctgggcaccgacaacagcgtggtgtgcgagc
aggaagtacaccagcttcccctggctgctgggctgcgccgcc
aactggatcctgagggggcaccagcttcgtgtacgtgcccagc
gccctgaaccccgccgacgacccagcaggggcaggctgggc
ctgagcaggcccctgctgaggctgcccttcaggcccaccacc
ggcaggaccagcctgtacgccgtgagccccagcgtggggccc
aaggccccatacacgagcaccctgctgcccccggagctgtcc
gagacccccaacgccacgcagccagaactcgccccggaagac
cccgaggattcggccctcttggaggaccccgtggggacggtg
gcgccgcaaatcccaccaaactggcacatcccgtcgatccag
gacgccgcgacgccttaccatccccggccacccgaacaac
atgggcctgatcgccggcgcggtgggcggcagtctcctggca
gccctggtcatttgcggaattgtgtactggatgcaccgccgc
actcggaaagccccaaagcgcatacgcctcccccacatccgg
gaagacgaccagccgtcctcgcaccagcccttgttttactag

| HBV PolN v2 amino acid sequence (SEQ ID NO: 173) | HFRKLLLLLDEEAGPLEEELPRLADEGLNRRVAEDLNLGNLPE WQTPSFPKIHLQEDIVDRCKQFVGPLTVNEKRRLKLIMPARF YPNVTKYLPLDKGIKPYYPEHAVNHYFQTRHYLHTLWKAGIL YKRETTRSASFCGSPYSWEQELQHGSCWWLQFRNSKPCSEYC LTHLVNLLEDWGPCDEHGEHHIRIPRTPARVT |

| HBV2 amino acid 174) (Pol N (italics)-Pol C (underlined)- Core) sequence (SEQ ID NO: | *YLPLDKGLKPYYPEHAVNHYFQTRHYLHTLWKAGLLYKRETT RSASFCGSPYSWEQELQHGSCWWLQFRNSKPCSEYCLTHLVN LLEDWGPCDEHGEHHIRIPRTPARVTGGVFLVDKNPHNTAES RLVVDFSQFSRGITRVSWPKFAVPNLQSLTNLLSSNLSWLSL DVQAFTFSPTYKAFLSKQYLNLYPVARQRPGLCQVFADATPT* <u>GWGLAMGHQRMRGTFVAPLPIHTAELLAACFARSRSGAKILG TDNSVVLSRKYTSFPWLLGCAANWILRGTSFVYVPSALNPAD DVGSNLEDPASRELVVSYVNVNMGLKIRQLLWFHISCLTFGR ETVIEYLVSFGVWIRTPPAYRPPNAPILSTLPETTVVRRRDR GR</u> |

| HBV3 amino acid sequence (SEQ ID NO: 175) (Pol N (italics)-Pol C (underlined)- Core) | *HFRKLLLLLDEEAGPLEEELPRLADEGLNRRVAEDLNLGNLPE WQTPSFPKIHLQEDIVDRCKQFVGPLTVNEKRRLKLIMPARF YPNVTKYLPLDKGIKPYYPEHAVNHYFQTRHYLHTLWKAGLL YKRETTRSASFCGSPYSWEQELQHGSCWWLQFRNSKPCSEYC LTHEVNLLEDWGPCDEHGEHHLRLPRTPARVT*<u>QAFTFSPTYK AFLSKQYLNLYPVARQRPGLCQVFADATPTGWGLAMGHQRMR GTFVAPLPIHTAELLAACFARSRSGAKILGTDNSVVLSRKYT SFPWLLGCAANWILRGTSFVYVPSALNPADDVGSNLEDPASR ELVVSYVNVNMGLKIRQLLWFHISCLTFGRETVIEYLVSFGV WIRTPPAYRPPNAPILSTLPETTVVRRRDRGR</u> |

| HBV2 nucleic acid sequence (SEQ ID NO: 176) | tatctgccgctggataaaggcattaaaccgtattatccggaacatgcggtgaaccattatttt cagacccgccattatctgcataccctgtggaaagcgggcattctgtataaacgcgaaacc acccgcagcgcgagcttttgcggcagcccgtatagctgggaacaggaactgcagcatg gcagctgctggtggctgcagtttcgcaacagcaaaccgtgcagcgaatattgcctgaccc atctggtgaacctgctggaagattgggggaccgtgcgatgaacatggcgaacatcatattc gcattccgcgcaccccggcgcgcgtgaccggcggcgtgtttctggtggataaaaacccg cataacaccgcggaaagccgcctggtggtggattttagccagtttagccgcgcggcattacc cgcgtgagctggccgaaatttgcggtgccgaacctgcagagcctgaccaacctgctgag cagcaacctgagctggctgagcctggatgtgcaggcgtttacctttagcccgacctataaa gcgtttctgagcaaacagtatctgaacctgtatccggtggcgcgccagcgcccgggcctg tgccaggtgtttgcggatgcgacccccgaccggctggggcctggcgatgggccatcagc gcatgcgcggcaccttgtggcgccgctgccgattcataccgcggaactgctggcggcg tgctttgcgcgcagccgcagcggcgcgaaaattctgggcaccgataacagcgtggtgct gagccgcaaatataccagctttccgtggctgctgggctgcgcggcgaactggattctgcg cggcaccagctttgtgtatgtgccgagcgcgctgaaccgcggcggatgatgtgggcagca acctggaagatccggcgagccgcgaactggtggtgagctatgtgaacgtgaacatggg cctgaaaattcgccagctgctgtggtttcatattagctgcctgacctttggccgcgcgaaaccg tgattgaatatctggtgagctttggcgtgtggattcgcaccccgccggcgtatcgcccgcc gaacgcgccgattctgagcaccctgccgagaaaccaccgtggtgcgccgccgcgatcgg ggccgc |

| HBV3 nucleic acid sequence (SEQ ID NO: 177) | cattttcgcaaactgctgctgctggatgaagaagcgggaccgctggaagaagaactgcc gcgcctggcggatgaaggcctgaaccgccgcgtggcggaagatctgaacctgggcaa cctgccggaatggcagacccccgagctttccgaaaattcatctgcaggaagatattgtggat cgctgcaaacagtttgtgggaccgctgaccgtgaacgaaaacgccgcctgaaactgatt atgccggcgcgcttttatccgaacgtgaccaaatatctgccgctggataaaggcattaaac |

TABLE 9-continued

| Sequences |
| --- |

| | Sequence |
| --- | --- |
| | cgtattatccggaacatgcggtgaaccattattttcagacccgccattatctgcataccctgt ggaaagcgggcattctgtataaacgcgaaaccacccgcagcgcgagctttgcggcagc ccgtatagctgggaacaggaactgcagcatggcagctgctggtggctgcagtttcgcaa cagcaaaccgtgcagcgaatattgcctgacccatctggtgaacctgctggaagattgggg accgtgcgatgaacatggcgaacatcatattcgcattccgcaccccggcgcgcgtga cccaggcgtttacctttagcccgacctataaagcgtttctgagcaaacagtatctgaacctg tatccggtggcgcgccagcgcccgggcctgtgccaggtgtttgcggatgcgaccccga ccggctggggcctggcgatgggccatcagcgcatgcgcggcacctttgtggcgccgct gccgattcataccgcggaactgctggcggcgtgctttgcgcgcagccgcagcggcgcg aaaattctgggcaccgataacagcgtggtgctgagccgcaaatataccagctttccgtgg ctgctgggctgcgcggcgaactggattctgcgcggcaccagctttgtgtatgtgccgagc gcgctgaacccggcggatgatgtgggcagcaacctggaagatccggcgagccgcgaa ctggtggtgagctatgtgaacgtgaacatgggcctgaaaattcgccagctgctgtggtttc atattagctgcctgacctttggccgcgaaaccgtgattgaatatctggtgagctttggcgtgt ggattcgcacccgccgggcgtatcgcccgccgaacgcgccgattctgagcaccctgcc ggaaaccaccgtggtgcgccgccgagatcgaggccgc |
| HBV2 PolN amino acid sequence (SEQ ID NO: 178) | YLPLDKGIKPYYPEHAVNHYFQTRHYLHTLWKAGILYKRETT RSASFCGSPYSWEQELQHGSCWWLQFRNSKPCSEYCLTHLVN LLEDWGPCDEHGEHHIRIPRTPARVTGGVFLVDKNPHNTAES RLVVDFSQFSRGITRVSWPKFAVPNLQSLTNLLSSNLSWLSL DV |
| HBV2 PolC amino acid sequence (SEQ ID NO: 179) | QAFTFSPTYKAFLSKQYLNLYPVARQRPGLCQVFADATPTGW GLAMGHQRMRGTFVAPLPIHTAELLAACFARSRSGAKILGTD NSVVLSRKYTSFPWLLGCAANWILRGTSFVYVPSALNPADD |
| HBV2 Core amino acid sequence (SEQ ID NO: 180) | VGSNLEDPASRELVVSYVNVNMGLKIRQLLWFHISCLTFGRE TVIEYLVSFGVWIRTPPAYRPPNAPILSTLPETTVVRRRDRG R |
| HBV3 PolN amino acid sequence (SEQ ID NO: 181) | HFRKLLLLLDEEAGPLEEELPRLADEGLNRRVAEDLNLGNLPE WQTPSFPKIHLQEDIVDRCKQFVGPLTVNEKRRLKLIMPARF YPNVTKYLPLDKGIKPYYPEHAVNHYFQTRHYLHTLWKAGIL YKRETTRSASFCGSPYSWEQELQHGSCWWLQFRNSKPCSEYC LTHLVNLLEDWGPCDEHGEHHIRIPRTPARVT |
| HBV3 PolC amino acid sequence (SEQ ID NO: 182) | QAFTFSPTYKAFLSKQYLNLYPVARQRPGLCQVFADATPTGW GLAMGHQRMRGTFVAPLPIHTAELLAACFARSRSGAKILGTD NSVVLSRKYTSFPWLLGCAANWILRGTSFVYVPSALNPADD |
| HBV3 Core amino sequence (SEQ ID NO: 183) | VGSNLEDPASRELVVSYVNVNMGLKIRQLLWFHISCLTFGRE TVIEYLVSFGVWIRTPPAYRPPNAPILSTLPETTVVRRRDRG R |
| gD-HBV2 nucleic acid sequence (SEQ ID NO: 184) | atggggggggctgccgccaggttggggggccgtgattttgttt gtcgtcatagtgggcctccatggggtccgcggcaaatatgcc ttggcggatgcctctctcaagatggccgacccccaatcgctttt cgcggcaaagaccttccggtcctggaccagctgaccgaccct ccgggggtccggcgcgtgtaccacatccaggcgggcctaccg gacccgttccagcccccagcctcccgatcacggtttactac gccgtgttggagcgcgcctgccgcagcgtgctcctaaacgca ccgtcggaggcccccagattgtccgcggggcctccgaagac gtccggaaacaaccctacaacctgaccatcgcttggtttcgg atgggaggcaactgtgctatccccatcacggtcatggagtac accgaatgctcctacaacaagtctctggggggcctgtcccatc cgaacgcagccccgctggaactactatgacagcttcagcgcc gtcagcgaggataacctggggttcctgatgcacgccccgcg tttgagaccgccggcacgtacctgcgggctcgtgaagataaac gactggacggagattacacagtttatcctggagcaccgagcc aagggctcctgtaagtacgccctcccgctgcgcatccccccg tcagcctgcctctccccccaggcctaccagcagggggtgacg gtggacagcatcgggatgctgccccgcttcatccccgagaac cagcgcaccgtcgccgtatacagcttgaagatcgccgggtgg cacgggccctatctgccgctggataaaggcattaaaccgtat tatccggaacatgcggtgaaccattattttcagacccgccat tatctgcataccctgtggaaagcgggcattctgtataaacgc gaaaccaccgcagcgcgagcttttgcggcagcccgtatagc tgggaacaggaactgcagcatggcagctgctggtggctgcag tttcgcaacagcaaaccgtgcagcgaatattgcctgacccat ctggtgaacctgctggaagattggggaccgtgcgatgaacat ggcgaacatcatattcgcattccgcgcaccccggcgcgcgtg |

TABLE 9-continued

| Sequences |
| --- |

| | Sequence |
| --- | --- |
| | accggcggcgtgtttctggtggataaaaacccgcataacacc |
| | gcggaaagccgcctggtggtggattttagccagtttagccgc |
| | ggcattacccgcgtgagctggccgaaatttgcggtgccgaac |
| | ctgcagagcctgaccaacctgctgagcagcaacctgagctgg |
| | ctgagcctggatgtgcaggcgtttacctttagcccgacctat |
| | aaagcgtttctgagcaaacagtatctgaacctgtatccggtg |
| | gcgcgccagcgcccgggcctgtgccaggtgtttgcggatgcg |
| | accccgaccggctggggcctggcgatgggccatcagcgcatg |
| | cgcggcacctttgtggcgccgctgccgattcataccgcggaa |
| | ctgctggcggcgtgctttgcgcgcagccgcagcggcgcgaaa |
| | attctgggcaccgataacagcgtggtgctgagccgcaaatat |
| | accagctttccgtggctgctgggctgcgcggcgaactggatt |
| | ctgcgcggcaccagctttgtgtatgtgccgagcgcgctgaac |
| | ccggcggatgatgtgggcagcaacctggaagatccggcgagc |
| | cgcgaactggtggtgagctatgtgaacgtgaacatgggcctg |
| | aaaattcgccagctgctgtggtttcatattagctgcctgacc |
| | tttggccgcgaaaccgtgattgaatatctggtgagctttggc |
| | gtgtggattcgcaccccgccggcgtatcgcccgccgaacgcg |
| | ccgattctgagcaccctgccggaaaccaccgtggtgcgccgc |
| | cgcgatcggggccgcgggcccaaggccccatacacgagcacc |
| | ctgctgccccccggagctgtccgagacccccaacgccacgcag |
| | ccagaactcgccccggaagaccccgaggattcggccctcttg |
| | gaggacccgtggggacggtggcgccgcaaatcccaccaaac |
| | tggcacatcccgtcgatccaggacgccgcgacgccttaccat |
| | cccccggccaccccgaacaacatgggcctgatcgccggcgcg |
| | gtgggcggcagtctcctggcagccctggtcatttgcggaatt |
| | gtgtactggatgcaccgccgcactcggaaagcccccaaagcgc |
| | atacgcctcccccacatccgggaagacgaccagccgtcctcg |
| | caccagcccttgttttactag |
| gD-HBV2 amino acid sequence (SEQ ID NO: 185) | MGGAAARLGAVILFVVIVGLHGVRGKYALADASLKMADPNRF RGKDLPVLDQLTDPPGVRRVYHIQAGLPDPFQPPSLPITVYY AVLERACRSVLLNAPSEAPQIVRGASEDVRKQPYNLTIAWFR MGGNCAIPITVMEYTECSYNKSLGACPIRTQPRWNYYDSFSA VSEDNLGFLMHAPAFETAGTYLRLVKINDWTEITQFILEHRA KGSCKYALPLRIPPSACLSPQAYQQGVTVDSIGMLPRFIPEN QRTVAVYSLKIAGWHGPYLPLDKGIKPYYPEHAVNHYFQTRH YLHTLWKAGILYKRETTRSASFCGSPYSWEQELQHGSCWWLQ FRNSKPCSEYCLTHLVNLLEDWGPCDEHGEHHIRIPRTPARV TGGVFLVDKNPHNTAESRLVVDFSQFSRGITRVSWPKFAVPN LQSLTNLLSSNLSWLSLDVQAFTFSPTYKAFLSKQYLNLYPV ARQRPGLCQVFADATPTGWGLAMGHQRMRGTFVAPLPIHTAE LLAACFARSRSGAKILGTDNSVVLSRKYTSFPWLLGCAANWI LRGTSFVYVPSALNPADDVGSNLEDPASRELVVSYVNVNMGL KIRQLLWFHISCLTFGRETVIEYLVSFGVWIRTPPAYRPPNA PILSTLPETTVVRRRDRGRGPKAPYTSTLLPPELSETPNATQ PELAPEDPEDSALLEDPVGTVAPQIPPNWHIPSIQDAATPYH PPATPNNMGLIAGAVGGSLLAALVICGIVYWMHRRTRKAPKR IRLPHIREDDQPSSHQPLFY* |
| gD-HBV3 nucleic acid sequence (SEQ ID NO: 186) | atggggggggctgccgccaggttggggggccgtgattttgtttt gtcgtcatagtgggcctccatggggtccgcggcaaatatgcc ttggcggatgcctctctcaagatggccgaccccaatcgcttt cgcggcaaagaccttccggtcctggaccagctgaccgaccct ccgggggtccggcgcgtgtaccacatccaggcgggcctaccg gacccgttccagcccccagcctcccgatcacggtttactac gccgtgttggagcgcgcctgccgcagcgtgctcctaaacgca ccgtcggaggccccccagattgtccgcgggggcctccgaagac gtccggaaacaaccctacaacctgaccatcgcttggtttcgg atgggaggcaactgtgctatccccatcacggtcatggagtac accgaatgctcctacaacaagtctctgggggcctgtcccatc cgaacgcagccccgctggaactactatgacagcttcagcgcc gtcagcgaggataacctggggttcctgatgcacgccccgcg tttgagaccgccggcacgtacctgcggctcgtgaagataaac gactggacggagattacacagtttatcctggagcaccgagcc aagggctcctgtaagtacgccctcccgctgcgcatcccccg tcagcctgcctctcccccaggcctaccagcaggggtgacg gtggacagcatcgggatgctgccccgcttcatccccgagaac cagcgcaccgtcgccgtatacagcttgaagatcgccgggtgg cacgggcccatttcgcaaactgctgctgctggatgaagaa gcgggaccgctggaagaagaactgccgcgcctggcggatgaa ggcctgaacgcccgcgtggcggaagatctgaacctgggcaac ctgccggaatggcagaccccgagctttccgaaaattcatctg caggaagatattgtggatcgctgcaaacagtttgtgggaccg ctgaccgtgaacgaaaaacgccgcctgaaactgattatgccg gcgcgctttttatccgaacgtgaccaaatatctgccgctggat |

TABLE 9-continued

Sequences

| Sequence |
| --- |

```
aaaggcattaaaccgtattatccggaacatgcggtgaaccat
tattttcagacccgccattatctgcataccctgtggaaagcg
ggcattctgtataaacgcgaaaccacccgcagcgcgagcttt
tgcggcagcccgtatagctgggaacaggaactgcagcatggc
agctgctggtggctgcagtttcgcaacagcaaaccgtgcagc
gaatattgcctgacccatctggtgaacctgctggaagattgg
ggaccgtgcgatgaacatggcgaacatcatattcgcattccg
cgcaccccggcgcgcgtgacccaggcgtttacctttagcccg
acctataaagcgtttctgagcaaacagtatctgaacctgtat
ccggtggcgcgccagcgcccgggcctgtgccaggtgtttgcg
gatgcgaccccgaccggctggggcctggcgatgggccatcag
cgcatgcgcggcacctttgtggcgccgctgccgattcatacc
gcggaactgctggcggcgtgctttgcgcgcagccgcagcggc
gcgaaaattctgggcaccgataacagcgtggtgctgagccgc
aaatataccagctttccgtggctgctgggctgcgcggcgaac
tggattctgcgcggcaccagctttgtgtatgtgccgagcgcg
ctgaacccggcggatgatgtgggcagcaacctggaagatccg
gcgagccgcgaactggtggtgagctatgtgaacgtgaacatg
ggcctgaaaattcgccagctgctgtggtttcatattagctgc
ctgacctttggccgcgaaaccgtgattgaatatctggtgagc
tttggcgtgtggattcgcacccogccggcgtatcgcccgccg
aacgcgccgattctgagcaccctgccggaaaccaccgtggtg
cgccgccgagatcgaggccgcgggccccaaggccccatacacg
agcaccctgctgccccccggagctgtccgagaccoccaacgcc
acgcagccagaactcgcccccggaagaccoccgaggattcggcc
ctcttggaggaccoccgtggggacggtggcgccgcaaatccca
ccaaactggcacatcccgtcgatccaggacgccgcgacgcct
taccatccoccggccaccoccgaacaacatgggcctgatcgcc
ggcgcggtgggcggcagtctcctggcagccctggtcatttgc
ggaattgtgtactggatgcaccgccgcactcggaaagcccca
aagcgcatacgcctcccccacatccgggaagacgaccagccg
tcctcgcaccagccottgttttactag
```

| gD-HBV3 amino acid sequence (SEQ ID NO: 187) | MGGAAARLGAVILFVVIVGLHGVRGKYALADASLKMADPNRF RGKDLPVLDQLTDPPGVRRVYHIQAGLPDPFQPPSLPITVYY AVLERACRSVLLNAPSEAPQIVRGASEDVRKQPYNLTIAWFR MGGNCAIPITVMEYTECSYNKSLGACPIRTQPRWNYYDSFSA VSEDNLGFLMHAPAFETAGTYLRLVKINDWTEITQFILEHRA KGSCKYALPLRIPPSACLSPQAYQQGVTVDSIGMLPRFIPEN QRTVAVYSLKIAGWHGPHFRKLLLLLDEEAGPLEEELPRLADE GLNRRVAEDLNLGNLPEWQTPSFPKIHLQEDIVDRCKQFVGP LTVNEKRRLKLIMPARFYPNVTKYLPLDKGIKPYYPEHAVNH YFQTRHYLHTLWKAGILYKRETTRSASFCGSPYSWEQELQHG SCWWLQFRNSKPCSEYCLTHLVNLLEDWGPCDEHGEHHIRIP RTPARVTQAFTFSPTYKAFLSKQYLNLYPVARQRPGLCQVFA DATPTGWGLAMGHQRMRGTFVAPLPIHTAELLAACFARSRSG AKILGTDNSVVLSRKYTSFPWLLGCAANWILRGTSFVYVPSA LNPADDVGSNLEDPASRELVVSYVNVNMGLKIRQLLWFHISC LTFGRETVIEYLVSFGVWIRTPPAYRPPNAPILSTLPETTVV RRRDRGRGPKAPYTSTLLPPELSETPNATQPELAPEDPEDSA LLEDPVGTVAPQIPPNWHIPSIQDAATPYHPPATPNNMGLIA GAVGGSLLAALVICGIVYWMHRRTRKAPKRIRLPHIREDDQP SSHQPLFY* |

EMBODIMENTS

The following list of embodiments is intended to complement, rather than displace or supersede, the previous descriptions.

Embodiment 1. A hepatitis B virus (HBV) Core protein comprising the amino acid sequence of SEQ ID NO: 6 or an immunogenic fragment thereof.

Embodiment 2. The HBV Core protein of embodiment 1, wherein the immunogenic fragment comprises any one of SEQ ID NOs: 20-54.

Embodiment 3. A hepatitis B virus (HBV) Core protein comprising the amino acid sequence of SEQ ID NO: 180 or an immunogenic fragment thereof, or the amino acid sequence of SEQ ID NO: 183 or an immunogenic fragment thereof.

Embodiment 4. A nucleic acid molecule encoding the HBV Core protein of any one of embodiments 1-3.

Embodiment 5. The nucleic acid molecule of embodiment 4, wherein the nucleic acid molecule comprises the nucleotide sequence of SEQ ID NO: 7.

Embodiment 6. A vector comprising the nucleic acid molecule of embodiment 4 or 5.

Embodiment 7. The vector of embodiment 6, wherein the vector is an adenoviral vector.

Embodiment 8. The vector of embodiment 7, wherein the adenoviral vector is an AdC6 vector or AdC7 vector.

Embodiment 9. A vaccine comprising the vector of any one of embodiments 6-8.

Embodiment 10. A HBV polymerase N-terminal domain comprising the amino acid sequence of SEQ ID NO: 8 or an immunogenic fragment thereof.

Embodiment 11. The HBV polymerase N-terminal domain of embodiment 10, wherein the immunogenic fragment comprises any one of SEQ ID NOs: 55-113.

Embodiment 12. A HBV polymerase N-terminal domain comprising the amino acid sequence of SEQ ID NO: 178 or an immunogenic fragment thereof, or the amino acid sequence of SEQ ID NO: 181 or an immunogenic fragment thereof.

Embodiment 13. A HBV polymerase C-terminal domain comprising the amino acid sequence of SEQ ID NO: 10 or an immunogenic fragment thereof.

Embodiment 14. The HBV polymerase C-terminal domain of embodiment 13, wherein the immunogenic fragment comprises any one of SEQ ID NOs: 114-172.

Embodiment 15. A HBV polymerase C-terminal domain comprising the amino acid sequence of SEQ ID NO: 179 or an immunogenic fragment thereof, or the amino acid sequence of SEQ ID NO: 182 or an immunogenic fragment thereof.

Embodiment 16. A nucleic acid molecule encoding the HBV polymerase of any one of embodiments 10-15.

Embodiment 17. The nucleic acid molecule of embodiment 16, wherein the nucleic acid molecule comprises the nucleotide sequence of SEQ ID NO: 9.

Embodiment 18. The nucleic acid molecule of embodiment 16, wherein the nucleic acid molecule comprises the nucleotide sequence of SEQ ID NO: 11.

Embodiment 19. A vector comprising the nucleic acid molecule of any one of embodiments 16-18.

Embodiment 20. The vector of embodiment 19, wherein the vector is an adenoviral vector.

Embodiment 21. The vector of embodiment 20, wherein the adenoviral vector is an AdC6 vector or AdC7 vector.

Embodiment 22. A vaccine comprising the vector of any one of embodiments 19-21.

Embodiment 23. A fusion protein comprising:

one or more of an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof.

Embodiment 24. The fusion protein of embodiment 23, comprising:

(1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;

(2) one or more of SEQ ID NOs: 20-54 (immunogenic fragments of SEQ ID NO: 6) and one or more of SEQ ID NOs: 55-113 (immunogenic fragments of SEQ ID NO: 8);

(3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;

(4) one or more of SEQ ID NOs: 20-54 (immunogenic fragments of SEQ ID NO: 6) and one or more of SEQ ID NOs: 114-172 (immunogenic fragments of SEQ ID NO: 10);

(5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;

(6) one or more of SEQ ID NOs: 55-113 (immunogenic fragments of SEQ ID NO: 8) and one or more of SEQ ID NOs: 114-172 (immunogenic fragments of SEQ ID NO: 10);

(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof; or (8) one or more of SEQ ID NOs: 20-54 (immunogenic fragments of SEQ ID NO: 6), one or more of SEQ ID NOs: 55-113 (immunogenic fragments of SEQ ID NO: 8), and one or more of SEQ ID NOs: 114-172 (immunogenic fragments of SEQ ID NO: 10).

Embodiment 25. A fusion protein comprising:

an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof.

Embodiment 26. The fusion protein of embodiment 25, comprising the amino acid sequence of SEQ ID NO: 174.

Embodiment 27. A fusion protein comprising:

an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof.

Embodiment 28. The fusion protein of embodiment 27, comprising the amino acid sequence of SEQ ID NO: 175.

Embodiment 29. A fusion protein comprising:

an N-terminal herpes simplex virus (HSV) glycoprotein (gD) sequence or a variant thereof;

an HBV Core protein comprising the amino acid sequence of SEQ ID NO: 6 or an immunogenic fragment thereof, and a C-terminal HSV gD sequence or a variant thereof.

Embodiment 30. The fusion protein of embodiment 29, wherein the immunogenic fragment comprises any one of SEQ ID NOs: 20-54.

Embodiment 31. A fusion protein comprising:

an N-terminal HSV gD sequence or a variant thereof;

an HBV polymerase N-terminal domain comprising the amino acid sequence of SEQ ID NO: 8 or an immunogenic fragment thereof, and a C-terminal HSV gD protein sequence or a variant thereof.

Embodiment 32. The fusion protein of embodiment 31, wherein the immunogenic fragment comprises any one of SEQ ID NOs: 55-113.

Embodiment 33. A fusion protein comprising:

an N-terminal HSV gD sequence or a variant thereof;

an HBV polymerase C-terminal domain comprising the amino acid sequence of SEQ ID NO: 10 or an immunogenic fragment thereof, and a C-terminal HSV gD protein sequence or a variant thereof.

Embodiment 34. The fusion protein of embodiment 33, wherein the immunogenic fragment comprises any one of SEQ ID NOs: 114-172.

Embodiment 35. A fusion protein comprising:

an N-terminal HSV gD sequence or a variant thereof;

an HBV sequence comprising:

(1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;

(2) one or more of SEQ ID NOs: 20-54 (immunogenic fragments of SEQ ID NO: 6) and one or more of SEQ ID NOs: 55-113 (immunogenic fragments of SEQ ID NO: 8);

(3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;

(4) one or more of SEQ ID NOs: 20-54 (immunogenic fragments of SEQ ID NO: 6) and one or more of SEQ ID NOs: 114-172 (immunogenic fragments of SEQ ID NO: 10);

(5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;

(6) one or more of SEQ ID NOs: 55-113 (immunogenic fragments of SEQ ID NO: 8) and one or more of SEQ ID NOs: 114-172 (immunogenic fragments of SEQ ID NO: 10);

(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof; or (8) one or more of SEQ ID NOs: 20-54 (immunogenic fragments of SEQ ID NO: 6), one or more of SEQ ID NOs: 55-113 (immunogenic fragments of SEQ ID NO: 8), and one or more of SEQ ID NOs: 114-172 (immunogenic fragments of SEQ ID NO: 10) and a C-terminal HSV gD protein sequence or a variant thereof.

Embodiment 36. A fusion protein comprising:

an N-terminal HSV gD sequence or a variant thereof;

an HBV Core protein comprising the amino acid sequence of SEQ ID NO: 180 or an immunogenic fragment thereof, or the amino acid sequence of SEQ ID NO: 183 or an immunogenic fragment thereof, and a C-terminal HSV gD sequence or a variant thereof.

Embodiment 37. A fusion protein comprising:

an N-terminal HSV gD sequence or a variant thereof;

an HBV polymerase N-terminal domain comprising the amino acid sequence of SEQ ID NO: 178 or an immunogenic fragment thereof, or the amino acid sequence of SEQ ID NO: 181 or an immunogenic fragment thereof, and a C-terminal HSV gD protein sequence or a variant thereof.

Embodiment 38. A fusion protein comprising:

an N-terminal HSV gD sequence or a variant thereof;

an HBV polymerase C-terminal domain comprising the amino acid sequence of SEQ ID NO: 179 or an immunogenic fragment thereof, or the amino acid sequence of SEQ ID NO: 182 or an immunogenic fragment thereof, and a C-terminal HSV gD protein sequence or a variant thereof.

Embodiment 39. A fusion protein comprising:

an N-terminal HSV gD sequence or a variant thereof;

an HBV sequence comprising:

(1) an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof, or (2) an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof, and a C-terminal HSV gD protein sequence or a variant thereof.

Embodiment 40. The fusion protein of embodiment 39, wherein the HBV sequence comprises an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof.

Embodiment 41. The fusion protein of embodiment 40, wherein the HBV sequence comprises the amino acid sequence of SEQ ID NO: 174.

Embodiment 42. The fusion protein of embodiment 39, wherein the HBV sequence comprises an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof Embodiment 43. The fusion protein of embodiment 42, wherein the HBV sequence comprises the amino acid sequence of SEQ ID NO: 175.

Embodiment 44. The fusion protein of any one of embodiments 29-43, wherein the N-terminal HSV gD sequence comprises the amino acid sequence of SEQ ID NO: 12.

Embodiment 45. The fusion protein of any one of embodiments 29-43, wherein the N-terminal HSV gD sequence comprises amino acid residues 26-269 of SEQ ID NO: 12.

Embodiment 46. The fusion protein of any one of embodiments 29-45, wherein the C-terminal HSV gD sequence comprises the transmembrane domain of the HSV gD.

Embodiment 47. The fusion protein of any one of embodiments 29-46, wherein the C-terminal HSV gD sequence comprises the amino acid sequence of SEQ ID NO: 13.

Embodiment 48. The fusion protein of any one of embodiments 29-47, wherein the fusion protein comprises the amino acid sequence of any one of SEQ ID NO: 14 or an immunogenic fragment thereof, SEQ ID NO: 16 or an immunogenic fragment thereof, or SEQ ID NO: 18 or an immunogenic fragment thereof.

Embodiment 49. The fusion protein of any one of embodiments 39-47, wherein the fusion protein comprises the amino acid sequence of SEQ ID NO: 185.

Embodiment 50. The fusion protein of any one of embodiments 39-47, wherein the fusion protein comprises the amino acid sequence of SEQ ID NO: 187.

Embodiment 51. A nucleic acid molecule encoding the fusion protein of any one of embodiments 23-50.

Embodiment 52. The nucleic acid molecule of embodiment 51, wherein the nucleic acid molecule comprises the nucleotide sequence of any one of SEQ ID NOs: 15, 17, or 19.

Embodiment 53. The nucleic acid molecule of embodiment 51, wherein the nucleic acid molecule comprises the nucleotide sequence of SEQ ID NO: 176.

Embodiment 54. The nucleic acid molecule of embodiment 51, wherein the nucleic acid molecule comprises the nucleotide sequence of SEQ ID NO: 177.

Embodiment 55. The nucleic acid molecule of embodiment 51, wherein the nucleic acid molecule comprises the nucleotide sequence of SEQ ID NO: 184.

Embodiment 56. The nucleic acid molecule of embodiment 51, wherein the nucleic acid molecule comprises the nucleotide sequence of SEQ ID NO: 186.

Embodiment 57. A vector comprising the nucleic acid molecule of any one of embodiments 51-56.

Embodiment 58. The vector of embodiment 57, wherein the vector is an adenoviral vector.

Embodiment 59. The vector of embodiment 58, wherein the adenoviral vector is an AdC6 vector or AdC7 vector.

Embodiment 60. A vaccine comprising the vector of any one of embodiments 57-59.

Embodiment 61. A method of inducing an immune response to HBV in a subject, the method comprising providing to the subject an effective amount of the fusion protein of any one of embodiments 23-50, the nucleic acid molecule of any one of embodiments 51-56, the vector of any one of embodiments 57-59, or the vaccine of embodiment 60 to thereby induce an immune response to HBV.

Embodiment 62. The method of embodiment 61, wherein the vaccine comprises an AdC6 vector comprising a fusion protein comprising the amino acid sequence of any one of SEQ ID NOs: 14, 16, or 18, or an immunogenic fragment thereof.

Embodiment 63. The method of embodiment 62, further comprising providing to the subject, subsequent to providing the vaccine comprising the AdC6 vector, a vaccine comprising an AdC7 vector comprising a fusion protein comprising the amino acid sequence of any one of SEQ ID NOs: 14, 16, or 18, or an immunogenic fragment thereof.

Embodiment 64. The method of embodiment 61, wherein the vaccine comprises an AdC7 vector comprising a fusion protein comprising the amino acid sequence of any one of SEQ ID NOs: 14, 16, or 18, or an immunogenic fragment thereof.

Embodiment 65. The method of embodiment 64, further comprising providing to the subject, subsequent to providing the vaccine comprising the AdC7 vector, a vaccine comprising an AdC6 vector comprising a fusion protein comprising the amino acid sequence of any one of SEQ ID NOs: 14, 16, or 18, or an immunogenic fragment thereof.

Embodiment 66. The method of embodiment 61, wherein the vaccine comprises an AdC6 vector comprising a fusion protein comprising the amino acid sequence of SEQ ID NO: 185.

Embodiment 67. The method of embodiment 66, further comprising providing to the subject, subsequent to providing the vaccine comprising the AdC6 vector, a vaccine comprising an AdC7 vector comprising a fusion protein comprising the amino acid sequence of SEQ ID NO: 185.

Embodiment 68. The method of embodiment 61, wherein the vaccine comprises an AdC7 vector comprising a fusion protein comprising the amino acid sequence of SEQ ID NO: 185.

Embodiment 69. The method of embodiment 68, further comprising providing to the subject, subsequent to providing the vaccine comprising the AdC7 vector, a vaccine comprising an AdC6 vector comprising a fusion protein comprising the amino acid sequence of SEQ ID NO: 185.

Embodiment 70. The method of embodiment 61, wherein the vaccine comprises an AdC6 vector comprising a fusion protein comprising the amino acid sequence of SEQ ID NO: 187.

Embodiment 71. The method of embodiment 70, further comprising providing to the subject, subsequent to providing the vaccine comprising the AdC6 vector, a vaccine comprising an AdC7 vector comprising a fusion protein comprising the amino acid sequence of SEQ ID NO: 187.

Embodiment 72. The method of embodiment 61, wherein the vaccine comprises an AdC7 vector comprising a fusion protein comprising the amino acid sequence of SEQ ID NO: 187.

Embodiment 73. The method of embodiment 72, further comprising providing to the subject, subsequent to providing the vaccine comprising the AdC7 vector, a vaccine comprising an AdC6 vector comprising a fusion protein comprising the amino acid sequence of SEQ ID NO: 187.

Embodiment 74. The method of any one of embodiments 61-73, wherein the amino acid sequence of any one of SEQ ID NOs: 14, 16, 18, 185, or 187, or an immunogenic fragment thereof, does not contain the N-terminal 25 amino acid signal peptide.

What is claimed:

1. A fusion protein comprising:

an HBV polymerase N-terminal domain comprising the amino acid sequence of SEQ ID NO: 178, an HBV polymerase C-terminal domain comprising the amino acid sequence of SEQ ID NO: 179, and an HBV Core protein comprising the amino acid sequence of SEQ ID NO: 180.

2. The fusion protein of claim 1, comprising the amino acid sequence of SEQ ID NO: 174.

3. The fusion protein of claim 1, further comprising an N-terminal HSV gD sequence, a C-terminal HSV gD sequence, or both.

4. The fusion protein of claim 3, comprising:

an N-terminal HSV gD sequence, an HBV sequence comprising an HBV polymerase N-terminal domain comprising the amino acid sequence of SEQ ID NO: 178, an HBV polymerase C-terminal domain comprising the amino acid sequence of SEQ ID NO: 179, and an HBV Core protein comprising the amino acid sequence of SEQ ID NO: 180; and a C-terminal HSV gD sequence.

5. The fusion protein of claim 4, wherein the HBV sequence comprises the amino acid sequence of SEQ ID NO: 174.

6. The fusion protein of claim 4, wherein the N-terminal HSV gD sequence comprises the amino acid sequence of SEQ ID NO: 12.

7. The fusion protein of claim 4, wherein the N-terminal HSV gD sequence comprises amino acid residues 26-269 of SEQ ID NO: 12.

8. The fusion protein of claim 4, wherein the C-terminal HSV gD sequence comprises the transmembrane domain of the HSV gD.

9. The fusion protein of claim 4, wherein the C-terminal HSV gD sequence comprises the amino acid sequence of SEQ ID NO: 13.

10. The fusion protein of claim 4, wherein the fusion protein comprises the amino acid sequence of SEQ ID NO: 185.

11. A nucleic acid molecule encoding the fusion protein of claim 1.

12. The nucleic acid molecule of claim 11, wherein the nucleic acid molecule comprises the nucleotide sequence of SEQ ID NO: 176.

13. The nucleic acid molecule of claim 11, wherein the nucleic acid molecule comprises the nucleotide sequence of SEQ ID NO: 184.

14. A vector comprising the nucleic acid molecule of claim 11.

15. The vector of claim 14, wherein the vector is an adenoviral vector.

16. The vector of claim 15, wherein the adenoviral vector is an AdC6 vector or AdC7 vector.

17. A vaccine comprising the vector of claim 14.

18. A method of inducing an immune response to HBV in a subject, the method comprising providing to the subject an effective amount of the vaccine of claim 17 to thereby induce an immune response to HBV.

19. The method of claim 18, wherein the vaccine comprises an AdC6 vector comprising a nucleic acid molecule encoding a fusion protein comprising the amino acid sequence of SEQ ID NO: 185.

20. The method of claim 19, further comprising providing to the subject, subsequent to providing the vaccine comprising the AdC6 vector, a vaccine comprising an AdC7 vector comprising a nucleic acid molecule encoding a fusion protein comprising the amino acid sequence of SEQ ID NO: 185.

21. The method of claim 18, wherein the vaccine comprises an AdC7 vector comprising a nucleic acid molecule encoding a fusion protein comprising the amino acid sequence of SEQ ID NO: 185.

22. The method of claim 21, further comprising providing to the subject, subsequent to providing the vaccine comprising the AdC7 vector, a vaccine comprising an AdC6 vector comprising a nucleic acid molecule encoding a fusion protein comprising the amino acid sequence of SEQ ID NO: 185.

23. The method of claim 18, wherein the vaccine comprising a vector encoding a fusion protein comprising the amino acid sequence of SEQ ID NO: 185 does not contain the N-terminal 25 amino acid signal peptide of the HSV gD.

*    *    *    *    *